United States Patent
Anderson et al.

(10) Patent No.: US 9,963,434 B2
(45) Date of Patent: May 8, 2018

(54) N-ARYLMETHYL SULFONAMIDE NEGATIVE MODULATORS OF NR2A

(71) Applicant: LUC THERAPEUTICS, Cambridge, MA (US)

(72) Inventors: David R Anderson, Salem, CT (US); Robert A Volkmann, Mystic, CT (US)

(73) Assignee: Luc Therapeutics, Inc., Cambridge, MA (US)

( * ) Notice: Subject to any disclaimer, the term of this patent is extended or adjusted under 35 U.S.C. 154(b) by 0 days. days.

(21) Appl. No.: 15/024,870

(22) PCT Filed: Sep. 26, 2014

(86) PCT No.: PCT/US2014/057795
§ 371 (c)(1),
(2) Date: Mar. 25, 2016

(87) PCT Pub. No.: WO2015/048503
PCT Pub. Date: Apr. 2, 2015

(65) Prior Publication Data
US 2016/0311782 A1    Oct. 27, 2016

Related U.S. Application Data

(60) Provisional application No. 61/882,964, filed on Sep. 26, 2013.

(51) Int. Cl.
| | | |
|---|---|---|
| *A61K 31/4965* | (2006.01) | |
| *C07D 241/24* | (2006.01) | |
| *C07D 401/12* | (2006.01) | |
| *C07D 403/12* | (2006.01) | |
| *C07D 417/12* | (2006.01) | |
| *C07D 213/81* | (2006.01) | |
| *C07D 213/82* | (2006.01) | |
| *C07D 237/24* | (2006.01) | |
| *C07D 405/12* | (2006.01) | |
| *C07D 409/12* | (2006.01) | |
| *C07D 413/12* | (2006.01) | |
| *C07D 417/14* | (2006.01) | |

(52) U.S. Cl.
CPC ......... *C07D 241/24* (2013.01); *C07D 213/81* (2013.01); *C07D 213/82* (2013.01); *C07D 237/24* (2013.01); *C07D 401/12* (2013.01); *C07D 403/12* (2013.01); *C07D 405/12* (2013.01); *C07D 409/12* (2013.01); *C07D 413/12* (2013.01); *C07D 417/12* (2013.01); *C07D 417/14* (2013.01)

(58) Field of Classification Search
CPC .. C07D 241/24; C07D 401/12; C07D 403/12; C07D 417/12
See application file for complete search history.

(56) References Cited

U.S. PATENT DOCUMENTS

2003/0114447 A1    6/2003    Choong et al.
2006/0014945 A1    1/2006    Galley et al.

OTHER PUBLICATIONS

International Search Report and Written Opinion, Patent Cooperation Treaty, Application No. PCT/US2014/057795, dated Feb. 19, 2015, 9 pages.

*Primary Examiner* — Brian McDowell
(74) *Attorney, Agent, or Firm* — Ziegler IP Law Group, LLC

(57) ABSTRACT

Compounds of the Formula

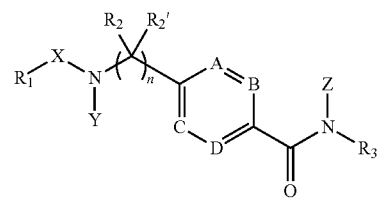

wherein A, B, C, D, X, Y, Z, $R_1$, $R_2$, $R_{2'}$, $R_3$ and n are described herein, selectively negatively modulate NMDA receptors containing an NR2A subunit, pharmaceutical compositions comprising the compounds, and methods of treating a disease using the compounds are disclosed.

25 Claims, No Drawings

N-ARYLMETHYL SULFONAMIDE NEGATIVE MODULATORS OF NR2A

PRIORITY

This is the National stage filing of PCT/US2014/057795 filed Sep. 26, 2014 and published as WO 2015/048503 which claims priority to U.S. Provisional Application 61/882,964 filed Sep. 26, 2013, the disclosures of which are incorporated herein by reference in their entirety.

FIELD

The present disclosure relates to compounds and compositions that negatively modulate the activity of an NR2A receptor, as well as methods of using these compounds and compositions for treating patients suffering from diseases associated with NR2A receptors.

BACKGROUND

The NMDA receptor is arguably an important signaling mechanism in the human brain. The brain processes a complex array of information to allow humans to function, storing information from the past and analyzing this information in the context of the present to respond and plan for the future. These incredibly complex computations are mediated at the molecular level by the continual adjustment of the strength of synapses, the nodes for communication between nerve cells (estimated at about 60 trillion in the human brain).

Glutamate is the major excitatory neurotransmitter in the brain, utilized at 80% of these synapses. NMDA receptors are one of three classes that mediate synaptic transmission using glutamate. NMDA receptors play a critical role in regulating the strength of synapses, that is, in regulating synaptic plasticity. Thus, the NMDA receptor is at the molecular core of brain function, and in particular the cognitive functions of learning and memory. These facts underlie the tremendous therapeutic utility of modulating NMDA receptor function with new drugs to treat a broad range of neuropsychiatric disease and cognitive dysfunction.

It is apparent that the molecular basis of NMDA receptor function is increasingly well understood. The NMDA receptor comprises four protein subunits: two NR1 subunits and two NR2 subunits. An NR1 subunit derived from a single gene is ubiquitously expressed throughout the brain and is common to all NMDA receptors. However, four different NR2 subunits, NR2A-D, are derived from separate genes that are differentially expressed in different brain regions and by distinct populations of neurons within a particular region. Furthermore, individual neurons may express more than one NR2 subunit and individual NMDA receptors expressed by such neurons may contain two of the same NR2 subunits (for example, 2 NR2A subunits) or two different subunits (one NR2A and one NR2B subunit). Therefore, a drug that selectively modulates the activity of one NR2 subunit may do so at receptors that express either one or two of the targeted subunits. Thus, there is a need for new treatments for diseases related to the NR2A receptor.

SUMMARY

In one aspect, there are provided compounds of Formula I:

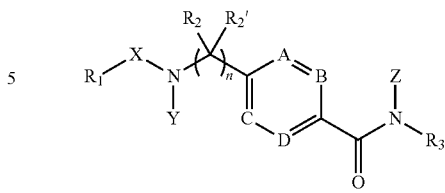

and pharmaceutically acceptable salts, prodrugs, solvates, hydrates, tautomers, or stereoisomers thereof
wherein:
A, B, C, and D are independently CR or N provided that at least one of A, B, C or D is N;
each R is independently selected from the group consisting of H, halogen, $C_1$-$C_5$ alkyl, $C_1$-$C_5$haloalkyl, CN and O-alkyl; or
when both A and B are CR, the R groups on A and B may form, with A and B, a fused 5,6 or 6,6 bicyclic aryl group or heteroaryl group;
$R_1$ is aryl or heteroaryl both of which are optionally substituted with one or more substituents selected from the group consisting of halogen, $C_1$-$C_5$ alkyl, —C(O)$C_1$-$C_5$alkyl, haloalklyl, CN, O-aryl, O-alkyl, aryl, and heteroaryl; or
$R_1$ is selected from the group consisting of optionally substituted alkyl, optionally substituted cycloalkyl, or optionally substituted heterocycloalkyl;
$R_2$ and $R_{2'}$ are independently selected from the group consisting of H, and $C_1$-$C_5$ alkyl; or
$R_2$ and $R_{2'}$ may form, with the carbon to which they are connected, a cycloalkane; X is C=O or $SO_2$;
Y is selected from the group consisting of H, $C_1$-$C_5$ alkyl, and a group —$CHP_1P_2$
$P_1$ is selected from the group consisting of H, and $C_1$-$C_5$ alkyl;
$P_2$ is O($C_1$-$C_5$)alkyl optionally substituted by one or more alkoxy and/or hydroxy groups; or $P_2$ is selected from the group consisting of OC(O)$R_4$, OC(O)O$R_4$, OC(O)NH$R_4$, OC(O)N$R_4R_5$, OC(O)-alkyl-N$R_4R_5$, and O(PO)$O_2^{-2}$; or $P_1$ and $P_2$, form a cycloalkyl or a heterocycle;
$R_4$ and $R_5$ are independently selected from the group consisting of H, and $C_1$-$C_5$ alkyl with the proviso that when $P_2$ is OC(O)O$R_4$, $R_4$ is not hydrogen;
$R_3$ is -$L_1$-$Ar_1$, $L_1$-N($C_1$-$C_6$alkyl)$_2$, or

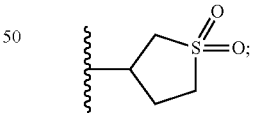

$L_1$ is straight or branched $C_1$-$C_5$ alkyl, optionally substituted with —OH, —O$C_1$-$C_6$alkyl, or (=O);
Z is selected from the group consisting of H and $C_1$-$C_5$ alkyl; or
Z and $R_3$, with the nitrogen to which they are connected, may form a heterocycle;
$Ar_1$ is aryl optionally substituted with one or more substitutents selected from the group consisting of $C_1$-$C_5$ alkyl, halogen, $C_1$-$C_6$haloalkyl, CN, and O-alkyl; or
$Ar_1$ is heteroaryl optionally substituted with one or more substitutents selected from the group consisting of $C_1$-$C_5$ alkyl, halogen, $C_1$-$C_6$haloalkyl, CN, and O-alkyl; and
n is 1 or 2.

In an embodiment, the present disclosure relates to and provides compounds that selectively modulate NMDA receptors that contain an NR2A subunit, which encompasses receptors containing two NR2A subunits or one NR2A subunit in combination with one other NR2 subunit (ie, NR2A/NR2B, NR2A/NR2C, or NR2A/NR2D receptors). Such compounds may either increase or decrease the activity of NR2A-containing NMDA receptors. The present disclosure also relates to the therapeutic uses of such compounds. Also described are pharmaceutical formulations comprising at least one disclosed compound.

Also described herein are methods of treating a disease susceptible to treatment with a disclosed compound in a patient in need thereof by administering to the patient an effective amount of a disclosed compound.

Also described herein are methods of treating a disease or a disorder by administering to a patient in need thereof an effective amount of a disclosed compound.

The disclosure also includes pharmaceutical compositions that comprise an effective amount of a disclosed compound and a pharmaceutically acceptable carrier. The compositions are useful for treating or preventing a disease or disorder. The invention includes a disclosed compound provided as a pharmaceutically acceptable prodrug, hydrate, salt, stereoisomer, or mixtures thereof.

Also described herein are methods of treating a disease susceptible to treatment with a disclosed compound in a patient in need thereof by administering to the patient an effective amount of a disclosed compound. Such diseases include, without limitation, neurological dysfunction such as Parkinson's disease, Huntington's disease, amyotrophic lateral sclerosis, multiple sclerosis, and seizure disorders; emotional disorders; depression; bipolar disorder; obsessive-compulsive disorder; and other anxiety disorders.

The compounds described may be useful in the treatment of diseases in which NMDA receptors containing the NR2A subunit are expressed outside the central nervous system contribute to pathophysiology. This may include, but is not limited to, diseases such as cancer, and particularly including melanomas, diseases of the lung or injury to the lung caused by toxins, diseases involving the peripheral nervous system. These compounds may also be useful in the treatment of autoimmune conditions in which antibodies develop that interact with NMDA receptors.

The disclosure also includes pharmaceutical compositions that comprise an effective amount of a disclosed compound and a pharmaceutically acceptable carrier. The compositions are useful for treating or preventing a disease or disorder. The invention includes a disclosed compound provided as a pharmaceutically acceptable prodrug, hydrate, salt, stereoisomer, or mixtures thereof.

DETAILED DESCRIPTION

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, $C_1$-$C_6$alkyl, —O$C_1$-$C_6$alkenyl, —O$C_1$-$C_6$alkynyl, —$C_1$-$C_6$alkenyl, —$C_1$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, NH$_2$, NH($C_1$-$C_6$alkyl), N($C_1$-$C_6$alkyl)$_2$, —S(O)$_2$—$C_1$-$C_6$alkyl, —S(O)NH$C_1$-$C_6$alkyl, and S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic or bicyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"$C_1$-$C_3$ alkyl" refers to a straight or branched chain saturated hydrocarbon containing 1-3 carbon atoms.

Examples of a $C_1$-$C_3$alkyl group include, but are not limited to, methyl, ethyl, propyl and isopropyl.

"$C_1$-$C_5$ alkyl" refers to a straight or branched chain saturated hydrocarbon containing 1-5 carbon atoms. Examples of a $C_1$-$C_5$alkyl group include, but are not limited to, methyl, ethyl, propyl, butyl, pentyl, isopropyl, isobutyl, sec-butyl and tert-butyl, isopentyl and neopentyl.

Alkyl is generally lower alkyl, or $C_1$-$C_6$ alkyl. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkylenyl" as herein defined refers to groups of general formula —$(CH_2)_n$— where n is an integer from 1 to 6. Suitable examples of alkylenyl groups include methylenyl, ethylenyl, and propylenyl.

The term "haloalkyl" refers to straight or branched saturated hydrocarbon chains containing 1-5 carbon atoms which are substituted at least one of the carbon with halogen groups such fluorine, chlorine, bromine, iodide. Examples of haloalkyl groups as herein defined include without limitation trifluoromethyl, tribromomethyl, and 1,1,1-trifluoroethyl.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" or"heterocycle" means monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl.

"Spirocycle" means bicyclic ring systems with both rings connected through a single atom. The ring can be different in size and nature, or identical in size and nature. Examples include spiropentane, spriohexane, spiroheptane, spirooctane, spirononane, or spirodecane.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diasteromers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diasteromers. The term "diasteromer" refers to any member of this set of compounds. In some examples presented, the synthetic route may produce a single diasteromer or a mixture of diasteromers. In some cases these diasteromers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

A "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

Compounds

In one aspect, there are provided compounds of Formula I:

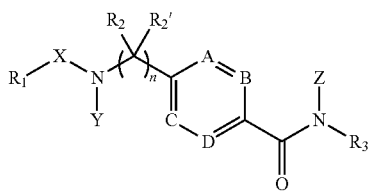

and pharmaceutically acceptable salts, prodrugs, solvates, hydrates, tautomers, or stereoisomers thereof
wherein
A, B, C, D, $R_1$, $R_2$, $R_{2'}$, X, Y, $R_3$, Z and n are defined as above.

In one embodiment, $R_1$ is aryl substituted with one or more substitutents selected from the group consisting of halogen, $C_1$-$C_5$ alkyl, CN and O-alkyl.

In another embodiment, $R_1$ is heteroaryl substituted with one or more substitutents selected from the group consisting of halogen, $C_1$-$C_5$ alkyl, CN and O-alkyl.

In another embodiment, $R_1$ is aryl substituted by one or more halogen.

In another embodiment, $R_1$ is heteroaryl substituted by one or more halogen.

In another embodiment, $R_1$ is aryl wherein the aryl is phenyl substituted by one or more halogen.

In another embodiment, $R_1$ is aryl wherein the aryl is phenyl substituted by two halogens.

In another embodiment, $R_1$ is aryl wherein the aryl is

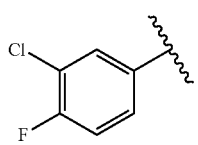 [SMILES: *c1ccc(F)c(Cl)c1]

In another embodiment, X is $SO_2$.
In another embodiment, Y is H.
In another embodiment, n is 1.
In another embodiment, $R_2$ is H.
In another embodiment, $R_{2'}$ is H.
In another embodiment, at least two of A, B, C, and D are N.
In another embodiment, A, B, C, D and the carbons to which they are attached is

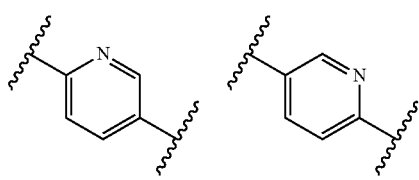

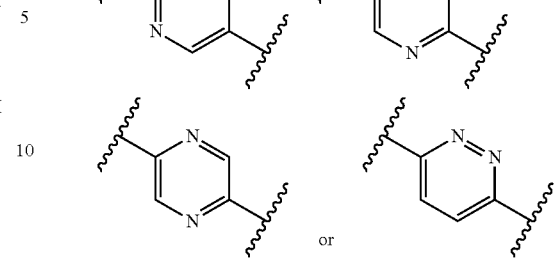

In another embodiment, Z is H.
In another embodiment, $L_1$ is $C_1$-$C_3$.
In another embodiment, $L_1$ is $CH_2$.
In another embodiment, $Ar_1$ is heteroaryl substituted with one or more of $C_1$-$C_5$ alkyl, CN, and O-alkyl.
In another embodiment, $Ar_1$ is heteroaryl wherein the heteroaryl is pyridyl substituted with one or more of $C_1$-$C_5$ alkyl, CN, and O-alkyl.
In another embodiment, $Ar_1$ is pyridinazyl substituted with one or more of $C_1$-$C_5$ alkyl, CN, and O-alkyl.
In another embodiment, $Ar_1$ is thiazolyl substituted with one or more of $C_1$-$C_5$ alkyl, CN, and O-alkyl.
In another embodiment, thiazolyl is bonded to $L_1$ at the 5 position of the thiazolyl ring:

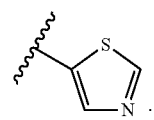

In an embodiment, the present disclosure includes Formula I compounds where any hydrogen atom may be replaced with a deuterium atom.
In another embodiment, Formula I tautomers are also provided.
In another aspect, there are provided compounds of Formula Ia:

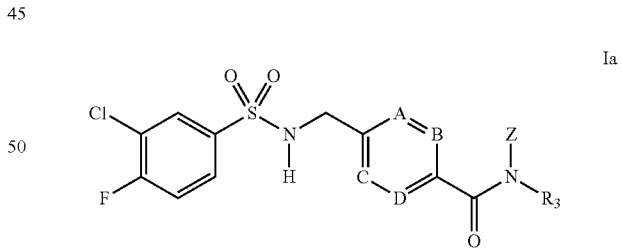

And pharmaceutically acceptable salts, prodrugs, solvates, hydrates, tautomers, or stereoisomers thereof,
wherein:
A, B, C, and D are independently CR or N provided that at least one of A, B, C or D is N;
R is independently selected from the group consisting of H, halogen, $C_1$-$C_5$ alkyl, CN and O-alkyl;
$R_3$ is -$L_1$-$Ar_1$;
$L_1$ is straight or branched $C_1$-$C_5$ alkyl;
Z is H or $C_1$-$C_5$ alkyl; or
Z and $R_3$, with the nitrogen to which they are connected, form a heterocycle;

$Ar_1$ is aryl optionally substituted with one or more substitutents selected from the group consisting of: $C_1$-$C_5$ alkyl, CN, and O-alkyl; or $Ar_1$ is a heteroaryl group substituted with one or more substitutents selected from the group consisting of $C_1$-$C_5$ alkyl, CN, and O-alkyl.

In another embodiment, at least two of A, B, C, and D are N.

In another embodiment, A, B, C, D and the carbons to which they are attached is

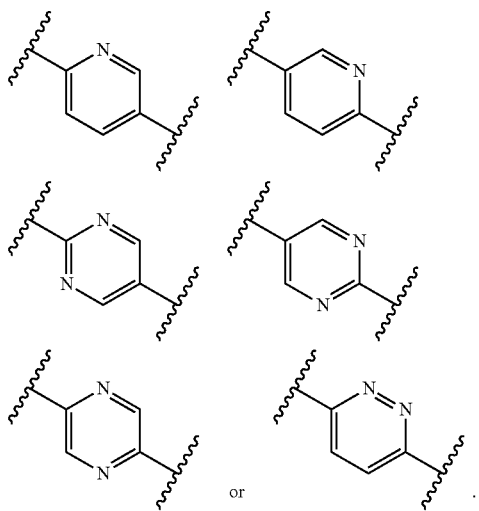

or.

In another embodiment, Z is H.
In another embodiment, $L_1$ is $C_1$-$C_3$.
In another embodiment, $L_1$ is $CH_2$.
In another embodiment, $Ar_1$ is heteroaryl substituted with one or more substitutents selected from the group consisting of $C_1$-$C_5$ alkyl, CN, and O-alkyl.

In another embodiment, $Ar_1$ is pyridyl substituted with one or more substitutents selected from the group consisting of $C_1$-$C_5$ alkyl, CN, and O-alkyl.

In another embodiment, $Ar_1$ is pyridinazyl substituted with one or more of the following features: $C_1$-$C_5$ alkyl, CN, and O-alkyl.

In another embodiment, $Ar_1$ is thiazolyl substituted with one or more of the following features: $C_1$-$C_5$ alkyl, CN, and O-alkyl.

In another embodiment, $Ar_1$ is

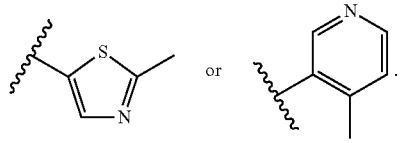

In an illustrative embodiment, a compound of Formula I may be:
5-[(3-chloro-4-fluorobenzene)sulfonamidomethyl]-N-[2-(4-methoxyphenyl)ethyl]pyridine-2-carboxamide;
5-[(3-chloro-4-fluorobenzene)sulfonamidomethyl]-N-[(3-methoxyphenyl)methyl]pyridine-2-carboxamide;
5-[(3-chloro-4-fluorobenzene)sulfonamidomethyl]-N-[(1-methyl-1H-pyrazol-4-yl)methyl]pyridine-2-carboxamide;
N-[(4-chloro-3-fluorophenyl)methyl]-5-[(3-chloro-4-fluorobenzene)sulfonamidomethyl]pyridine-2-carboxamide;
5-[(3-chloro-4-fluorobenzene)sulfonamidomethyl]-N-(1,3-thiazol-5-ylmethyl)pyridine-2-carboxamide;
5-[(3-chloro-4-fluorobenzene)sulfonamidomethyl]-N-[(4-methylpyridin-3-yl)methyl]pyridine-2-carboxamide;
5-[(3-chloro-4-fluorobenzene)sulfonamidomethyl]-N-[(2-methyl-1,3-thiazol-4-yl)methyl]pyridine-2-carboxamide;
5-[(3-chloro-4-fluorobenzene)sulfonamidomethyl]-N-(1,3-thiazol-5-ylmethyl)pyrazine-2-carboxamide;
5-[(3-chloro-4-fluorobenzene)sulfonamidomethyl]-N-[(4-methoxyphenyl)methyl]pyrazine-2-carboxamide;
5-[(3-chloro-4-fluorobenzene)sulfonamidomethyl]-N-(pyridin-3-ylmethyl)pyridine-2-carboxamide;
5-[(3-chloro-4-fluorobenzene)sulfonamidomethyl]-N-[(4-methoxyphenyl)methyl]pyridine-2-carboxamide;
5-[(3-chloro-4-fluorobenzene)sulfonamidomethyl]-N-(pyrimidin-4-ylmethyl)pyridine-2-carboxamide;
5-[(3-chloro-4-fluorobenzene)sulfonamidomethyl]-N-[(2-methyl-1,3-thiazol-5-yl)methyl]pyridine-2-carboxamide;
5-[(3-chloro-4-fluorobenzene)sulfonamidomethyl]-N-(1,3-oxazol-4-ylmethyl)pyridine-2-carboxamide;
5-(((3-chloro-4-fluorophenyl)sulfonamido)methyl)-N-(1,1-dioxidotetrahydrothiophen-3-yl)picolinamide;
6-[(3-chloro-4-fluorobenzene)sulfonamidomethyl]-N-(1,3-thiazol-5-ylmethyl)pyridine-3-carboxamide;
5-[(3-chloro-4-fluorobenzene)sulfonamidomethyl]-N-[(4-methyl-1,3-thiazol-5-yl)methyl]pyridine-2-carboxamide;
5-[(3-chloro-4-fluorobenzene)sulfonamidomethyl]-N-[(dimethyl-1,3-thiazol-5-yl)methyl]pyridine-2-carboxamide;
5-[(3-chloro-4-fluorobenzene)sulfonamidomethyl]-N-(thiophen-2-ylmethyl)pyridine-2-carboxamide;
5-[(3-chloro-4-fluorobenzene)sulfonamidomethyl]-N-[(4-methylpyridin-3-yl)methyl]pyrazine-2-carboxamide;
5-[(3-chloro-4-fluorobenzene)sulfonamidomethyl]-N-(pyrimidin-4-ylmethyl)pyrazine-2-carboxamide;
5-[(3-chloro-4-fluorobenzene)sulfonamidomethyl]-N-(1,3-oxazol-4-ylmethyl)pyrazine-2-carboxamide;
5-[(3-chloro-4-fluorobenzene)sulfonamidomethyl]-N-[(2-methyl-1,3-thiazol-4-yl)methyl]pyrazine-2-carboxamide;
5-(((3-chloro-4-fluorophenyl)sulfonamido)methyl)-N-(1,1-dioxidotetrahydrothiophen-3-yl)pyrazine-2-carboxamide;
5-[(3-chloro-4-fluorobenzene)sulfonamidomethyl]-N-[(1-methyl-1H-imidazol-4-yl)methyl]pyrazine-2-carboxamide;
5-[(3-chloro-4-fluorobenzene)sulfonamidomethyl]-N-[(2-methyl-1,3-thiazol-5-yl)methyl]pyrazine-2-carboxamide;
5-[(3-chloro-4-fluorobenzene)sulfonamidomethyl]-N-[1-(furan-2-yl)ethyl]pyridine-2-carboxamide;
5-[(3-chloro-4-fluorobenzene)sulfonamidomethyl]-N-(1,3-oxazol-5-ylmethyl)pyridine-2-carboxamide;
6-[(3-chloro-4-fluorobenzene)sulfonamidomethyl]-N-[(4-methoxyphenyl)methyl]pyridine-3-carboxamide;
5-[(3-chloro-4-fluorobenzene)sulfonamidomethyl]-N-(thiophen-3-ylmethyl)pyridine-2-carboxamide;
6-[(3-chloro-4-fluorobenzene)sulfonamidomethyl]-N-[2-(dimethylamino)ethyl]pyridine-3-carboxamide;
6-[(3-chloro-4-fluorobenzene)sulfonamidomethyl]-N-[3-(dimethylamino)propyl]pyridine-3-carboxamide;
6-[(3-chloro-4-fluorobenzene)sulfonamidomethyl]-N-[4-(dimethylamino)butyl]pyridine-3-carboxamide;
6-[(3-chloro-4-fluorobenzene)sulfonamidomethyl]-N-(pyridin-4-ylmethyl)pyridine-3-carboxamide;
6-[(3-chloro-4-fluorobenzene)sulfonamidomethyl]-N-(pyridin-3-ylmethyl)pyridine-3-carboxamide;
6-[(3-chloro-4-fluorobenzene)sulfonamidomethyl]-N-[(4-methylpyridin-3-yl)methyl]pyridine-3-carboxamide;

6-[(3-chloro-4-fluorobenzene)sulfonamidomethyl]-N-[(1-methyl-1H-imidazol-4-yl)methyl]pyridine-3-carboxamide;
6-[(3-chloro-4-fluorobenzene)sulfonamidomethyl]-N-(1,3-oxazol-4-ylmethyl)pyridine-3-carboxamide;
6-[(3-chloro-4-fluorobenzene)sulfonamidomethyl]-N-(pyridin-2-ylmethyl)pyridine-3-carboxamide;
6-[(3-chloro-4-fluorobenzene)sulfonamidomethyl]-N-(pyrazin-2-ylmethyl)pyridine-3-carboxamide;
6-[(3-chloro-4-fluorobenzene)sulfonamidomethyl]-N-[(5-methylpyrazin-2-yl)methyl]pyridine-3-carboxamide;
6-[(3-chloro-4-fluorobenzene)sulfonamidomethyl]-N-[(1-methyl-1H-imidazol-2-yl)methyl]pyridine-3-carboxamide;
5-[(3-chloro-4-fluorobenzene)sulfonamidomethyl]-N-[1-(thiophen-2-yl)ethyl]pyridine-2-carboxamide;
5-[(3-chloro-4-fluorobenzene)sulfonamidomethyl]-N-[(1-methyl-1H-imidazol-4-yl)methyl]pyridine-2-carboxamide;
6-[(3-chloro-4-fluorobenzene)sulfonamidomethyl]-N-(pyrimidin-4-ylmethyl)pyridine-3-carboxamide;
5-[(3-chloro-4-fluorobenzene)sulfonamidomethyl]-N-(pyridin-3-ylmethyl)pyrazine-2-carboxamide;
5-[(3-chloro-4-fluorobenzene)sulfonamidomethyl]-N-[(4-methyl-1,3-thiazol-5-yl)methyl]pyrazine-2-carboxamide;
5-[(3-chloro-4-fluorobenzene)sulfonamidomethyl]-N-(pyridin-4-ylmethyl)pyrazine-2-carboxamide;
5-[(3-chloro-4-fluorobenzene)sulfonamidomethyl]-N-(pyrazin-2-ylmethyl)pyrazine-2-carboxamide;
5-[(3-chloro-4-fluorobenzene)sulfonamidomethyl]-N-[(1-methyl-1H-pyrrol-2-yl)methyl]pyrazine-2-carboxamide;
5-[(3-chloro-4-fluorobenzene)sulfonamidomethyl]-N-[(1,5-dimethyl-1H-pyrrol-2-yl)methyl]pyrazine-2-carboxamide;
5-[(3-chloro-4-fluorobenzene)sulfonamidomethyl]-N-[(1-methyl-1H-pyrazol-5-yl)methyl]pyrazine-2-carboxamide;
6-[(3-chloro-4-fluorobenzene)sulfonamidomethyl]-N-[(2-methyl-1,3-thiazol-4-yl)methyl]pyridine-3-carboxamide;
6-[(3-chloro-4-fluorobenzene)sulfonamidomethyl]-N-[(dimethyl-1,3-thiazol-5-yl)methyl]pyridine-3-carboxamide;
6-[(3-chloro-4-fluorobenzene)sulfonamidomethyl]-N-[(6-methylpyridin-2-yl)methyl]pyridine-3-carboxamide;
6-[(3-chloro-4-fluorobenzene)sulfonamidomethyl]-N-[(1-methyl-1H-pyrrol-2-yl)methyl]pyridine-3-carboxamide;
6-[(3-chloro-4-fluorobenzene)sulfonamidomethyl]-N-[(1,5-dimethyl-1H-pyrrol-2-yl)methyl]pyridine-3-carboxamide;
5-[(3-chloro-4-fluorobenzene)sulfonamidomethyl]-N-(furan-3-ylmethyl)pyridine-2-carboxamide;
6-[(3-chloro-4-fluorobenzene)sulfonamidomethyl]-N-[(1-methyl-1H-pyrazol-5-yl)methyl]pyridine-3-carboxamide;
6-[(3-chloro-4-fluorobenzene)sulfonamidomethyl]-N-[(2-methoxypyridin-4-yl)methyl]pyridine-3-carboxamide;
6-[(3-chloro-4-fluorobenzene)sulfonamidomethyl]-N-[(6-methoxypyridin-3-yl)methyl]pyridine-3-carboxamide;
6-[(3-chloro-4-fluorobenzene)sulfonamidomethyl]-N-[(5-methylthiophen-2-yl)methyl]pyridine-3-carboxamide;
6-[(3-chloro-4-fluorobenzene)sulfonamidomethyl]-N-(1,3-thiazol-2-ylmethyl)pyridine-3-carboxamide;
5-[(3-chloro-4-fluorobenzene)sulfonamidomethyl]-N-[(1-methyl-1H-imidazol-5-yl)methyl]pyrazine-2-carboxamide;
6-[(3-chloro-4-fluorobenzene)sulfonamidomethyl]-N-(pyrimidin-2-ylmethyl)pyridine-3-carboxamide;
6-[(3-chloro-4-fluorobenzene)sulfonamidomethyl]-N-[(2-methoxyphenyl)methyl]pyridine-3-carboxamide;
5-[(3-chloro-4-fluorobenzene)sulfonamidomethyl]-N-(pyridin-2-ylmethyl)pyrazine-2-carboxamide;
5-[(3-chloro-4-fluorobenzene)sulfonamidomethyl]-N-[(5-methylpyrazin-2-yl)methyl]pyrazine-2-carboxamide;
5-[(3-chloro-4-fluorobenzene)sulfonamidomethyl]-N-[(6-methylpyridin-2-yl)methyl]pyrazine-2-carboxamide;
6-[(3-chloro-4-fluorobenzene)sulfonamidomethyl]-N-[(1R)-1-(1,3-thiazol-5-yl)ethyl]pyridine-3-carboxamide;
6-[(3-chloro-4-fluorobenzene)sulfonamidomethyl]-N-(pyrimidin-5-ylmethyl)pyridine-3-carboxamide;
6-[(3-chloro-4-fluorobenzene)sulfonamidomethyl]-N-[(5-methyl-1,3,4-thiadiazol-2-yl)methyl]pyridine-3-carboxamide;
6-[(3-chloro-4-fluorobenzene)sulfonamidomethyl]-N-{[3-(trifluoromethyl)pyridin-2-yl]methyl}pyridine-3-carboxamide;
5-[(3-chloro-4-fluorobenzene)sulfonamidomethyl]-N-[2-(dimethylamino)ethyl]pyridine-2-carboxamide;
6-[(3-chloro-4-fluorobenzene)sulfonamidomethyl]-N-(1,3-thiazol-5-ylmethyl)pyridazine-3-carboxamide;
6-[(3-chloro-4-fluorobenzene)sulfonamidomethyl]-N-(pyridin-2-ylmethyl)pyridazine-3-carboxamide;
6-[(3-chloro-4-fluorobenzene)sulfonamidomethyl]-N-[(2-methyl-1,3-thiazol-5-yl)methyl]pyridazine-3-carboxamide;
5-[(3-chloro-4-fluorobenzene)sulfonamidomethyl]-N-[(1R)-1-(1,3-thiazol-5-yl)ethyl]pyridine-2-carboxamide;
5-[(3-chloro-4-fluorobenzene)sulfonamidomethyl]-N-(furan-2-ylmethyl)pyridine-2-carboxamide;
5-[(3-chloro-4-fluorobenzene)sulfonamidomethyl]-N-(pyridin-4-ylmethyl)pyridine-2-carboxamide;
5-[(3-chloro-4-fluorobenzene)sulfonamidomethyl]-N-(pyrazin-2-ylmethyl)pyridine-2-carboxamide;
5-[(3-chloro-4-fluorobenzene)sulfonamidomethyl]-N-(pyrimidin-5-ylmethyl)pyridine-2-carboxamide;
5-[(3-chloro-4-fluorobenzene)sulfonamidomethyl]-N-(pyrimidin-2-ylmethyl)pyridine-2-carboxamide;
5-[(3-chloro-4-fluorobenzene)sulfonamidomethyl]-N-[(6-methylpyridin-2-yl)methyl]pyridine-2-carboxamide;
5-[(3-chloro-4-fluorobenzene)sulfonamidomethyl]-N-{[3-(trifluoromethyl)pyridin-2-yl]methyl}pyridine-2-carboxamide;
5-[(3-chloro-4-fluorobenzene)sulfonamidomethyl]-N-{[3-chloro-5-(trifluoromethyl)pyridin-2-yl]methyl}pyridine-2-carboxamide;
5-[(3-chloro-4-fluorobenzene)sulfonamidomethyl]-N-[(2-methoxypyridin-4-yl)methyl]pyridine-2-carboxamide;
5-[(3-chloro-4-fluorobenzene)sulfonamidomethyl]-N-[(6-methoxypyridin-3-yl)methyl]pyridine-2-carboxamide;
5-[(3-chloro-4-fluorobenzene)sulfonamidomethyl]-N-[(1-methyl-1H-imidazol-5-yl)methyl]pyridine-2-carboxamide;
5-[(3-chloro-4-fluorobenzene)sulfonamidomethyl]-N-[(5-methylthiophen-2-yl)methyl]pyridine-2-carboxamide;
5-[(3-chloro-4-fluorobenzene)sulfonamidomethyl]-N-[(1-methyl-1H-pyrrol-2-yl)methyl]pyridine-2-carboxamide;
5-[(3-chloro-4-fluorobenzene)sulfonamidomethyl]-N-(pyridin-2-ylmethyl)pyridine-2-carboxamide;
6-[(3-chloro-4-fluorobenzene)sulfonamidomethyl]-N-[(4-methoxyphenyl)methyl]pyridazine-3-carboxamide;
6-[(3-chloro-4-fluorobenzene)sulfonamidomethyl]-N-(furan-2-ylmethyl)pyridazine-3-carboxamide;
6-[(3-chloro-4-fluorobenzene)sulfonamidomethyl]-N-(pyridin-4-ylmethyl)pyridazine-3-carboxamide;
6-[(3-chloro-4-fluorobenzene)sulfonamidomethyl]-N-[(4-methylpyridin-3-yl)methyl]pyridazine-3-carboxamide;

6-[(3-chloro-4-fluorobenzene)sulfonamidomethyl]-N-(thiophen-2-ylmethyl)pyridazine-3-carboxamide;
6-[(3-chloro-4-fluorobenzene)sulfonamidomethyl]-N-(pyrimidin-4-ylmethyl)pyridazine-3-carboxamide;
6-[(3-chloro-4-fluorobenzene)sulfonamidomethyl]-N-[(1-methyl-1H-imidazol-4-yl)methyl]pyridazine-3-carboxamide;
6-[(3-chloro-4-fluorobenzene)sulfonamidomethyl]-N-(1,3-oxazol-4-ylmethyl)pyridazine-3-carboxamide;
6-[(3-chloro-4-fluorobenzene)sulfonamidomethyl]-N-[(2-methyl-1,3-thiazol-4-yl)methyl]pyridazine-3-carboxamide;
6-[(3-chloro-4-fluorobenzene)sulfonamidomethyl]-N-[(1R)-1-(1,3-thiazol-5-yl)ethyl]pyridazine-3-carboxamide;
6-[(3-chloro-4-fluorobenzene)sulfonamidomethyl]-N-[(4-methyl-1,3-thiazol-5-yl)methyl]pyridazine-3-carboxamide;
6-[(3-chloro-4-fluorobenzene)sulfonamidomethyl]-N-[(dimethyl-1,3-thiazol-5-yl)methyl]pyridazine-3-carboxamide;
6-[(3-chloro-4-fluorobenzene)sulfonamidomethyl]-N-[1-(furan-2-yl)ethyl]pyridazine-3-carboxamide;
6-[(3-chloro-4-fluorobenzene)sulfonamidomethyl]-N-(furan-3-ylmethyl)pyridazine-3-carboxamide;
6-[(3-chloro-4-fluorobenzene)sulfonamidomethyl]-N-(pyrazin-2-ylmethyl)pyridazine-3-carboxamide;
6-[(3-chloro-4-fluorobenzene)sulfonamidomethyl]-N-(pyrimidin-2-ylmethyl)pyridazine-3-carboxamide;
5-[(3-chloro-4-fluorobenzene)sulfonamidomethyl]-N-[3-(dimethylamino)propyl]pyridine-2-carboxamide;
6-[(3-chloro-4-fluorobenzene)sulfonamidomethyl]-N-[2-(4-methoxyphenyl)ethyl]pyridazine-3-carboxamide;
6-[(3-chloro-4-fluorobenzene)sulfonamidomethyl]-N-(pyridin-3-ylmethyl)pyridazine-3-carboxamide;
6-[(3-chloro-4-fluorobenzene)sulfonamidomethyl]-N-[1-(thiophen-2-yl)ethyl]pyridazine-3-carboxamide;
6-[(3-chloro-4-fluorobenzene)sulfonamidomethyl]-N-[(5-methylpyrazin-2-yl)methyl]pyridazine-3-carboxamide;
6-[(3-chloro-4-fluorobenzene)sulfonamidomethyl]-N-(pyrimidin-5-ylmethyl)pyridazine-3-carboxamide;
6-[(3-chloro-4-fluorobenzene)sulfonamidomethyl]-N-[(3-methoxyphenyl)methyl]pyridazine-3-carboxamide;
6-[(3-chloro-4-fluorobenzene)sulfonamidomethyl]-N-(1,2-oxazol-5-ylmethyl)pyridine-3-carboxamide;
5-[(3-chloro-4-fluorobenzene)sulfonamidomethyl]-N-(1,3-thiazol-2-ylmethyl)pyrazine-2-carboxamide;
5-[(3-chloro-4-fluorobenzene)sulfonamidomethyl]-N-[(4-methyl-1,3-thiazol-2-yl)methyl]pyrazine-2-carboxamide;
5-[(3-chloro-4-fluorobenzene)sulfonamidomethyl]-N-[(5-methyl-1,3,4-oxadiazol-2-yl)methyl]pyridine-2-carboxamide;
5-[(3-chloro-4-fluorobenzene)sulfonamidomethyl]-N-[(5-methyl-1,3,4-thiadiazol-2-yl)methyl]pyridine-2-carboxamide;
5-[(3-chloro-4-fluorobenzene)sulfonamidomethyl]-N-(1,3-thiazol-2-ylmethyl)pyridine-2-carboxamide;
5-[(3-chloro-4-fluorobenzene)sulfonamidomethyl]-N-[(4-methyl-1,3-thiazol-2-yl)methyl]pyridine-2-carboxamide;
5-[(3-chloro-4-fluorobenzene)sulfonamidomethyl]-N-[(1R)-1-(1,3-thiazol-5-yl)ethyl]pyrazine-2-carboxamide;
5-[(3-chloro-4-fluorobenzene)sulfonamidomethyl]-N-(pyrimidin-5-ylmethyl)pyrazine-2-carboxamide;
5-[(3-chloro-4-fluorobenzene)sulfonamidomethyl]-N-[(dimethyl-1,3-thiazol-5-yl)methyl]pyrazine-2-carboxamide;
5-[(3-chloro-4-fluorobenzene)sulfonamidomethyl]-N-{[3-chloro-5-(trifluoromethyl)pyridin-2-yl]methyl}pyrazine-2-carboxamide;
5-[(3-chloro-4-fluorobenzene)sulfonamidomethyl]-N-[(2-methoxypyridin-4-yl)methyl]pyrazine-2-carboxamide;
5-[(3-chloro-4-fluorobenzene)sulfonamidomethyl]-N-[(1-methyl-1H-imidazol-2-yl)methyl]pyrazine-2-carboxamide;
5-[(3-chloro-4-fluorobenzene)sulfonamidomethyl]-N-[(5-methylthiophen-2-yl)methyl]pyrazine-2-carboxamide;
5-[(3-chloro-4-fluorobenzene)sulfonamidomethyl]-N-[(5-methyl-1,3,4-oxadiazol-2-yl)methyl]pyrazine-2-carboxamide;
5-[(3-chloro-4-fluorobenzene)sulfonamidomethyl]-N-[(5-methyl-1,3,4-thiadiazol-2-yl)methyl]pyrazine-2-carboxamide;
5-[(3-chloro-4-fluorobenzene)sulfonamidomethyl]-N-[(1,3-dimethyl-1H-pyrazol-5-yl)methyl]pyrazine-2-carboxamide;
5-[(3-chloro-4-fluorobenzene)sulfonamidomethyl]-N-[(6-methoxypyridin-3-yl)methyl]pyrazine-2-carboxamide;
6-[(3-chloro-4-fluorobenzene)sulfonamidomethyl]-N-[(5-methyl-1,3,4-oxadiazol-2-yl)methyl]pyridine-3-carboxamide;
5-[(3-chloro-4-fluorobenzene)sulfonamidomethyl]-N-(1,2-oxazol-5-ylmethyl)pyridine-2-carboxamide;
5-[(3-chloro-4-fluorobenzene)sulfonamidomethyl]-N-[(1-methyl-1H-pyrazol-5-yl)methyl]pyridine-2-carboxamide;
5-[(3-chloro-4-fluorobenzene)sulfonamidomethyl]-N-[1-(2-methyl-1,3-thiazol-5-yl)ethyl]pyrazine-2-carboxamide;
5-[(3-chloro-4-fluorobenzene)sulfonamidomethyl]-N-{[3-(trifluoromethyl)pyridin-2-yl]methyl}pyrazine-2-carboxamide;
5-[(3-chloro-4-fluorobenzene)sulfonamidomethyl]-N-[(1,3-dimethyl-1H-pyrazol-5-yl)methyl]pyridine-2-carboxamide;
6-[(3-chloro-4-fluorobenzene)sulfonamidomethyl]-N-{[3-chloro-5-(trifluoromethyl)pyridin-2-yl]methyl}pyridine-3-carboxamide;
6-[(3-chloro-4-fluorobenzene)sulfonamidomethyl]-N-[(4-methyl-1,3-thiazol-2-yl)methyl]pyridine-3-carboxamide;
6-[(3-chloro-4-fluorobenzene)sulfonamidomethyl]-N-[(1,3-dimethyl-1H-pyrazol-5-yl)methyl]pyridine-3-carboxamide;
6-(((3-chloro-4-fluorophenyl)sulfonamido)methyl)-N-(1,1-dioxidotetrahydrothiophen-3-yl)nicotinamide;
5-[(2-fluorobenzene)sulfonamidomethyl]-N-[(2-methyl-1,3-thiazol-5-yl)methyl]pyridine-2-carboxamide;
5-[(5-chloro-2-fluorobenzene)sulfonamidomethyl]-N-[(2-methyl-1,3-thiazol-5-yl)methyl]pyridine-2-carboxamide;
5-[(3-chlorobenzene)sulfonamidomethyl]-N-[(2-methyl-1,3-thiazol-5-yl)methyl]pyridine-2-carboxamide;
5-[(3-chloro-4-fluorobenzene)sulfonamidomethyl]-N-[(5-fluoropyridin-3-yl)methyl]pyrazine-2-carboxamide;
5-[(3-chloro-4-fluorobenzene)sulfonamidomethyl]-3-methyl-N-(pyridin-3-ylmethyl)pyridine-2-carboxamide;
5-[(4-chloro-3-fluorobenzene)sulfonamidomethyl]-N-[(2-methyl-1,3-thiazol-5-yl)methyl]pyrazine-2-carboxamide;
5-[(3,4-difluorobenzene)sulfonamidomethyl]-N-[(2-methyl-1,3-thiazol-5-yl)methyl]pyrazine-2-carboxamide;
5-[(3,5-difluorobenzene)sulfonamidomethyl]-N-[(2-methyl-1,3-thiazol-5-yl)methyl]pyrazine-2-carboxamide;
6-[(3-chloro-4-fluorobenzene)sulfonamidomethyl]-N-[(4-methyl-1,3-thiazol-5-yl)methyl]pyridine-3-carboxamide;
N-[(2-methyl-1,3-thiazol-5-yl)methyl]-5-{[4-(trifluoromethyl)benzene]sulfonamidomethyl}pyridine-2-carboxamide;

5-[(3,5-dichlorobenzene)sulfonamidomethyl]-N-[(2-methyl-1,3-thiazol-5-yl)methyl]pyrazine-2-carboxamide;
5-[(3,4-dichlorobenzene)sulfonamidomethyl]-N-[(2-methyl-1,3-thiazol-5-yl)methyl]pyrazine-2-carboxamide;
5-[(3-chloro-4-fluorobenzene)sulfonamidomethyl]-N-(pyridin-3-ylmethyl)pyrimidine-2-carboxamide;
5-[(3-chloro-4-fluorobenzene)sulfonamidomethyl]-N-[(2-methyl-1,3-thiazol-5-yl)methyl]pyrimidine-2-carboxamide; or
5-[(2-fluorobenzene)sulfonamidomethyl]-N-[(2-methyl-1,3-thiazol-5-yl)methyl]pyrazine-2-carboxamide.

Methods for Using the Disclosed Compounds

In one aspect, the present disclosure relates to and provides compounds that selectively modulate NMDA receptors that contain an NR2A subunit, which encompasses receptors containing two NR2A subunits or one NR2A subunit in combination with one other NR2 subunit (ie, NR2A/NR2B, NR2A/NR2C, or NRSA/NRSD receptors). The present disclosure also relates to the therapeutic uses of such compounds.

One therapeutic use of a compound of the present invention that modulates the activity of NR2A-containing NMDA receptors is to treat patients suffering from Major Depressive Disorder (MDD, or depression). Depression is the prolonged experience of sadness, hopelessness, or worthlessness to a degree that significantly impairs quality of life and the ability to function Major Depressive Disorder is now commonly treated with Selective Serotonin Reuptake Inhibitors (SSRIs) such as Prozac, Zoloft and newer variants, but these agents are of limited effectiveness. Of additional concern is that even when these drugs are effective, the onset of action is may be delayed 4-6 weeks or more, during which time patients are at increased risk of suicide. Consequently, the Food and Drug Administration has inserted a black-box warning on all antidepressants concerning suicide risk. There is a need for new agents with greater antidepressant efficacy and faster onset of action.

Another therapeutic use for compounds of the present invention is in the treatment of schizophrenia. Schizophrenia is a debilitating mental disorder encompassing three symptom domains: positive (hallucination, delusions), negative (withdrawal), and cognitive (pervasive reduction in cognitive ability). Schizophrenia typically strikes in early adulthood with the emergence of positive symptoms; however, it is the chronic cognitive deficits that prevent patients from resuming normal activities after the initial onset of symptoms and largely accounts for a lifetime disability.

Given the fundamental role of NR2A containing NMDA receptors in brain function (vide supra), there are many other therapeutic uses for compounds of the present invention that modulate the activity of NR2A-containing NMDA receptors. Compounds of the present invention may improve cognitive function in individuals suffering from cognitive deficits in addition to schizophrenia, including but not limited to those suffering from Alzheimer's disease. Such compounds may also be used in the treatment of post-traumatic stress syndrome. Compounds of the present invention may be used to treat individuals suffering from neurological dysfunction, including but not limited to those suffering from Parkinson's disease, Huntington's disease, amyotrophic lateral sclerosis, multiple sclerosis, and seizure disorders. Compounds of the present invention may be used to treat individuals suffering from emotional disorders in addition to depression, including but not limited to those suffering from bipolar disorder, obsessive-compulsive disorder and other anxiety disorders. Compounds of the present invention may be used to treat individuals that experience dysfunction caused by abnormal brain development, including but not limited to those suffering from autism and autism spectrum disorders, Fragile X syndrome, tuberous sclerosis, Down's syndrome and other forms of mental retardation. Such compounds may also be used to treat abnormal brain function that results from infections of the central nervous system, exposure to toxic agents or other xenobiotics or naturally occurring toxins.

The disclosure includes methods for treating diseases including but not limited to Alzheimer's disease, Parkinson's disease, epilepsy, schizophrenia, depression, manic depression, neurodevelopmental disorder, autism, Huntington's disease, stroke, cerebral palsy, traumatic brain injury, dementia, progressive muscular atrophy, amyotrophic lateral sclerosis, post-polio syndrome, tabes dorsalis, multiple sclerosis, arm peripheral nerve disease, leg peripheral nerve disease, facial nerve palsy, Guillian-Barre's syndrome, Friedreich's ataxia, Charcot-Marie-Tooth disease, spina bifida, hydrocephalus, Down's syndrome, Rett syndrome, Fragile X syndrome Attention deficit/hyperactivity disorder (ADHD), Tourette's syndrome, tuberous sclerosis and chorea.

Stroke is the focal loss of blood supply to the brain, caused by clots or hemorrhage that results in brain ischemia. In the US, approximately 800,000 people suffer a stroke each year and stroke is the leading cause of long-term disability. The estimated economic burden from stroke is projected to exceed $45 B per year through 2050. Head trauma causes both mechanical damage to the brain and ischemia.

Traumatic brain injury (TBI) may be treated with the compounds of the present disclosure. TBI necessitates acute intensive medical support that affects approximately 200,000 people in the US annually. There is also a growing awareness of the long term consequences of mild TBI caused by concussions suffered by an estimated 1.5M people in the US per year. The total costs to society of the resultant disabilities may exceed $60 B per year. TBI has also become recognized as the 'signature injury' of soldiers returning from Iraq and Afghanistan, affecting as many as 18% of the veterans of these wars. It is estimated that the care for these veterans may approach $1.0 B annually. Currently, there are very few treatment options to reduce disability in patients surviving TBI and stroke and costs to society. The only available therapy, tPA, which reduces brain tissue loss by restoring brain perfusion after embolic stroke, is appropriate for only 2-3% of stroke patients. Other approaches to prevent or reduce brain tissue loss after injury have failed, largely because brain damage occurs rapidly and neuroprotectant treatment cannot be administered in a time frame to be effective.

A new approach to reduce disability and improve long-term outcomes for brain injury survivors is to promote the natural process of recovery after brain injury by treating such patients with the compounds of the present disclosure that selectively inhibit NMDA receptors containing the NR2A subunit. Despite permanent brain damage, brain injury survivors often partially recover lost function resulting from reorganization of surviving brain tissue to assume the function of damaged tissue. This process is mechanistically similar to brain organization during development, which includes synapse formation and strengthening. During development, NR2B-containing NMDA receptors predominate to mediate initial synapse formation and strengthening. NR2A receptors subsequently predominate to stabilize synapses in the adult brain. However, after adult brain injury, NR2A receptors limit synapse reformation between surviving neurons. Thus, inhibiting NR2A receptors will reduce this limitation, thereby promoting brain reorganization to facilitate the natural process of recovery after injury. Of note, since the mechanism of NR2A inhibitors is to promote recovery, the therapeutic window for initiating treatment is days after brain injury, not minutes to hours as is the case for neuroprotective therapies.

In an embodiment, one therapeutic use of a compound of the present disclosure that inhibits NR2A-containing NMDA receptors is to facilitate recovery of function after brain injury. Damage to the brain can result in lifelong disability.

In an embodiment, another therapeutic use of a compound of the present disclosure that inhibits NR2A-containing NMDA receptors is to treat patients suffering from Rett Syndrome. Rett Syndrome (RTT) is a severe developmental disorder affecting 1 in 10,000 girls. RTT is caused by disruptions in the X-linked transcriptional repressor MECP2. Carriers develop with a normal trajectory for 6-12 months and then suffer a developmental regression that leaves them speech and hand control deficits, seizures, and autonomic deficits. The symptoms of RTT are well replicated by genetic lesion of MECP2 in mice. Studies in which such lesions are restricted to forebrain neurons, and the pathophysiological, neurochemical, and behavioral consequences of such lesions indicate that failure or regression in cortical development accounts for many, if not all, of the symptoms of RTT. Thus, remediating cortical dysfunction in RTT is a clear therapeutic goal. Given the fundamental role of NMDA receptors in cortical development (vide supra), NMDA receptors are a target of high interest in the development of new treatments for RTT. In fact evidence indicates that manipulations that decrease the level of NR2A receptor expression in mice for which the MeCP2 gene has been deleted remediates the cortical dysfunction caused by MeCP2 lesion. In fact, lowering NR2A expression ameliorates many of the functional and behavioral deficits caused by MeCP2 deletion, and prolongs lifespan in MeCP2 knock out mice. These findings can be extrapolated to support the development of compounds of the present disclosure that inhibit NR2A-containing NMDA receptor modulators to prevent or delay the consequences of the developmental regression suffered by RTT patients.

In an embodiment, given the fundamental role of NR2A-containing NMDA receptors in brain function (vide supra), there may be many other therapeutic uses for compounds of the present disclosure that inhibit the activity of NR2A-containing NMDA receptors. For example, compounds of the present disclosure may improve cognitive function in individuals suffering from cognitive deficits, including but not limited to those suffering from Alzheimer's disease and schizophrenia. Compounds of the present disclosure may be used to treat individuals suffering from neurological dysfunction, including but not limited to those suffering from Parkinson's disease, Huntington's disease, amyotrophic lateral sclerosis, multiple sclerosis, and seizure disorders. Compounds of the present disclosure may be used to treat individuals suffering from emotional disorders, including but not limited to those suffering from depression, bipolar disorder, obsessive compulsive disorder and other anxiety disorders. Compounds of the present disclosure may be used to treat individuals that experience dysfunction caused by abnormal brain development, including but not limited to those suffering from autism and autism spectrum disorders, Fragile X syndrome, tuberous sclerosis, Down's syndrome and other forms of mental retardation. Such compounds may also be used to treat abnormal brain function that results from infections of the central nervous system, exposure to toxic agents or other xenobiotics or naturally occurring toxins.

In an embodiment, another therapeutic use of a compound of the present disclosure that inhibits NR2A-containing NMDA receptors is to treat patients suffering from cancer such as melanoma. The compounds described may be useful in the treatment of diseases in which NMDA receptors containing the NR2A subunit are expressed outside the central nervous system and contribute to pathophysiology. This may include, but is not limited to, diseases such as cancer, and particularly including melanomas. Mutation of the gene for the NR2A subunit of the NMDA receptor, GRIN2A, is mutated in a high percentage of melanoma samples (Wei, D'Meillo), strongly implicating aberrant NR2A activity in melanoma tumorogenesis, stasis, and or metastasis. This conclusion is validated with the finding that blockade of NMDA receptors inhibit the growth of melanoma in an in vivo animal model system. Together, these human genetic data and proof of concept animal model data support the use of NR2A NAMs in the treatment of melanoma.

The disclosed compound can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

In another embodiment, effective dosage amounts of the disclosed compounds, when used for the indicated effects, range from about 0.5 mg to about 5000 mg of the disclosed compound per day, or as needed per episode of the disorder. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Methods of Making

Compounds of formula I may be prepared from a compound of formula II:

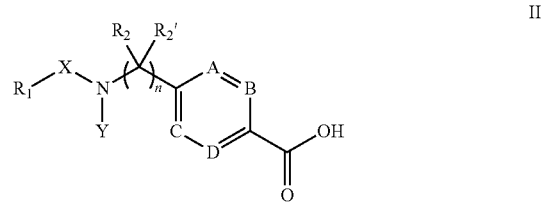

II wherein the substitutents $R_1$, X, Y, $R_2$, $R_{2'}$, n, A, B, C, and D have the meanings as understood in formula I, by reaction of the compound of formula II with an amine of formula III

$R_3$—NH—Z          III after activation of the carboxylic acid moiety of the formula II compound with a carbodiimide, e.g., 1-ethyl-3-(3-dimethylaminopropyl)carbodiimide in the presence of a base.

The compound of formula II may be prepared from a compound of formula IV:

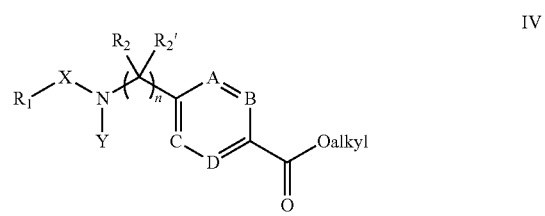

IV wherein the substitutents $R_1$, X, Y, $R_2$, $R_{2'}$, n, A, B, C, and D have the meanings as understood in formula I, by basic hydrolysis of the compound of formula IV.

The compound of formula II may be prepared by reaction of a compound of formula V:

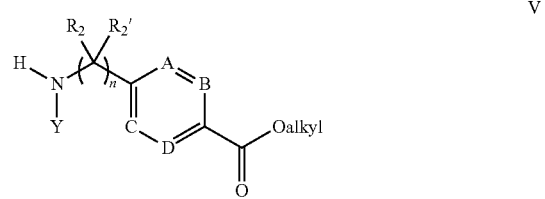

V wherein the substitutents Y, $R_2$, $R_{2'}$, n, A, B, C, and D have the meanings as understood in formula I, with an acyl halide or sulfonyl halide of formula VI:

$R_1$X-halo          VI wherein the substitutents $R_1$ and X have the have the meanings as understood in formula I, in the presence of a base, e.g., triethylamine.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1—Preparation of 5-[(3-chloro-4-fluorobenzene)sulfonamidomethyl]-N-[2-(4-methoxyphenyl)ethyl]pyridine-2-carboxamide

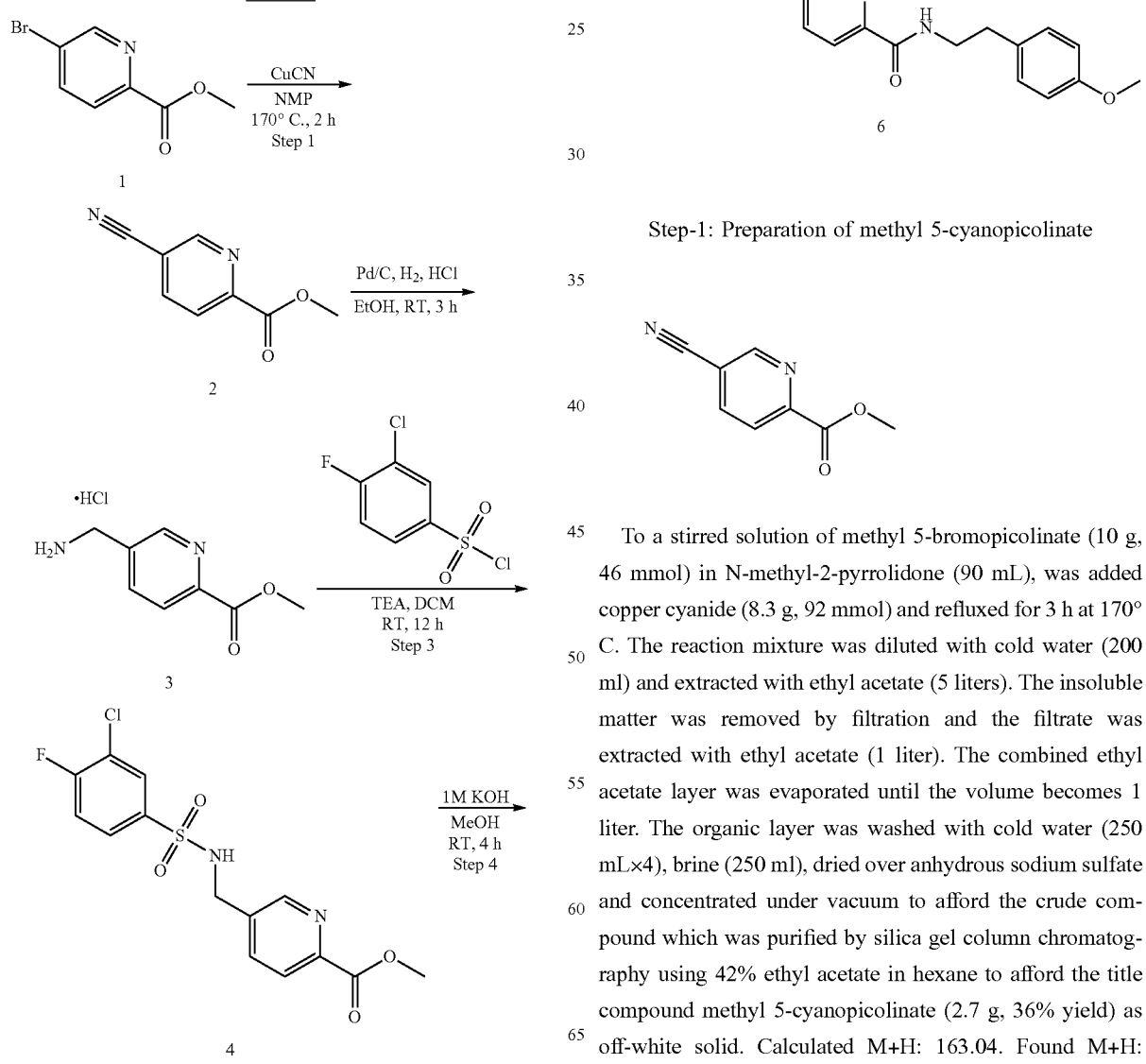

Step-1: Preparation of methyl 5-cyanopicolinate

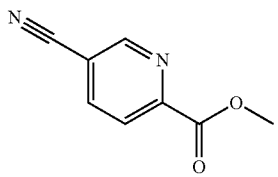

To a stirred solution of methyl 5-bromopicolinate (10 g, 46 mmol) in N-methyl-2-pyrrolidone (90 mL), was added copper cyanide (8.3 g, 92 mmol) and refluxed for 3 h at 170° C. The reaction mixture was diluted with cold water (200 ml) and extracted with ethyl acetate (5 liters). The insoluble matter was removed by filtration and the filtrate was extracted with ethyl acetate (1 liter). The combined ethyl acetate layer was evaporated until the volume becomes 1 liter. The organic layer was washed with cold water (250 mL×4), brine (250 ml), dried over anhydrous sodium sulfate and concentrated under vacuum to afford the crude compound which was purified by silica gel column chromatography using 42% ethyl acetate in hexane to afford the title compound methyl 5-cyanopicolinate (2.7 g, 36% yield) as off-white solid. Calculated M+H: 163.04. Found M+H: 163.2.

Step-2: Preparation of methyl 5-(aminomethyl)picolinate hydrochloride

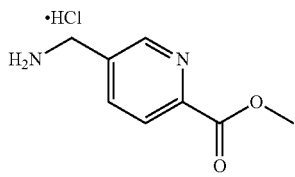

To a solution of methyl 5-cyanopicolinate (2.4 g, 14 mmol) in ethanol (60 mL) was added concentrated hydrochloric acid (10.3 mL) followed by 10% Pd/C (0.4 g). The reaction vessel was evacuated and backfilled with hydrogen three times and then stirred for a total of 3 h. The solution was filtered through celite, and the filter pad rinsed with methanol. The filtrate was evaporated and recrystallized with ether:ethanol mixture (10:1) to obtain the title compound methyl 5-(aminomethyl)picolinate hydrochloride (2.6 g, 89% yield) as a pale yellow solid. Calculated M+H: 167.07. Found M+H: 167.20.

Step-3: Preparation of methyl 5-((3-chloro-4-fluorophenylsulfonamido)methyl)picolinate

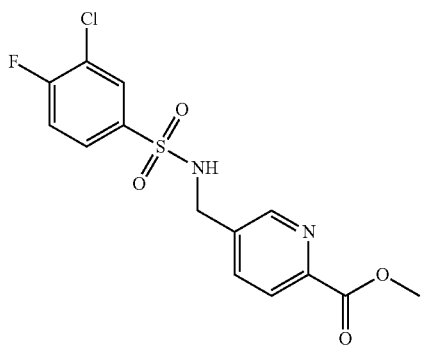 [SMILES: COC(=O)c1ccc(CNS(=O)(=O)c2ccc(F)c(Cl)c2)cn1]

To a stirred solution of methyl 5-(aminomethyl)picolinate hydrochloride (2.6 g, 12 mmol) in dichloromethane (780 mL) at 0° C. were added triethylamine (5.3 mL, 38 mmol) and 3-chloro-4-fluorobenzene-1-sulfonyl chloride (2.9 g, 12 mmol) respectively and stirred at 0° C. for 4 h. The reaction mixture was diluted with water and extracted with dichloromethane. The combined organic layer was washed with brine, dried over anhydrous sodium sulfate and concentrated under vacuum to afford the crude compound which was purified by silica gel column chromatography, using 30% ethyl acetate in dichloromethane to obtain the title compound methyl 5-((3-chloro-4-fluorophenylsulfonamido) methyl)picolinate (2.1 g, 45% yield) as off-white semisolid. Calculated M+H: 359.02. Found M+H: 359.20.

Step-4: Preparation of 5-((3-chloro-4-fluorophenylsulfonamido)methyl)picolinic acid

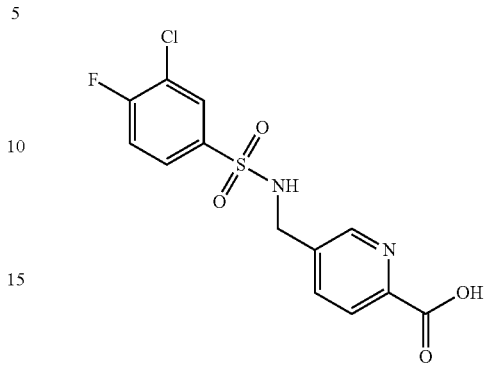

To a stirred solution of methyl 5-((3-chloro-4-fluorophenylsulfonamido)methyl)picolinate (1.5 g, 4 mmol) in methanol (70 mL), was added 1 M potassium hydroxide solution (21 mL, 20 mmol) and stirred at room temperature for 4 h. The reaction mixture was evaporated and acidified using 1 N hydrochloric acid solution (pH: 2) to get a solid. The obtained solid was filtered and washed with ether and pentane to get the title compound 5-((3-chloro-4-fluorophenylsulfonamido)methyl)picolinic acid (1.3 g, 90% yield) as an off-white solid. Calculated M+H: 345.00. Found M+H: 345.20.

Step-5: Preparation of 5-[(3-chloro-4-fluorobenzene)sulfonamidomethyl]-N-[2-(4-methoxyphenyl)ethyl]pyridine-2-carboxamide

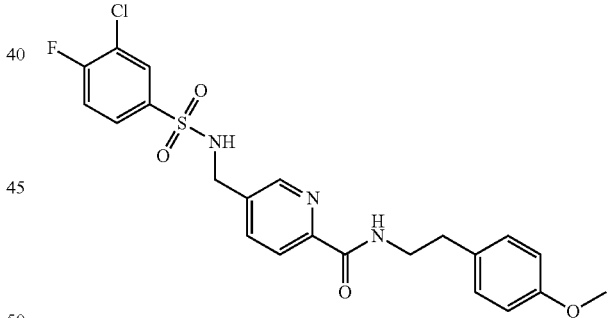

To a solution of 5-((3-chloro-4-fluorophenylsulfonamido)methyl)picolinic acid (0.050 g, 0.15 mmol) and 2-(4-methoxyphenyl)ethan-1-amine (0.021 g, 0.15 mmol) in N,N-dimethylformamide (2 mL) was added triethylamine (0.040 mL, 0.29 mmol) and 1-propanephosphonic acid cyclic anhydride (0.185 mL, 0.290 moles) and the resulting suspension was stirred at room temperature for 18 h. After completion of the reaction (monitored by TLC), reaction mass was diluted with water (2 mL). The organic compound was extracted with ethyl acetate (5 mL×3), washed with brine (10 mL×2), dried over sodium sulfate and concentrated to get the crude material which was purified by prep HPLC to get the title compound 5-[(3-chloro-4-fluorobenzene) sulfonamidomethyl]-N-[2-(4-methoxyphenyl)ethyl]pyridine-2-carboxamide (0.021 g, 99.94% yield) as off-white solid. Calculated M−H: 476.09. Found M−H: 476.27.

TABLE 1

| Structure | IUPAC Name | Calculated M + H | Found M + H |
|---|---|---|---|
| 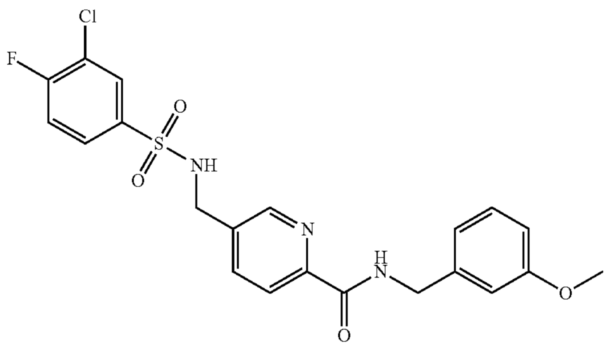 [SMILES: COc1cccc(CNC(=O)c2ccc(CNS(=O)(=O)c3ccc(F)c(Cl)c3)cn2)c1] | 5-[(3-chloro-4-fluorobenzene)sulfonamidomethyl]-N-[(3-methoxyphenyl)methyl]pyridine-2-carboxamide | 462.08 (M − H) | 462.25 (M − H) |
| 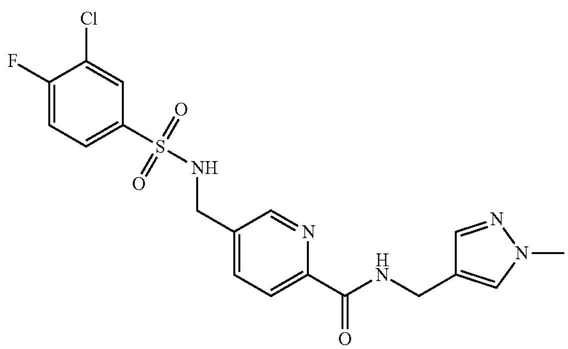 [SMILES: Cn1cc(CNC(=O)c2ccc(CNS(=O)(=O)c3ccc(F)c(Cl)c3)cn2)cn1] | 5-[(3-chloro-4-fluorobenzene)sulfonamidomethyl]-N-[(1-methyl-1H-pyrazol-4-yl)methyl]pyridine-2-carboxamide | 436.07 (M − H) | 436.25 (M − H) |
| 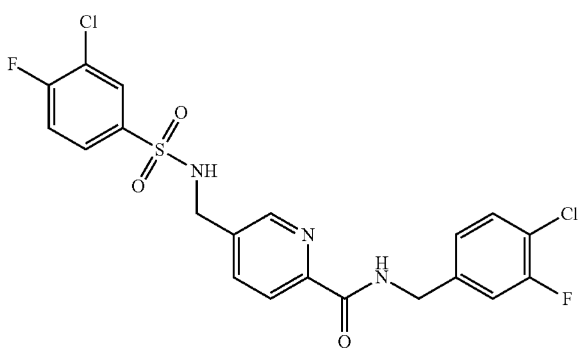 [SMILES: O=C(NCc1ccc(Cl)c(F)c1)c1ccc(CNS(=O)(=O)c2ccc(F)c(Cl)c2)cn1] | N-[(4-chloro-3-fluorophenyl)methyl]-5-[(3-chloro-4-fluorobenzene)sulfonamidomethyl]pyridine-2-carboxamide | 484.02 (M − H) | 484.17 (M − H) |
| 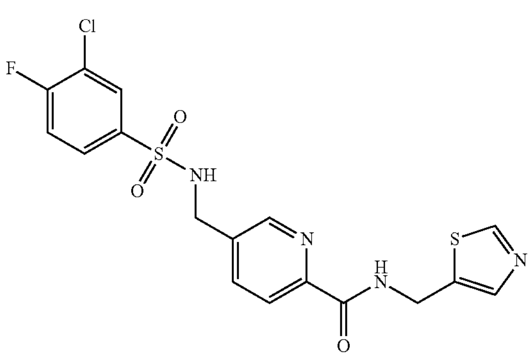 | 5-[(3-chloro-4-fluorobenzene)sulfonamidomethyl]-N-(1,3-thiazol-5-ylmethyl)pyridine-2-carboxamide | 441.02 | 441 |

The following compounds were prepared by the method described above

TABLE 1-continued

The following compounds were prepared by the method described above

| Structure | IUPAC Name | Calculated M + H | Found M + H |
|---|---|---|---|
| 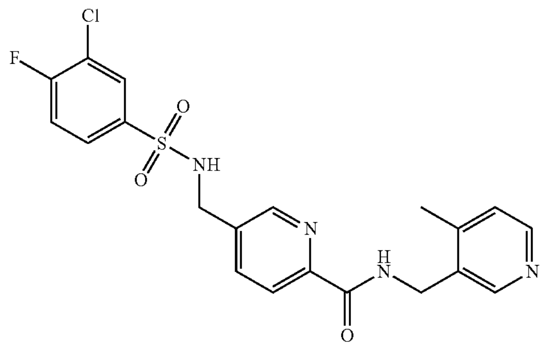 [SMILES: Cc1ccncc1CNC(=O)c1ccc(CNS(=O)(=O)c2ccc(F)c(Cl)c2)cn1] | 5-[(3-chloro-4-fluorobenzene)sulfonamidomethyl]-N-[(4-methylpyridin-3-yl)methyl]pyridine-2-carboxamide | 449.08 | 449.34 |
| 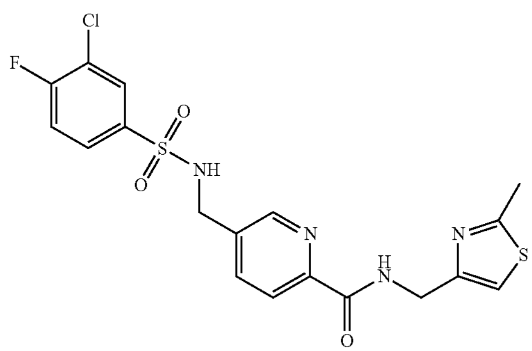 [SMILES: Cc1nc(CNC(=O)c2ccc(CNS(=O)(=O)c3ccc(F)c(Cl)c3)cn2)cs1] | 5-[(3-chloro-4-fluorobenzene)sulfonamidomethyl]-N-[(2-methyl-1,3-thiazol-4-yl)methyl]pyridine-2-carboxamide | 455.03 | 454.95 |
| 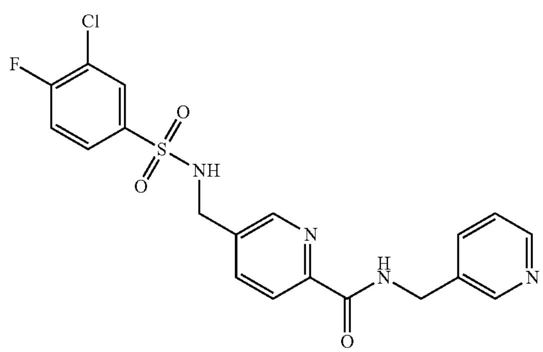 [SMILES: O=C(NCc1cccnc1)c1ccc(CNS(=O)(=O)c2ccc(F)c(Cl)c2)cn1] | 5-[(3-chloro-4-fluorobenzene)sulfonamidomethyl]-N-(pyridin-3-ylmethyl)pyridine-2-carboxamide | 435.06 | 435.13 |
| 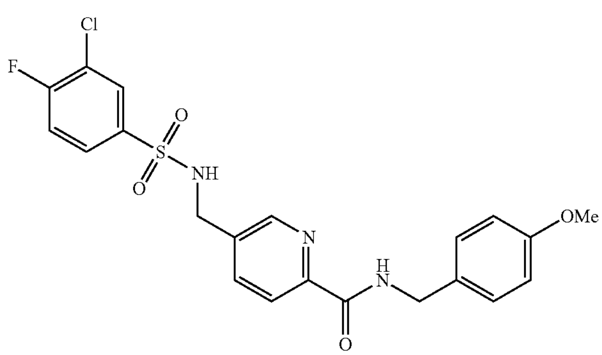 [SMILES: COc1ccc(CNC(=O)c2ccc(CNS(=O)(=O)c3ccc(F)c(Cl)c3)cn2)cc1] | 5-[(3-chloro-4-fluorobenzene)sulfonamidomethyl]-N-[(4-methoxyphenyl)methyl]pyridine-2-carboxamide | 464.08 | 464.17 |

TABLE 1-continued

The following compounds were prepared by the method described above

| Structure | IUPAC Name | Calculated M + H | Found M + H |
|---|---|---|---|
| 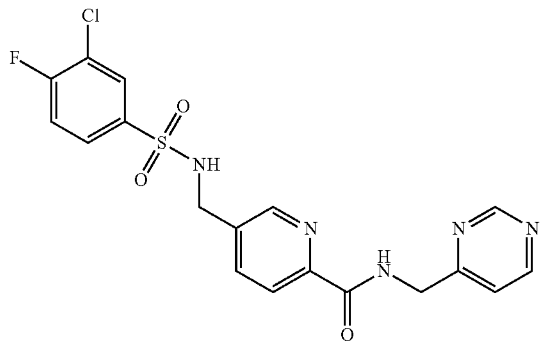 [SMILES: O=C(NCc1ccncn1)c1ccc(CNS(=O)(=O)c2ccc(F)c(Cl)c2)cn1] | 5-[(3-chloro-4-fluorobenzene)sulfonamidomethyl]-N-(pyrimidin-4-ylmethyl)pyridine-2-carboxamide | 436.06 | 436.14 |
| 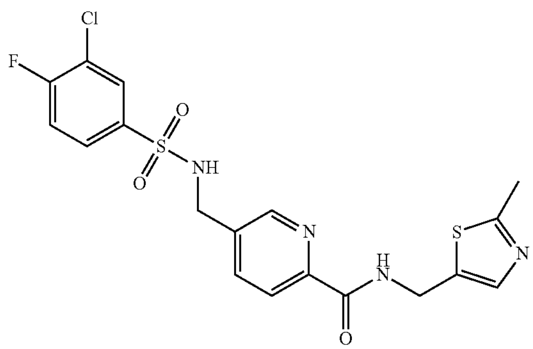 | 5-[(3-chloro-4-fluorobenzene)sulfonamidomethyl]-N-[(2-methyl-1,3-thiazol-5-yl)methyl]pyridine-2-carboxamide | 453.03 (M − H) | 453.3 (M − H) |
| | 5-[(3-chloro-4-fluorobenzene)sulfonamidomethyl]-N-(1,3-oxazol-4-ylmethyl)pyridine-2-carboxamide | 425.04 | 425.32 |
| | 5-[(3-chloro-4-fluorobenzene)sulfonamidomethyl]-N-(1,3-oxazol-4-ylmethyl)pyridine-2-carboxamide | 460.03 (M − H) | 460.3 (M − H) |

TABLE 1-continued

The following compounds were prepared by the method described above

| Structure | IUPAC Name | Calculated M + H | Found M + H |
|---|---|---|---|
| 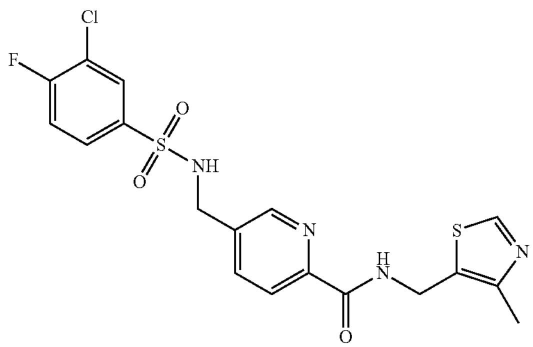 [SMILES: Cc1ncsc1CNC(=O)c1ccc(CNS(=O)(=O)c2ccc(F)c(Cl)c2)cn1] | 5-[(3-chloro-4-fluorobenzene)sulfonamidomethyl]-N-[(4-methyl-1,3-thiazol-5-yl)methyl]pyridine-2-carboxamide | 455.03 | 455.29 |
| 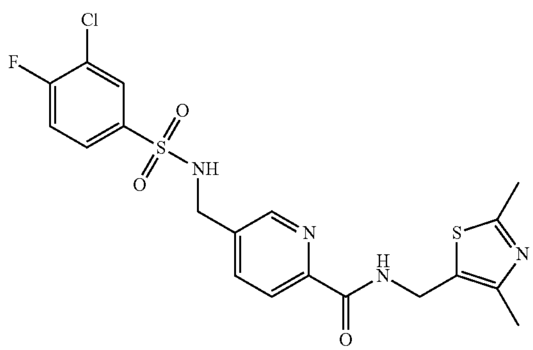 [SMILES: Cc1nc(C)c(CNC(=O)c2ccc(CNS(=O)(=O)c3ccc(F)c(Cl)c3)cn2)s1] | 5-[(3-chloro-4-fluorobenzene)sulfonamidomethyl]-N-[(dimethyl-1,3-thiazol-5-yl)methyl]pyridine-2-carboxamide- | 469.05 | 469.33 |
| 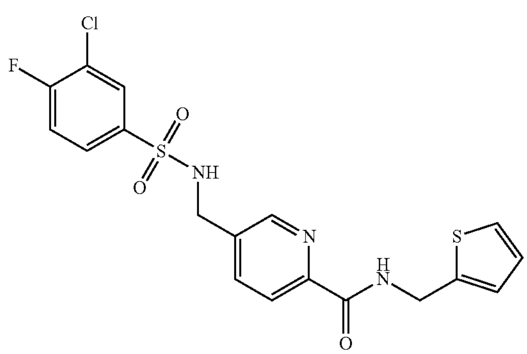 | 5-[(3-chloro-4-fluorobenzene)sulfonamidomethyl]-N-(thiophen-2-ylmethyl)pyridine-2-carboxamide | 440.02 | 440.3 |
| 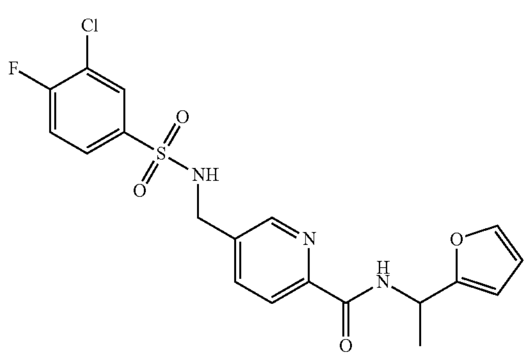 | 5-[(3-chloro-4-fluorobenzene)sulfonamidomethyl]-N-[1-(furan-2-yl)ethyl]pyridine-2-carboxamide | 438.06 | 438.32 |

TABLE 1-continued

The following compounds were prepared by the method described above

| Structure | IUPAC Name | Calculated M + H | Found M + H |
|---|---|---|---|
| 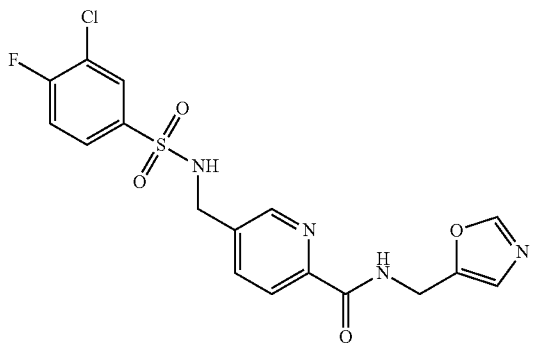 | 5-[(3-chloro-4-fluorobenzene)sulfonamidomethyl]-N-(1,3-oxazol-5-ylmethyl)pyridine-2-carboxamide | 425.04 | 425.89 |
| 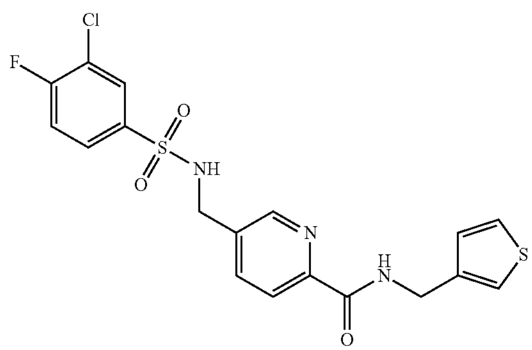 [SMILES: O=C(NCc1ccsc1)c1ccc(CNS(=O)(=O)c2ccc(F)c(Cl)c2)cn1] | 5-[(3-chloro-4-fluorobenzene)sulfonamidomethyl]-N-(thiophen-3-ylmethyl)pyridine-2-carboxamide | 440.02 | 440.24 |
| 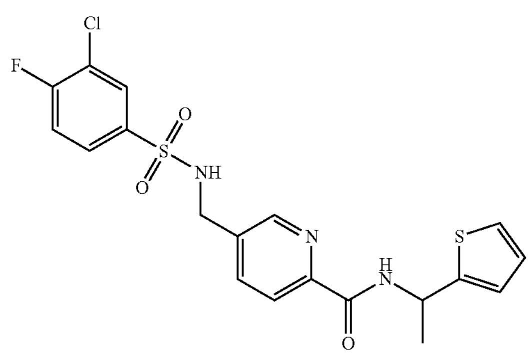 | 5-[(3-chloro-4-fluorobenzene)sulfonamidomethyl]-N-[1-(thiophen-2-yl)ethyl]pyridine-2-carboxamide | 454.04 | 454.24 |
| 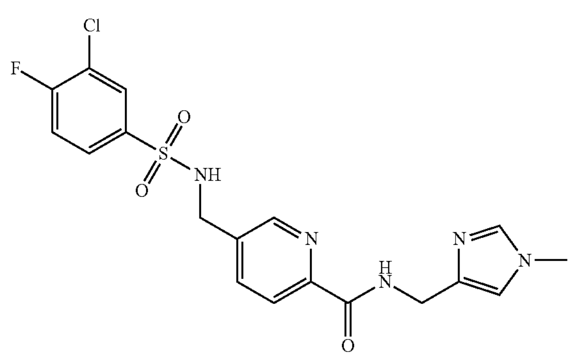 [SMILES: Cn1cnc(CNC(=O)c2ccc(CNS(=O)(=O)c3ccc(F)c(Cl)c3)cn2)c1] | 5-[(3-chloro-4-fluorobenzene)sulfonamidomethyl]-N-[(1-methyl-1H-imidazol-4-yl)methyl]pyridine-2-carboxamide | 438.07 | 438.29 |

TABLE 1-continued

The following compounds were prepared by the method described above

| Structure | IUPAC Name | Calculated M + H | Found M + H |
|---|---|---|---|
| 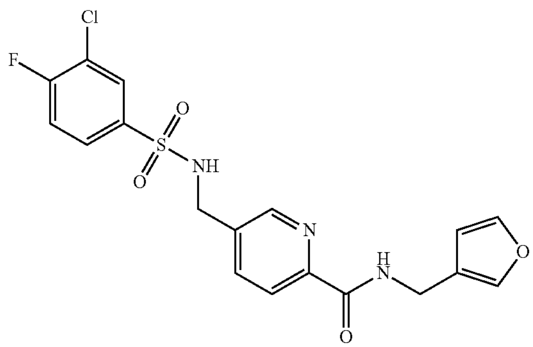 | 5-[(3-chloro-4-fluorobenzene)sulfonamidomethyl]-N-(furan-3-ylmethyl)pyridine-2-carboxamide | 424.05 | 424.28 |
|  | 5-[(3-chloro-4-fluorobenzene)sulfonamidomethyl]-N-[2-(dimethylamino)ethyl]pyridine-2-carboxamide | 415.09 | 415.31 |
| 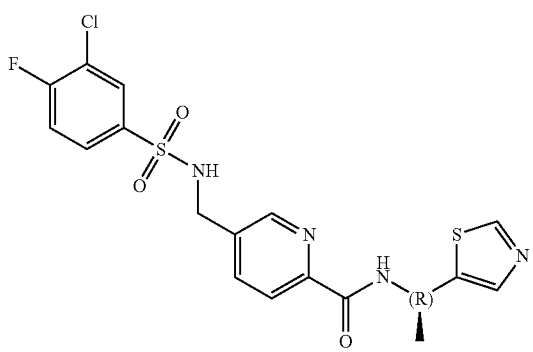 | 5-[(3-chloro-4-fluorobenzene)sulfonamidomethyl]-N-[(1R)-1-(1,3-thiazol-5-yl)ethyl]pyridine-2-carboxamide | 453.03 (M − H) | 453.13 (M − H) |
| 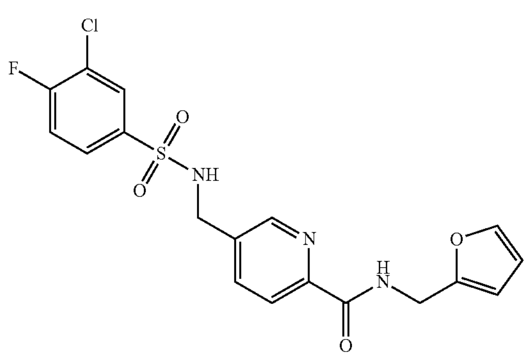 | 5-[(3-chloro-4-fluorobenzene)sulfonamidomethyl]-N-(furan-2-ylmethyl)pyridine-2-carboxamide | 422.05 (M − H) | 422.14 (M − H) |

TABLE 1-continued

The following compounds were prepared by the method described above

| Structure | IUPAC Name | Calculated M + H | Found M + H |
|---|---|---|---|
| 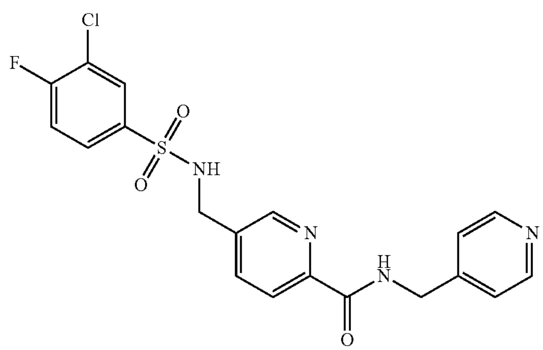 [SMILES: O=C(NCc1ccncc1)c1ccc(CNS(=O)(=O)c2ccc(F)c(Cl)c2)cn1] | 5-[(3-chloro-4-fluorobenzene)sulfonamidomethyl]-N-(pyridin-4-ylmethyl)pyridine-2-carboxamide | 433.06 (M − H) | 433.17 (M − H) |
| 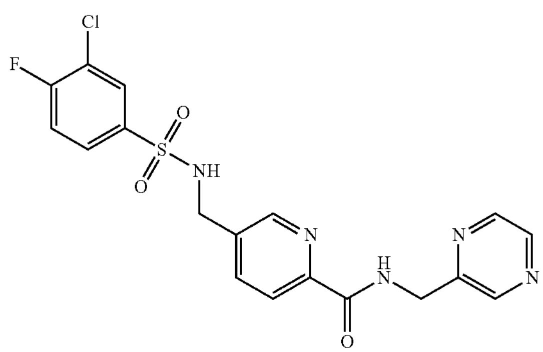 [SMILES: O=C(NCc1cnccn1)c1ccc(CNS(=O)(=O)c2ccc(F)c(Cl)c2)cn1] | 5-[(3-chloro-4-fluorobenzene)sulfonamidomethyl]-N-(pyrazin-2-ylmethyl)pyridine-2-carboxamide | 436.06 | 436.03 |
| 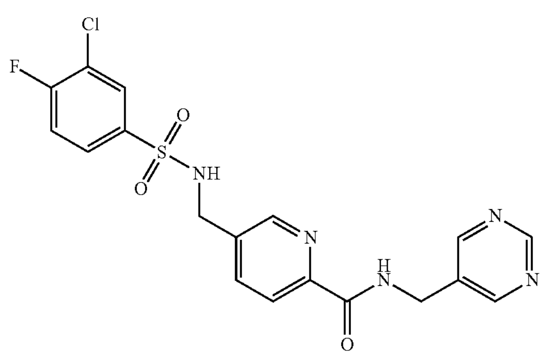 [SMILES: O=C(NCc1cncnc1)c1ccc(CNS(=O)(=O)c2ccc(F)c(Cl)c2)cn1] | 5-[(3-chloro-4-fluorobenzene)sulfonamidomethyl]-N-(pyrimidin-5-ylmethyl)pyridine-2-carboxamide | 436.06 | 436.03 |
| 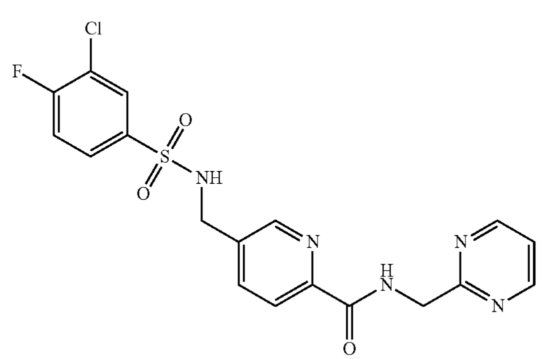 [SMILES: O=C(NCc1ncccn1)c1ccc(CNS(=O)(=O)c2ccc(F)c(Cl)c2)cn1] | 5-[(3-chloro-4-fluorobenzene)sulfonamidomethyl]-N-(pyrimidin-2-ylmethyl)pyridine-2-carboxamide | 434.06 (M − H) | 434.16 (M − H) |

TABLE 1-continued

The following compounds were prepared by the method described above

| Structure | IUPAC Name | Calculated M + H | Found M + H |
|---|---|---|---|
| 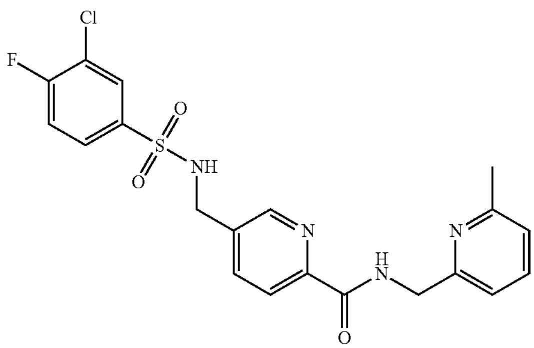 [SMILES: Cc1cccc(CNC(=O)c2ccc(CNS(=O)(=O)c3ccc(F)c(Cl)c3)cn2)n1] | 5-[(3-chloro-4-fluorobenzene)sulfonamidomethyl]-N-[(6-methylpyridin-2-yl)methyl]pyridine-2-carboxamide | 449.08 | 449.05 |
| 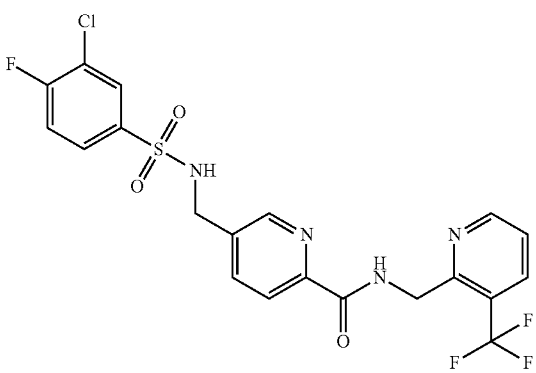 [SMILES: O=C(NCc1ncccc1C(F)(F)F)c1ccc(CNS(=O)(=O)c2ccc(F)c(Cl)c2)cn1] | 5-[(3-chloro-4-fluorobenzene)sulfonamidomethyl]-N-{[3-(trifluoromethyl)pyridin-2-yl]methyl}pyridine-2-carboxamide | 503.05 | 503.01 |
| 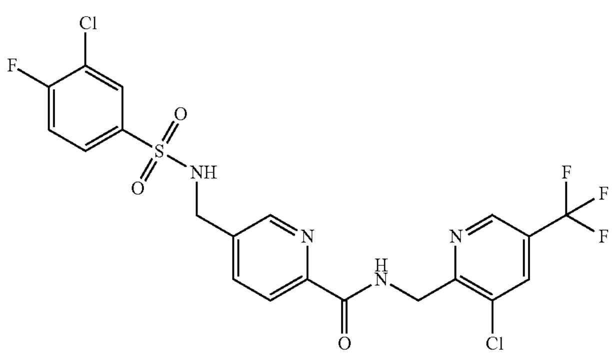 [SMILES: O=C(NCc1ncc(C(F)(F)F)cc1Cl)c1ccc(CNS(=O)(=O)c2ccc(F)c(Cl)c2)cn1] | 5-[(3-chloro-4-fluorobenzene)sulfonamidomethyl]-N-{[3-chloro-5-(trifluoromethyl)pyridin-2-yl]methyl}pyridine-2-carboxamide | 535.01 (M − H) | 535.09 (M − H) |
| 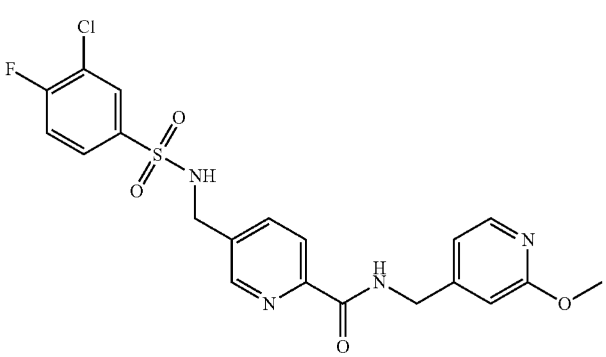 [SMILES: COc1cc(CNC(=O)c2ccc(CNS(=O)(=O)c3ccc(F)c(Cl)c3)cn2)ccn1] | 5-[(3-chloro-4-fluorobenzene)sulfonamidomethyl]-N-[(2-methoxypyridin-4-yl)methyl]pyridine-2-carboxamide | 465.07 | 465.07 |

TABLE 1-continued

The following compounds were prepared by the method described above

| Structure | IUPAC Name | Calculated M + H | Found M + H |
|---|---|---|---|
| 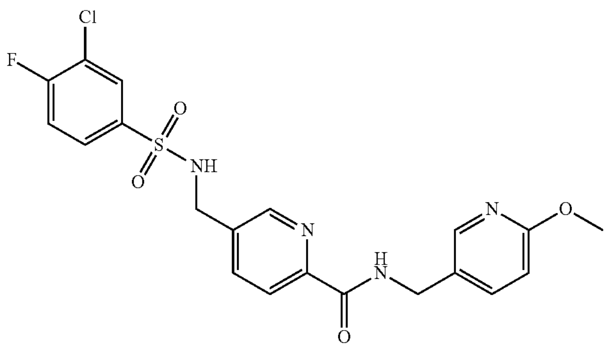 [SMILES: COc1ccc(CNC(=O)c2ccc(CNS(=O)(=O)c3ccc(F)c(Cl)c3)cn2)cn1] | 5-[(3-chloro-4-fluorobenzene)sulfonamidomethyl]-N-[(6-methoxypyridin-3-yl)methyl]pyridine-2-carboxamide | 465.07 | 465.04 |
| 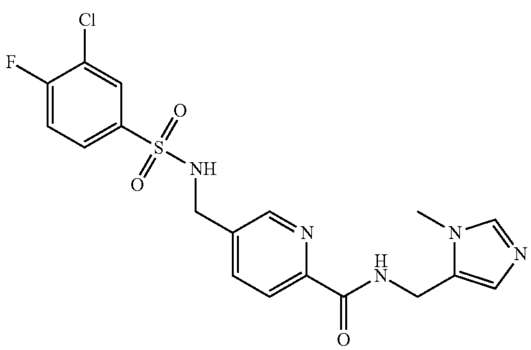 [SMILES: Cn1cncc1CNC(=O)c1ccc(CNS(=O)(=O)c2ccc(F)c(Cl)c2)cn1] | 5-[(3-chloro-4-fluorobenzene)sulfonamidomethyl]-N-[(1-methyl-1H-imidazol-5-yl)methyl]pyridine-2-carboxamide | 436.07 (M − H) | 436.13 (M − H) |
| 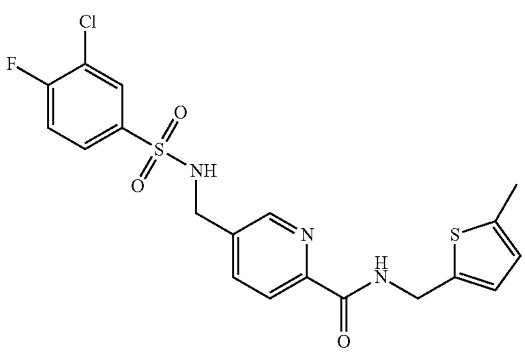 [SMILES: Cc1ccc(CNC(=O)c2ccc(CNS(=O)(=O)c3ccc(F)c(Cl)c3)cn2)s1] | 5-[(3-chloro-4-fluorobenzene)sulfonamidomethyl]-N-[(5-methyl-thiophen-2-yl)methyl]pyridine-2-carboxamide | 454.04 | 454.22 |
| 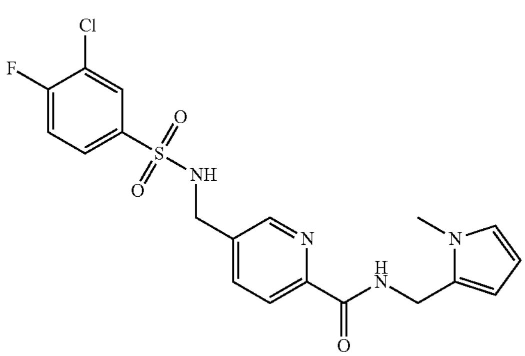 | 5-[(3-chloro-4-fluorobenzene)sulfonamidomethyl]-N-[(1-methyl-1H-pyrrol-2-yl)methyl]pyridine-2-carboxamide | 437.08 | 437.28 |

TABLE 1-continued

The following compounds were prepared by the method described above

| Structure | IUPAC Name | Calculated M + H | Found M + H |
|---|---|---|---|
| 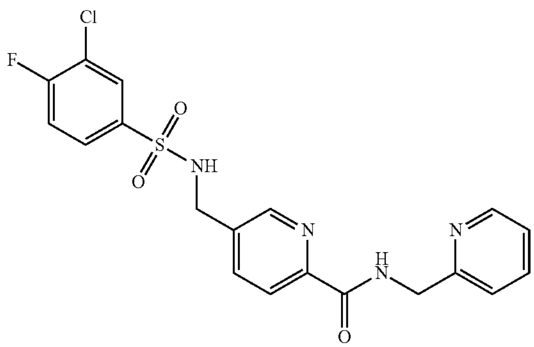 [SMILES: O=C(NCc1ccccn1)c1ccc(CNS(=O)(=O)c2ccc(F)c(Cl)c2)cn1] | 5-[(3-chloro-4-fluorobenzene)sulfonamidomethyl]-N-(pyridin-2-ylmethyl)pyridine-2-carboxamide | 435.06 | 435.21 |
| | 5-[(3-chloro-4-fluorobenzene)sulfonamidomethyl]-N-[3-(dimethylamino)propyl]pyridine-2-carboxamide | 429.11 | 429.16 |
| 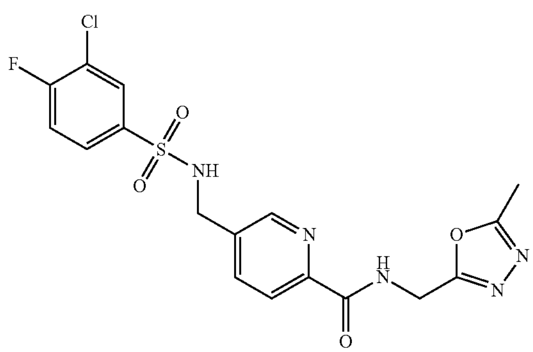 | 5-[(3-chloro-4-fluorobenzene)sulfonamidomethyl]-N-[(5-methyl-1,3,4-oxadiazol-2-yl)methyl]pyridine-2-carboxamide | 438.05 (M − H) | 438.17 (M − H) |
| 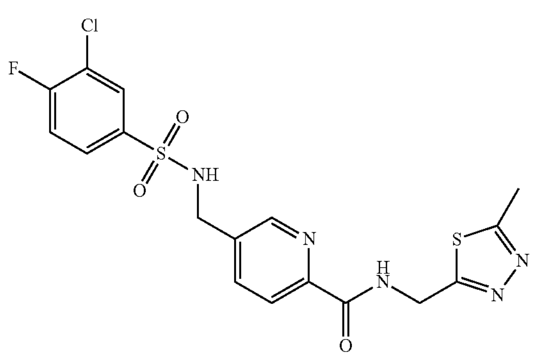 | 5-[(3-chloro-4-fluorobenzene)sulfonamidomethyl]-N-[(5-methyl-1,3,4-thiadiazol-2-yl)methyl]pyridine-2-carboxamide | 454.03 (M − H) | 454.12 (M − H) |

TABLE 1-continued

The following compounds were prepared by the method described above

| Structure | IUPAC Name | Calculated M + H | Found M + H |
|---|---|---|---|
| 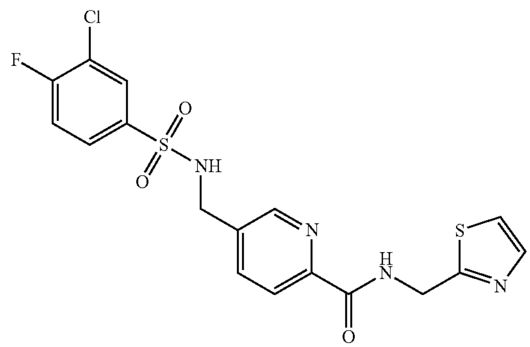 | 5-[(3-chloro-4-fluorobenzene)sulfonamidomethyl]-N-(1,3-thiazol-2-ylmethyl)pyridine-2-carboxamide | 441.02 | 441.17 |
| 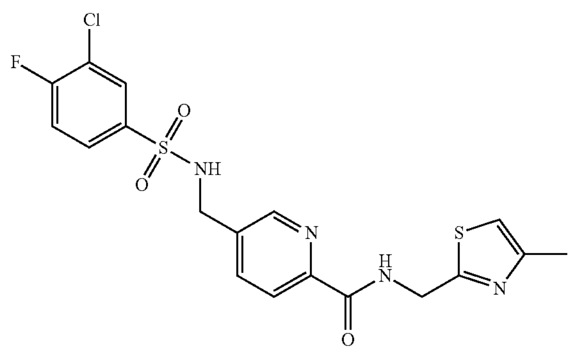 [SMILES: Cc1csc(CNC(=O)c2ccc(CNS(=O)(=O)c3ccc(F)c(Cl)c3)cn2)n1] | 5-[(3-chloro-4-fluorobenzene)sulfonamidomethyl]-N-[(4-methyl-1,3-thiazol-2-yl)methyl]pyridine-2-carboxamide | 455.03 | 455.18 |
| 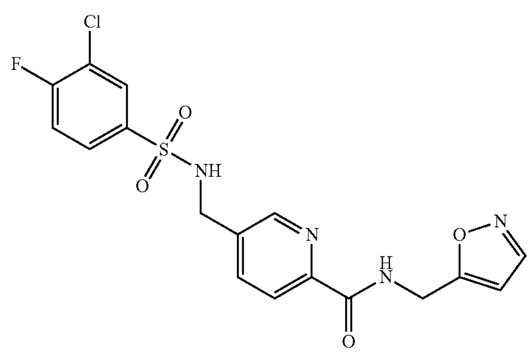 | 5-[(3-chloro-4-fluorobenzene)sulfonamidomethyl]-N-(1,2-oxazol-5-ylmethyl)pyridine-2-carboxamide | 425.04 | 425.2 |
| 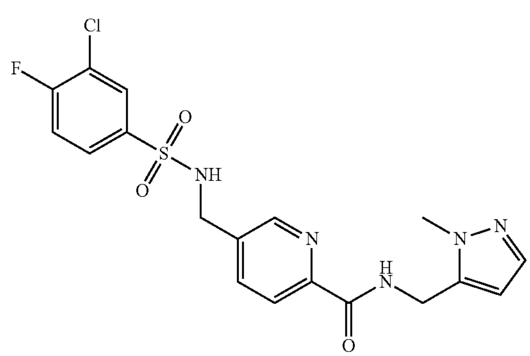 | 5-[(3-chloro-4-fluorobenzene)sulfonamidomethyl]-N-[(1-methyl-1H-pyrazol-5-yl)methyl]pyridine-2-carboxamide | 438.07 | 438.39 |

TABLE 1-continued

The following compounds were prepared by the method described above

| Structure | IUPAC Name | Calculated M + H | Found M + H |
|---|---|---|---|
| 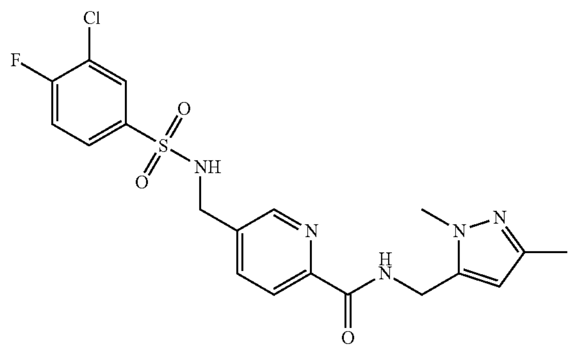 [SMILES: Cc1cc(CNC(=O)c2ccc(CNS(=O)(=O)c3ccc(F)c(Cl)c3)cn2)n(C)n1] | 5-[(3-chloro-4-fluorobenzene)sulfonamidomethyl]-N-[(1,3-dimethyl-1H-pyrazol-5-yl)methyl]pyridine-2-carboxamide | 452.09 | 452.16 |
| 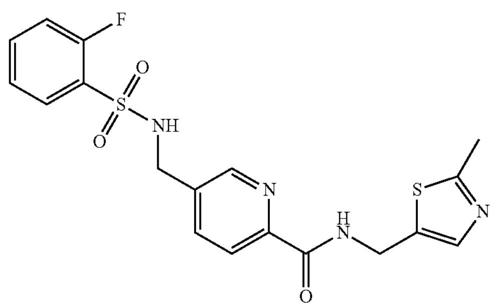 [SMILES: Cc1ncc(CNC(=O)c2ccc(CNS(=O)(=O)c3ccccc3F)cn2)s1] | 5-[(2-fluorobenzene)sulfonamidomethyl]-N-[(2-methyl-1,3-thiazol-5-yl)methyl]pyridine-2-carboxamide | 421.07 | 421.25 |
| 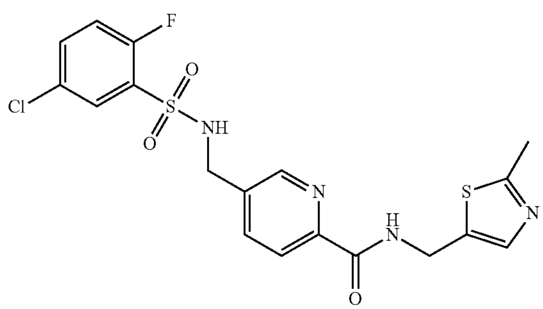 [SMILES: Cc1ncc(CNC(=O)c2ccc(CNS(=O)(=O)c3cc(Cl)ccc3F)cn2)s1] | 5-[(5-chloro-2-fluorobenzene)sulfonamidomethyl]-N-[(2-methyl-1,3-thiazol-5-yl)methyl]pyridine-2-carboxamide | 455.03 | 455.03 |
| 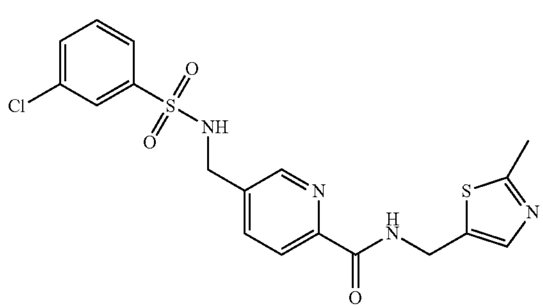 [SMILES: Cc1ncc(CNC(=O)c2ccc(CNS(=O)(=O)c3cccc(Cl)c3)cn2)s1] | 5-[(3-chlorobenzene)sulfonamidomethyl]-N-[(2-methyl-1,3-thiazol-5-yl)methyl]pyridine-2-carboxamide | 437.04 | 437.24 |

TABLE 1-continued

The following compounds were prepared by the method described above

| Structure | IUPAC Name | Calculated M + H | Found M + H |
|---|---|---|---|
| 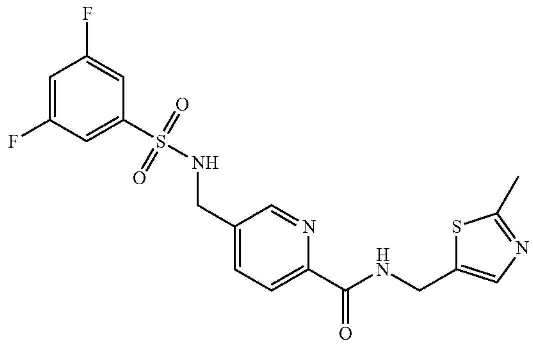 [SMILES: Cc1ncc(CNC(=O)c2ccc(CNS(=O)(=O)c3cc(F)cc(F)c3)cn2)s1] | 5-[(3,5-difluorobenzene)sulfonamidomethyl]-N-[(2-methyl-1,3-thiazol-5-yl)methyl]pyridine-2-carboxamide | 439.06 | 439.3 |
|  | N-[(2-methyl-1,3-thiazol-5-yl)methyl]-5-{[4-(trifluoromethyl)benzene]sulfonamidomethyl}pyridine-2-carboxamide | 471.07 | 471.24 |

Example 2—Preparation of 6-[(3-chloro-4-fluorobenzene)sulfonamidomethyl]-N-(1,3-thiazol-5-ylmethyl)pyridine-3-carboxamide

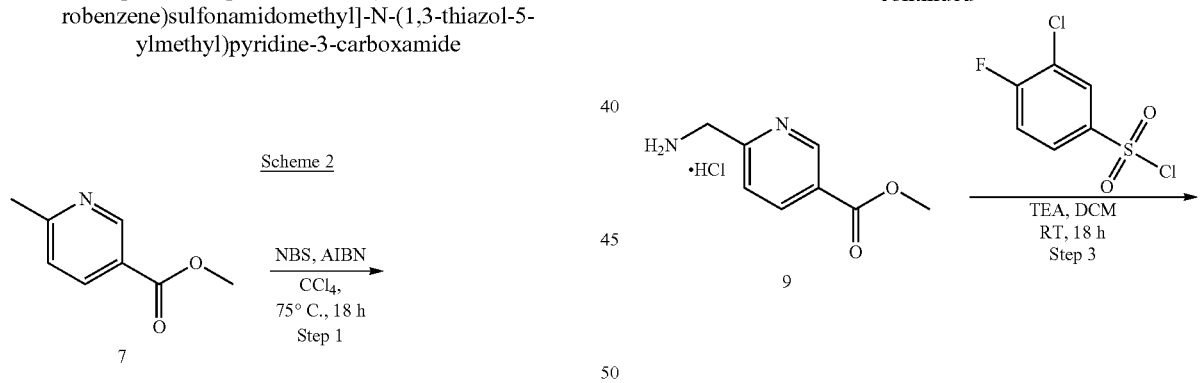

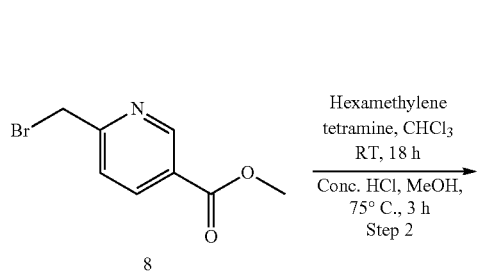

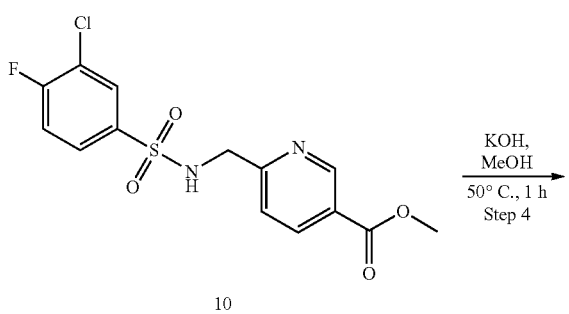

-continued

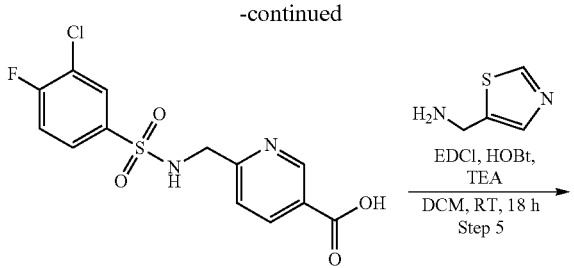

11

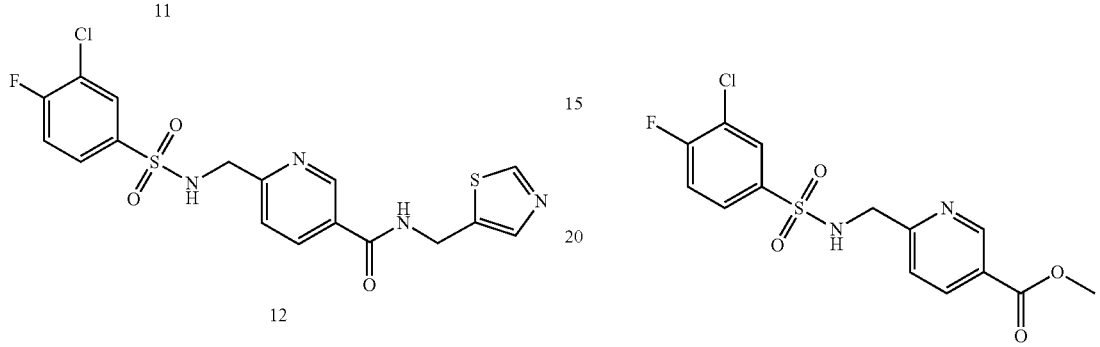

12

Step-1: Preparation of methyl 6-(bromomethyl)nicotinate

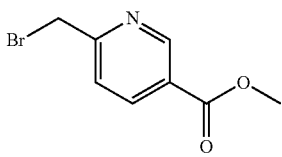

To a solution of methyl 6-methylnicotinate (0.5 g, 3.31 mmol) in carbon tetrachloride (15 mL) was added N-bromosuccinimide (0.647 g, 3.63 mmol) followed by azobisisobutyronitrile (0.054 g, 0.33 mmol). The reaction mixture was heated at 75° C. for 18 h. The reaction mixture was diluted with dichloromethane, washed with water, dried over anhydrous sodium sulfate, filtered and concentrated. The crude was purified by silica gel column chromatography, using 50% ethyl acetate in hexane to afford methyl 6-(bromomethyl)nicotinate (0.28 g, 37% yield) as a brownish solid. Calculated M+H: 229.97. Found M+H: 230.01.

Step-2: Preparation of methyl 6-(aminomethyl)nicotinate hydrochloride

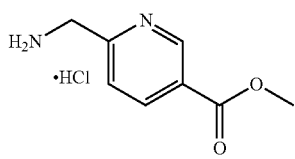

To a solution of methyl 6-(bromomethyl)nicotinate (0.28 g, 1.22 mmol) in chloroform (20 mL) was added hexamethylene tetramine (0.175 g, 1.24 mmol) and the reaction mixture was stirred at room temperature for 18 h. The solid formed was filtered and dried. The solid was suspended in methanol (20 mL), concentrated hydrochloric acid (0.3 mL) was added and the reaction mixture was heated at 75° C. for 3 h. The reaction mixture was concentrated, the residue was triturated with diethyl ether and dried to afford methyl 6-(aminomethyl)nicotinate hydrochloride (0.4 g, crude) as a brownish solid. Calculated M+H: 167.07. Found M+H: 167.0.

Step-3: Preparation of methyl 6-((3-chloro-4-fluorophenylsulfonamido)methyl)nicotinate

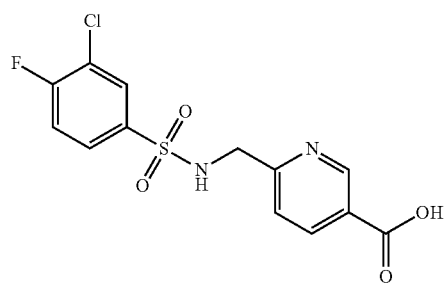 [SMILES: O=C(O)c1ccc(CNS(=O)(=O)c2ccc(F)c(Cl)c2)nc1]

To a solution of methyl 6-(aminomethyl)nicotinate hydrochloride (0.4 g, 1.67 mmol) in dichloromethane (20 mL) was added triethylamine (1.2 mL, 8.37 mmol)) followed by 4-fluoro-3-chlorobenzenesulfonyl chloride (0.24 ml, 1.67 mmol). The reaction mixture was stirred at room temperature for 18 h. The reaction mixture was diluted with dichloromethane, washed with water, dried over anhydrous sodium sulfate, filtered and concentrated. The crude was purified by silica gel column chromatography, using 40% ethyl acetate in hexane to afford the title compound methyl 6-((3-chloro-4-fluorophenylsulfonamido)methyl)nicotinate (0.22 g, 37% yield) as a brownish solid. Calculated M+H: 359.02. Found M+H: 359.1.

Step-4: Preparation of 6-((3-chloro-4-fluorophenylsulfonamido)methyl)nicotinic acid To a solution of methyl 6-((3-chloro-4-fluorophenylsulfonamido)methyl)nicotinate (0.22 g, 0.61 mmol) in methanol (20 mL) was added a 1M potassium hydroxide solution (0.172 g, 3.07 mmol) and the reaction mixture was heated at 50° C. for 1 h. The reaction mixture was concentrated, the residue was diluted with water and acidified with 1.5 M hydrochloric acid to pH 6 and the solid separated was filtered. The precipitate was washed with ice water and dried to afford 6-((3-chloro-4-fluorophenylsulfonamido)methyl) nicotinic acid (0.2 g, 94% yield) as a brownish solid. Calculated M+H: 345.0. Found M+H: 345.0.

Step-5: Preparation of 6-[(3-chloro-4-fluorobenzene)sulfonamidomethyl]-N-(1,3-thiazol-5-ylmethyl)pyridine-3-carboxamide

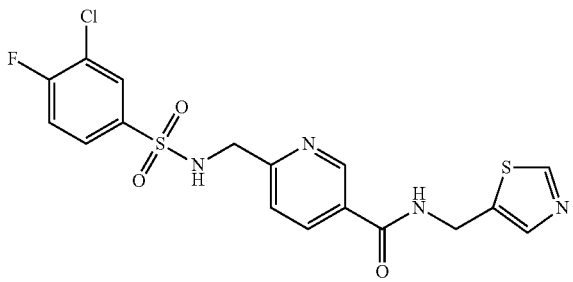 [SMILES: O=C(NCc1cncs1)c1ccc(CNS(=O)(=O)c2ccc(F)c(Cl)c2)nc1]

To a solution of 6-((3-chloro-4-fluorophenylsulfonamido)methyl)nicotinic acid (0.1 g, 0.29 mmol) and triethylamine (0.12 ml, 0.87 mmol) in dichloromethane (20 mL) were added 1-ethyl-3-(3-dimethylaminopropyl)carbodiimide (0.084 g, 0.44 mmol) and 1-hydroxybenzotriazole (0.047 g, 0.35 mmol) at 0° C. The reaction mixture was stirred at 0° C. for 30 min. A solution of thiazol-5-ylmethanamine (0.044 g, 0.29 mmol) in dichloromethane was added dropwise to the reaction mixture and was stirred at room temperature for 18 h. The reaction mixture was diluted with dichloromethane, washed with water, dried over anhydrous sodium sulfate, filtered and concentrated. The crude was purified by silica gel column chromatography using 2% methanol in dichloromethane to afford the title compound 6-[(3-chloro-4-fluorobenzene)sulfonamidomethyl]-N-(1,3-thiazol-5-ylmethyl)pyridine-3-carboxamide (0.025 g, 20%) as an off-white solid. Calculated M+H: 441.02. Found M+H: 441.1.

TABLE 2

The following compounds were prepared by the method described above

| Structure | IUPAC Name | Calculated M + H | Found M + H |
|---|---|---|---|
|  | 6-[(3-chloro-4-fluorobenzene)sulfonamidomethyl]-N-[(4-methoxyphenyl)methyl]pyridine-3-carboxamide | 464.08 | 464.1 |
|  | 6-[(3-chloro-4-fluorobenzene)sulfonamidomethyl]-N-[2-(dimethylamino)ethyl]pyridine-3-carboxamide | 415.09 | 415.4 |
|  | 6-[(3-chloro-4-fluorobenzene)sulfonamidomethyl]-N-[3-(dimethylamino)propyl]pyridine-3-carboxamide | 429.11 | 429.2 |

TABLE 2-continued

The following compounds were prepared by the method described above

| Structure | IUPAC Name | Calculated M + H | Found M + H |
|---|---|---|---|
| | 6-[(3-chloro-4-fluorobenzene)sulfonamidomethyl]-N-[4-(dimethylamino)butyl]pyridine-3-carboxamide | 443.12 | 443.2 |
| 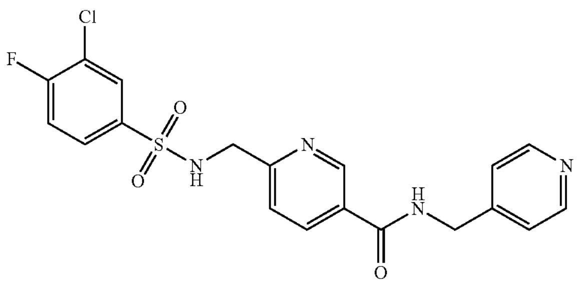 [SMILES: O=C(NCc1ccncc1)c1ccc(CNS(=O)(=O)c2ccc(F)c(Cl)c2)nc1] | 6-[(3-chloro-4-fluorobenzene)sulfonamidomethyl]-N-(pyridin-4-ylmethyl)pyridine-3-carboxamide | 435.06 | 435.2 |
| 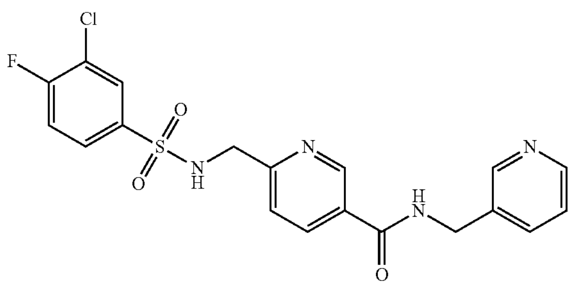 | 6-[(3-chloro-4-fluorobenzene)sulfonamidomethyl]-N-(pyridin-3-ylmethyl)pyridine-3-carboxamide | 435.06 | 435.26 |
| 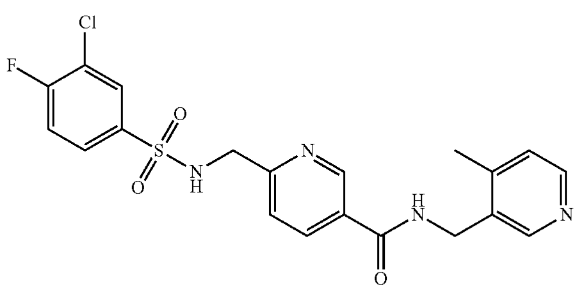 [SMILES: Cc1ccncc1CNC(=O)c1ccc(CNS(=O)(=O)c2ccc(F)c(Cl)c2)nc1] | 6-[(3-chloro-4-fluorobenzene)sulfonamidomethyl]-N-[(4-methylpyridin-3-yl)methyl]pyridine-3-carboxamide | 449.08 | 449.31 |
| 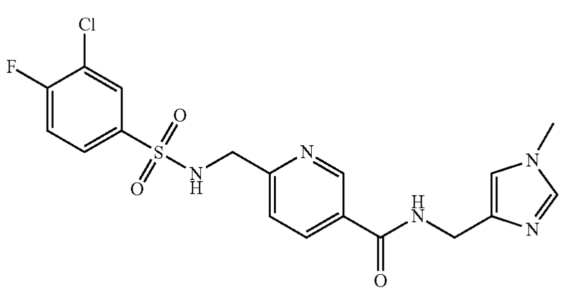 | 6-[(3-chloro-4-fluorobenzene)sulfonamidomethyl]-N-[(1-methyl-1H-imidazol-4-yl)methyl]pyridine-3-carboxamide | 438.07 | 438.29 |

TABLE 2-continued

The following compounds were prepared by the method described above

| Structure | IUPAC Name | Calculated M + H | Found M + H |
|---|---|---|---|
| 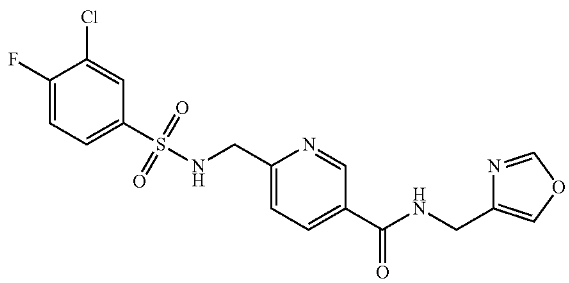 [SMILES: O=C(NCc1cocn1)c1ccc(CNS(=O)(=O)c2ccc(F)c(Cl)c2)nc1] | 6-[(3-chloro-4-fluorobenzene)sulfonamidomethyl]-N-(1,3-oxazol-4-ylmethyl)pyridine-3-carboxamide | 425.04 | 425.25 |
| 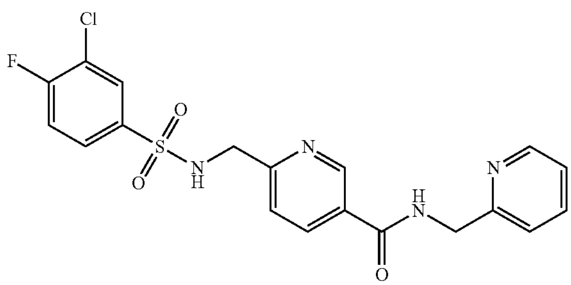 | 6-[(3-chloro-4-fluorobenzene)sulfonamidomethyl]-N-(pyridin-2-ylmethyl)pyridine-3-carboxamide | 435.06 | 435.26 |
| 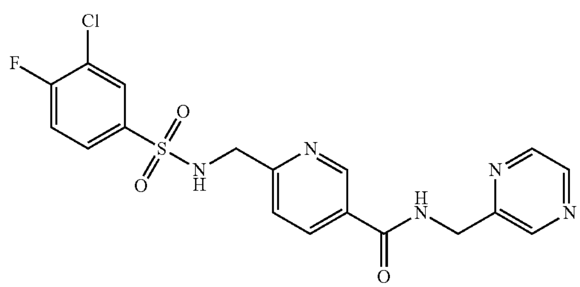 [SMILES: O=C(NCc1cnccn1)c1ccc(CNS(=O)(=O)c2ccc(F)c(Cl)c2)nc1] | 6-[(3-chloro-4-fluorobenzene)sulfonamidomethyl]-N-(pyrazin-2-ylmethyl)pyridine-3-carboxamide | 436.06 | 436.27 |
| 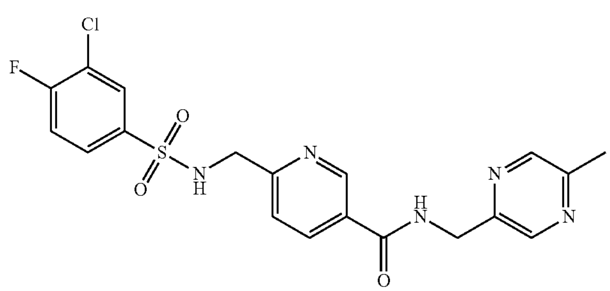 | 6-[(3-chloro-4-fluorobenzene)sulfonamidomethyl]-N-[(5-methylpyrazin-2-yl)methyl]pyridine-3-carboxamide | 450.07 | 450.28 |
| 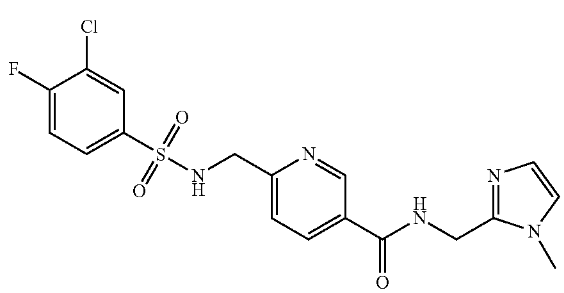 | 6-[(3-chloro-4-fluorobenzene)sulfonamidomethyl]-N-[(1-methyl-1H-imidazol-2-yl)methyl]pyridine-3-carboxamide | 438.07 | 438.3 |

TABLE 2-continued

The following compounds were prepared by the method described above

| Structure | IUPAC Name | Calculated M + H | Found M + H |
|---|---|---|---|
| 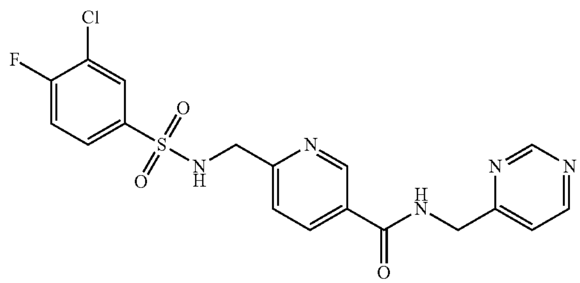 [SMILES: O=C(NCc1ccncn1)c1ccc(CNS(=O)(=O)c2ccc(F)c(Cl)c2)nc1] | 6-[(3-chloro-4-fluorobenzene)sulfonamidomethyl]-N-(pyrimidin-4-ylmethyl)pyridine-3-carboxamide | 436.06 | 436.27 |
| 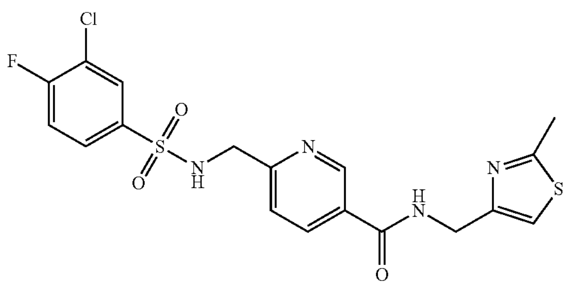 | 6-[(3-chloro-4-fluorobenzene)sulfonamidomethyl]-N-[(2-methyl-1,3-thiazol-4-yl)methyl]pyridine-3-carboxamide | 455.03 | 455.25 |
| 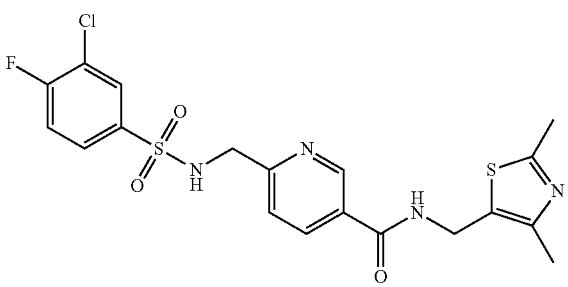 [SMILES: Cc1nc(C)c(CNC(=O)c2ccc(CNS(=O)(=O)c3ccc(F)c(Cl)c3)nc2)s1] | 6-[(3-chloro-4-fluorobenzene)sulfonamidomethyl]-N-[(dimethyl-1,3-thiazol-5-yl)methyl]pyridine-3-carboxamide | 469.05 | 469.27 |
| 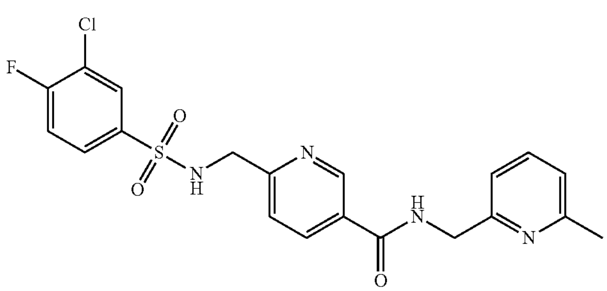 [SMILES: Cc1cccc(CNC(=O)c2ccc(CNS(=O)(=O)c3ccc(F)c(Cl)c3)nc2)n1] | 6-[(3-chloro-4-fluorobenzene)sulfonamidomethyl]-N-[(6-methylpyridin-2-yl)methyl]pyridine-3-carboxamide | 449.08 | 449.31 |
| 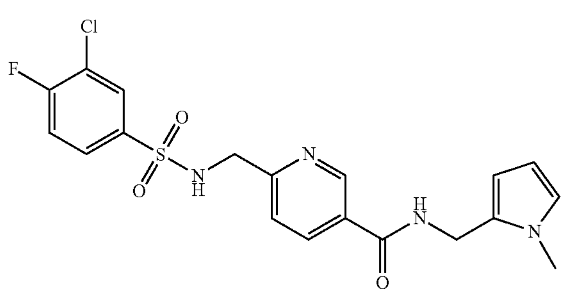 | 6-[(3-chloro-4-fluorobenzene)sulfonamidomethyl]-N-[(1-methyl-1H-pyrrol-2-yl)methyl]pyridine-3-carboxamide | 437.08 | 437.32 |

TABLE 2-continued

The following compounds were prepared by the method described above

| Structure | IUPAC Name | Calculated M + H | Found M + H |
|---|---|---|---|
| 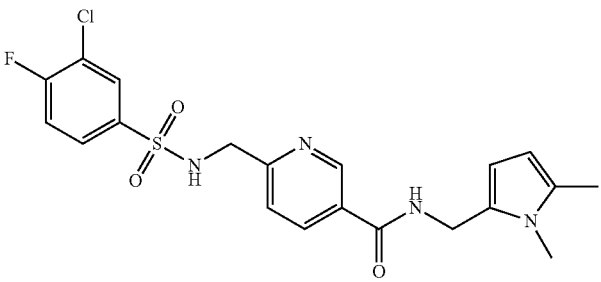 [SMILES: Cc1ccc(CNC(=O)c2ccc(CNS(=O)(=O)c3ccc(F)c(Cl)c3)nc2)n1C] | 6-[(3-chloro-4-fluorobenzene)sulfonamidomethyl]-N-[(1,5-dimethyl-1H-pyrrol-2-yl)methyl]pyridine-3-carboxamide | 451.09 | 451.3 |
| 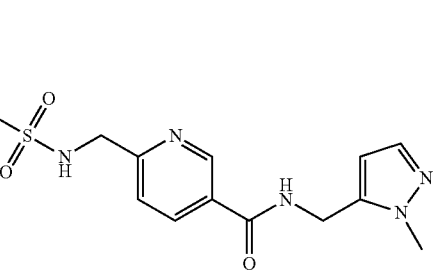 | 6-[(3-chloro-4-fluorobenzene)sulfonamidomethyl]-N-[(1-methyl-1H-pyrazol-5-yl)methyl]pyridine-3-carboxamide | 438.07 | 438.28 |
| 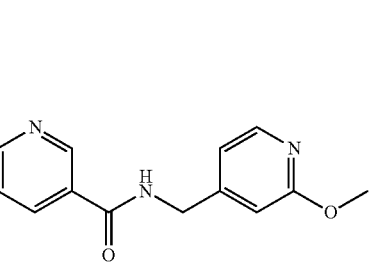 | 6-[(3-chloro-4-fluorobenzene)sulfonamidomethyl]-N-[(2-methoxypyridin-4-yl)methyl]pyridine-3-carboxamide | 465.07 | 466.29 |
| 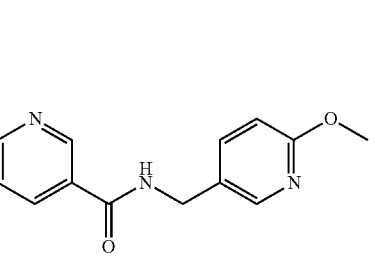 | 6-[(3-chloro-4-fluorobenzene)sulfonamidomethyl]-N-[(6-methoxypyridin-3-yl)methyl]pyridine-3-carboxamide | 465.07 | 465.33 |
| 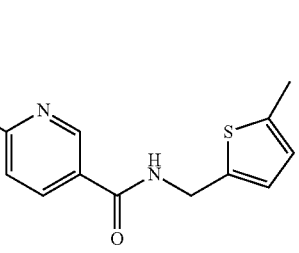 | 6-[(3-chloro-4-fluorobenzene)sulfonamidomethyl]-N-[(5-methylthiophen-2-yl)methyl]pyridine-3-carboxamide | 454.04 | 454.27 |

TABLE 2-continued

The following compounds were prepared by the method described above

| Structure | IUPAC Name | Calculated M + H | Found M + H |
|---|---|---|---|
| 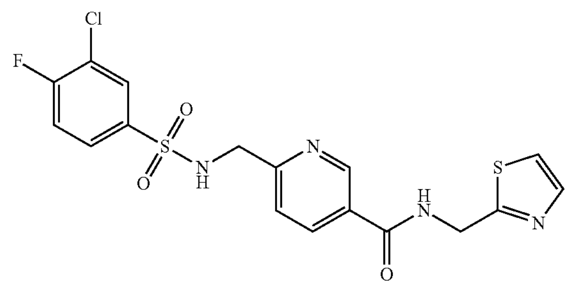 | 6-[(3-chloro-4-fluorobenzene)sulfonamidomethyl]-N-(1,3-thiazol-2-ylmethyl)pyridine-3-carboxamide | 441.02 | 441.26 |
| 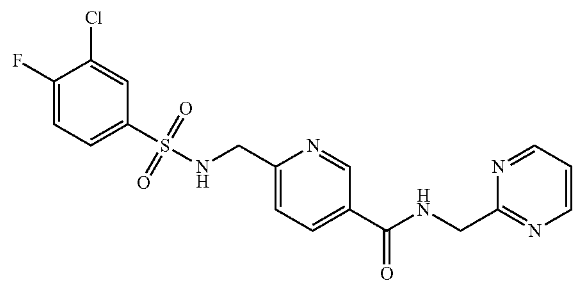 [SMILES: O=C(NCc1ncccn1)c1ccc(CNS(=O)(=O)c2ccc(F)c(Cl)c2)nc1] | 6-[(3-chloro-4-fluorobenzene)sulfonamidomethyl]-N-(pyrimidin-2-ylmethyl)pyridine-3-carboxamide | 436.06 | 436.3 |
|  | 6-[(3-chloro-4-fluorobenzene)sulfonamidomethyl]-N-[(2-methoxyphenyl)methyl]pyridine-3-carboxamide | 464.08 | 464.1 |
| 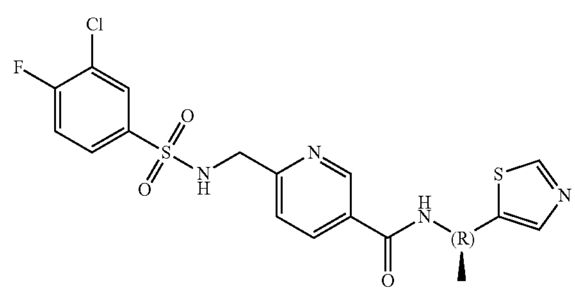 | 6-[(3-chloro-4-fluorobenzene)sulfonamidomethyl]-N-[(1R)-1-(1,3-thiazol-5-yl)ethyl]pyridine-3-carboxamide | 455.03 | 455.27 |
| 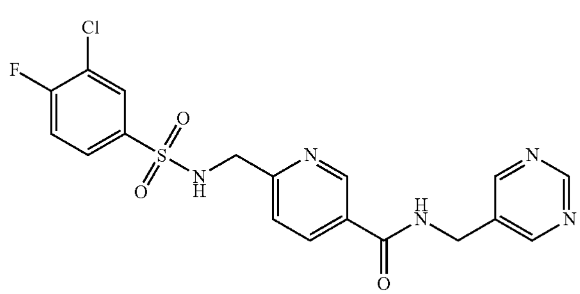 | 6-[(3-chloro-4-fluorobenzene)sulfonamidomethyl]-N-(pyrimidin-5-ylmethyl)pyridine-3-carboxamide | 436.06 | 436.31 |

TABLE 2-continued

The following compounds were prepared by the method described above

| Structure | IUPAC Name | Calculated M + H | Found M + H |
|---|---|---|---|
| 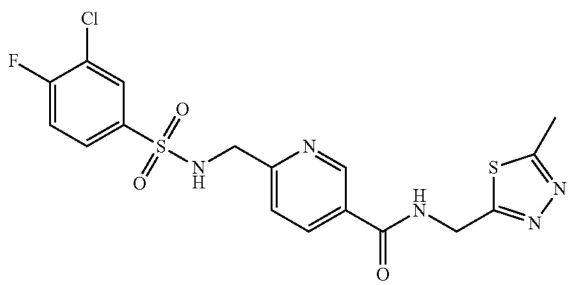 [SMILES: Cc1nnc(CNC(=O)c2ccc(CNS(=O)(=O)c3ccc(F)c(Cl)c3)nc2)s1] | 6-[(3-chloro-4-fluorobenzene)sulfonamidomethyl]-N-[(5-methyl-1,3,4-thiadiazol-2-yl)methyl]pyridine-3-carboxamide | 456.03 | 456.29 |
| | 6-[(3-chloro-4-fluorobenzene)sulfonamidomethyl]-N-{[3-(trifluoromethyl)pyridin-2-yl]methyl}pyridine-3-carboxamide | 503.05 | 503.31 |
| 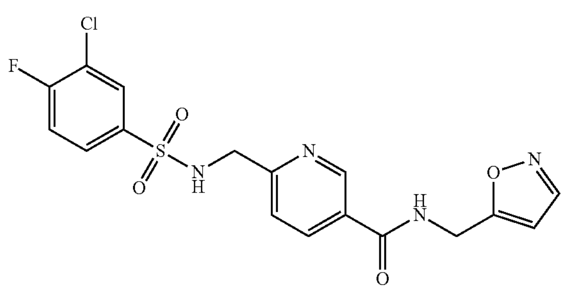 [SMILES: O=C(NCc1ccno1)c1ccc(CNS(=O)(=O)c2ccc(F)c(Cl)c2)nc1] | 6-[(3-chloro-4-fluorobenzene)sulfonamidomethyl]-N-(1,2-oxazol-5-ylmethyl)pyridine-3-carboxamide | 423.04 (M − H) | 423.3 (M − H) |
| 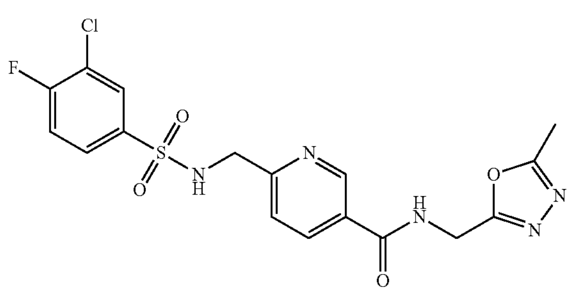 [SMILES: Cc1nnc(CNC(=O)c2ccc(CNS(=O)(=O)c3ccc(F)c(Cl)c3)nc2)o1] | 6-[(3-chloro-4-fluorobenzene)sulfonamidomethyl]-N-[(5-methyl-1,3,4-oxadiazol-2-yl)methyl]pyridine-3-carboxamide | 440.05 | 440.29 |
| 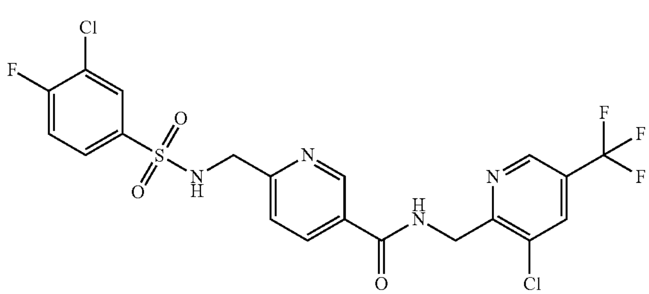 [SMILES: O=C(NCc1ncc(C(F)(F)F)cc1Cl)c1ccc(CNS(=O)(=O)c2ccc(F)c(Cl)c2)nc1] | 6-[(3-chloro-4-fluorobenzene)sulfonamidomethyl]-N-{[3-chloro-5-(trifluoromethyl)pyridin-2-yl]methyl}pyridine-3-carboxamide | 537.01 | 537.18 |

TABLE 2-continued

The following compounds were prepared by the method described above

| Structure | IUPAC Name | Calculated M + H | Found M + H |
|---|---|---|---|
| 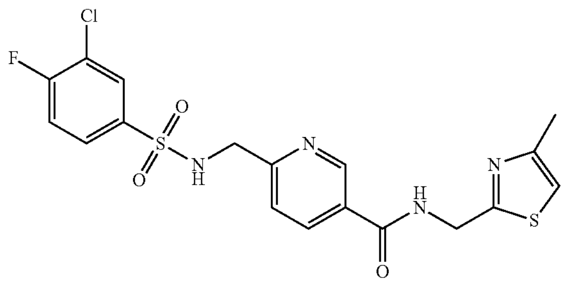 [SMILES: Cc1csc(CNC(=O)c2ccc(CNS(=O)(=O)c3ccc(F)c(Cl)c3)nc2)n1] | 6-[(3-chloro-4-fluorobenzene)sulfonamidomethyl]-N-[(4-methyl-1,3-thiazol-2-yl)methyl]pyridine-3-carboxamide | 455.03 | 455.24 |
| 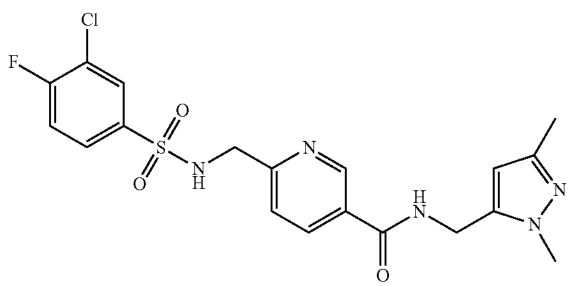 [SMILES: Cc1cc(CNC(=O)c2ccc(CNS(=O)(=O)c3ccc(F)c(Cl)c3)nc2)n(C)n1] | 6-[(3-chloro-4-fluorobenzene)sulfonamidomethyl]-N-[(1,3-dimethyl-1H-pyrazol-5-yl)methyl]pyridine-3-carboxamide | 452.09 | 452.17 |
| 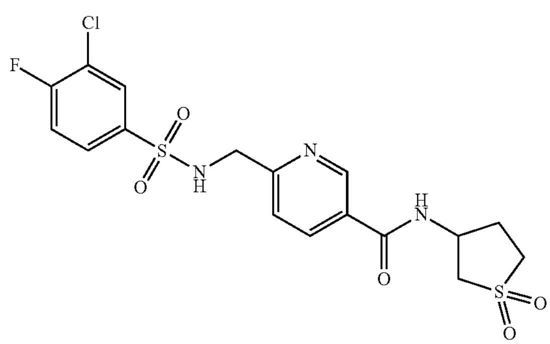 [SMILES: O=C(NC1CCS(=O)(=O)C1)c1ccc(CNS(=O)(=O)c2ccc(F)c(Cl)c2)nc1] | 6-(((3-chloro-4-fluorophenyl)sulfonamido)methyl)-N-(1,1-dioxido-tetrahydrothiophen-3-yl)nicotinamide | 462.03 | 462.2 |
| 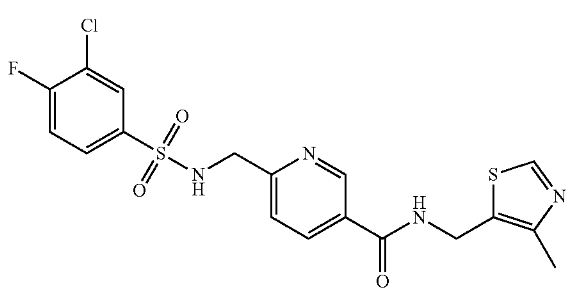 | 6-[(3-chloro-4-fluorobenzene)sulfonamidomethyl]-N-[(4-methyl-1,3-thiazol-5-yl)methyl]pyridine-3-carboxamide | 455.03 | 455.28 |

Example 3—Preparation of 5-[(3-chloro-4-fluorobenzene)sulfonamidomethyl]-N-(1,3-thiazol-5-ylmethyl)pyrazine-2-carboxamide

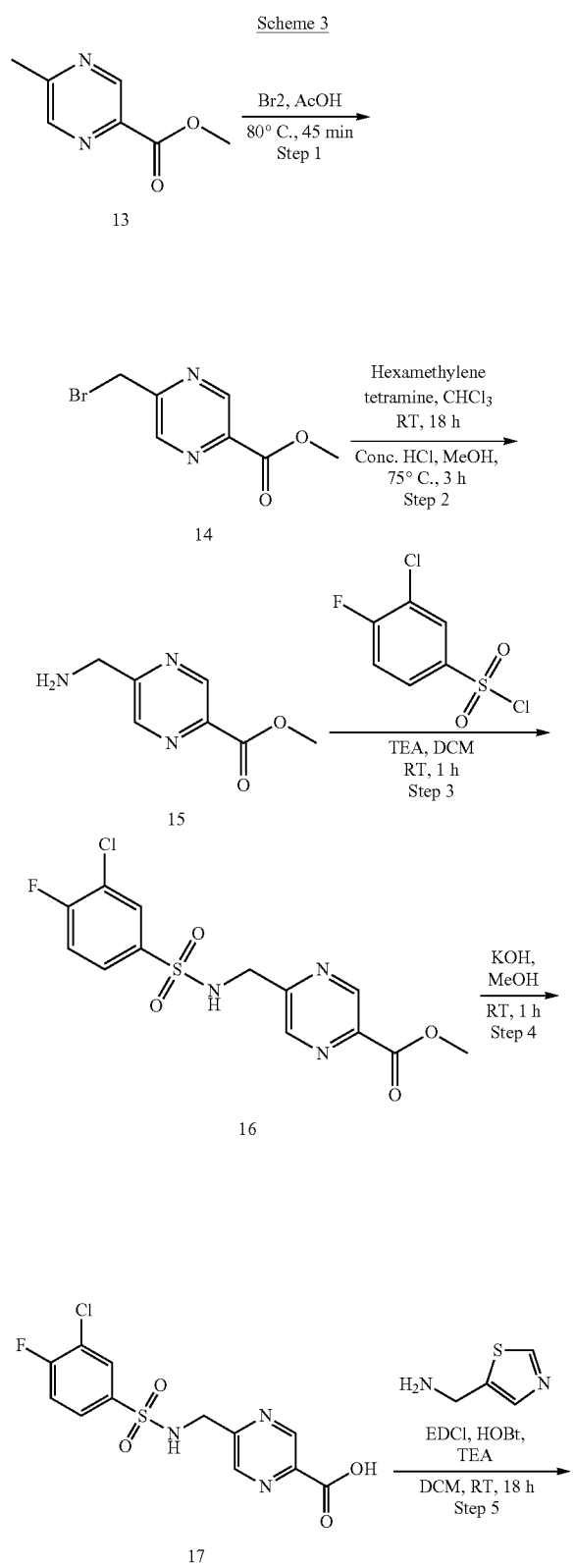

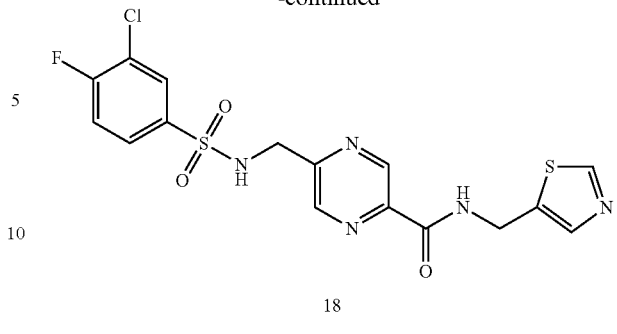

Step-1: Preparation of methyl 5-(bromomethyl)pyrazine-2-carboxylate

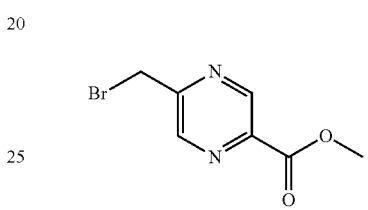

To a solution of methyl 5-methylpyrazine-2-carboxylate (0.5 g, 3.28 mmol) in acetic acid (5 ml) was added bromine (0.19 ml, 3.61 mmol) at room temperature. The reaction mixture was heated at 80° C. for 45 min. The reaction mixture was concentrated to remove acetic acid. The residue was basified with saturated sodium bicarbonate solution and extracted with ethyl acetate. The organic layer was dried and concentrated. The crude was purified by silica gel column chromatography using 20% ethyl acetate in hexane to afford the title compound methyl 5-(bromomethyl)pyrazine-2-carboxylate (0.3 g, 40%) as a brownish liquid. Calculated M+H: 230.97. Found M+H: 231.0.

Step-2: Preparation of methyl 5-(aminomethyl)pyrazine-2-carboxylate hydrochloride

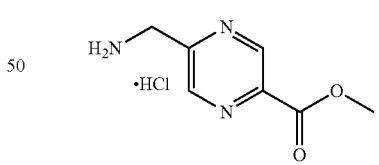

To a solution of methyl 5-(bromomethyl)pyrazine-2-carboxylate (0.15 g, 0.65 mmol) in chloroform (10 mL) was added hexamethylene tetramine (0.093 g, 0.66 mmol) and the reaction mixture was stirred at room temperature for 18 h. The solid formed was filtered and dried. The solid was suspended in methanol (10 mL), concentrated hydrochloric acid (0.3 ml) was added and the reaction mixture was heated at 75° C. for 3 h. The reaction mixture was concentrated, the residue was triturated with diethyl ether and dried to afford the title compound methyl 5-(aminomethyl)pyrazine-2-carboxylate hydrochloride (0.15 g, crude) as a brownish solid. Calculated M+H: 168.07. Found M+H: 168.1.

Step-3: Preparation of methyl 5-((3-chloro-4-fluorophenylsulfonamido)methyl)pyrazine-2-carboxylate

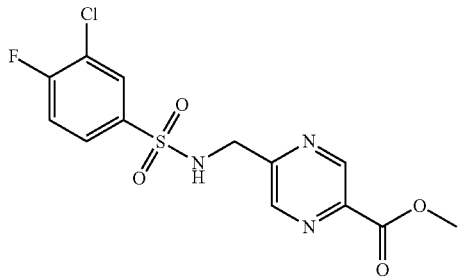 [SMILES: COC(=O)c1cnc(CNS(=O)(=O)c2ccc(F)c(Cl)c2)cn1]

To a suspension of methyl 5-(aminomethyl)pyrazine-2-carboxylate hydrochloride (4 g, 19.73 mmol) in dichloromethane (200 mL) was added triethylamine (14 mL, 98.68 mmol) followed by 4-fluor-3-chlorobenzenesulfonyl chloride (2.81 ml, 19.73 mmol). The reaction mixture was stirred at room temperature for 1 h. Then the reaction mixture was diluted with dichloromethane, washed with water, dried over anhydrous sodium sulfate, filtered and concentrated. The crude was purified by silica gel column chromatography using 40% ethyl acetate in hexane to afford the title compound methyl 5-((3-chloro-4-fluorophenylsulfonamido)methyl)pyrazine-2-carboxylate (1.5 g, 21%) as a brownish solid. Calculated M+H: 360.01. Found M+H: 360.1.

Step-4: Preparation of 5-((3-chloro-4-fluorophenylsulfonamido)methyl)pyrazine-2-carboxylic acid

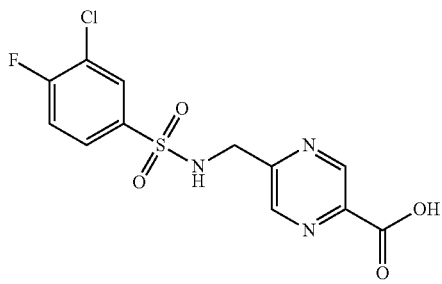 [SMILES: O=C(O)c1cnc(CNS(=O)(=O)c2ccc(F)c(Cl)c2)cn1]

To a solution of methyl 5-((3-chloro-4-fluorophenylsulfonamido)methyl)pyrazine-2-carboxylate (0.5 g, 1.39 mmol) in methanol (30 mL) was added 1M potassium hydroxide solution (7 ml, 6.96 mmol) and the reaction mixture was stirred at room temperature for 1 h. The reaction mixture was concentrated and the residue was diluted with water, acidified with 1.5 M hydrochloric acid to pH 6 and the solid separated was filtered. The precipitate was washed with ice water and dried to afford the title compound 5-((3-chloro-4-fluorophenylsulfonamido)methyl)pyrazine-2-carboxylic acid (0.45 g, 94%) as a brownish solid. Calculated M+H: 346.0. Found M+H: 346.0.

Step-5: Preparation of 5-[(3-chloro-4-fluorobenzene)sulfonamidomethyl]-N-(1,3-thiazol-5-ylmethyl)pyrazine-2-carboxamide

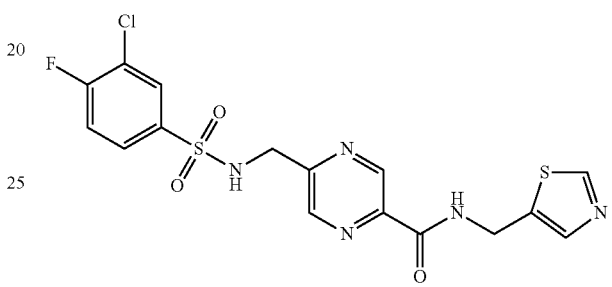

To a solution of 5-((3-chloro-4-fluorophenylsulfonamido)methyl)pyrazine-2-carboxylic acid (0.12 g, 0.35 mmol) and triethylamine (0.15 ml, 1.04 mmol) in dichloromethane (20 mL) were added 1-ethyl-3-(3-dimethylaminopropyl)carbodiimide (0.1 g, 0.52 mmol) and 1-hydroxybenzotriazole (0.056 g, 0.42 mmol) at 0° C. The reaction mixture was stirred at 0° C. for 30 min. A solution of thiazol-5-ylmethanamine (0.04 g, 0.35 mmol) in dichloromethane was added dropwise to the reaction mixture and stirred at room temperature for 18 h. The reaction mixture was diluted with dichloromethane, washed with water, dried over anhydrous sodium sulfate, filtered and concentrated. The crude was purified by silica gel column chromatography using 2% methanol in dichloromethane to afford the title compound 5-[(3-chloro-4-fluorobenzene)sulfonamidomethyl]-N-(1,3-thiazol-5-ylmethyl)pyrazine-2-carboxamide (0.045 g, 30%) as off-white solid. Calculated M+H: 442.01. Found M+H: 442.1.

TABLE 3

The following compounds were prepared by the method described above

| Structure | IUPAC Name | Calculated M + H | Found M + H |
|---|---|---|---|
| 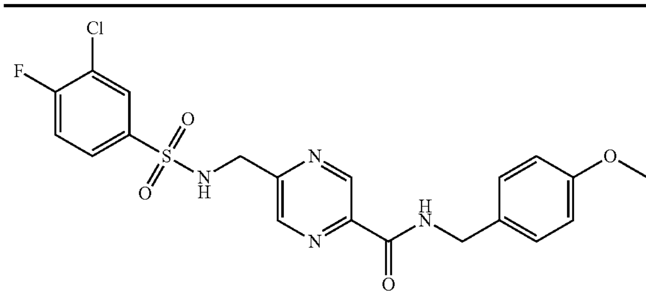 | 5-[(3-chloro-4-fluorobenzene)sulfonamidomethyl]-N-[(4-methoxyphenyl)methyl]pyrazine-2-carboxamide | 465.07 | 465.1 |

TABLE 3-continued

The following compounds were prepared by the method described above

| Structure | IUPAC Name | Calculated M + H | Found M + H |
|---|---|---|---|
| 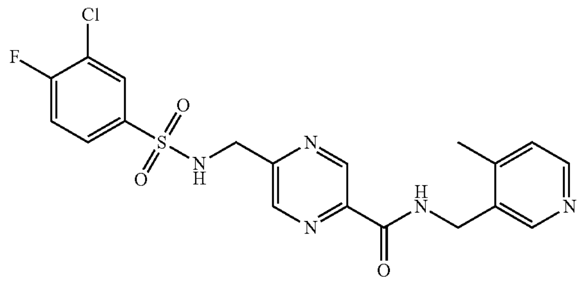 | 5-[(3-chloro-4-fluorobenzene)sulfonamidomethyl]-N-[(4-methylpyridin-3-yl)methyl]pyrazine-2-carboxamide | 450.07 | 450.36 |
| 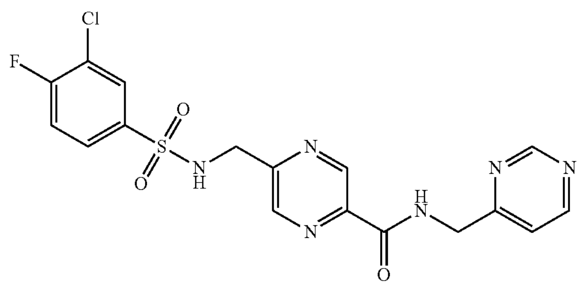 [SMILES: O=C(NCc1ccncn1)c1cnc(CNS(=O)(=O)c2ccc(F)c(Cl)c2)cn1] | 5-[(3-chloro-4-fluorobenzene)sulfonamidomethyl]-N-(pyrimidin-4-ylmethyl)pyrazine-2-carboxamide | 435.05 (M − H) | 435.3 (M − H) |
| 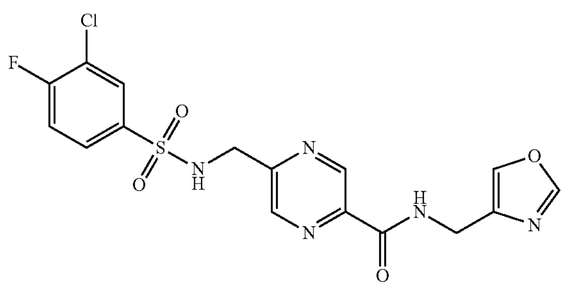 [SMILES: O=C(NCc1cocn1)c1cnc(CNS(=O)(=O)c2ccc(F)c(Cl)c2)cn1] | 5-[(3-chloro-4-fluorobenzene)sulfonamidomethyl]-N-(1,3-oxazol-4-ylmethyl)pyrazine-2-carboxamide | 424.04 (M − H) | 424.3 (M − H) |
| 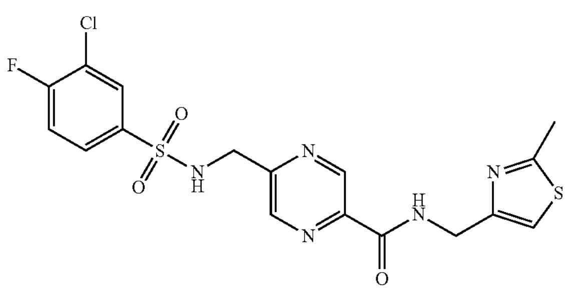 [SMILES: Cc1nc(CNC(=O)c2cnc(CNS(=O)(=O)c3ccc(F)c(Cl)c3)cn2)cs1] | 5-[(3-chloro-4-fluorobenzene)sulfonamidomethyl]-N-[(2-methyl-1,3-thiazol-4-yl)methyl]pyrazine-2-carboxamide | 456.03 | 456.29 |
| | 5-(((3-chloro-4-fluorophenyl)sulfonamido)methyl)-N-1,1-dioxidotetrahydrothiophen-3-yl)pyrazine-2-carboxamide | 461.02 (M − H) | 461.28 (M − H) |

TABLE 3-continued

The following compounds were prepared by the method described above

| Structure | IUPAC Name | Calculated M + H | Found M + H |
|---|---|---|---|
| 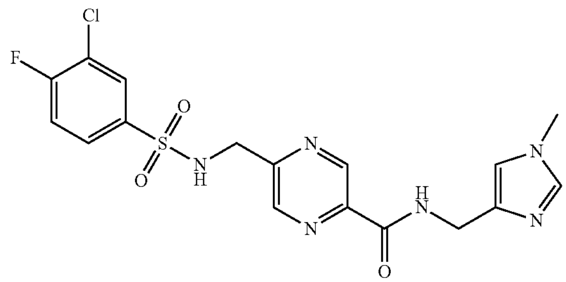 [SMILES: Cn1cnc(CNC(=O)c2cnc(CNS(=O)(=O)c3ccc(F)c(Cl)c3)cn2)c1] | 5-[(3-chloro-4-fluorobenzene)sulfonamidomethyl]-N-[(1-methyl-1H-imidazol-4-yl)methyl]pyrazine-2-carboxamide | 439.07 | 439.37 |
| 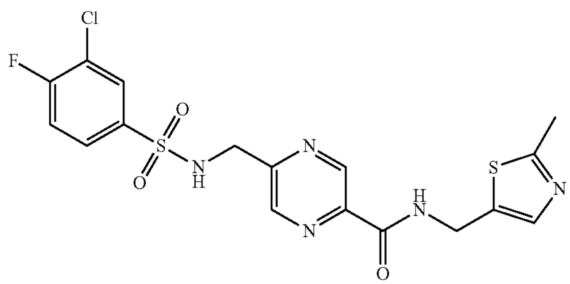 [SMILES: Cc1ncc(CNC(=O)c2cnc(CNS(=O)(=O)c3ccc(F)c(Cl)c3)cn2)s1] | 5-[(3-chloro-4-fluorobenzene)sulfonamidomethyl]-N-[(2-methyl-1,3-thiazol-5-yl)methyl]pyrazine-2-carboxamide | 456.03 | 456.1 |
| 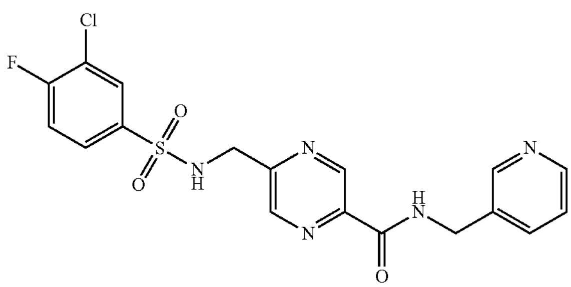 [SMILES: O=C(NCc1cccnc1)c1cnc(CNS(=O)(=O)c2ccc(F)c(Cl)c2)cn1] | 5-[(3-chloro-4-fluorobenzene)sulfonamidomethyl]-N-(pyridin-3-ylmethyl)pyrazine-2-carboxamide | 436.06 | 436.27 |
| 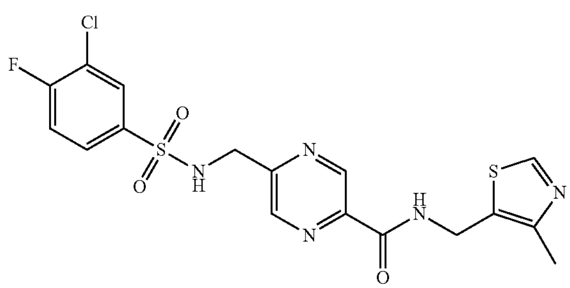 [SMILES: Cc1ncsc1CNC(=O)c1cnc(CNS(=O)(=O)c2ccc(F)c(Cl)c2)cn1] | 5-[(3-chloro-4-fluorobenzene)sulfonamidomethyl]-N-[(4-methyl-1,3-thiazol-5-yl)methyl]pyrazine-2-carboxamide | 456.03 | 456.26 |
| 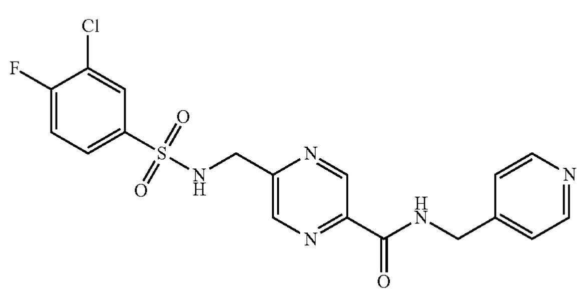 [SMILES: O=C(NCc1ccncc1)c1cnc(CNS(=O)(=O)c2ccc(F)c(Cl)c2)cn1] | 5-[(3-chloro-4-fluorobenzene)sulfonamidomethyl]-N-(pyridin-4-ylmethyl)pyrazine-2-carboxamide | 436.06 | 436.27 |

TABLE 3-continued

The following compounds were prepared by the method described above

| Structure | IUPAC Name | Calculated M + H | Found M + H |
|---|---|---|---|
| 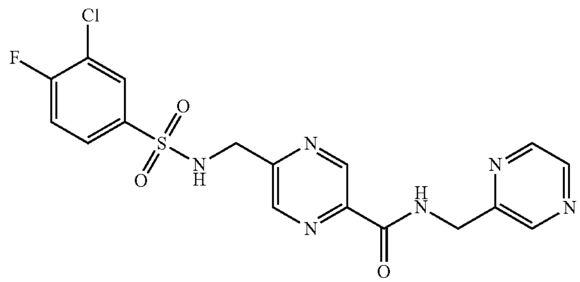 [SMILES: O=C(NCc1cnccn1)c1cnc(CNS(=O)(=O)c2ccc(F)c(Cl)c2)cn1] | 5-[(3-chloro-4-fluorobenzene)sulfonamidomethyl]-N-(pyrazin-2-ylmethyl)pyrazine-2-carboxamide | 437.05 | 437.28 |
| 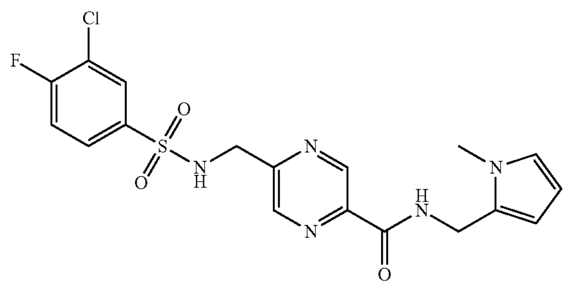 [SMILES: Cn1cccc1CNC(=O)c1cnc(CNS(=O)(=O)c2ccc(F)c(Cl)c2)cn1] | 5-[(3-chloro-4-fluorobenzene)sulfonamidomethyl]-N-[(1-methyl-1H-pyrrol-2-yl)methyl]pyrazine-2-carboxamide | 438.07 | 438.29 |
| 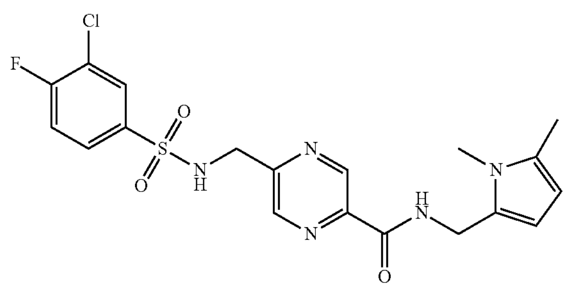 [SMILES: Cc1ccc(CNC(=O)c2cnc(CNS(=O)(=O)c3ccc(F)c(Cl)c3)cn2)n1C] | 5-[(3-chloro-4-fluorobenzene)sulfonamidomethyl]-N-[(1,5-dimethyl-1H-pyrrol-2-yl)methyl]pyrazine-2-carboxamide | 452.09 | 452.3 |
| 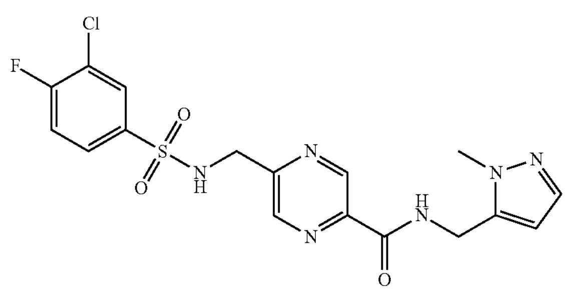 [SMILES: Cn1nccc1CNC(=O)c1cnc(CNS(=O)(=O)c2ccc(F)c(Cl)c2)cn1] | 5-[(3-chloro-4-fluorobenzene)sulfonamidomethyl]-N-[(1-methyl-1H-pyrazol-5-yl)methyl]pyrazine-2-carboxamide | 439.07 | 439.29 |
| 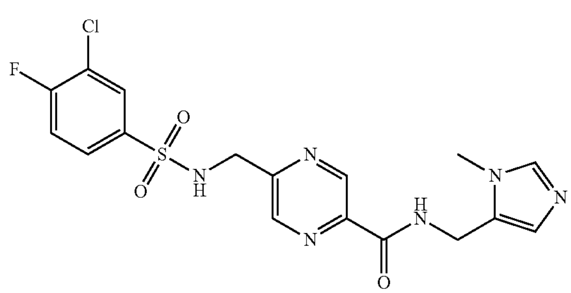 [SMILES: Cn1cncc1CNC(=O)c1cnc(CNS(=O)(=O)c2ccc(F)c(Cl)c2)cn1] | 5-[(3-chloro-4-fluorobenzene)sulfonamidomethyl]-N-[(1-methyl-1H-imidazol-5-yl)methyl]pyrazine-2-carboxamide | 439.07 | 439.33 |

TABLE 3-continued

The following compounds were prepared by the method described above

| Structure | IUPAC Name | Calculated M + H | Found M + H |
|---|---|---|---|
| 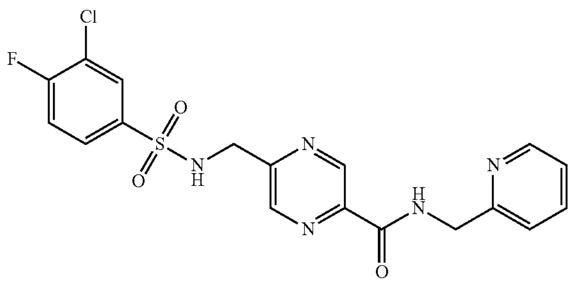 [SMILES: O=C(NCc1ccccn1)c1cnc(CNS(=O)(=O)c2ccc(F)c(Cl)c2)cn1] | 5-[(3-chloro-4-fluorobenzene)sulfonamidomethyl]-N-(pyridin-2-ylmethyl)pyrazine-2-carboxamide | 436.06 | 436.3 |
| 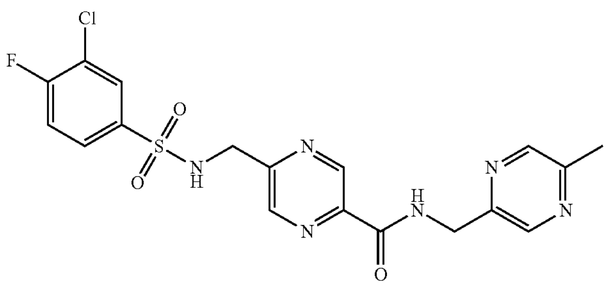 [SMILES: Cc1cnc(CNC(=O)c2cnc(CNS(=O)(=O)c3ccc(F)c(Cl)c3)cn2)cn1] | 5-[(3-chloro-4-fluorobenzene)sulfonamidomethyl]-N-[(5-methylpyrazin-2-yl)methyl]pyrazine-2-carboxamide | 451.07 | 451.29 |
| 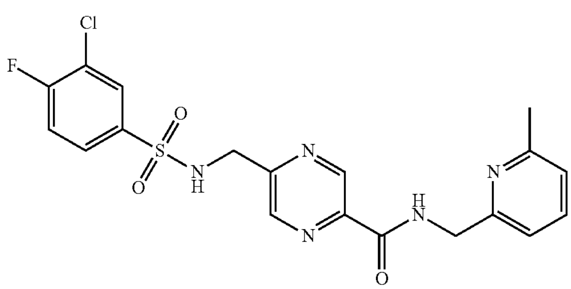 [SMILES: Cc1cccc(CNC(=O)c2cnc(CNS(=O)(=O)c3ccc(F)c(Cl)c3)cn2)n1] | 5-[(3-chloro-4-fluorobenzene)sulfonamidomethyl]-N-[(6-methylpyridin-2-yl)methyl]pyrazine-2-carboxamide | 450.07 | 450.28 |
| 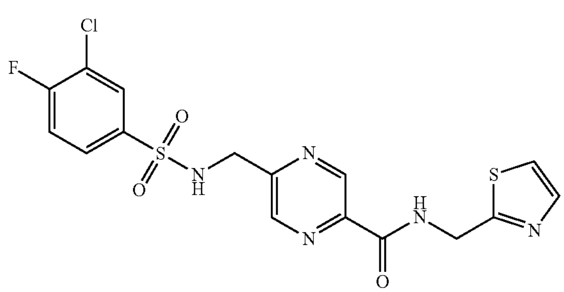 [SMILES: O=C(NCc1nccs1)c1cnc(CNS(=O)(=O)c2ccc(F)c(Cl)c2)cn1] | 5-[(3-chloro-4-fluorobenzene)sulfonamidomethyl]-N-(1,3-thiazol-2-ylmethyl)pyrazine-2-carboxamide | 440.01 (M − H) | 440.23 (M − H) |
| 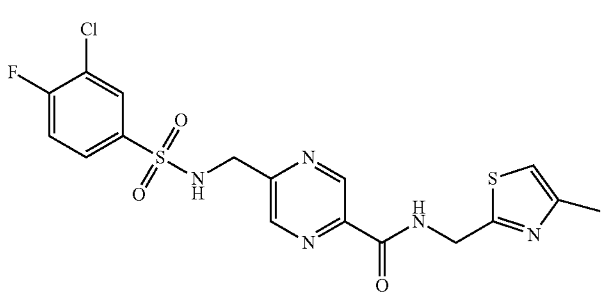 [SMILES: Cc1csc(CNC(=O)c2cnc(CNS(=O)(=O)c3ccc(F)c(Cl)c3)cn2)n1] | 5-[(3-chloro-4-fluorobenzene)sulfonamidomethyl]-N-[(4-methyl-1,3-thiazol-2-yl)methyl]pyrazine-2-carboxamide | 454.03 (M − H) | 454.27 (M − H) |

TABLE 3-continued

The following compounds were prepared by the method described above

| Structure | IUPAC Name | Calculated M + H | Found M + H |
|---|---|---|---|
| 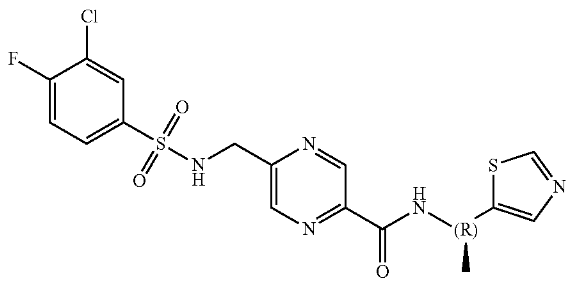 | 5-[(3-chloro-4-fluorobenzene)sulfonamidomethyl]-N-[(1R)-1-(1,3-thiazol-5-yl)ethyl]pyrazine-2-carboxamide | 456.03 | 456.15 |
| 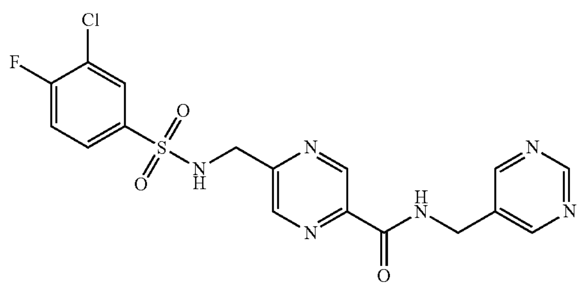 [SMILES: O=C(NCc1cncnc1)c1cnc(CNS(=O)(=O)c2ccc(F)c(Cl)c2)cn1] | 5-[(3-chloro-4-fluorobenzene)sulfonamidomethyl]-N-(pyrimidin-5-ylmethyl)pyrazine-2-carboxamide | 437.05 | 437.3 |
| 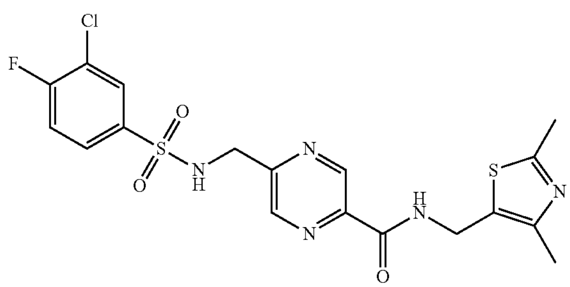 [SMILES: Cc1nc(C)c(CNC(=O)c2cnc(CNS(=O)(=O)c3ccc(F)c(Cl)c3)cn2)s1] | 5-[(3-chloro-4-fluorobenzene)sulfonamidomethyl]-N-[(dimethyl-1,3-thiazol-5-yl)methyl]pyrazine-2-carboxamide | 468.04 (M − H) | 468.25 (M − H) |
| 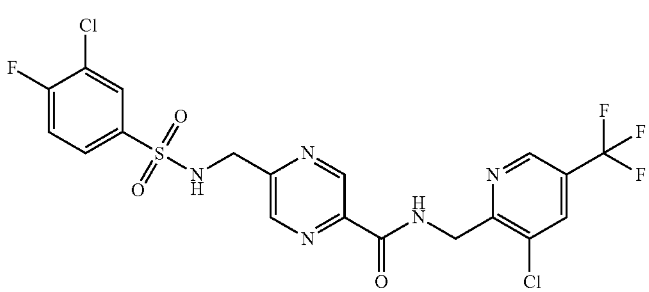 [SMILES: O=C(NCc1ncc(C(F)(F)F)cc1Cl)c1cnc(CNS(=O)(=O)c2ccc(F)c(Cl)c2)cn1] | 5-[(3-chloro-4-fluorobenzene)sulfonamidomethyl]-N-{[3-chloro-5-(trifluoromethyl)pyridin-2-yl]methyl}pyrazine-2-carboxamide | 536.01 | 536.2 |
| 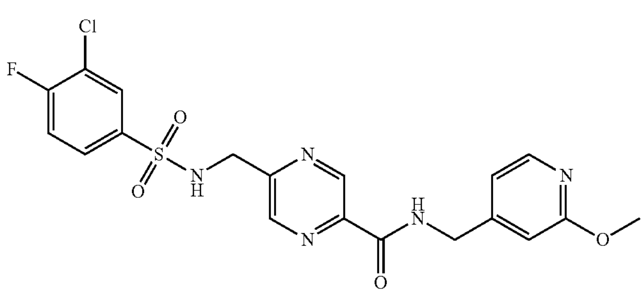 [SMILES: COc1cc(CNC(=O)c2cnc(CNS(=O)(=O)c3ccc(F)c(Cl)c3)cn2)ccn1] | 5-[(3-chloro-4-fluorobenzene)sulfonamidomethyl]-N-[(2-methoxypyridin-4-yl)methyl]pyrazine-2-carboxamide | 464.07 (M − H) | 464.42 (M − H) |

TABLE 3-continued

The following compounds were prepared by the method described above

| Structure | IUPAC Name | Calculated M + H | Found M + H |
|---|---|---|---|
| 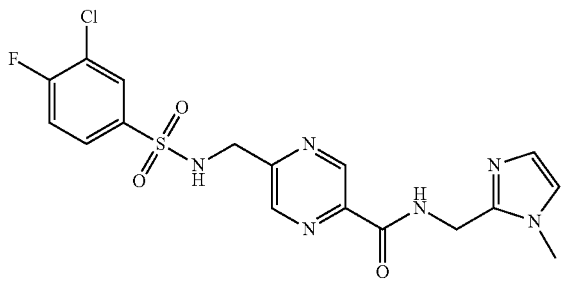 [SMILES: Cn1ccnc1CNC(=O)c1cnc(CNS(=O)(=O)c2ccc(F)c(Cl)c2)cn1] | 5-[(3-chloro-4-fluorobenzene)sulfonamidomethyl]-N-[(1-methyl-1H-imidazol-2-yl)methyl]pyrazine-2-carboxamide | 437.07 (M − H) | 437.23 (M − H) |
| 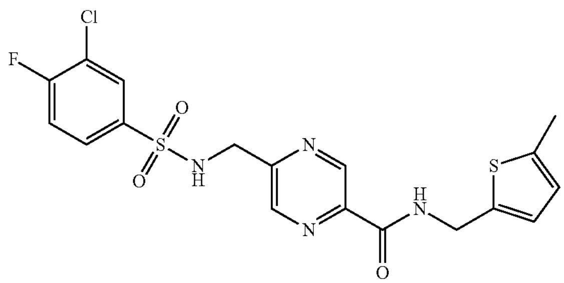 [SMILES: Cc1ccc(CNC(=O)c2cnc(CNS(=O)(=O)c3ccc(F)c(Cl)c3)cn2)s1] | 5-[(3-chloro-4-fluorobenzene)sulfonamidomethyl]-N-[(5-methylthiophen-2-yl)methyl]pyrazine-2-carboxamide | 453.03 (M − H) | 453.23 (M − H) |
| 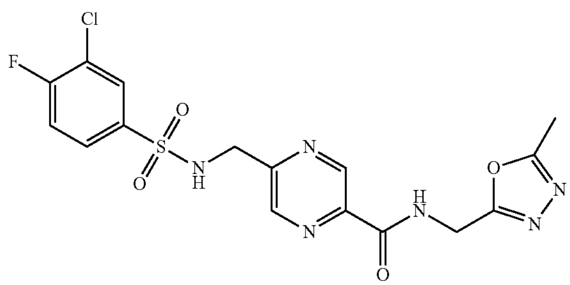 [SMILES: Cc1nnc(CNC(=O)c2cnc(CNS(=O)(=O)c3ccc(F)c(Cl)c3)cn2)o1] | 5-[(3-chloro-4-fluorobenzene)sulfonamidomethyl]-N-[(5-methyl-1,3,4-oxadiazol-2-yl)methyl]pyrazine-2-carboxamide | 439.05 (M − H) | 438.8 (M − H) |
| 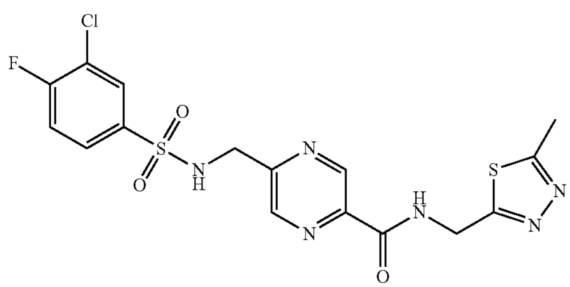 | 5-[(3-chloro-4-fluorobenzene)sulfonamidomethyl]-N-[(5-methyl-1,3,4-thiadiazol-2-yl)methyl]pyrazine-2-carboxamide | 455.02 (M − H) | 454.8 (M − H) |
| 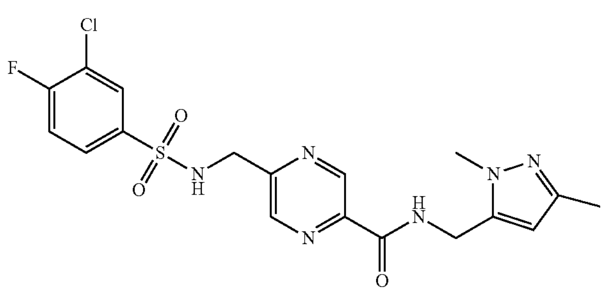 [SMILES: Cc1cc(CNC(=O)c2cnc(CNS(=O)(=O)c3ccc(F)c(Cl)c3)cn2)n(C)n1] | 5-[(3-chloro-4-fluorobenzene)sulfonamidomethyl]-N-[(1,3-dimethyl-1H-pyrazol-5-yl)methyl]pyrazine-2-carboxamide | 451.08 (M − H) | 451.29 (M − H) |

TABLE 3-continued

The following compounds were prepared by the method described above

| Structure | IUPAC Name | Calculated M + H | Found M + H |
|---|---|---|---|
| 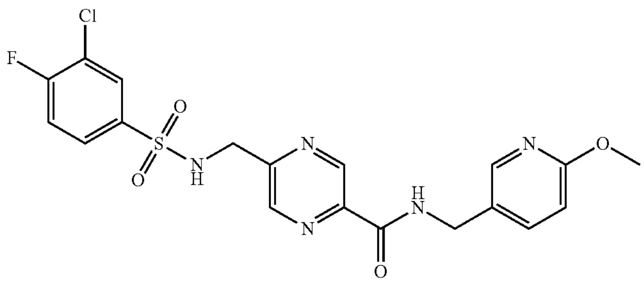 | 5-[(3-chloro-4-fluorobenzene)sulfonamidomethyl]-N-[(6-methoxypyridin-3-yl)methyl]pyrazine-2-carboxamide | 466.07 | 466.3 |
| 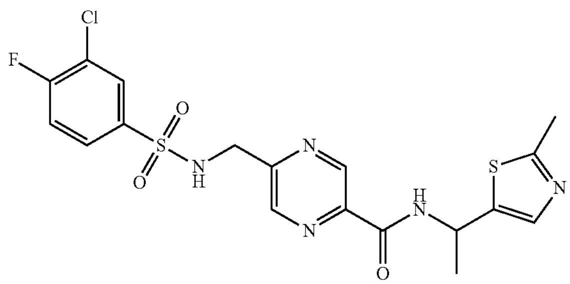 [SMILES: Cc1ncc(C(C)NC(=O)c2cnc(CNS(=O)(=O)c3ccc(F)c(Cl)c3)cn2)s1] | 5-[(3-chloro-4-fluorobenzene)sulfonamidomethyl]-N-[1-(2-methyl-1,3-thiazol-5-yl)ethyl]pyrazine-2-carboxamide | 470.04 | 470.1 |
| 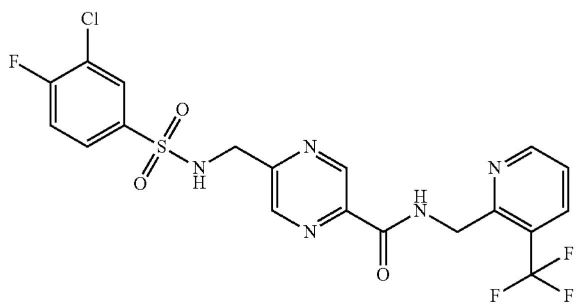 [SMILES: O=C(NCc1ncccc1C(F)(F)F)c1cnc(CNS(=O)(=O)c2ccc(F)c(Cl)c2)cn1] | 5-[(3-chloro-4-fluorobenzene)sulfonamidomethyl]-N-{[3-(trifluoromethyl)pyridin-2-yl]methyl}pyrazine-2-carboxamide | 504.04 | 504.08 |
| 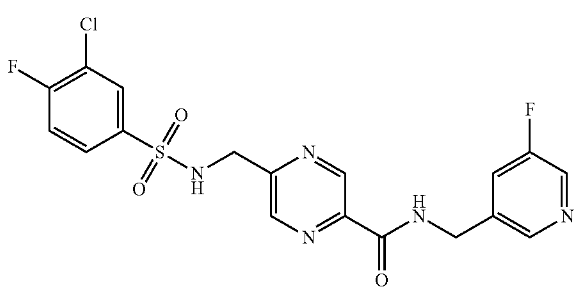 [SMILES: O=C(NCc1cncc(F)c1)c1cnc(CNS(=O)(=O)c2ccc(F)c(Cl)c2)cn1] | 5-[(3-chloro-4-fluorobenzene)sulfonamidomethyl]-N-[(5-fluoropyridin-3-yl)methyl]pyrazine-2-carboxamide | 454.05 | 454.1 |
| 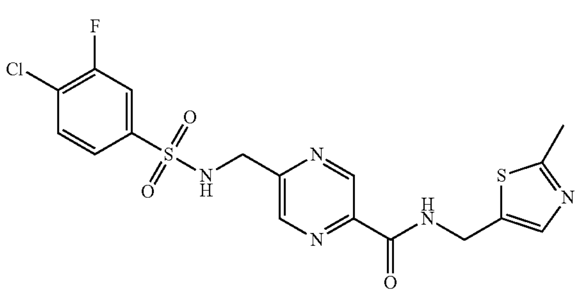 [SMILES: Cc1ncc(CNC(=O)c2cnc(CNS(=O)(=O)c3ccc(Cl)c(F)c3)cn2)s1] | 5-[(4-chloro-3-fluorobenzene)sulfonamidomethyl]-N-[(2-methyl-1,3-thiazol-5-yl)methyl]pyrazine-2-carboxamide | 454.03 (M − H) | 454.1 (M − H) |

TABLE 3-continued

The following compounds were prepared by the method described above

| Structure | IUPAC Name | Calculated M + H | Found M + H |
|---|---|---|---|
| 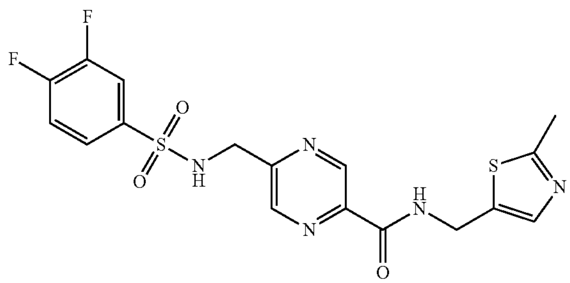 [SMILES: Cc1ncc(CNC(=O)c2cnc(CNS(=O)(=O)c3ccc(F)c(F)c3)cn2)s1] | 5-[(3,4-difluorobenzene)sulfonamidomethyl]-N-[(2-methyl-1,3-thiazol-5-yl)methyl]pyrazine-2-carboxamide | 440.06 | 440.1 |
| 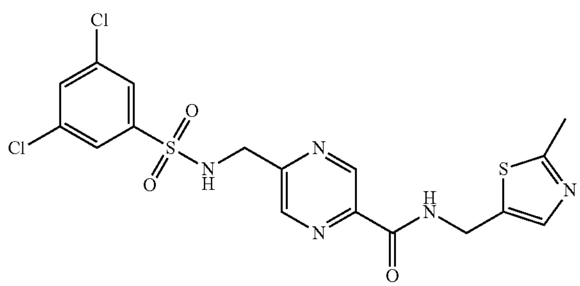 [SMILES: Cc1ncc(CNC(=O)c2cnc(CNS(=O)(=O)c3cc(Cl)cc(Cl)c3)cn2)s1] | 5-[(3,5-dichlorobenzene)sulfonamidomethyl]-N-[(2-methyl-1,3-thiazol-5-yl)methyl]pyrazine-2-carboxamide | 472.0 | 472.37 |
| 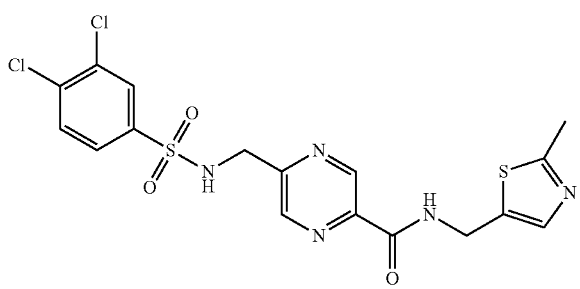 [SMILES: Cc1ncc(CNC(=O)c2cnc(CNS(=O)(=O)c3ccc(Cl)c(Cl)c3)cn2)s1] | 5-[(3,4-dichlorobenzene)sulfonamidomethyl]-N-[(2-methyl-1,3-thiazol-5-yl)methyl]pyrazine-2-carboxamide | 472.0 | 472.37 |
| 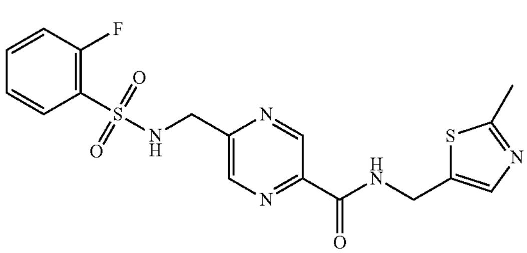 [SMILES: Cc1ncc(CNC(=O)c2cnc(CNS(=O)(=O)c3ccccc3F)cn2)s1] | 5-[(2-fluorobenzene)sulfonamidomethyl]-N-[(2-methyl-1,3-thiazol-5-yl)methyl]pyrazine-2-carboxamide | 422.07 | 422.4 |

Example 4—Preparation of 6-[(3-chloro-4-fluorobenzene)sulfonamidomethyl]-N-(1,3-thiazol-5-ylmethyl)pyridazine-3-carboxamide Scheme 4

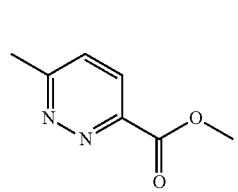
19

NBS, AIBN
DMF, 80° C.,
30 min
Step 1

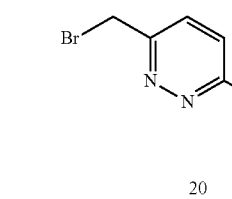
20

Hexamethylene
tetramine, CHCl₃
RT, 18 h

Conc. HCl. MeOH,
75° C., 3 h
Step 2

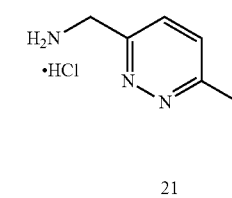
21

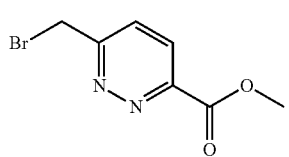

TEA, DCM
RT, 18 h
Step 3

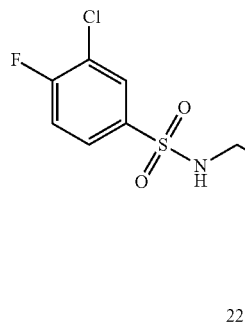
22

1 M KOH.
MeOH
RT, 3 h
Step 4

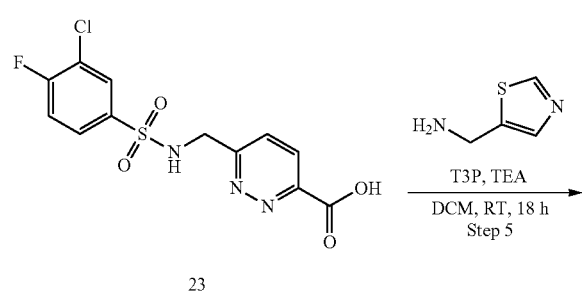
23

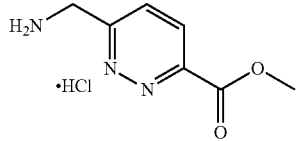

T3P, TEA
DCM, RT, 18 h
Step 5

-continued

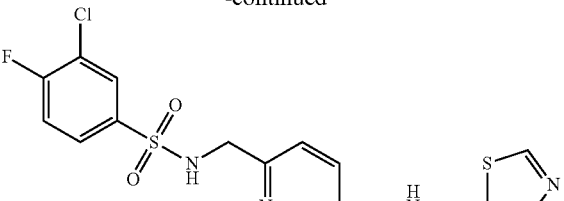

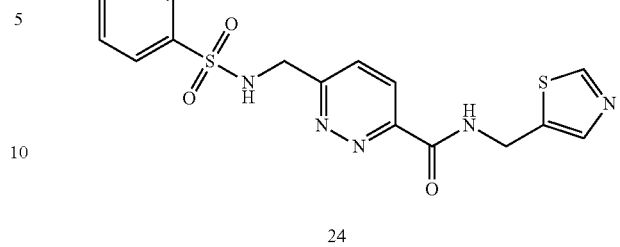
24

Step-1: Preparation of methyl 6-(bromomethyl)pyridazine-3-carboxylate

To a solution of methyl 6-methylpyridazine-3-carboxylate (0.1 g, 0.66 mmol) in N,N-dimethylformamide (6 mL) was added N-bromosuccinimide (0.14 g, 0.79 mmol) followed by azobisisobutyronitrile (0.010 g, 0.07 mmol). The reaction mixture was heated at 80° C. for 45 min. The reaction mixture was diluted with water, extracted with ethyl acetate. The combined organic layer was dried over anhydrous sodium sulfate, filtered and concentrated. The crude was purified by silica gel column chromatography using 10% ethyl acetate in hexane to afford the title compound methyl 6-(bromomethyl)pyridazine-3-carboxylate (0.08 g, 53% yield) as a brownish solid. Calculated M+H: 230.97. Found M+H: 231.

Step-2: Preparation of methyl 6-(aminomethyl)pyridazine-3-carboxylate hydrochloride To a solution of methyl 6-(bromomethyl)pyridazine-3-carboxylate (0.08 g, 0.35 mmol) in chloroform (5 mL) was added hexamethylene tetramine (0.05 g, 0.35 mmol) and the reaction mixture was stirred at room temperature for 18 h. The solid formed was filtered and dried. The solid was suspended in methanol (5 mL), concentrated hydrochloric acid (0.15 mL) was added and the reaction mixture was heated at 75° C. for 3 h. The reaction mixture was concentrated, the residue was triturated with diethyl ether and dried to afford the title compound methyl 6-(aminomethyl)pyridazine-3-carboxylate hydrochloride (0.08 g, crude) as a brownish solid. Calculated M+H: 168.07. Found M+H: 168.2.

Step-3: Preparation of methyl 6-((3-chloro-4-fluorophenylsulfonamido)methyl)pyridazine-3-carboxylate

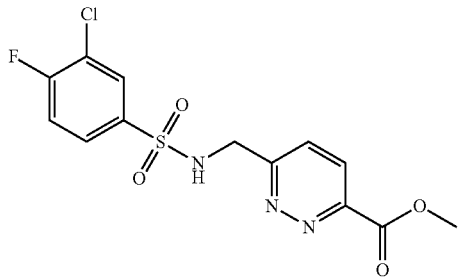 [SMILES: COC(=O)c1ccc(CNS(=O)(=O)c2ccc(F)c(Cl)c2)nn1]

To a solution of methyl 6-(aminomethyl)pyridazine-3-carboxylate hydrochloride (4.75 g, 19.87 mmol) in dichloromethane (100 mL) was added triethylamine (14 mL, 99.37 mmol)) followed by 4-fluoro-3-chlorobenzene sulphonyl chloride (2.83 mL, 19.87 mmol). After stirring for 18 h at room temperature the reaction mixture was diluted with dichloromethane, washed with water, dried over anhydrous sodium sulfate, filtered and concentrated. The crude was purified by silica gel column chromatography using 3% methanol in dichloromethane to afford the title compound methyl 6-((3-chloro-4-fluorophenylsulfonamido)methyl)pyridazine-3-carboxylate (2.9 g, 40% yield) as a brownish solid. Calculated M+H: 360.01. Found M+H: 360.1.

Step-4: Preparation of 6-((3-chloro-4-fluorophenylsulfonamido)methyl)pyridazine-3-carboxylic acid

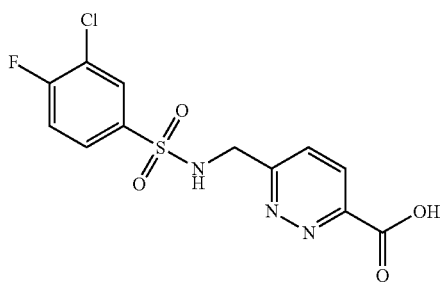 [SMILES: O=C(O)c1ccc(CNS(=O)(=O)c2ccc(F)c(Cl)c2)nn1]

To a solution of methyl 6-((3-chloro-4-fluorophenylsulfonamido)methyl)pyridazine-3-carboxylate (0.2 g, 0.56 mmol) in methanol (20 mL) was added 1M potassium hydroxide solution (0.158 g, 2.78 mmol) and the reaction mixture was stirred at room temperature for 3 h. The reaction mixture was concentrated and the residue was diluted with water. It was acidified with 1.5 M hydrochloric acid to pH 6 and extracted with ethyl acetate. The combined organic layer was dried and concentrated. The crude was triturated with diethyl ether and dried to afford the title compound 6-((3-chloro-4-fluorophenylsulfonamido)methyl) pyridazine-3-carboxylic acid (0.15 g, 78% yield) as a brownish solid. Calculated M+H: 346.0. Found M+H: 346.

Step-5: Preparation of 6-[(3-chloro-4-fluorobenzene)sulfonamidomethyl]-N-(1,3-thiazol-5-ylmethyl)pyridazine-3-carboxamide To a solution of 6-((3-chloro-4-fluorophenylsulfonamido)methyl)pyridazine-3-carboxylic acid (0.07 g, 0.20 mmol), thiazol-5-ylmethanamine (0.031 g, 0.20 mmol) and triethylamine (0.23 mL, 1.61 mmol) cooled at 0° C., was added a solution of 1-propane phosphonic acid cyclic anhydride (0.46 mL, 0.61 mmol) and the reaction mixture was stirred at room temperature for 18 h. The reaction mixture was diluted with dichloromethane, washed with water, brine, dried over anhydrous sodium sulfate, filtered and concentrated. The crude was purified by silica gel column chromatography using 5% methanol in dichloromethane to afford the title compound 6-[(3-chloro-4-fluorobenzene)sulfonamidomethyl]-N-(1,3-thiazol-5-ylmethyl)pyridazine-3-carboxamide (0.041 g, 46% yield) as off-white solid. Calculated M+H: 442.01. Found M+H: 442.1.

TABLE 4

The following compounds were prepared by the method described above.

| Structure | IUPAC Name | Calculated M + H | Found M + H |
|---|---|---|---|
| 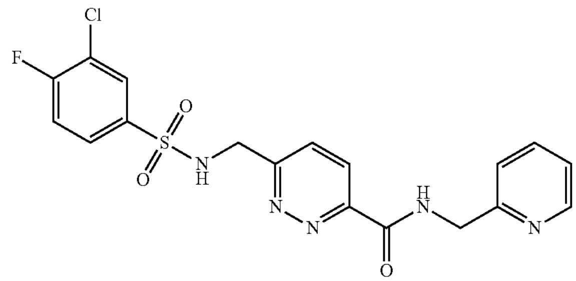 [SMILES: O=C(NCc1ccccn1)c1ccc(CNS(=O)(=O)c2ccc(F)c(Cl)c2)nn1] | 6-[(3-chloro-4-fluorobenzene)sulfonamidomethyl]-N-(pyridin-2-ylmethyl)pyridazine-3-carboxamide | 436.06 | 436.1 |
| 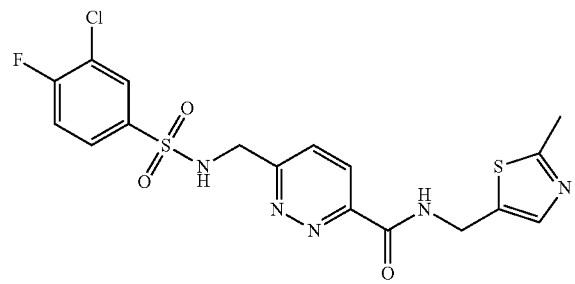 [SMILES: Cc1ncc(CNC(=O)c2ccc(CNS(=O)(=O)c3ccc(F)c(Cl)c3)nn2)s1] | 6-[(3-chloro-4-fluorobenzene)sulfonamidomethyl]-N-[(2-methyl-1,3-thiazol-5-yl)methyl]pyridazine-3-carboxamide | 456.03 | 456.1 |
| 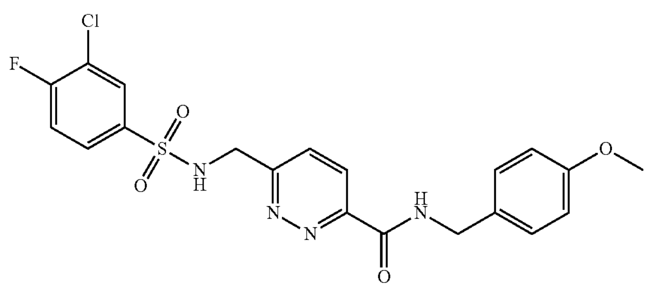 [SMILES: COc1ccc(CNC(=O)c2ccc(CNS(=O)(=O)c3ccc(F)c(Cl)c3)nn2)cc1] | 6-[(3-chloro-4-fluorobenzene)sulfonamidomethyl]-N-[(4-methoxyphenyl)methyl]pyridazine-3-carboxamide | 465.07 | 465.1 |
| 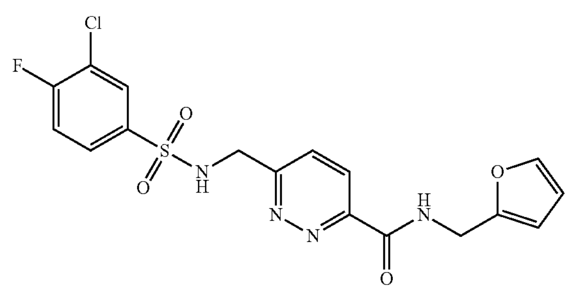 | 6-[(3-chloro-4-fluorobenzene)sulfonamidomethyl]-N-(furan-2-ylmethyl)pyridazine-3-carboxamide | 425.04 | 425 |
| 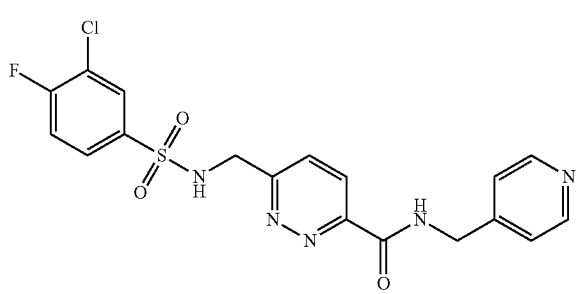 [SMILES: O=C(NCc1ccncc1)c1ccc(CNS(=O)(=O)c2ccc(F)c(Cl)c2)nn1] | 6-[(3-chloro-4-fluorobenzene)sulfonamidomethyl]-N-(pyridin-4-ylmethyl)pyridazine-3-carboxamide | 436.06 | 436.1 |

TABLE 4-continued

The following compounds were prepared by the method described above.

| Structure | IUPAC Name | Calculated M + H | Found M + H |
|---|---|---|---|
| 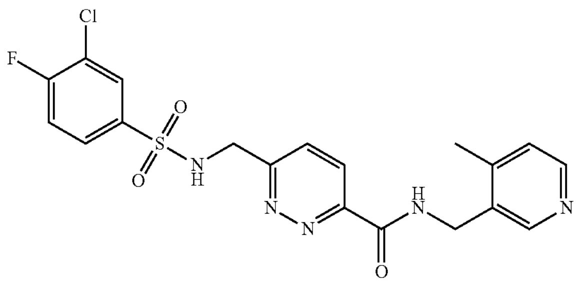 [SMILES: Cc1ccncc1CNC(=O)c1ccc(CNS(=O)(=O)c2ccc(F)c(Cl)c2)nn1] | 6-[(3-chloro-4-fluorobenzene)sulfonamidomethyl]-N-[(4-methylpyridin-3-yl)methyl]pyridazine-3-carboxamide | 450.07 | 450.1 |
| 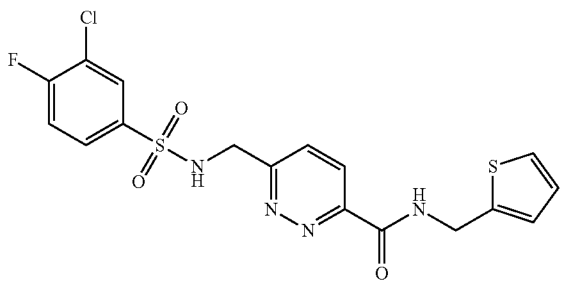 [SMILES: O=C(NCc1cccs1)c1ccc(CNS(=O)(=O)c2ccc(F)c(Cl)c2)nn1] | 6-[(3-chloro-4-fluorobenzene)sulfonamidomethyl]-N-(thiophen-2-ylmethyl)pyridazine-3-carboxamide | 441.02 | 441.1 |
| 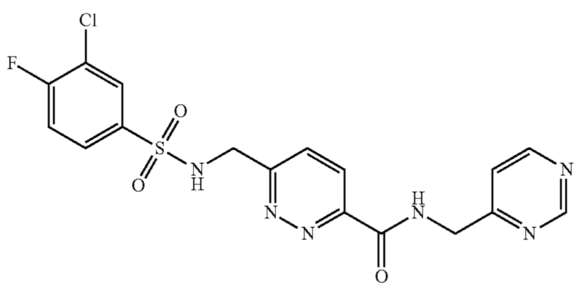 [SMILES: O=C(NCc1ccncn1)c1ccc(CNS(=O)(=O)c2ccc(F)c(Cl)c2)nn1] | 6-[(3-chloro-4-fluorobenzene)sulfonamidomethyl]-N-(pyrimidin-4-ylmethyl)pyridazine-3-carboxamide | 437.05 | 437.28 |
| 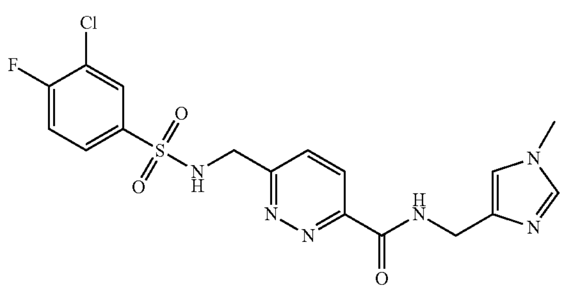 [SMILES: Cn1cnc(CNC(=O)c2ccc(CNS(=O)(=O)c3ccc(F)c(Cl)c3)nn2)c1] | 6-[(3-chloro-4-fluorobenzene)sulfonamidomethyl]-N-[(1-methyl-1H-imidazol-4-yl)methyl]pyridazine-3-carboxamide | 439.07 | 439.29 |
| 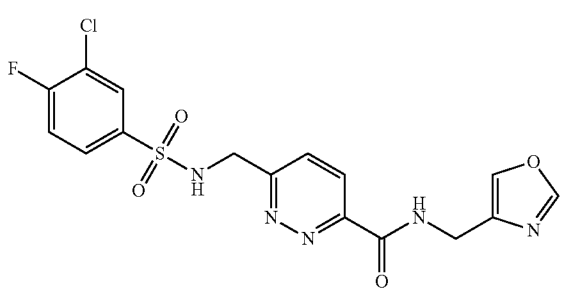 [SMILES: O=C(NCc1cocn1)c1ccc(CNS(=O)(=O)c2ccc(F)c(Cl)c2)nn1] | 6-[(3-chloro-4-fluorobenzene)sulfonamidomethyl]-N-(1,3-oxazol-4-ylmethyl)pyridazine-3-carboxamide | 426.04 | 426.26 |

TABLE 4-continued

The following compounds were prepared by the method described above.

| Structure | IUPAC Name | Calculated M + H | Found M + H |
|---|---|---|---|
| 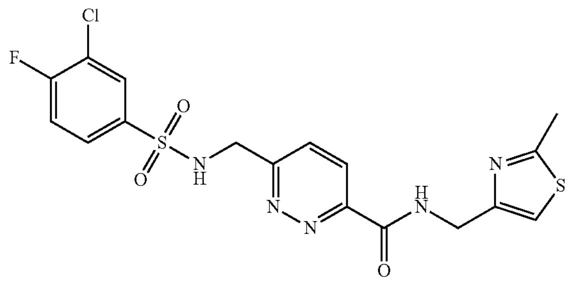 [SMILES: Cc1nc(CNC(=O)c2ccc(CNS(=O)(=O)c3ccc(F)c(Cl)c3)nn2)cs1] | 6-[(3-chloro-4-fluorobenzene)sulfonamidomethyl]-N-[(2-methyl-1,3-thiazol-4-yl)methyl]pyridazine-3-carboxamide | 456.03 | 456.26 |
| 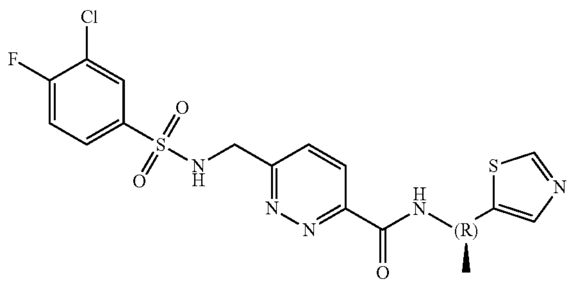 | 6-[(3-chloro-4-fluorobenzene)sulfonamidomethyl]-N-[(1R)-1-(1,3-thiazol-5-yl)ethyl]pyridazine-3-carboxamide | 456.03 | 456.26 |
| 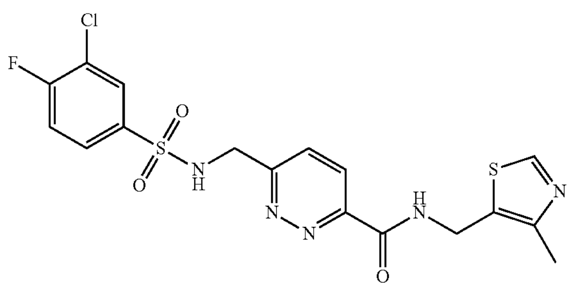 [SMILES: Cc1ncsc1CNC(=O)c1ccc(CNS(=O)(=O)c2ccc(F)c(Cl)c2)nn1] | 6-[(3-chloro-4-fluorobenzene)sulfonamidomethyl]-N-[(4-methyl-1,3-thiazol-5-yl)methyl]pyridazine-3-carboxamide | 456.03 | 456.25 |
| 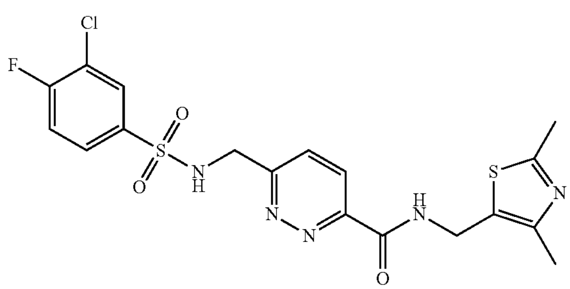 [SMILES: Cc1nc(C)c(CNC(=O)c2ccc(CNS(=O)(=O)c3ccc(F)c(Cl)c3)nn2)s1] | 6-[(3-chloro-4-fluorobenzene)sulfonamidomethyl]-N-[(dimethyl-1,3-thiazol-5-yl)methyl]pyridazine-3-carboxamide | 470.04 | 470.26 |
| 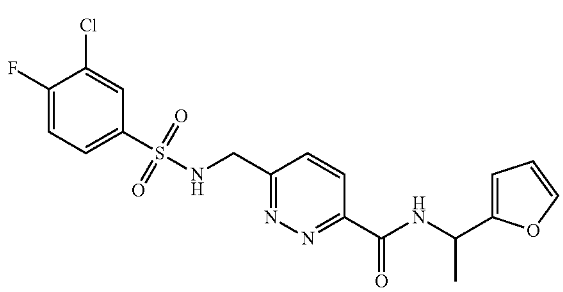 [SMILES: CC(NC(=O)c1ccc(CNS(=O)(=O)c2ccc(F)c(Cl)c2)nn1)c1ccco1] | 6-[(3-chloro-4-fluorobenzene)sulfonamidomethyl]-N-[1-(furan-2-yl)ethyl]pyridazine-3-carboxamide | 437.06 (M − H) | 437.32 (M − H) |

TABLE 4-continued

The following compounds were prepared by the method described above.

| Structure | IUPAC Name | Calculated M + H | Found M + H |
|---|---|---|---|
| 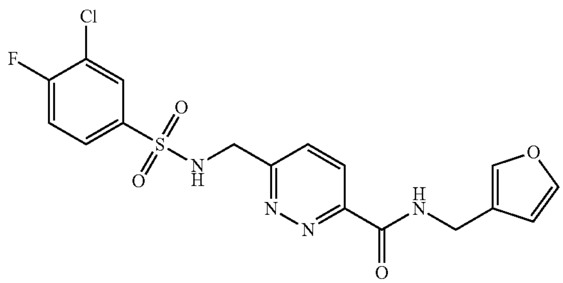 [SMILES: O=C(NCc1ccoc1)c1ccc(CNS(=O)(=O)c2ccc(F)c(Cl)c2)nn1] | 6-[(3-chloro-4-fluorobenzene)sulfonamidomethyl]-N-(furan-3-ylmethyl)pyridazine-3-carboxamide | 425.04 | 425.25 |
| 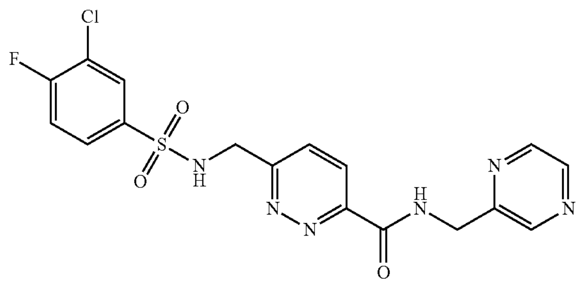 [SMILES: O=C(NCc1cnccn1)c1ccc(CNS(=O)(=O)c2ccc(F)c(Cl)c2)nn1] | 6-[(3-chloro-4-fluorobenzene)sulfonamidomethyl]-N-(pyrazin-2-ylmethyl)pyridazine-3-carboxamide | 437.05 | 437.31 |
| 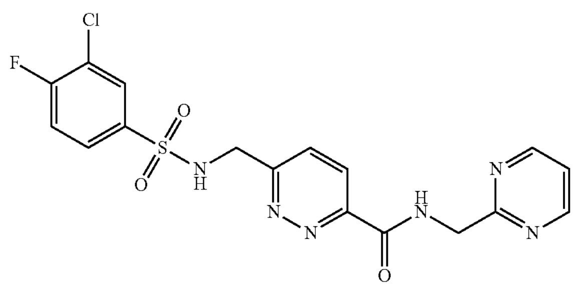 [SMILES: O=C(NCc1ncccn1)c1ccc(CNS(=O)(=O)c2ccc(F)c(Cl)c2)nn1] | 6-[(3-chloro-4-fluorobenzene)sulfonamidomethyl]-N-(pyrimidin-2-ylmethyl)pyridazine-3-carboxamide | 437.05 | 437.35 |
| 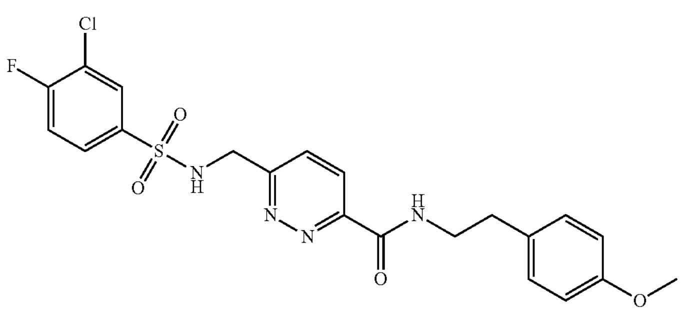 [SMILES: COc1ccc(CCNC(=O)c2ccc(CNS(=O)(=O)c3ccc(F)c(Cl)c3)nn2)cc1] | 6-[(3-chloro-4-fluorobenzene)sulfonamidomethyl]-N-[2-(4-methoxyphenyl)ethyl]pyridazine-3-carboxamide | 479.09 | 479.34 |
| 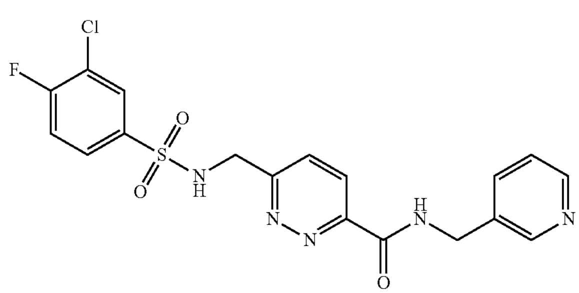 [SMILES: O=C(NCc1cccnc1)c1ccc(CNS(=O)(=O)c2ccc(F)c(Cl)c2)nn1] | 6-[(3-chloro-4-fluorobenzene)sulfonamidomethyl]-N-(pyridin-3-ylmethyl)pyridazine-3-carboxamide | 436.06 | 436.34 |

TABLE 4-continued

The following compounds were prepared by the method described above.

| Structure | IUPAC Name | Calculated M + H | Found M + H |
|---|---|---|---|
| 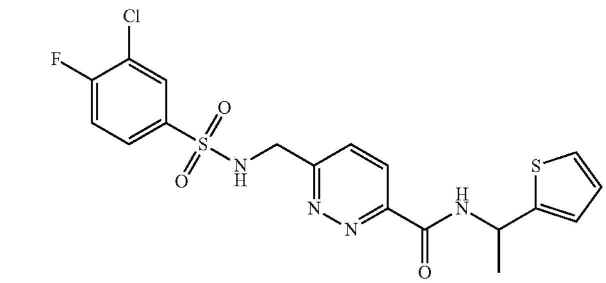 [SMILES: CC(NC(=O)c1ccc(CNS(=O)(=O)c2ccc(F)c(Cl)c2)nn1)c1cccs1] | 6-[(3-chloro-4-fluorobenzene)sulfonamidomethyl]-N-[1-(thiophen-2-yl)ethyl]pyridazine-3-carboxamide | 455.03 | 455.31 |
| 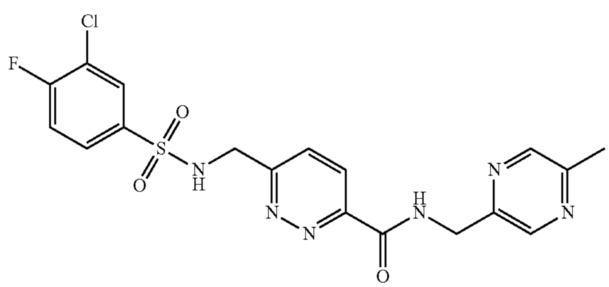 [SMILES: Cc1cnc(CNC(=O)c2ccc(CNS(=O)(=O)c3ccc(F)c(Cl)c3)nn2)cn1] | 6-[(3-chloro-4-fluorobenzene)sulfonamidomethyl]-N-[(5-methylpyrazin-2-yl)methyl]pyridazine-3-carboxamide | 451.07 | 451.36 |
| 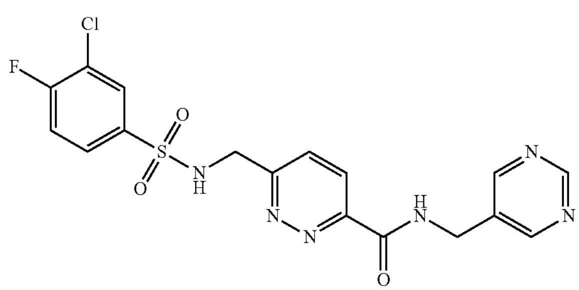 [SMILES: O=C(NCc1cncnc1)c1ccc(CNS(=O)(=O)c2ccc(F)c(Cl)c2)nn1] | 6-[(3-chloro-4-fluorobenzene)sulfonamidomethyl]-N-(pyrimidin-5-ylmethyl)pyridazine-3-carboxamide | 437.05 | 437.32 |
| 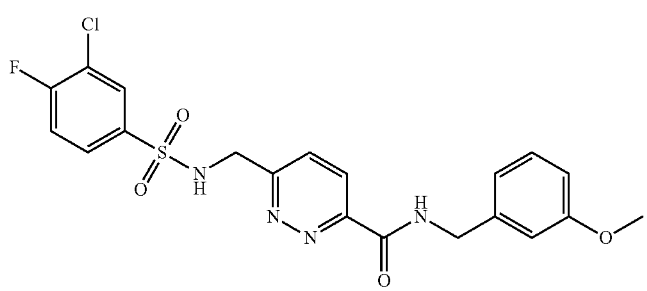 [SMILES: COc1cccc(CNC(=O)c2ccc(CNS(=O)(=O)c3ccc(F)c(Cl)c3)nn2)c1] | 6-[(3-chloro-4-fluorobenzene)sulfonamidomethyl]-N-[(3-methoxyphenyl)methyl]pyridazine-3-carboxamide | 463.07 (M − H) | 463.31 (M − H) |

Example 5—Preparation of 5-[(3-chloro-4-fluorobenzene)sulfonamidomethyl]-N-(pyridin-3-ylmethyl)pyrimidine-2-carboxamide Scheme 5

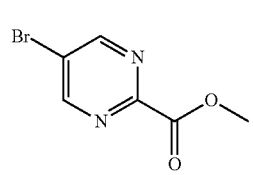
25

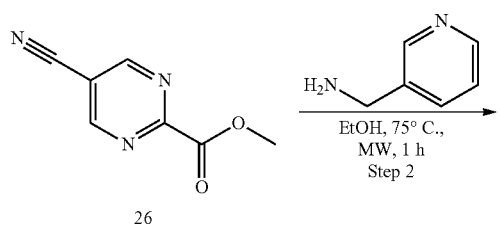
26

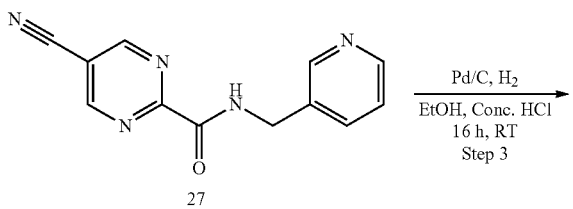
27

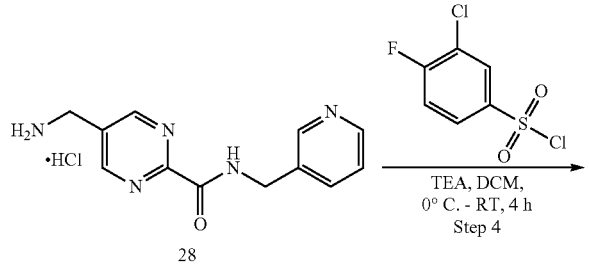
28

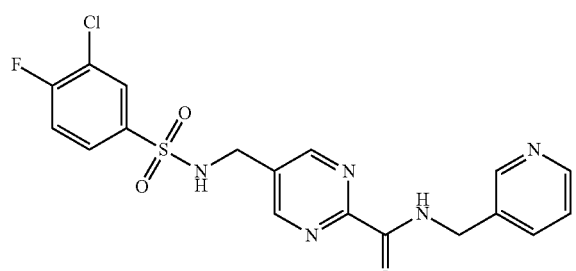
29

Step-1: Preparation of methyl 5-cyanopyrimidine-2-carboxylate

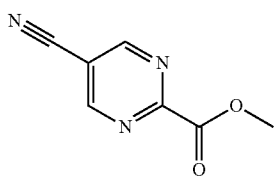

A solution of methyl 5-bromopyrimidine-2-carboxylate (5 g, 23.04 mmol) in N,N-dimethylformamide (90 mL) was purged with argon for 10 min. Zinc cyanide (2.03 g, 17.28 mmol), 1,1'-Bis(diphenylphosphino)ferrocene (0.562 g, 1.01 mmol), and tris(dibenzylideneacetone)dipalladium(0) (0.464 g, 0.51 mmol) were added and the reaction mixture was heated at 130° C. for 1.5 h. The reaction mixture was cooled to room temperature, diluted with water and extracted with ethyl acetate. The combined organic layer was dried over anhydrous sodium sulfate, filtered and concentrated. The crude was purified by silica gel column chromatography using 30% ethyl acetate in hexane to afford the title compound methyl 5-cyanopyrimidine-2-carboxylate (2.35 g, 56% yield) as a brown solid. Calculated M+H: 164.04. Found M+H: 164.1.

Step-2: Preparation of 5-cyano-N-(pyridin-3-ylmethyl)pyrimidine-2-carboxamide

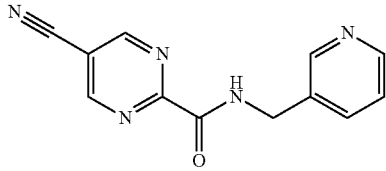 [SMILES: N#Cc1cnc(C(=O)NCc2cccnc2)nc1]

A mixture of methyl 5-cyanopyrimidine-2-carboxylate (0.6 g, 3.68 mmol) and pyridin-3-ylmethanamine (1.2 g, 11.03 mmol) in ethanol was heated at 75° C. for 1 h under microwave conditions. The reaction mixture was concentrated and the residue was purified by silica gel column chromatography using 5% methanol in dichloromethane to afford the title compound methyl 5-cyano-N-(pyridin-3-ylmethyl)pyrimidine-2-carboxamide (0.401 g, 45% yield) as an off-white solid. Calculated M+H: 240.08. Found M+H: 240.1.

Step-3: Preparation of 5-(aminomethyl)-N-(pyridin-3-ylmethyl)pyrimidine-2-carboxamide hydrochloride

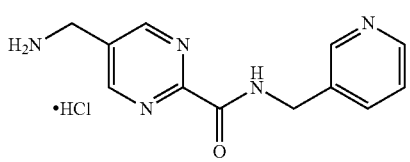 [SMILES: NCc1cnc(C(=O)NCc2cccnc2)nc1 ; Cl]

To a solution of methyl 5-cyano-N-(pyridin-3-ylmethyl)pyrimidine-2-carboxamide (0.1 g, 0.41 mmol) in ethanol (20 mL) was added concentrated hydrochloric acid (0.1 mL) followed by 10% Pd/C (0.05 g). The reaction vessel was evacuated and backfilled with hydrogen three times and then stirred for 6 h. The solution was filtered through celite, and the filter pad rinsed with methanol. The filtrate was evaporated and recrystallized with ether:ethanol mixture (10:1) to obtain the title compound 5-(aminomethyl)-N-(pyridin-3-ylmethyl)pyrimidine-2-carboxamide hydrochloride (0.08 g, crude) as a brownish semisolid. Calculated M+H: 244.11. Found M+H: 244.2.

Step-4: Preparation of 5-[(3-chloro-4-fluorobenzene)sulfonamidomethyl]-N-(pyridin-3-ylmethyl)pyrimidine-2-carboxamide

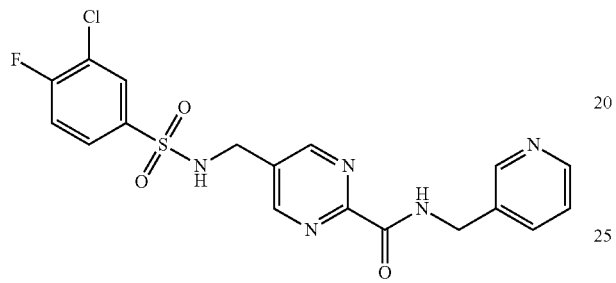

To a solution of 5-(aminomethyl)-N-(pyridin-3-ylmethyl)pyrimidine-2-carboxamide hydrochloride (0.08 g, 0.29 mmol) in dichloromethane (30 mL) was added triethylamine (0.09 g, 0.86 mmol). The reaction mixture was cooled to 0° C. and 4-fluoro-3-chlorobenzenesulfonyl chloride (0.04 g, 0.17 mmol) was added and the reaction mixture was stirred at room temperature for 4 h. The reaction mixture was diluted with dichloromethane, washed with water, dried over anhydrous sodium sulfate, filtered and concentrated. The crude was purified by preparative HPLC (analytical conditions: column: Xbridge C8 (250 mm×4.6 mm×5 µm), mobile phase (A): 0.01% TFA in water, mobile phase (B): Acetonitrile, flow rate: 1.0 mL/min, gradient T/% B: 0/20, 10/70, 25/70, 27/20, 30/20) to afford the title compound 5-[(3-chloro-4-fluorobenzene)sulfonamidomethyl]-N-(pyridin-3-ylmethyl)pyrimidine-2-carboxamide (0.019 g, 15% yield) as off-white solid. Calculated M+H: 436.06. Found M+H: 436.3.

Example 6—Preparation of 5-((3,5-difluorobenzamido)methyl)-N-(thiazol-5-ylmethyl)picolinamide

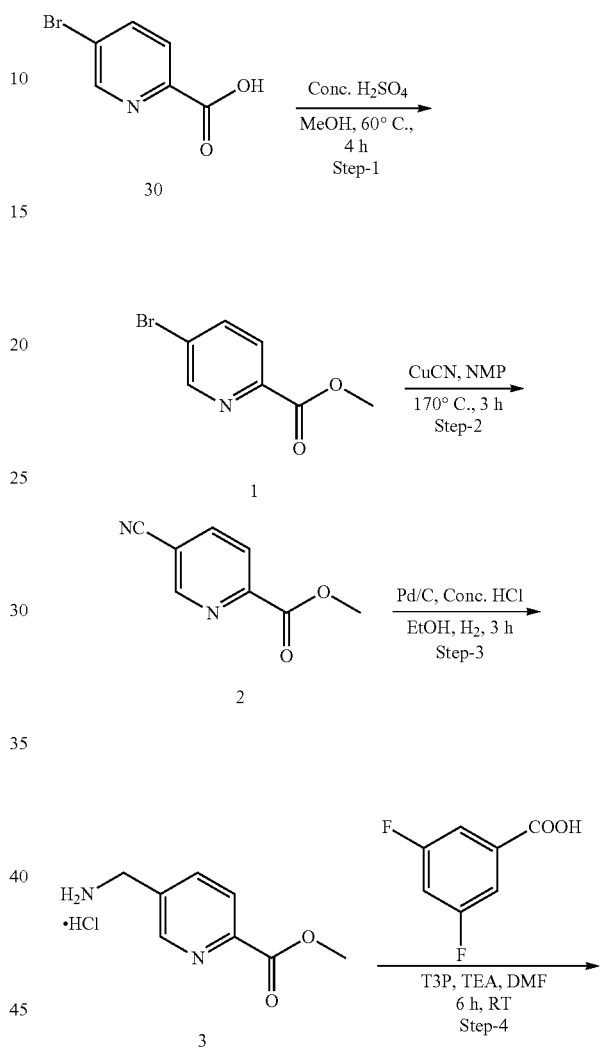

Scheme 6

TABLE 5

The following compound was prepared by the method described above

| Structure | IUPAC Name | Calculated M + H | Found M + H |
|---|---|---|---|
| 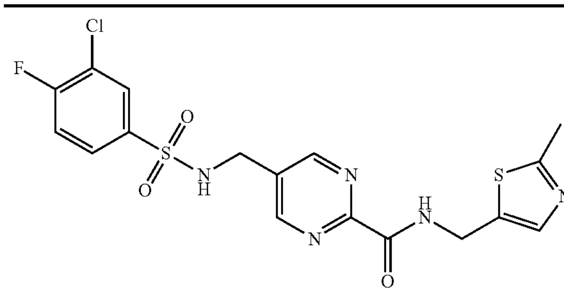 | 5-[(3-chloro-4-fluorobenzene)sulfonamidomethyl]-N-[(2-methyl-1,3-thiazol-5-yl)methyl]pyrimidine-2-carboxamide | 456.03 | 456.1 |

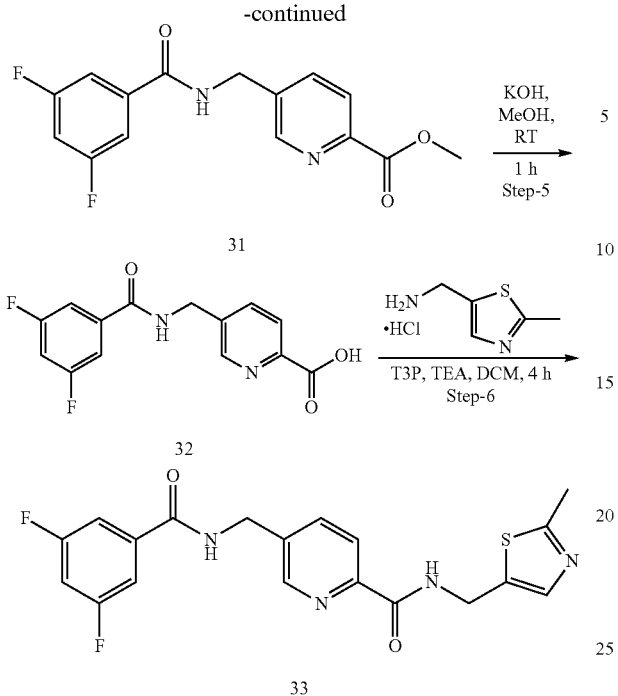

Step-1: Preparation of methyl 5-bromopicolinate

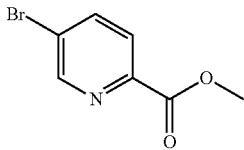

To a solution of 5-bromopicolinic acid (5 g, 24.7 mmol) in methanol (50 mL) was added concentrated sulfuric acid (1 mL) at 0° C. and the resulting solution was stirred at 60° C. for 4 h. The reaction mixture was cooled to room temperature and concentrated under vacuum. The residue was dissolved in ethyl acetate (300 mL) and washed with saturated sodium bicarbonate solution (200 mL×2), brine (300 mL), dried over sodium sulfate and concentrated under vacuum to afford the title compound methyl 5-bromopicolinate (5.1 g, crude) as an off-white solid which was used for the next step without further purification. Calculated M+H: 216.03. Found M+H: 216.01.

Step-2: Preparation of methyl 5-cyanopicolinate

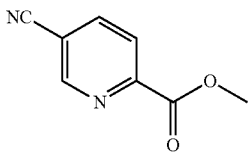

To a solution of methyl 5-bromopicolinate (5 g, 23.25 mmol) in N-methyl-2-pyrrolidone (40 mL) was added copper(I)cyanide (4.23 g, 47.5 mmol) at room temperature and the resulting suspension was stirred at 170° C. for 3 h. The reaction mixture was cooled to room temperature, poured into ice cold water (300 mL) and extracted with dichloromethane (300 mL×3). The combined organic layer was washed with brine (500 mL×2), dried over sodium sulfate and concentrated under vacuum to obtain the crude material which was purified by column chromatography using 100-200 mesh silica gel with 40% ethyl acetate in hexane to afford the title compound methyl 5-cyanopicolinate (0.7 g, 19% yield) as a light yellow solid. Calculated M+H: 163.04. Found M+H: 163.05.

Step-3: Preparation of methyl 5-(aminomethyl)picolinate hydrochloride

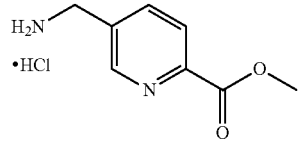

To a solution of methyl 5-cyanopicolinate (0.6 g, 3.7 mmol) in ethanol (15 mL) was added Pd/C (0.20 g) and concentrated hydrochloric acid (2 mL) and resulting suspension was stirred at room temperature under a hydrogen atmosphere for 3 h. The reaction mixture was filtered through a celite pad and filtrate obtained was concentrated under vacuum to afford the title compound methyl 5-(aminomethyl)picolinate hydrochloride (0.370 g, 49% yield) as a light yellow gum which was used for the next step without further purification. Calculated M+H: 167.05. Found M+H: 167.02.

Step-4: Preparation of methyl 5-((3,5-difluorobenzamido)methyl)picolinate

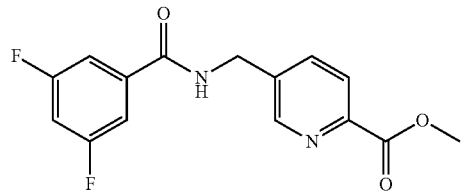 [SMILES: COC(=O)c1ccc(CNC(=O)c2cc(F)cc(F)c2)cn1]

To a solution of methyl 5-(aminomethyl)picolinate hydrochloride (0.050 g, 0.24 mmol) and 3,5-difluorobenzoic acid (0.034 g, 0.24 mmol) in N,N-dimethylformamide (1 mL) was added 1-propanephosphonic anhydride (50% solution in ethyl acetate, 0.4 mL, 0.72 mmol) and triethylamine (0.5 mL, 0.48 mmol) and resulting suspension was stirred at room temperature for 6 h. The reaction mixture was poured into ice-cold water (5 mL) and extracted with ethyl acetate (10 mL×3). The combined organic phase was washed with brine (20 mL×2), dried over sodium sulfate and concentrated under vacuum to obtain the crude material which was purified by column chromatography using 100-200 mesh silica with 4% methanol in dichloromethane to afford the title compound methyl 5-((3,5-difluorobenzamido)methyl)picolinate (0.035 g, 47% yield) as an off-white solid. Calculated M+H: 307.18. Found M+H: 307.22.

Step-5: Preparation of 5-((3,5-difluorobenzamido)methyl)picolinic acid

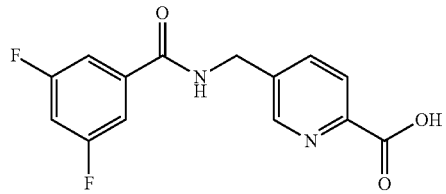 [SMILES: O=C(NCc1ccc(C(=O)O)nc1)c1cc(F)cc(F)c1]

To a solution of methyl 5-((3,5-difluorobenzamido)methyl)picolinate (0.035 g, 0.114 mmol) in methanol (3 mL) was added 1M potassium hydroxide solution (2 mL) and resulting suspension was stirred at room temperature for 1 h. The reaction mixture was concentrated under vacuum and residue obtained was dissolved in water (1 mL). The aqueous layer was acidified by 1N hydrochloric acid to pH 7 and extracted with 10% methanol in dichloromethane (15 mL×3). The combined organic layer was washed with brine (20 mL×2), dried over sodium sulfate and concentrated under vacuum to afford the title compound 5-((3,5-difluorobenzamido)methyl)picolinic acid (0.030 g, 91% yield) as an off-white solid which was used for the next step without further purification. Calculated M+H: 293.06. Found M+H: 293.26.

Step-6: Preparation of 5-((3,5-difluorobenzamido)methyl)-N-(thiazol-5-ylmethyl)picolinamide

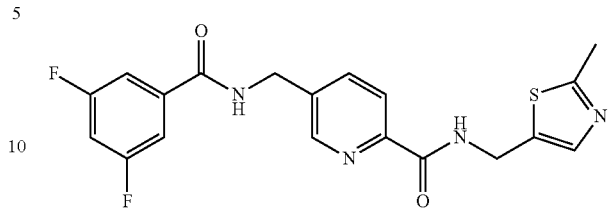

To a solution of 5-((3,5-difluorobenzamido)methyl)picolinic acid (0.030 g, 0.10 mmol) and (2-methylthiazol-5-yl)methanamine hydrochloride (0.018 g, 0.11 mmol) in N,N-dimethylformamide (1 mL) were added 1-propanephosphonic anhydride (50% solution in ethyl acetate, 0.2 mL, 0.33 mmol) and triethylamine (0.1 mL, 0.2 mmol) and the resulting suspension was stirred at room temperature for 4 h. The reaction mixture was cooled to room temperature, poured into ice-cold water (10 mL) and extracted with dichloromethane (10 mL×3). The combined organic extract was washed with brine (20 mL×2), dried over sodium sulfate and concentrated under vacuum to obtain the crude material which was purified by column chromatography using 100-200 mesh silica with 3% methanol in dichloromethane to afford the title compound 5-((3,5-difluorobenzamido)methyl)-N-(thiazol-5-ylmethyl)picolinamide (0.018 g, 41% yield) as an off-white solid. Calculated M+H: 403.43. Found M+H: 403.02.

TABLE 6

The following compounds were prepared by the method described above:

| Structure | IUPAC Name | Calculated M + H | Found M + H |
|---|---|---|---|
| 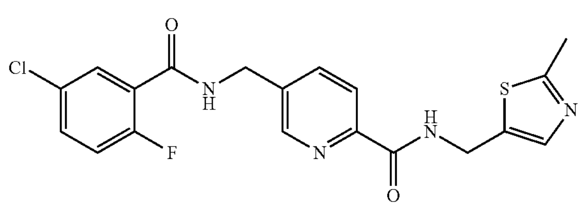 [SMILES: Cc1ncc(CNC(=O)c2ccc(CNC(=O)c3cc(Cl)ccc3F)cn2)s1] | 5-{[(5-chloro-2-fluorophenyl)formamido]methyl}-N-[(2-methyl-1,3-thiazol-5-yl)methyl]pyridine-2-carboxamide | 419.07 | 419.11 |
| 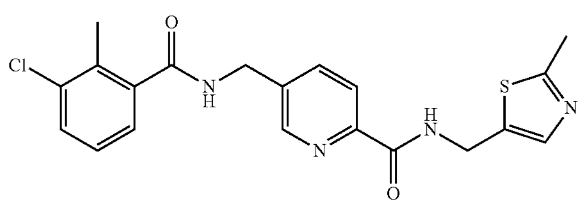 [SMILES: Cc1ncc(CNC(=O)c2ccc(CNC(=O)c3cccc(Cl)c3C)cn2)s1] | 5-((3-chloro-2-methylbenzamido)methyl)-N-((2-methylthiazol-5-yl)methyl)picolinamide | 415.09 | 415.22 |
| 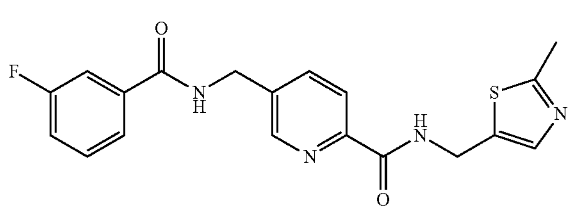 [SMILES: Cc1ncc(CNC(=O)c2ccc(CNC(=O)c3cccc(F)c3)cn2)s1] | 5-{[(3-fluorophenyl)formamido]methyl}-N-[(2-methyl-1,3-thiazol-5-yl)methyl]pyridine-2-carboxamide | 385.11 | 385.13 |

TABLE 6-continued

The following compounds were prepared by the method described above:

| Structure | IUPAC Name | Calculated M + H | Found M + H |
|---|---|---|---|
| 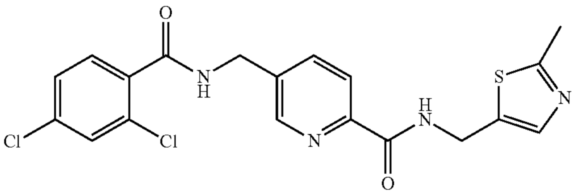 [SMILES: Cc1ncc(CNC(=O)c2ccc(CNC(=O)c3ccc(Cl)cc3Cl)cn2)s1] | 5-{[(2,4-dichlorophenyl)form-amido]methyl}-N-[(2-methyl-1,3-thiazol-5-yl)methyl]pyridine-2-carboxamide | 435.04 | 435.09 |
| 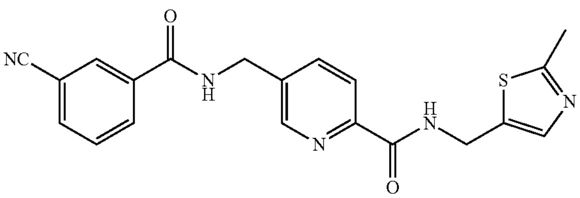 [SMILES: Cc1ncc(CNC(=O)c2ccc(CNC(=O)c3cccc(C#N)c3)cn2)s1] | 5-{[(3-cyanophenyl)form-amido]methyl}-N-[(2-methyl-1,3-thiazol-5-yl)methyl]pyridine-2-carboxamide | 392.11 | 392.13 |
| 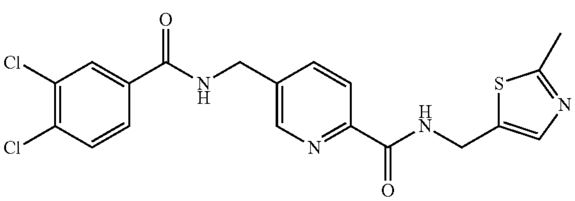 [SMILES: Cc1ncc(CNC(=O)c2ccc(CNC(=O)c3ccc(Cl)c(Cl)c3)cn2)s1] | 5-{[(3,4-dichlorophenyl)form-amido]methyl}-N-[(2-methyl-1,3-thiazol-5-yl)methyl]pyridine-2-carboxamide | 435.04 | 435.16 |

Example 7—Preparation of 5-((4-fluorophenylsulfo-namido)methyl)-N-((2-methylthiazol-5-yl)methyl) picolinamide

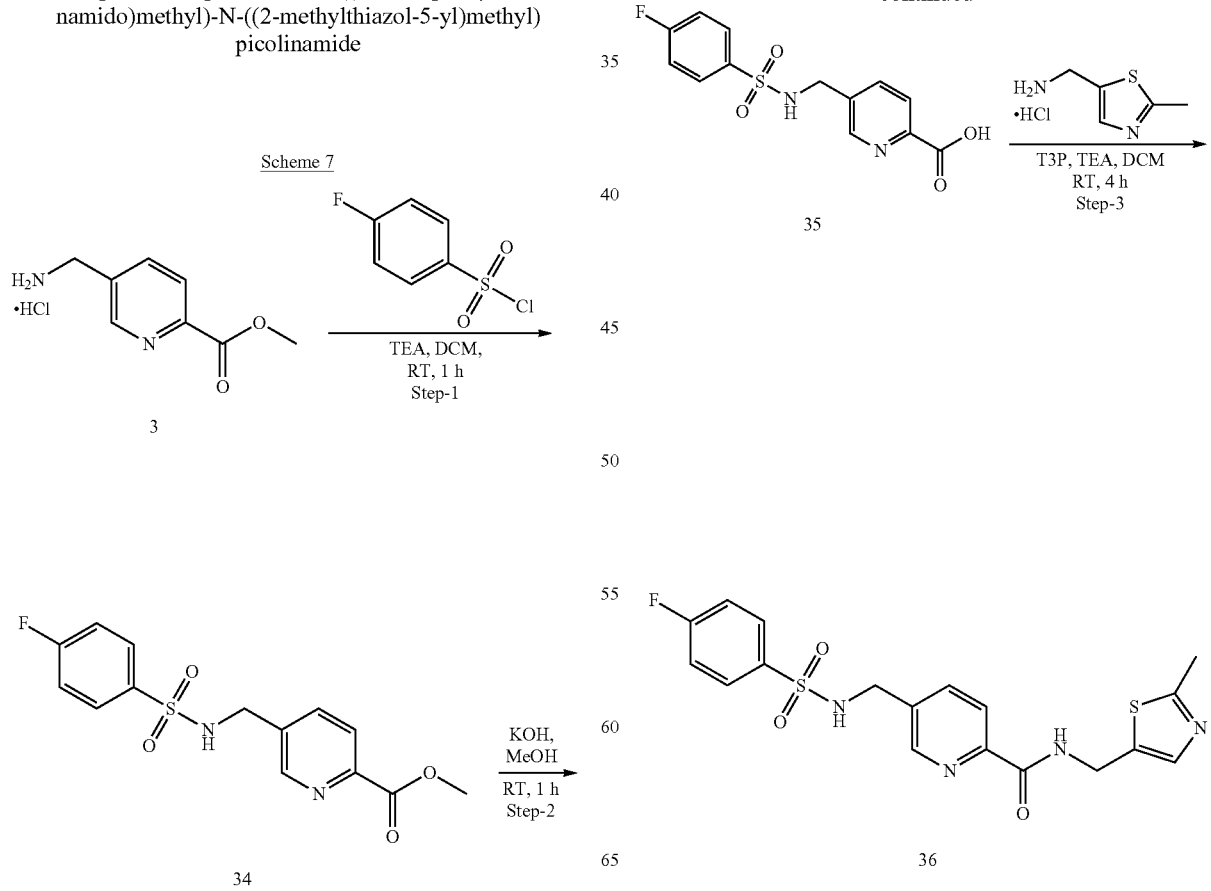

Step-1: Preparation of methyl 5-((((4-fluorophenyl)sulfonamido)methyl)picolinate

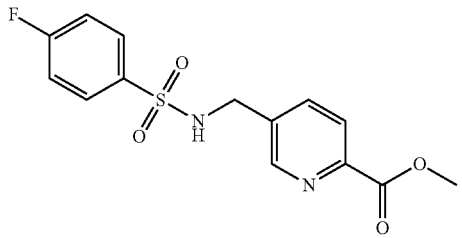 [SMILES: COC(=O)c1ccc(CNS(=O)(=O)c2ccc(F)cc2)cn1]

To a solution of methyl 5-(aminomethyl)picolinate hydrochloride (0.050 g, 0.24 mmol) and 4-fluorobenzenesulfonyl chloride (0.046 g, 0.24 mmol) in dichloromethane (2 mL) was added triethylamine (0.1 mL, 0.48 mmol) at 0° C. and resulting solution was stirred at room temperature for 1 h. Then the reaction mixture was diluted with water (10 mL) and extracted with dichloromethane (5 mL×3). The combined organic layer was washed with saturated sodium bicarbonate solution (10 mL×2), brine (20 mL), dried over sodium sulfate and concentrated under vacuum to get the crude material which was purified by column chromatography using 100-200 mesh silica with 60% ethyl acetate in hexane to afford the title compound methyl 5-((((4-fluorophenyl)sulfonamido)methyl)picolinate (0.032 g, 21%) as a greenish gum. Calculated M+H: 325.06. Found M+H: 325.11.

Step-2: Preparation of 5-((((4-fluorophenyl)sulfonamido)methyl)picolinic acid

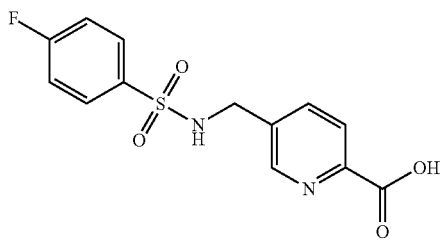 [SMILES: O=C(O)c1ccc(CNS(=O)(=O)c2ccc(F)cc2)cn1]

To a solution of 5-((((4-fluorophenyl)sulfonamido)methyl)picolinate (0.032 g, 0.09 mmol) in methanol (3 mL) was added 1M potassium hydroxide solution (2 mL) and the resulting suspension was stirred at room temperature for 1 h. The reaction mixture was concentrated under vacuum and the residue obtained was dissolved in water (1 mL), acidified with 1N hydrochloric acid to pH=7 and extracted with 10% methanol in dichloromethane (15 mL×3). The combined organic extract was washed with brine (20 mL×2), dried over sodium sulfate and concentrated under vacuum to afford the title compound 5-((((4-fluorophenyl)sulfonamido)methyl)picolinic acid (0.020 g, 61% yield) as an off-white solid which was used for next step without further purification. Calculated M+H: 311.04. Found M+H: 311.06.

Step-3: Preparation of 5-((4-fluorophenylsulfonamido)methyl)-N-((2-methylthiazol-5-yl)methyl)picolinamide

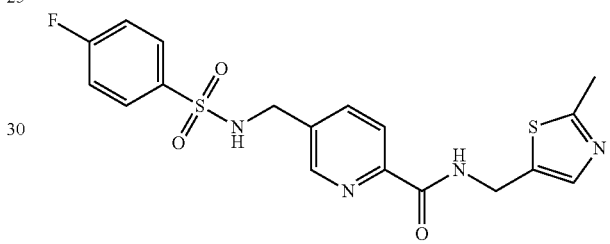

To a solution of 5-((((4-fluorophenyl)sulfonamido)methyl)picolinic acid (0.020 g, 0.06 mmol) and (2-methylthiazol-5-yl)methanamine hydrochloride (0.01 g, 0.06 mmol) in N,N-dimethylformamide (1 mL) were added 1-propanephosphonic anhydride (50% solution in ethyl acetate, 0.2 mL, 0.133 mmol) and triethylamine (0.1 mL, 0.133 mmol) and resulting suspension was stirred at room temperature for 4 h. The reaction mixture was cooled to room temperature, poured into ice-cold water (10 mL) and extracted with dichloromethane (10 mL×3). The combined organic extract was washed with brine (20 mL×2), dried over sodium sulfate and concentrated under vacuum to obtain the crude material which was purified by preparative HPLC (analytical conditions: column: Xbridge C18 (19 mm×250 mm×5 µm), mobile phase (A): 5 mM ammonium acetate in water, mobile phase (B): HPLC grade acetonitrile. Elution gradient: 0-20 min, 5-95% B in A) to afford the title compound 5-((4-fluorophenylsulfonamido)methyl)-N-((2-methylthiazol-5-yl)methyl)picolinamide (0.002 g, 7% yield) as an off-white solid. Calculated M+H: 421.07. Found M+H: 421.11.

TABLE 7

| Structure | IUPAC Name | Calculated M + H | Found M + H |
|---|---|---|---|
| 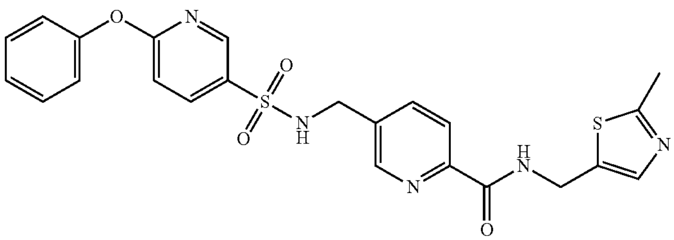 [SMILES: Cc1ncc(CNC(=O)c2ccc(CNS(=O)(=O)c3ccc(Oc4ccccc4)nc3)cn2)s1] | N-[(2-methyl-1,3-thiazol-5-yl)methyl]-5-(6-phenoxypyridine-3-sulfonamidomethyl)pyridine-2-carboxamide | 496.10 | 496.18 |
| 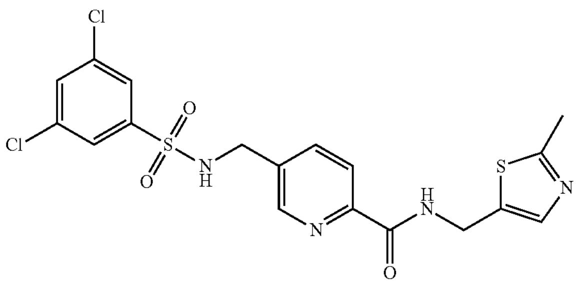 [SMILES: Cc1ncc(CNC(=O)c2ccc(CNS(=O)(=O)c3cc(Cl)cc(Cl)c3)cn2)s1] | 5-(3,5-dichlorobenzene-sulfonamidomethyl)-N-[(2-methyl-1,3-thiazol-5-yl)methyl]pyridine-2-carboxamide | 471.00 | 471.19 |
| 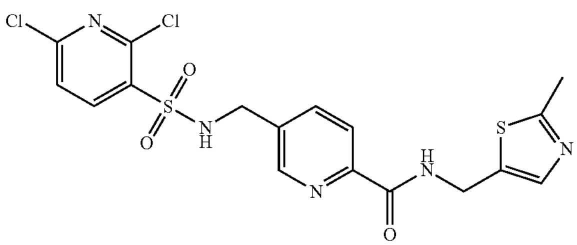 [SMILES: Cc1ncc(CNC(=O)c2ccc(CNS(=O)(=O)c3ccc(Cl)nc3Cl)cn2)s1] | 5-(2,6-dichloropyridine-3-sulfonamidomethyl)-N-[(2-methyl-1,3-thiazol-5-yl)methyl]pyridine-2-carboxamide | 472.00 | 472.10 |
| 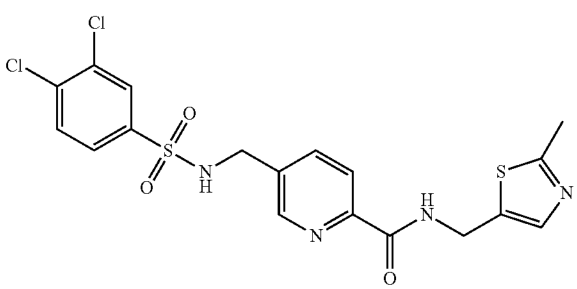 [SMILES: Cc1ncc(CNC(=O)c2ccc(CNS(=O)(=O)c3ccc(Cl)c(Cl)c3)cn2)s1] | 5-(3,4-dichlorobenzene-sulfonamidomethyl)-N-[(2-methyl-1,3-thiazol-5-yl)methyl]pyridine-2-carboxamide | 471.00 | 470.11 |
| 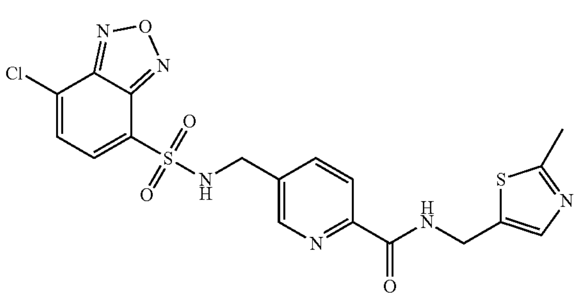 [SMILES: Cc1ncc(CNC(=O)c2ccc(CNS(=O)(=O)c3ccc(Cl)c4nonc34)cn2)s1] | 5-(7-chloro-2,1,3-benzoxadiazole-4-sulfonamidomethyl)-N-[(2-methyl-1,3-thiazol-5-yl)methyl]pyridine-2-carboxamide | 479.03 | 479.00 |

TABLE 7-continued

The following compounds were prepared by the method described above:

| Structure | IUPAC Name | Calculated M + H | Found M + H |
|---|---|---|---|
| 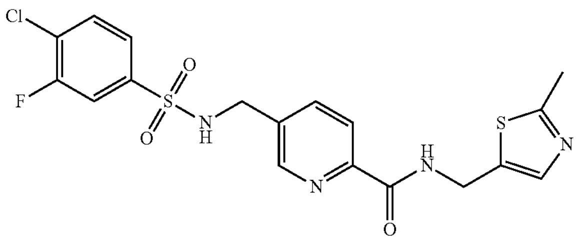 [SMILES: Cc1ncc(CNC(=O)c2ccc(CNS(=O)(=O)c3ccc(Cl)c(F)c3)cn2)s1] | 5-(4-chloro-3-fluorobenzene-sulfonamidomethyl)-N-[(2-methyl-1,3-thiazol-5-yl)methyl]pyridine-2-carboxamide | 455.03 | 455.14 |
| 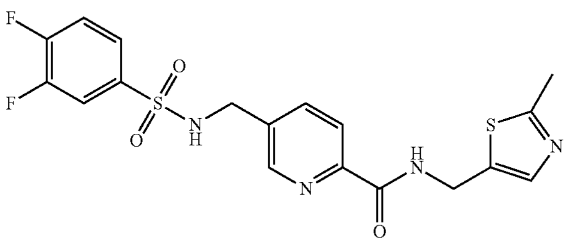 [SMILES: Cc1ncc(CNC(=O)c2ccc(CNS(=O)(=O)c3ccc(F)c(F)c3)cn2)s1] | 5-(3,4-difluorobenzene-sulfonamidomethyl)-N-[(2-methyl-1,3-thiazol-5-yl)methyl]pyridine-2-carboxamide | 439.06 | 439.22 |
| 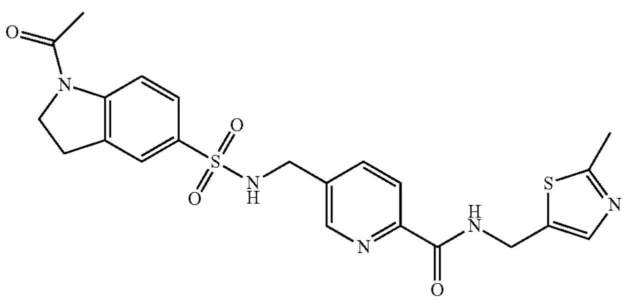 [SMILES: CC(=O)N1CCc2cc(S(=O)(=O)NCc3ccc(C(=O)NCc4cnc(C)s4)nc3)ccc21] | 5-(1-acetyl-2,3-dihydro-1H-indole-5-sulfonamidomethyl)-N-[(2-methyl-1,3-thiazol-5-yl)methyl]pyridine-2-carboxamide | 486.12 | 486.19 |
| 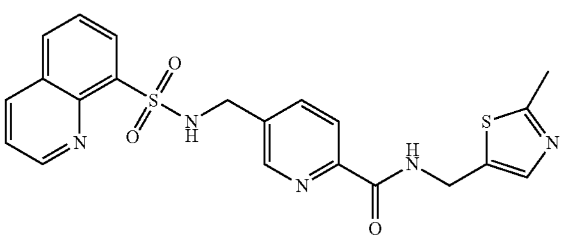 [SMILES: Cc1ncc(CNC(=O)c2ccc(CNS(=O)(=O)c3cccc4cccnc34)cn2)s1] | N-[(2-methyl-1,3-thiazol-5-yl)methyl]-5-(quinoline-8-sulfonamidomethyl)pyridine-2-carboxamide | 454.09 | 454.22 |
| 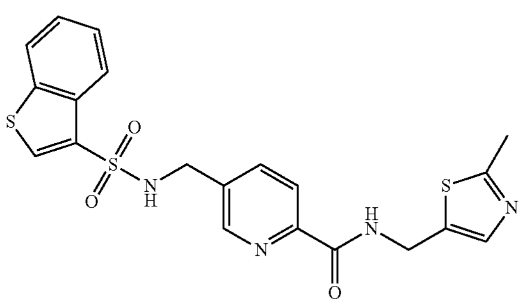 [SMILES: Cc1ncc(CNC(=O)c2ccc(CNS(=O)(=O)c3csc4ccccc34)cn2)s1] | 5-(1-benzothiophene-3-sulfonamidomethyl)-N-[(2-methyl-1,3-thiazol-5-yl)methyl]pyridine-2-carboxamide | 459.05 | 459.07 |

TABLE 7-continued

The following compounds were prepared by the method described above:

| Structure | IUPAC Name | Calculated M + H | Found M + H |
|---|---|---|---|
| 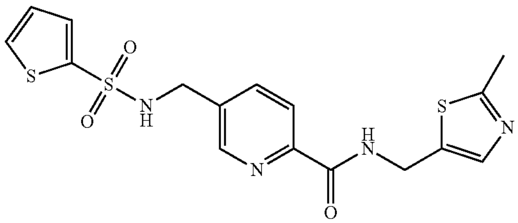 [SMILES: Cc1ncc(CNC(=O)c2ccc(CNS(=O)(=O)c3cccs3)cn2)s1] | N-[(2-methyl-1,3-thiazol-5-yl)methyl]-5-(thiophene-2-sulfonamidomethyl)pyridine-2-carboxamide | 409.04 | 409.13 |
| 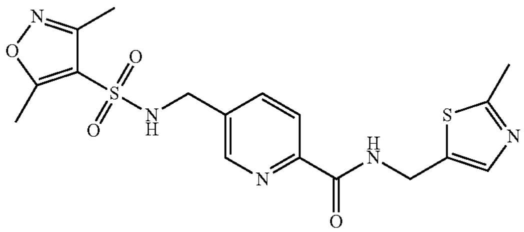 [SMILES: Cc1ncc(CNC(=O)c2ccc(CNS(=O)(=O)c3c(C)noc3C)cn2)s1] | 5-(dimethyl-1,2-oxazole-4-sulfonamidomethyl)-N-[(2-methyl-1,3-thiazol-5-yl)methyl]pyridine-2-carboxamide | 422.09 | 422.10 |
| 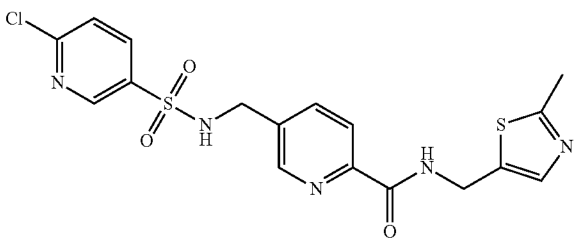 [SMILES: Cc1ncc(CNC(=O)c2ccc(CNS(=O)(=O)c3ccc(Cl)nc3)cn2)s1] | 5-(6-chloropyridine-3-sulfonamidomethyl)-N-[(2-methyl-1,3-thiazol-5-yl)methyl]pyridine-2-carboxamide | 438.04 | 438.19 |
| 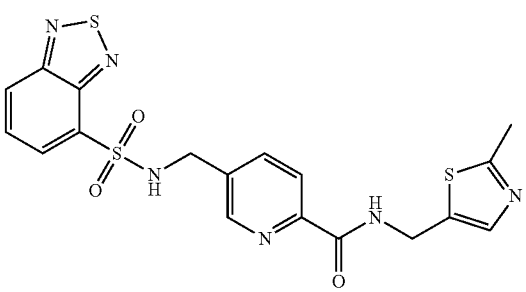 [SMILES: Cc1ncc(CNC(=O)c2ccc(CNS(=O)(=O)c3cccc4nsnc34)cn2)s1] | 5-(2,1,3-benzothiadiazole-4-sulfonamidomethyl)-N-[(2-methyl-1,3-thiazol-5-yl)methyl]pyridine-2-carboxamide | 461.04 | 461.33 |
| 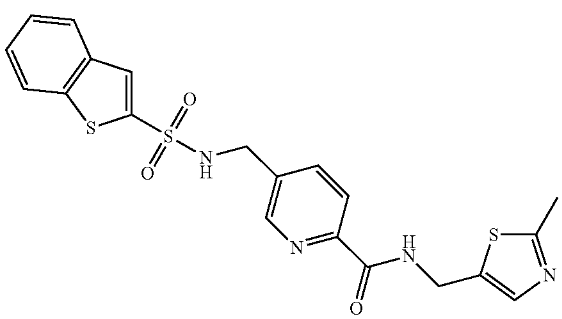 [SMILES: Cc1ncc(CNC(=O)c2ccc(CNS(=O)(=O)c3cc4ccccc4s3)cn2)s1] | 5-(1-benzothiophene-2-sulfonamidomethyl)-N-[(2-methyl-1,3-thiazol-5-yl)methyl]pyridine-2-carboxamide | 459.05 | 459.04 |
| 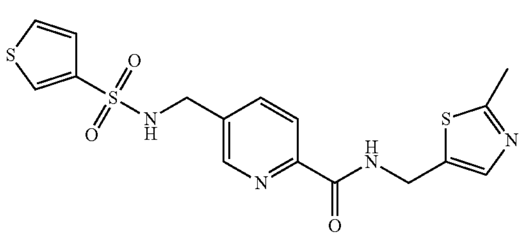 [SMILES: Cc1ncc(CNC(=O)c2ccc(CNS(=O)(=O)c3ccsc3)cn2)s1] | N-[(2-methyl-1,3-thiazol-5-yl)methyl]-5-(thiophene-3-sulfonamidomethyl)pyridine-2-carboxamide | 407.04 | 407.07 |

TABLE 7-continued

The following compounds were prepared by the method described above:

| Structure | IUPAC Name | Calculated M + H | Found M + H |
|---|---|---|---|
| 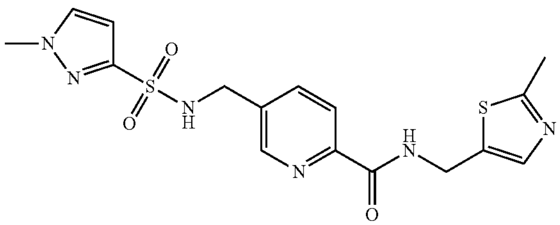 [SMILES: Cc1ncc(CNC(=O)c2ccc(CNS(=O)(=O)c3ccn(C)n3)cn2)s1] | N-[(2-methyl-1,3-thiazol-5-yl)methyl]-5-(1-methyl-1H-pyrazole-3-sulfonamidomethyl)pyridine-2-carboxamide | 407.09 | 407.12 |
| 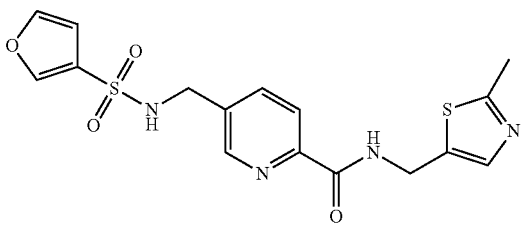 [SMILES: Cc1ncc(CNC(=O)c2ccc(CNS(=O)(=O)c3ccoc3)cn2)s1] | 5-(furan-3-sulfonamidomethyl)-N-[(2-methyl-1,3-thiazol-5-yl)methyl]pyridine-2-carboxamide | 393.06 | 393.12 |
| 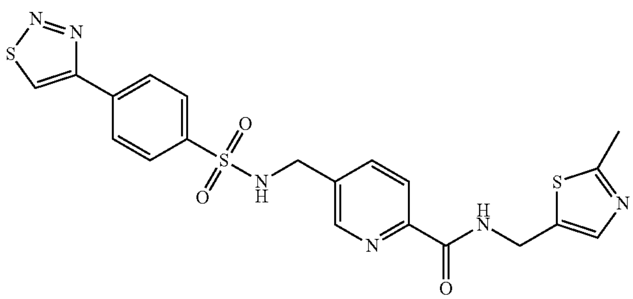 [SMILES: Cc1ncc(CNC(=O)c2ccc(CNS(=O)(=O)c3ccc(-c4csnn4)cc3)cn2)s1] | N-[(2-methyl-1,3-thiazol-5-yl)methyl]-5-[4-(1,2,3-thiadiazol-4-yl)benzenesulfonamidomethyl]pyridine-2-carboxamide | 487.06 | 487.10 |
| 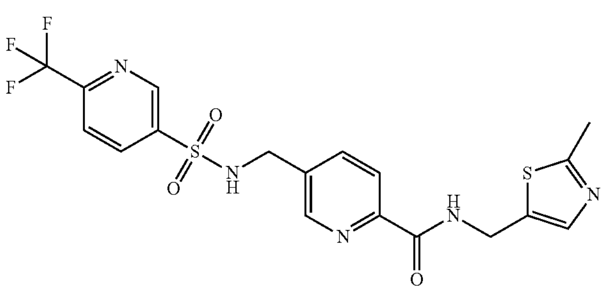 [SMILES: Cc1ncc(CNC(=O)c2ccc(CNS(=O)(=O)c3ccc(C(F)(F)F)nc3)cn2)s1] | N-[(2-methyl-1,3-thiazol-5-yl)methyl]-5-[6-(trifluoromethyl)pyridine-3-sulfonamidomethyl]pyridine-2-carboxamide | 472.06 | 472.33 |
| 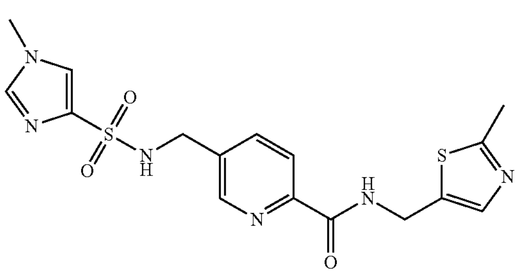 [SMILES: Cc1ncc(CNC(=O)c2ccc(CNS(=O)(=O)c3cn(C)cn3)cn2)s1] | N-[(2-methyl-1,3-thiazol-5-yl)methyl]-5-(1-methyl-1H-imidazole-4-sulfonamidomethyl)pyridine-2-carboxamide | 407.09 | 407.10 |

TABLE 7-continued

The following compounds were prepared by the method described above:

| Structure | IUPAC Name | Calculated M + H | Found M + H |
|---|---|---|---|
| 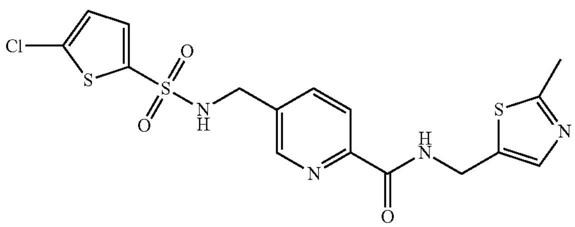 [SMILES: Cc1ncc(CNC(=O)c2ccc(CNS(=O)(=O)c3ccc(Cl)s3)cn2)s1] | 5-(5-chlorothiophene-2-sulfonamidomethyl)-N-[(2-methyl-1,3-thiazol-5-yl)methyl]pyridine-2-carboxamide | 443.01 | 443.08 |

Example 8—Preparation of 5-((5-chloro-2-fluorobenzamido)methyl)-N-((2-methylthiazol-5-yl)methyl)pyrazine-2-carboxamide Scheme 8

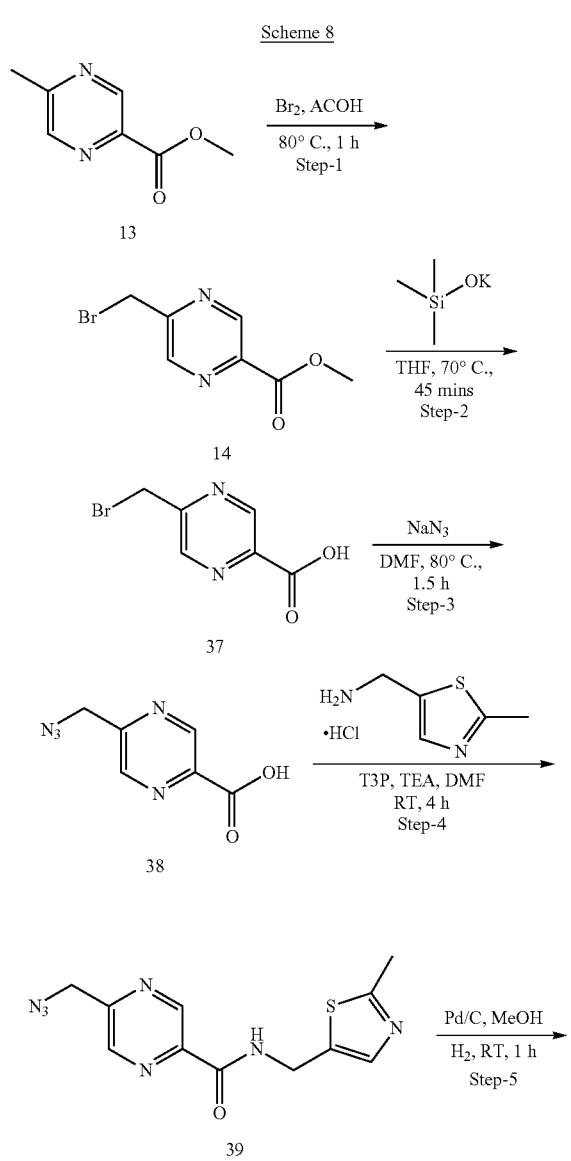

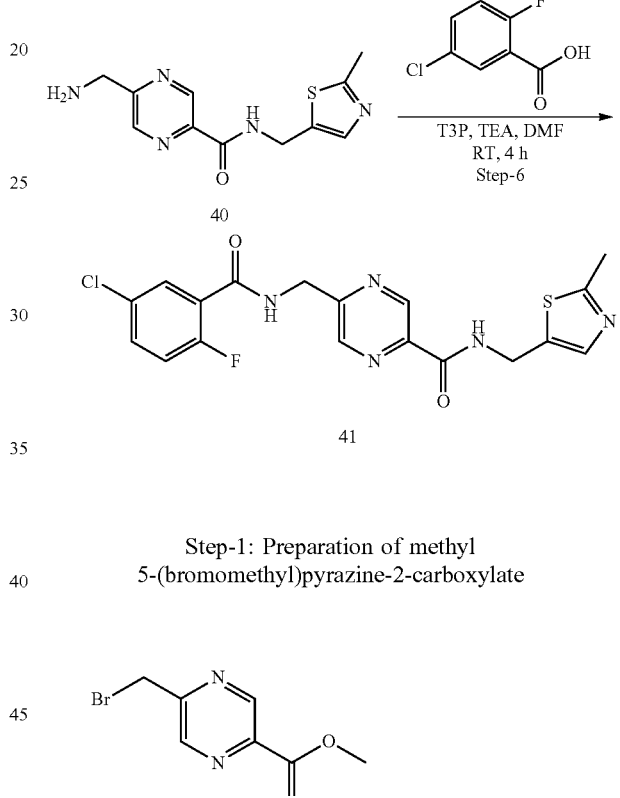

Step-1: Preparation of methyl 5-(bromomethyl)pyrazine-2-carboxylate

To a solution of methyl 5-methylpyrazine-2-carboxylate (10 g, 65.7 mmol) in acetic acid (200 mL) was added bromine (3.72 ml, 72.2 mmol) at room temperature. The reaction mixture was stirred at 80° C. for 1 h and concentrated to remove acetic acid. The residue was basified with sodium bicarbonate solution and extracted with ethyl acetate (300 mL×2). The combined organic layer was dried over anhydrous sodium sulfate, filtered and concentrated under vacuum. The crude was purified by silica gel column chromatography, using 21% ethyl acetate in hexane as eluant, to afford the title compound methyl 5-(bromomethyl)pyrazine-2-carboxylate (7.08 g, 46% yield) as a brown solid. Calculated M+H: 232.05. Found M+H: 232.

Step-2: Preparation of 5-(bromomethyl)pyrazine-2-carboxylic acid

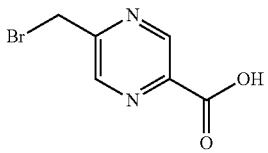

To a solution of methyl 5-(bromomethyl)pyrazine-2-carboxylate (0.5 g, 2.16 mmol) in tetrahydrofuran (20 mL) was added potassium trimethylsilanolate (0.11 g, 0.80 mmol) and the reaction mixture was stirred at 70° C. for 45 minutes. The reaction mixture was diluted with water (30 mL), acidified with 1.5 M hydrochloric acid (pH 2-3) and extracted with ethyl acetate (50 mL×3). The combined organic layer was dried over anhydrous sodium sulfate, filtered and concentrated under vacuum. The crude was purified by silica gel column chromatography using 3% methanol in dichloromethane as eluant, to afford the title compound 5-(bromomethyl)pyrazine-2-carboxylic acid (0.174 g, 37% yield) as a yellow solid. Calculated M+H: 218.02. Found M+H: 218.1.

Step-3: Preparation 5-(azidomethyl)pyrazine-2-carboxylic acid

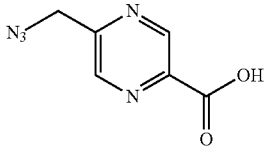 [SMILES: [N-]=[N+]=NCc1cnc(C(=O)O)cn1]

To a solution 5-(bromomethyl)pyrazine-2-carboxylic acid (2 g, 9.21 mmol) in N,N-dimethylformamide (40 mL) was added sodium azide (0.718 g, 11.05 mmol) and the reaction mixture was stirred at 80° C. for 1.5 h. The reaction mixture was diluted with water (70 mL) and extracted with ethyl acetate (100 mL×2). The combined organic layer was dried over anhydrous sodium sulfate, filtered and concentrated under vacuum to afford the title compound 5-(azidomethyl) pyrazine-2-carboxylic acid (1 g, 60% yield) as a yellow solid. Calculated M−H: 178.14. Found M−H: 178.1.

Step-4: Preparation of 5-(azidomethyl)-N-((2-methylthiazol-5-yl)methyl)pyrazine-2-carboxamide

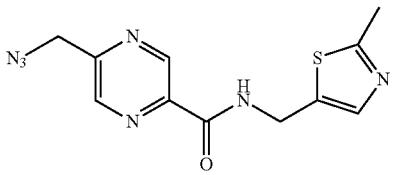 [SMILES: Cc1ncc(CNC(=O)c2cnc(CN=[N+]=[N-])cn2)s1]

To a solution of 5-(azidomethyl)pyrazine-2-carboxylic acid (0.500 g, 2.79 mmol) and (2-methylthiazol-5-yl)methanamine hydrochloride (0.457 g, 2.79 mmol) in N,N-dimethylformamide (5 mL) were added 1-propanephosphonic anhydride (50% solution in ethyl acetate, 3.5 mL, 5.58 mmol) and triethylamine (0.7 mL, 5.58 mmol) and the resulting suspension was stirred at room temperature for 4 h. The reaction mixture was poured into ice cold water (20 mL) and extracted with ethyl acetate (50 mL×3). The combined organic extract was washed with brine (100 mL), dried over sodium sulfate and concentrated under vacuum to obtain the crude material which was purified by column chromatography using 100-200 mesh silica gel with 40% ethyl acetate in hexane to afford the title compound of 5-(azidomethyl)-N-((2-methylthiazol-5-yl)methyl)pyrazine-2-carboxamide (0.320 g, 40% yield) as a pale yellow solid. Calculated M+H: 290.07. Found M+H: 290.22.

Step-5: Preparation of 5-(aminomethyl)-N-((2-methylthiazol-5-yl)methyl)pyrazine-2-carboxamide

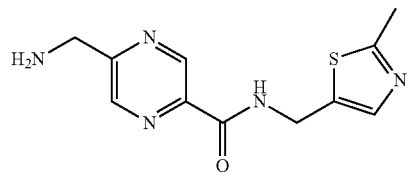 [SMILES: Cc1ncc(CNC(=O)c2cnc(CN)cn2)s1]

To a solution of 5-(azidomethyl)-N-((2-methylthiazol-5-yl)methyl)pyrazine-2-carboxamide (0.360 g, 1.24 mmol) in methanol (10 mL) was added Pd/C (0.036 g) and resulting solution was stirred at room temperature under hydrogen atmosphere for 1 h. The reaction mixture was filtered through a celite pad and filtrate obtained was concentrated to afford the title compound 5-(aminomethyl)-N-((2-methylthiazol-5-yl)methyl)pyrazine-2-carboxamide (0.270 g, crude) as a greenish semi-solid which was used for next step without further purification. Calculated M+H: 264.08. Found M+H: 264.11.

Step-6: Preparation of 5-((5-chloro-2-fluorobenzamido)methyl)-N-((2-methylthiazol-5-yl)methyl)pyrazine-2-carboxamide

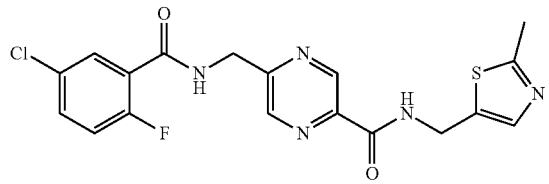 [SMILES: Cc1ncc(CNC(=O)c2cnc(CNC(=O)c3cc(Cl)ccc3F)cn2)s1]

To a solution of 5-(aminomethyl)-N-((2-methylthiazol-5-yl)methyl)pyrazine-2-carboxamide (0.050 g, 0.19 mmol) and 5-chloro-2-fluorobenzoic acid (0.033 g, 0.19 mmol) in N,N-dimethylformamide (2 mL) were added 1-propanephosphonic anhydride (50% solution in ethyl acetate, 0.4 mL, 0.38 mmol) and triethylamine (0.1 mL, 0.38 mmol) and resulting suspension was stirred at room temperature for 4 h. Then the reaction mixture was poured into ice-cold water (20 mL) and extracted with ethyl acetate (10 mL×3). The combined organic extract was washed with brine (20 mL), dried over sodium sulfate and concentrated under vacuum to obtain the crude material which was purified by preparative HPLC (analytical conditions: column: Xbridge C18 (19 mm×250 mm×5 μm), mobile phase (A): 5 mM ammonium acetate in water, mobile phase (B): HPLC grade acetonitrile. Elution gradient: 0-20 min, 5-95% B in A) to afford the title compound 5-((5-chloro-2-fluorobenzamido)methyl)-N-((2-methylthiazol-5-yl)methyl)pyrazine-2-carboxamide (0.009 g, 11% yield) as an off-white solid. Calculated M+H: 420.06. Found M+H: 420.13.

TABLE 8

The following compounds were prepared by the method described above:

| Structure | IUPAC Name | Calculated M + H | Found M + H |
|---|---|---|---|
| 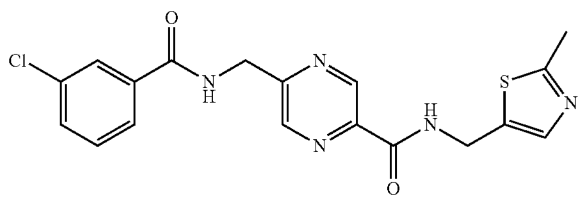 [SMILES: Cc1ncc(CNC(=O)c2cnc(CNC(=O)c3cccc(Cl)c3)cn2)s1] | 5-{[(3-chlorophenyl)form-amido]methyl}-N-[(2-methyl-1,3-thiazol-5-yl)methyl]pyrazine-2-carboxamide | 402.07 | 402.11 |
| 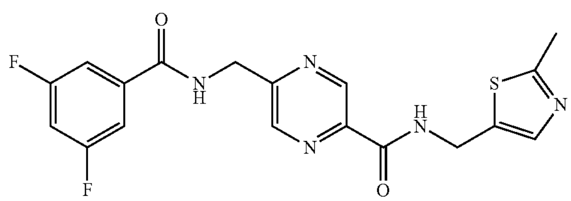 | 5-{[(3,5-difluorophenyl)formamido]methyl}-N-[(2-methyl-1,3-thiazol-5-yl)methyl]pyrazine-2-carboxamide | 404.09 | 404.05 |
| 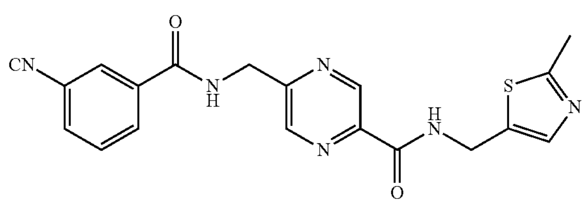 | 5-{[(3-cyanophenyl)form-amido]methyl}-N-[(2-methyl-1,3-thiazol-5-yl)methyl]pyrazine-2-carboxamide | 393.11 | 393.00 |
| 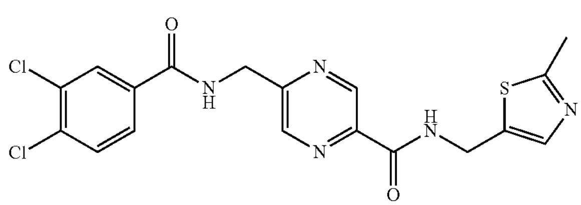 [SMILES: Cc1ncc(CNC(=O)c2cnc(CNC(=O)c3ccc(Cl)c(Cl)c3)cn2)s1] | 5-{[(3,4-dichlorophenyl)formamido]methyl}-N-[(2-methyl-1,3-thiazol-5-yl)methyl]pyrazine-2-carboxamide | 436.03 | 436.14 |
| 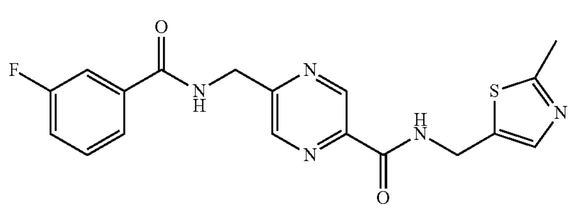 [SMILES: Cc1ncc(CNC(=O)c2cnc(CNC(=O)c3cccc(F)c3)cn2)s1] | 5-{[(3-fluorophenyl)form-amido]methyl}-N-[(2-methyl-1,3-thiazol-5-yl)methyl]pyrazine-2-carboxamide | 386.10 | 386.22 |
| 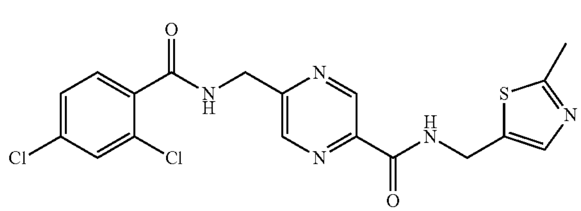 [SMILES: Cc1ncc(CNC(=O)c2cnc(CNC(=O)c3ccc(Cl)cc3Cl)cn2)s1] | 5-{[(2,4-dichlorophenyl)form-amido]methyl}-N-[(2-methyl-1,3-thiazol-5-yl)methyl]pyrazine-2-carboxamide | 436.03 | 436.13 |

Example 9—Preparation of 5-(((3,5-difluorophenyl)sulfonamido)methyl)-N-((2-methylthiazol-5-yl)methyl)pyrazine-2-carboxamide

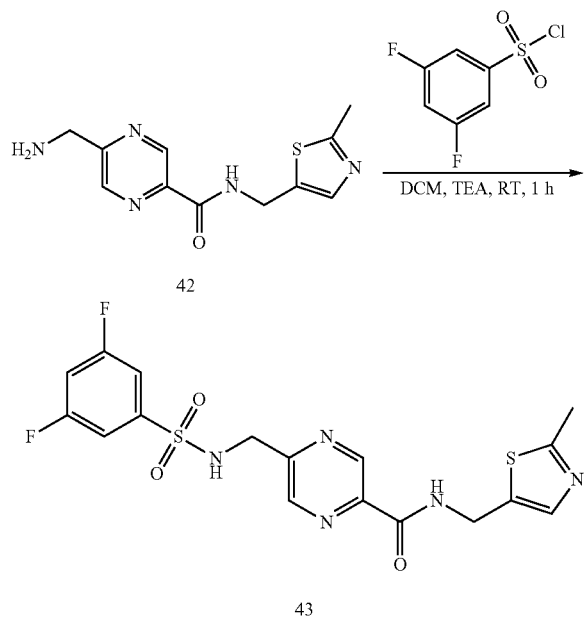

To a solution of 5-(aminomethyl)-N-((2-methylthiazol-5-yl)methyl)pyrazine-2-carboxamide (0.070 g, 0.26 mmol) and 3,5-difluorobenzenesulfonyl chloride (0.056 g, 0.26 mmol) in dichloromethane (2 mL) was added triethylamine (0.1 mL, 0.53 mmol) at 0° C. and resulting solution was stirred at room temperature for 1 h. The reaction mixture was diluted with water (20 mL) and extracted with dichloromethane (15 mL×3). The organic layer was washed with saturated sodium bicarbonate solution (10 mL×2), brine (20 mL), dried over sodium sulfate and concentrated under vacuum to get the crude material which was purified by preparative HPLC (analytical conditions: column: Xbridge C18 (19 mm×250 mm×5 μm), mobile phase (A): 5 mM ammonium acetate in water, mobile phase (B): HPLC grade acetonitrile. Elution gradient: 0-20 min, 5-95% B in A) to afford the title compound 5-(((3,5-difluorophenyl)sulfonamido)methyl)-N-((2-methylthiazol-5-yl)methyl)pyrazine-2-carboxamide (0.013 g, 12% yield) as an off-white solid. Calculated M+H: 440.06. Found M+H: 440.13.

TABLE 9

| The following compounds were prepared by the method described above: | | | |
|---|---|---|---|
| Structure | IUPAC Name | Calculated M + H | Found M + H |
| *(structure with 3-chlorobenzenesulfonamide)* | 5-(3-chlorobenzenesulfon-amidomethyl)-N-[(2-methyl-1,3-thiazol-5-yl)methyl]pyrazine-2-carboxamide | 438.04 | 438.11 |
| *(structure with 4-fluorobenzenesulfonamide)* | 5-(4-fluorobenzenesulfon-amidomethyl)-N-[(2-methyl-1,3-thiazol-5-yl)methyl]pyrazine-2-carboxamide | 422.07 | 422.00 |

TABLE 9-continued

The following compounds were prepared by the method described above:

| Structure | IUPAC Name | Calculated M + H | Found M + H |
|---|---|---|---|
| 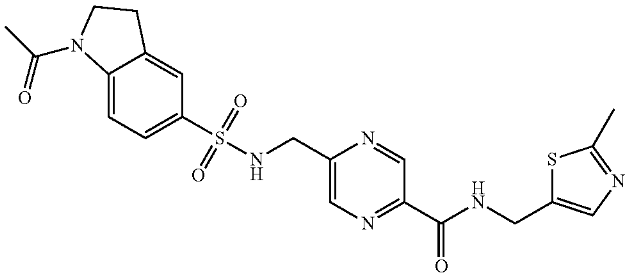 [SMILES: CC(=O)N1CCc2cc(S(=O)(=O)NCc3cnc(C(=O)NCc4cnc(C)s4)cn3)ccc21] | 5-(1-acetyl-2,3-dihydro-1H-indole-5-sulfonamidomethyl)-N-[(2-methyl-1,3-thiazol-5-yl)methyl]pyrazine-2-carboxamide | 487.11 | 487.22 |
| 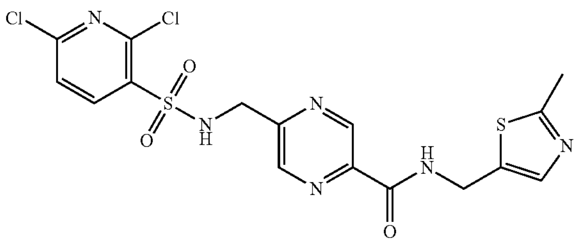 [SMILES: Cc1ncc(CNC(=O)c2cnc(CNS(=O)(=O)c3ccc(Cl)nc3Cl)cn2)s1] | 5-(2,6-dichloropyridine-3-sulfonamidomethyl)-N-[(2-methyl-1,3-thiazol-5-yl)methyl]pyrazine-2-carboxamide | 473.10 | 473.13 |
| 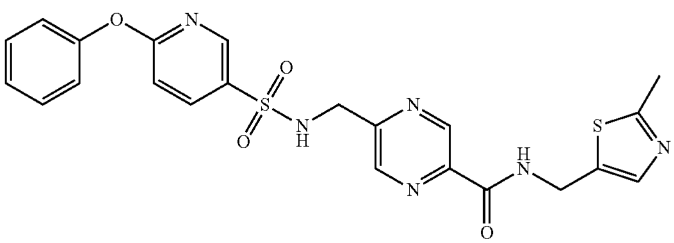 [SMILES: Cc1ncc(CNC(=O)c2cnc(CNS(=O)(=O)c3ccc(Oc4ccccc4)nc3)cn2)s1] | N-[(2-methyl-1,3-thiazol-5-yl)methyl]-5-(6-phenoxypyridine-3-sulfonamidomethyl)pyrazine-2-carboxamide | 497.10 | 497.11 |
| | 5-(5-chloro-2-fluorobenzenesulfonamidomethyl)-N-[(2-methyl-1,3-thiazol-5-yl)methyl]pyrazine-2-carboxamide | 456.03 | 456.14 |
| 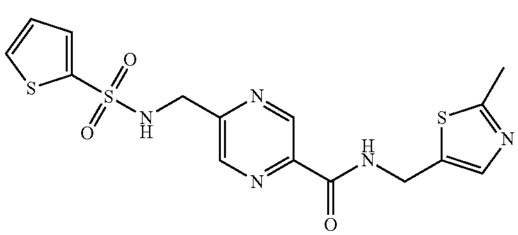 [SMILES: Cc1ncc(CNC(=O)c2cnc(CNS(=O)(=O)c3cccs3)cn2)s1] | N-[(2-methyl-1,3-thiazol-5-yl)methyl]-5-(thiophene-2-sulfonamidomethyl)pyrazine-2-carboxamide | 410.03 | 410.15 |
| 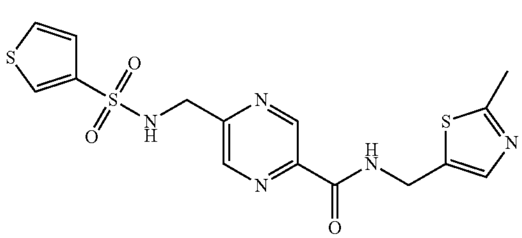 [SMILES: Cc1ncc(CNC(=O)c2cnc(CNS(=O)(=O)c3ccsc3)cn2)s1] | N-[(2-methyl-1,3-thiazol-5-yl)methyl]-5-(thiophene-3-sulfonamidomethyl)pyrazine-2-carboxamide | 410.03 | 410.21 |

TABLE 9-continued

The following compounds were prepared by the method described above:

| Structure | IUPAC Name | Calculated M + H | Found M + H |
|---|---|---|---|
| 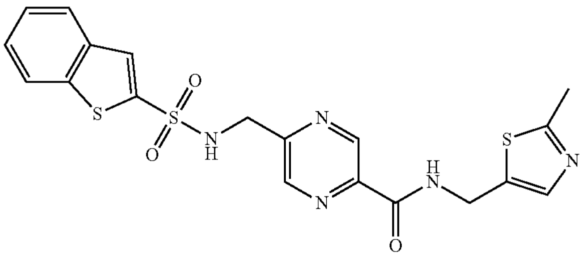 [SMILES: Cc1ncc(CNC(=O)c2cnc(CNS(=O)(=O)c3cc4ccccc4s3)cn2)s1] | 5-(1-benzothiophene-2-sulfonamidomethyl)-N-[(2-methyl-1,3-thiazol-5-yl)methyl]pyrazine-2-carboxamide | 460.05 | 460.12 |

Example 10—Preparation of 5-((3-chloro-2-methyl-benzamido)methyl)-6-methyl-N-((2-methylthiazol-5-yl)methyl)pyrazine-2-carboxamide Scheme 10

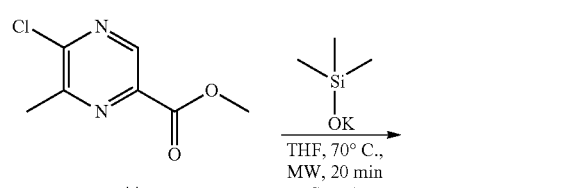

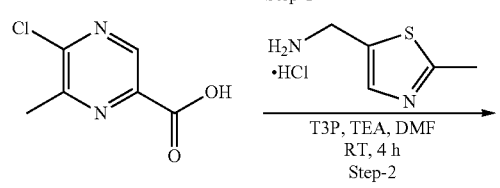

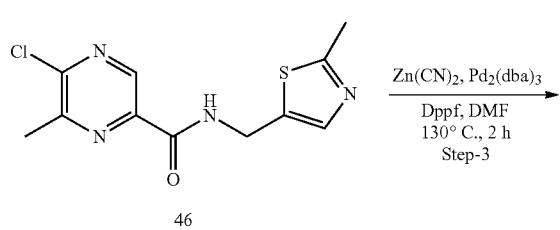

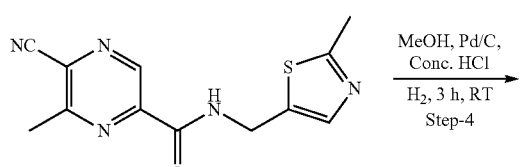

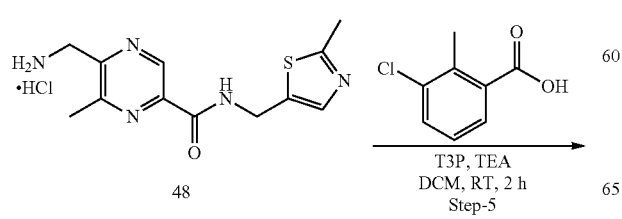

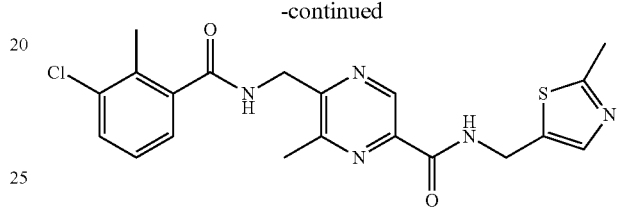

49

Step-1: Preparation of 5-chloro-6-methylpyrazine-2-carboxylic acid

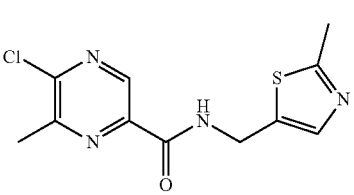 [SMILES: Cc1ncc(CNC(=O)c2cnc(Cl)c(C)n2)s1]

A solution of methyl 5-chloro-6-methylpyrazine-2-carboxylate (1 g, 5.37 mmol) and potassium trimethyl silanolate (1.3 g, 10.7 mmol) in tetrahydrofuran (15 mL) was stirred at 70° C. under microwave irradiation for 20 minutes. Then the reaction mixture was acidified with 1N hydrochloric acid to pH 3 and extracted with ethyl acetate (100 mL×2). The combined organic extract was washed with brine (200 mL), dried over sodium sulfate and concentrated under vacuum to afford the title compound 5-chloro-6-methylpyrazine-2-carboxylic acid (0.800 g, crude) as a light yellow solid which was used for next step without further purification. Calculated M+H: 173.03. Found M+H: 173.33.

Step-2: Preparation of 5-chloro-6-methyl-N-((2-methylthiazol-5-yl)methyl)pyrazine-2-carboxamide To a solution of 5-chloro-6-methylpyrazine-2-carboxylic acid (0.800 g, 4.6 mmol) and (2-methylthiazol-5-yl)methanamine hydrochloride (0.760 g, 4.6 mmol) in N,N-dimethylformamide (10 mL) were added 1-propanephosphonic anhydride (50% solution in ethyl acetate, 8.8 mL, 13.8 mmol) and triethylamine (1.2 mL, 9.2 mmol) and resulting suspension was stirred at room temperature for 4 h. Then the reaction mixture was poured into ice-cold water (100 mL) and extracted with ethyl acetate (100 mL×3). The combined organic extract was washed with brine (200 mL), dried over sodium sulfate and concentrated under vacuum to afford the title compound 5-chloro-6-methyl-N-((2-methylthiazol-5-yl)methyl)pyrazine-2-carboxamide (0.900 g, crude) as a light yellow solid, which was used for the next step without further purification. Calculated M+H: 283.03. Found M+H: 283.33.

Step-3: Preparation of 5-cyano-6-methyl-N-((2-methylthiazol-5-yl)methyl)pyrazine-2-carboxamide

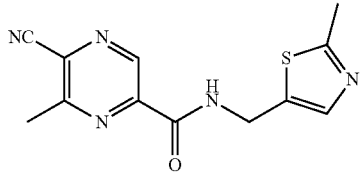 [SMILES: Cc1ncc(CNC(=O)c2cnc(C#N)c(C)n2)s1]

To a solution of 5-chloro-6-methyl-N-((2-methylthiazol-5-yl)methyl)pyrazine-2-carboxamide (0.900 g, 3.19 mmol) in N,N-dimethylformamide (10 ml) was added zinc cyanide (0.740 g, 6.38 mmol) and the reaction mixture was purged with nitrogen for 10 minutes. Then tris(dibenzylideneacetone)dipalladium (0.500 g, 0.54 mmol) and 1,1'-bis(diphenylphosphanyl) ferrocene (0.88 g, 1.5 mmol) were added and the resulting mixture was stirred at 130° C. for 2 h. The reaction mixture was cooled to room temperature, poured into ice cold water (50 mL) and extracted with ethyl acetate (100 mL×3). The combined organic extract was washed with brine (200 mL), dried over sodium sulfate and concentrated under vacuum to obtain crude material which was purified by column chromatography using 100-200 mesh silica with 70% ethyl acetate in hexane to afford the title compound 5-cyano-6-methyl-N-((2-methylthiazol-5-yl)methyl)pyrazine-2-carboxamide (0.500 g, 57.4% yield) as a light yellow solid. Calculated M+H: 274.07. Found M+H: 274.10.

Step-4: Preparation of 5-(aminomethyl)-6-methyl-N-((2-methylthiazol-5-yl)methyl)pyrazine-2-carboxamide hydrochloride

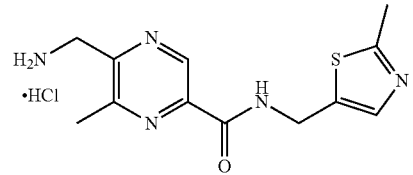 [SMILES: Cl ; Cc1ncc(CNC(=O)c2cnc(CN)c(C)n2)s1]

To a solution of 5-cyano-6-methyl-N-((2-methylthiazol-5-yl)methyl)pyrazine-2-carboxamide (0.500 g, 1.83 mmol) in methanol (30 mL) was added Pd/C (0.400 g) and concentrated hydrochloric acid (2.5 mL) and the resulting suspension was stirred at room temperature under hydrogen atmosphere for 3 h. Then the reaction mixture was filtered through a celite pad and filtrate obtained was concentrated under vacuum to afford the title compound 5-(aminomethyl)-6-methyl-N-((2-methylthiazol-5-yl)methyl)pyrazine-2-carboxamide hydrochloride (0.460 g, crude) as light yellow gum which was used for the next step without further purification. Calculated M+H: 278.07. Found M+H: 278.14.

Step-5: Preparation of 5-((3-chloro-2-methylbenzamido)methyl)-6-methyl-N-((2-methylthiazol-5-yl)methyl)pyrazine-2-carboxamide

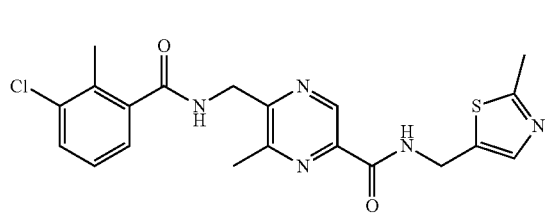 [SMILES: Cc1ncc(CNC(=O)c2cnc(CNC(=O)c3cccc(Cl)c3C)c(C)n2)s1]

To a solution of 5-(aminomethyl)-6-methyl-N-((2-methylthiazol-5-yl)methyl)pyrazine-2-carboxamide hydrochloride (0.100 g, 0.36 mmol) and 3-chloro-2-methylbenzoic acid (0.048 g, 0.36 mmol) in dichloromethane (2 mL) were added 1-propanephosphonic anhydride (50% solution in ethyl acetate, 0.6 mL, 0.63 mmol) and triethylamine (0.1 mL, 0.63 mmol) and the resulting suspension was stirred at room temperature for 2 h. The reaction mixture was poured into ice cold water (20 mL) and extracted with dichloromethane (10 mL×3). The combined organic extract was washed with brine (20 mL), dried over sodium sulfate and concentrated under vacuum to obtain the crude material which was purified by preparative HPLC (analytical conditions: column: Xbridge C18 (19 mm×250 mm×5 μm), mobile phase (A): 5 mM ammonium acetate in water, mobile phase (B): HPLC grade acetonitrile. Elution gradient: 0-20 min, 5-95% B in A) to afford the title compound 5-((3-chloro-2-methylbenzamido)methyl)-6-methyl-N-((2-methylthiazol-5-yl)methyl)pyrazine-2-carboxamide (0.013 g, 13% yield) as off-white solid. Calculated M+H: 430.07. Found M+H: 430.11.

TABLE 10

The following compounds were prepared by the method described above:

| Structure | IUPAC Name | Calculated M + H | Found M + H |
|---|---|---|---|
| | 5-{[(3,5-difluorophenyl)formamido]methyl}-6-methyl-N-[(2-methyl-1,3-thiazol-5-yl)methyl]pyrazine-2-carboxamide | 418.11 | 418.01 |
| | 5-{[(5-chloro-2-fluorophenyl)formamido]methyl}-6-methyl-N-[(2-methyl-1,3-thiazol-5-yl)methyl]pyrazine-2-carboxamide | 434.08 | 434.11 |
| | 5-{[(3-cyanophenyl)formamido]methyl}-6-methyl-N-[(2-methyl-1,3-thiazol-5-yl)methyl]pyrazine-2-carboxamide | 407.12 | 407.13 |

Example 11—Preparation of 5-((3-chloro-4-fluorophenylsulfonamido)methyl)-6-methyl-N-((2-methylthiazol-5-yl)methyl)pyrazine-2-carboxamide

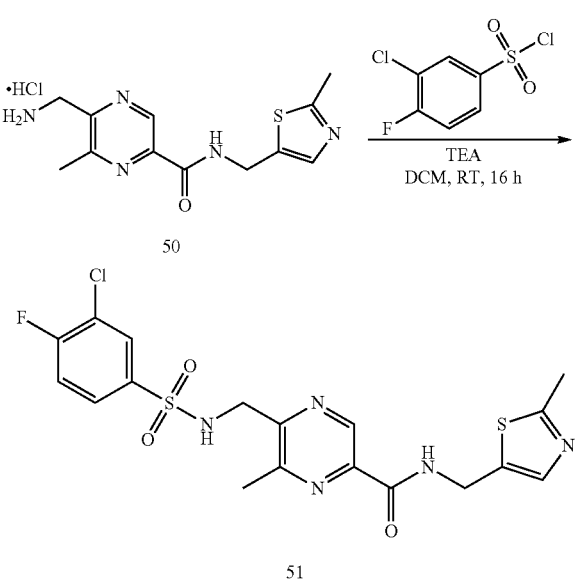

To a solution of 6-(aminomethyl)-5-methyl-N-((2-methylthiazol-5-yl)methyl)nicotinamide hydrochloride (0.06 g, 0.191 mmol) and triethylamine (0.07 mL, 0.573 mmol) in dichloromethane (15 mL) cooled at 0° C. was added a solution of 3-chloro-4-fluorobenzene-1-sulfonyl chloride (0.026 g, 0.114 mmol) in dichloromethane (5 mL) dropwise. The resulting solution was stirred at room temperature for 16 h. The reaction mixture was diluted with water (20 mL) and extracted with dichloromethane (30 mL×3). The combined organic layer was washed with brine (30 mL), dried over sodium sulfate and concentrated under vacuum to get the crude material which was purified preparative HPLC (analytical conditions: column: Xbridge C8 (250 mm×4.6 mm×5 µm), mobile phase (A): water, mobile phase (B): acetonitrile, flow rate: 1.0 mL/min, T/% B: 0/20, 10/70, 25/70, 27/20, 30/20) to afford the title compound 5-((3-chloro-4-fluorophenylsulfonamido)methyl)-6-methyl-N-((2-methylthiazol-5-yl)methyl)pyrazine-2-carboxamide (0.005 g, 5% yield) as a white solid. Calculated M+H: 470.94. Found M+H: 470.1.

TABLE 11

The following compounds were prepared by the method described above:

| Structure | IUPAC Name | Calculated M + H | Found M + H |
|---|---|---|---|
| 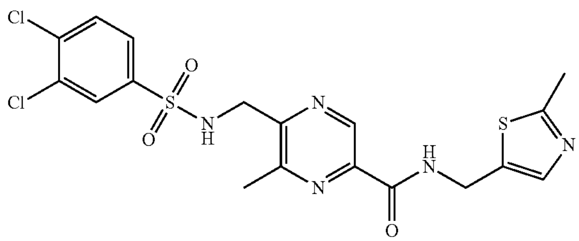 [SMILES: Cc1ncc(CNC(=O)c2cnc(CNS(=O)(=O)c3ccc(Cl)c(Cl)c3)c(C)n2)s1] | 5-(3,4-dichlorobenzene-sulfonamidomethyl)-6-methyl-N-[(2-methyl-1,3-thiazol-5-yl)methyl]pyrazine-2-carboxamide | 486.01 | 486.12 |
| 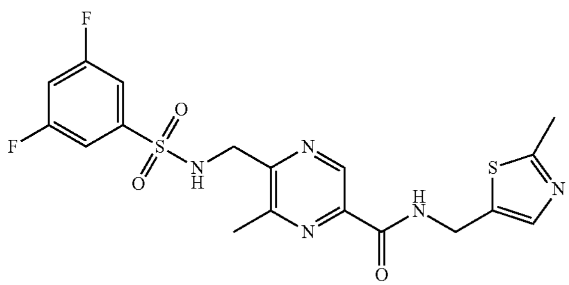 [SMILES: Cc1ncc(CNC(=O)c2cnc(CNS(=O)(=O)c3cc(F)cc(F)c3)c(C)n2)s1] | 5-(3,5-difluorobenzene-sulfonamidomethyl)-6-methyl-N-[(2-methyl-1,3-thiazol-5-yl)methyl]pyrazine-2-carboxamide | 454.07 | 454.10 |
| 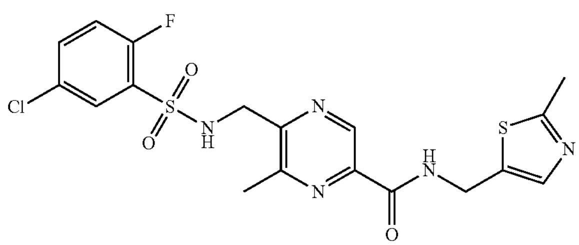 [SMILES: Cc1ncc(CNC(=O)c2cnc(CNS(=O)(=O)c3cc(Cl)ccc3F)c(C)n2)s1] | 5-(5-chloro-2-fluorobenzenesulfon-amidomethyl)-6-methyl-N-[(2-methyl-1,3-thiazol-5-yl)methyl]pyrazine-2-carboxamide | 470.04 | 470.11 |
| 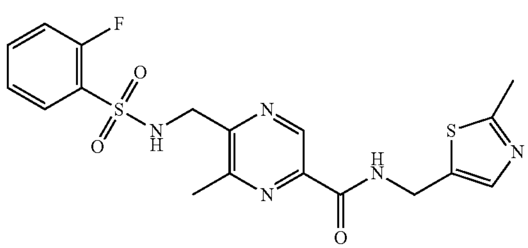 [SMILES: Cc1ncc(CNC(=O)c2cnc(CNS(=O)(=O)c3ccccc3F)c(C)n2)s1] | 5-(2-fluorobenzenesulfon-amidomethyl)-6-methyl-N-[(2-methyl-1,3-thiazol-5-yl)methyl]pyrazine-2-carboxamide | 436.08 | 436.21 |
| 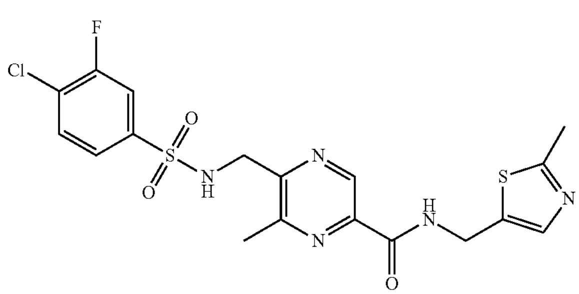 [SMILES: Cc1ncc(CNC(=O)c2cnc(CNS(=O)(=O)c3ccc(Cl)c(F)c3)c(C)n2)s1] | 5-(4-chloro-3-fluorobenzenesulfon-amidomethyl)-6-methyl-N-[(2-methyl-1,3-thiazol-5-yl)methyl]pyrazine-2-carboxamide | 470.04 | 470.14 |

TABLE 11-continued

The following compounds were prepared by the method described above:

| Structure | IUPAC Name | Calculated M + H | Found M + H |
|---|---|---|---|
| | 5-(3,5-dichlorobenzene-sulfonamidomethyl)-6-methyl-N-[(2-methyl-1,3-thiazol-5-yl)methyl]pyrazine-2-carboxamide | 486.01 | 486.04 |
| | 5-(3-chlorobenzenesulfon-amidomethyl)-6-methyl-N-[(2-methyl-1,3-thiazol-5-yl)methyl]pyrazine-2-carboxamide | 452.05 | 452.22 |
| | 5-(4-fluorobenzenesulfon-amidomethyl)-6-methyl-N-[(2-methyl-1,3-thiazol-5-yl)methyl]pyrazine-2-carboxamide | 436.08 | 436.06 |
| | 5-(3,4-difluorobenzene-sulfonamidomethyl)-6-methyl-N-[(2-methyl-1,3-thiazol-5-yl)methyl]pyrazine-2-carboxamide | 454.07 | 454.01 |

Example 12—Preparation of 5-((3-chloro-4-fluoro-phenylsulfonamido)methyl)-6-ethyl-N-((2-methyl-thiazol-5-yl)methyl)pyrazine-2-carboxamide Scheme 12

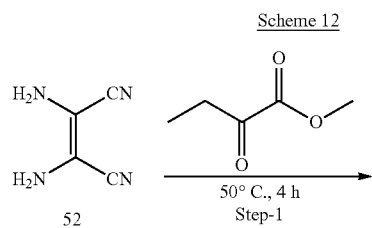

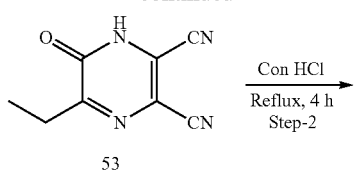

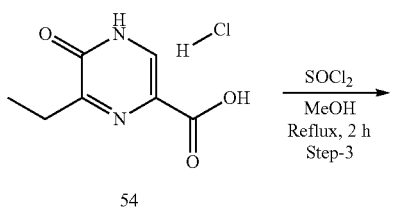

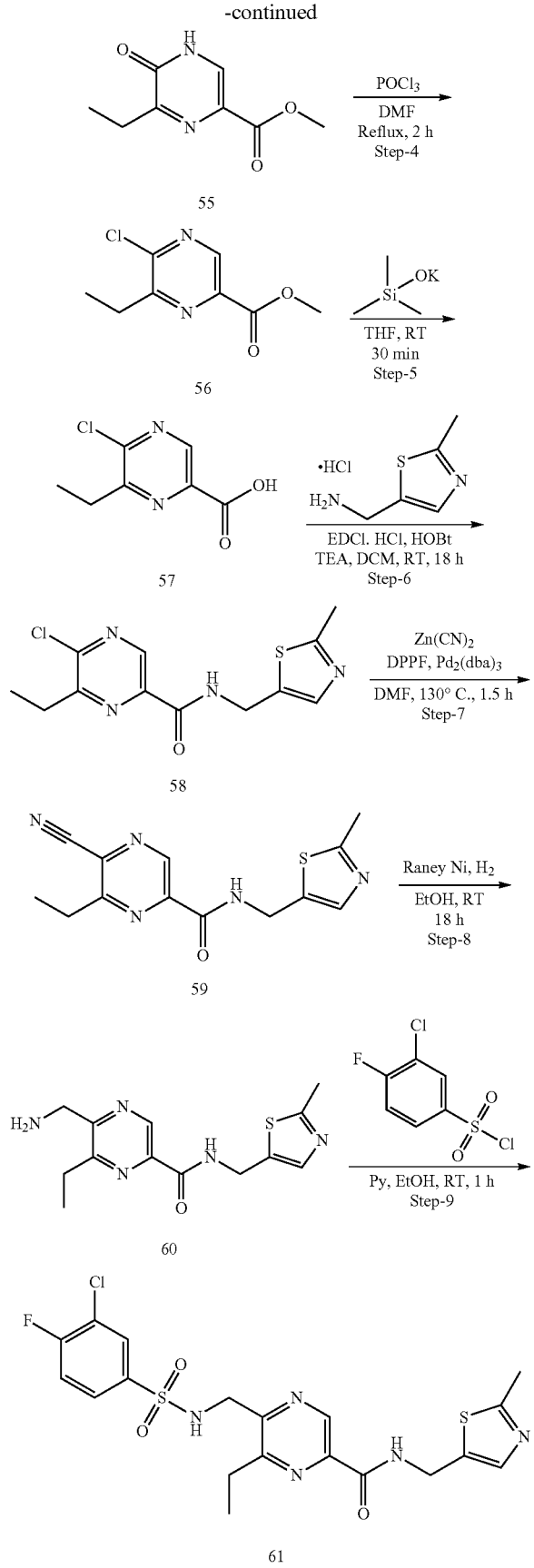

Step-1: Preparation of 5-ethyl-6-oxo-1,6-dihydropyrazine-2,3-dicarbonitrile

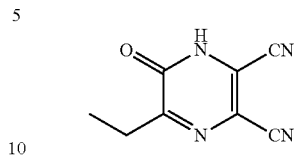

To a solution of 2,3-diaminomaleonitrile (20 g, 185.013 mmol) in water (400 mL) heated at 50° C. was added methyl 2-oxobutanoate (21.48 g, 185.013 mmol) dropwise and the reaction mixture was stirred at the same temperature for 4 h. The reaction mixture was cooled to room temperature and allowed to precipitate for overnight. The solid formed was filtered, washed with n-pentane and dried to afford the title compound 5-ethyl-6-oxo-1,6-dihydropyrazine-2,3-dicarbonitrile (27 g, 84% yield) as a brown solid. Calculated M−H: 173.16. Found M−H: 173.2.

Step-2: Preparation of 6-ethyl-5-oxo-4,5-dihydropyrazine-2-carboxylic acid hydrochloride

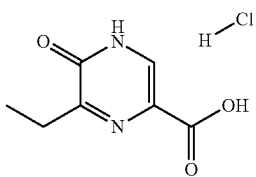

A mixture of 5-ethyl-6-oxo-1,6-dihydropyrazine-2,3-dicarbonitrile (32 g, 183.908 mmol) and concentrated hydrochloric acid (320 mL) was refluxed for 4 h. The reaction mixture was concentrated and dried. The residue was washed with diethyl ether to afford the title compound 6-ethyl-5-oxo-4,5-dihydropyrazine-2-carboxylic acid hydrochloride (28 g, crude) as a brownish solid. The compound was as such taken into the next steps without further purification. Calculated M+H: 169.15. Found M+H: 169.1.

Step-3: Preparation of methyl 6-ethyl-5-oxo-4,5-dihydropyrazine-2-carboxylate

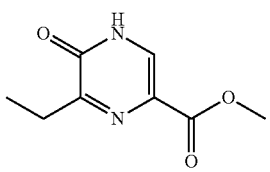

Thionyl chloride (23 mL, 316.668 mmol) was added dropwise to methanol (650 mL) at −20° C. to −10 OC and the solution was stirred at the same temperature for 30 minutes. Then 6-ethyl-5-oxo-4,5-dihydropyrazine-2-carboxylic acid hydrochloride (14 g, 68.627 mmol) was added and the reaction mixture was refluxed for 2 h. The solution was concentrated; the residue was basified with saturated sodium bicarbonate solution and extracted with ethyl acetate (300 mL×2). The combined organic layer was washed with brine, dried over anhydrous sodium sulfate, filtered and concentrated under vacuum to afford the crude compound which was purified by silica gel column chromatography, using 5% methanol in dichloromethane to obtain the title compound methyl 6-ethyl-5-oxo-4,5-dihydropyrazine-2-carboxylate (6.7 g, 54% yield) as a brownish solid. Calculated M+H: 183.18. Found M+H: 183.1.

Step-4: Preparation of methyl 5-chloro-6-ethylpyrazine-2-carboxylate

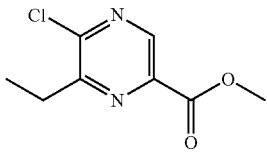

A mixture of methyl 6-ethyl-5-oxo-4,5-dihydropyrazine-2-carboxylate (6.7 g, 36.776 mmol), phosphorous oxychloride (35 mL) and N,N-dimethylformamide (0.1 mL) was refluxed for 2 h. The cooled reaction mixture was poured into ice-water and extracted with chloroform (200 mL×2). The combined organic layer was washed with brine, dried over anhydrous sodium sulfate, filtered and concentrated under vacuum to afford the crude compound which was purified by silica gel column chromatography, using 15% ethyl acetate in hexane to obtain the title compound methyl 5-chloro-6-ethylpyrazine-2-carboxylate (6.2 g, 84% yield) as a colorless liquid. Calculated M+H: 201.62. Found M+H: 201.1.

Step-5: Preparation of 5-chloro-6-ethylpyrazine-2-carboxylic acid

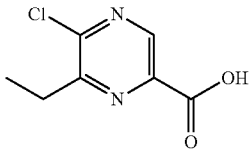

To a solution of methyl 5-chloro-6-ethylpyrazine-2-carboxylate (1.5 g, 7.50 mmol) in tetrahydrofuran (15 mL) was added potassium trimethylsilanolate (1.935 g, 15.00 mmol) and the reaction mixture was stirred at room temperature for 30 minutes. The reaction mixture was diluted with water (60 mL), acidified with 1.5N hydrochloric acid and extracted with ethyl acetate (100 mL×2). The combined organic layer was washed with brine, dried over anhydrous sodium sulfate, filtered and concentrated under vacuum to afford the title compound 5-chloro-6-ethylpyrazine-2-carboxylic acid (1.2 g, 86% yield) as a brownish semi solid. Calculated M+H: 187.60. Found M+H: 187.0.

Step-6: Preparation of 5-chloro-6-ethyl-N-((2-methylthiazol-5-yl)methyl)pyrazine-2-carboxamide

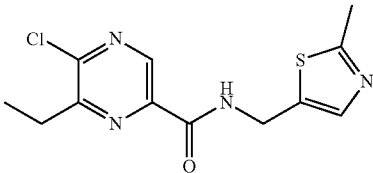 [SMILES: CCc1nc(C(=O)NCc2cnc(C)s2)cnc1Cl]

To a solution of 5-chloro-6-ethylpyrazine-2-carboxylic acid (1.1 g, 5.894 mmol) and triethylamine (2.5 ml, 17.684 mmol) in dichloromethane (100 mL) were added 1-ethyl-3-(3-dimethylaminopropyl)carbodiimide (1.697 g, 8.84 mmol) and 1-hydroxybenzotriazole (0.955 g, 7.07 mmol) at 0° C. The reaction mixture was stirred at 0° C. for 30 minutes. A solution of (2-methylthiazol-5-yl)methanamine hydrochloride (0.972 g, 5.894 mmol) and triethylamine (2.5 ml, 17.684 mmol) in dichloromethane (50 mL) was added dropwise to the reaction mixture and stirred at room temperature for 18 h. The reaction mixture was diluted with dichloromethane (100 mL), washed with water (50 mL), dried over anhydrous sodium sulfate, filtered and concentrated. The crude was purified by silica gel column chromatography using 3% methanol in dichloromethane to afford the title compound 5-chloro-6-ethyl-N-((2-methylthiazol-5-yl)methyl)pyrazine-2-carboxamide (0.9 g, 51% yield) as a brownish solid. Calculated M+H: 297.78. Found M+H: 297.1.

Step-7: Preparation of 5-cyano-6-ethyl-N-((2-methylthiazol-5-yl)methyl)pyrazine-2-carboxamide

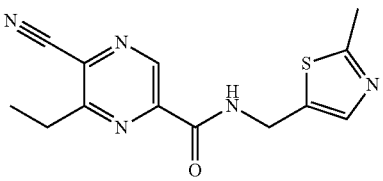 [SMILES: CCc1nc(C(=O)NCc2cnc(C)s2)cnc1C#N]

To a solution of 5-chloro-6-ethyl-N-((2-methylthiazol-5-yl)methyl)pyrazine-2-carboxamide (0.35 g, 1.179 mmol) in N,N-dimethylformamide (20 mL) was purged with argon for 10 minutes. Zinc cyanide (0.097 g, 0.825 mmol), 1,1'-bis(diphenylphosphino)ferrocene (0.029 g, 0.051 mmol) and tris(dibenzylideneacetone)dipalladium (0.024 g, 0.025 mmol) were added and the reaction mixture was heated at 130° C. for 1.5 h. The reaction mixture was diluted with water (50 mL) and extracted with ethyl acetate (100 mL×2). The combined organic layer was washed with brine, dried over anhydrous sodium sulfate, filtered and concentrated under vacuum to afford the crude compound which was purified by silica gel column chromatography, using 15% ethyl acetate in hexane to obtain the title compound 5-cyano-6-ethyl-N-((2-methylthiazol-5-yl)methyl)pyrazine-2-carboxamide (0.32 g, 94% yield) as a brownish solid. Calculated M+H: 288.34. Found M+H: 288.0.

Step-8: Preparation of 5-(aminomethyl)-6-ethyl-N-((2-methylthiazol-5-yl)methyl)pyrazine-2-carboxamide

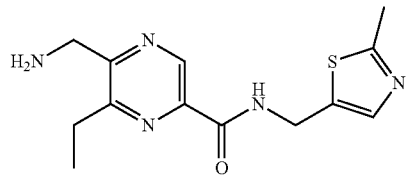 [SMILES: CCc1nc(C(=O)NCc2cnc(C)s2)cnc1CN]

To a solution of 5-cyano-6-ethyl-N-((2-methylthiazol-5-yl)methyl)pyrazine-2-carboxamide (0.05 g) in ethanol (10 mL) was added Raney nickel (0.01 g) and the reaction mixture was hydrogenated at room temperature for 18 h using a balloon. After the completion of reaction (as monitored by TLC), the reaction mixture was filtered through celite, the celite bed was washed with methanol and the combined filtrate was concentrated to afford the title compound 5-(aminomethyl)-6-ethyl-N-((2-methylthiazol-5-yl)methyl)pyrazine-2-carboxamide (0.05 g, crude) as a brownish gum. The crude was as such taken for next step without further purification. Calculated M+H: 292.37. Found M+H: 292.3.

Step-9: Preparation of 5-((3-chloro-4-fluorophenylsulfonamido)methyl)-6-ethyl-N-((2-methylthiazol-5-yl)methyl)pyrazine-2-carboxamide

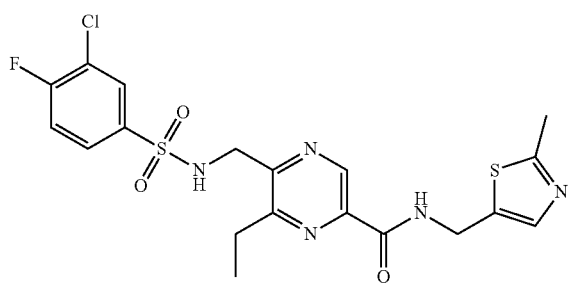 [SMILES: CCc1nc(C(=O)NCc2cnc(C)s2)cnc1CNS(=O)(=O)c1ccc(F)c(Cl)c1]

To a solution of 5-(aminomethyl)-6-ethyl-N-((2-methylthiazol-5-yl)methyl)pyrazine-2-carboxamide (0.055 g, 0.188 mmol) and pyridine (0.045 mL, 0.566 mmol) in ethanol (20 mL) cooled at 0° C., was added 3-chloro-4-fluorobenzene-1-sulfonyl chloride (0.016 mL, 0.113 mmol) dropwise at room temperature and the reaction mixture was stirred at room temperature for 1 h. The solution was concentrated. The residue was dissolved in ethyl acetate (50 mL), washed with 10% citric acid solution (30 mL), water (30 mL), saturated sodium bicarbonate solution (30 mL), dried and concentrated. The crude was purified by preparative HPLC (analytical conditions: column: Zorbax XDB C18 (150 mm×4.6 mm×3.5 μm), mobile phase (A): 0.01% ammonia in water, mobile phase (B): acetonitrile, flow rate: 1.0 mL/min, T/% B: 0/20, 10/70, 25/70, 27/20, 30/20) to afford the title compound 5-((3-chloro-4-fluorophenylsulfonamido)methyl)-6-ethyl-N-((2-methylthiazol-5-yl)methyl)pyrazine-2-carboxamide (0.013 g, 14% yield) as a off-white solid. Calculated M+H: 484.97. Found M+H: 484.1.

Example 13—Preparation of 5-((3-chloro-4-fluorophenylsulfonamido)methyl)-N-((2-methylthiazol-5-yl)methyl)-6-(trifluoromethyl)pyrazine-2-carboxamide

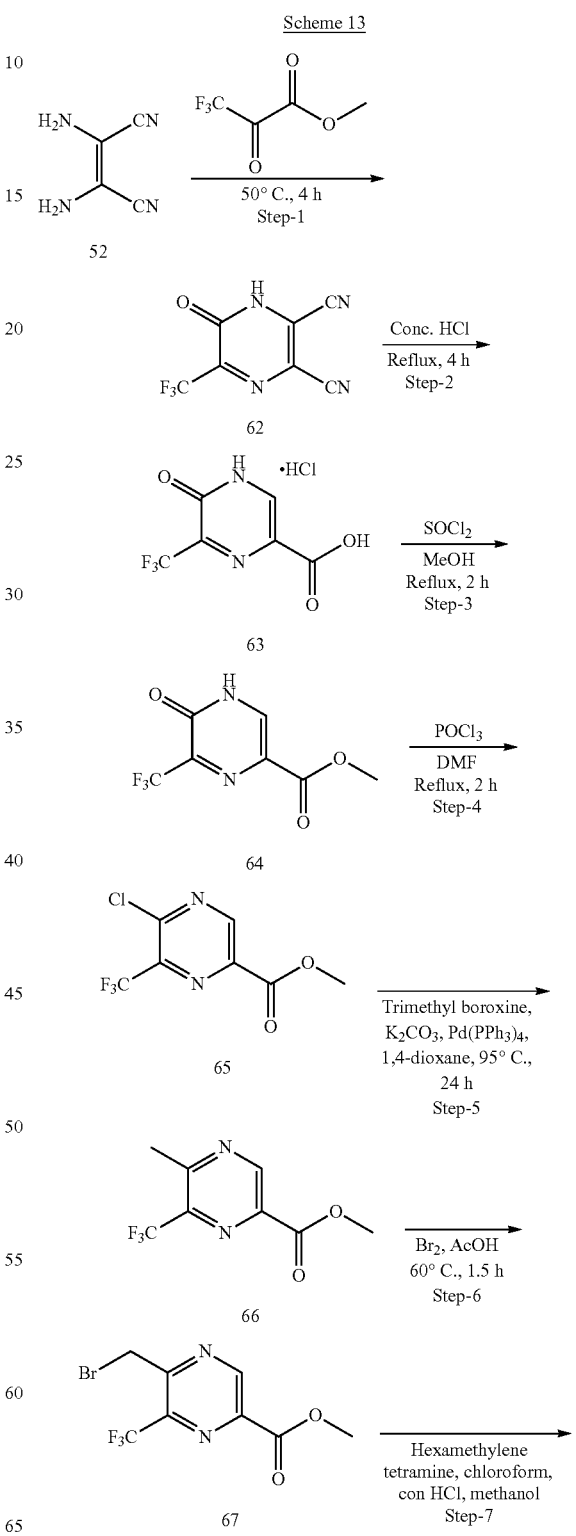

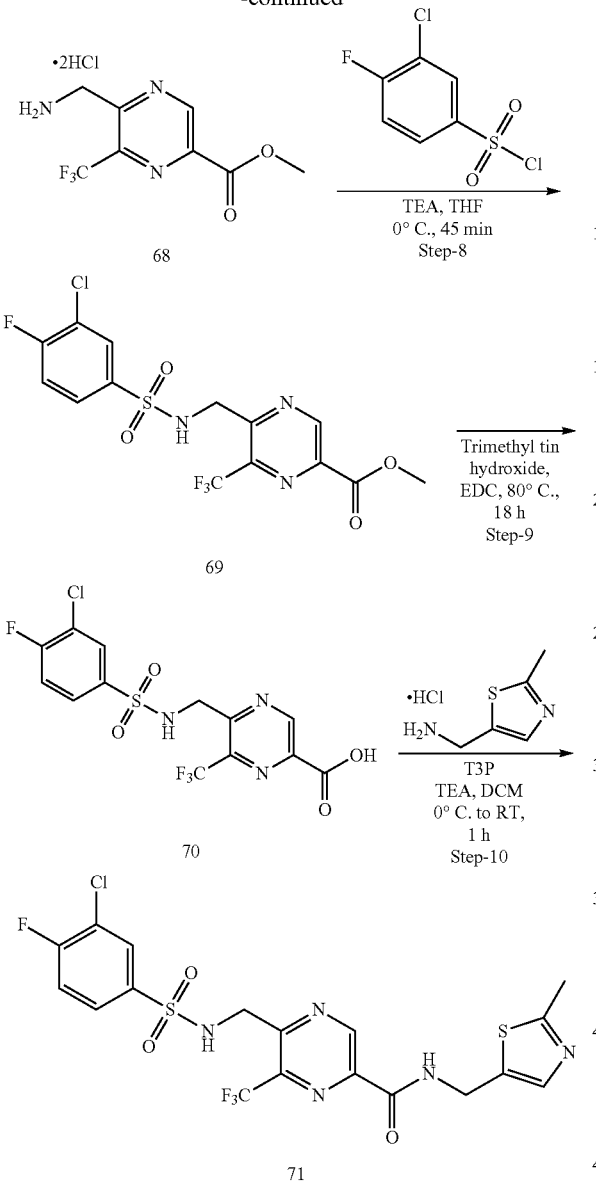

Step-1: Preparation of 6-oxo-5-(trifluoromethyl)-1,6-dihydropyrazine-2,3-dicarbonitrile

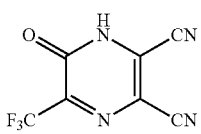

To a solution of 2,3-diaminomaleonitrile (15 g, 138.76 mmol) in water (300 mL) heated at 50° C. was added methyl 3,3,3-trifluoro-2-oxopropanoate (14.25 g, 138.76 mmol) dropwise and the reaction mixture was stirred at the same temperature for 4 h. The reaction mixture was cooled to room temperature and allowed to precipitate overnight. The solid formed was filtered, washed with n-pentane and dried to afford the title compound 6-oxo-5-(trifluoromethyl)-1,6-dihydropyrazine-2,3-dicarbonitrile (23 g, crude) as a brownish solid. The crude was as such taken for next step without further purification. Calculated M−H: 213.10. Found M−H: 213.0.

Step-2: Preparation of 5-oxo-6-(trifluoromethyl)-4,5-dihydropyrazine-2-carboxylic acid hydrochloride

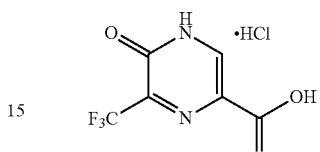

A mixture of -oxo-5-(trifluoromethyl)-1,6-dihydropyrazine-2,3-dicarbonitrile (29 g, 135.450 mmol) and concentrated hydrochloric acid (290 mL) was refluxed for 4 h. The reaction mixture was concentrated and dried. The residue was washed with diethyl ether to afford the title compound 5-oxo-6-(trifluoromethyl)-4,5-dihydropyrazine-2-carboxylic acid hydrochloride (26 g, crude) as a brownish solid. The compound was as such taken for next step without further purification. Calculated M−H: 207.09. Found M−H: 207.0.

Step-3: Preparation of methyl 5-oxo-6-(trifluoromethyl)-4,5-dihydropyrazine-2-carboxylate

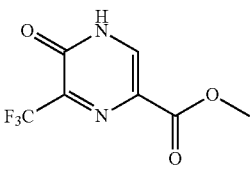

Thionyl chloride (24 mL, 330.436 mmol) was added dropwise to methanol (500 mL) at −20° C. to −10° C. and the solution was stirred at the same temperature for 30 minutes. Then 5-oxo-6-(trifluoromethyl)-4,5-dihydropyrazine-2-carboxylic acid hydrochloride (14 g, 67.278 mmol) was added and the reaction mixture was refluxed for 2 h. The solution was concentrated; the residue was basified with saturated sodium bicarbonate solution and extracted with ethyl acetate (300 mL×2). The combined organic layer was washed with brine, dried over anhydrous sodium sulfate, filtered and concentrated under vacuum to afford the crude compound which was purified by silica gel column chromatography, using 5% methanol in dichloromethane to obtain the title compound methyl 5-oxo-6-(trifluoromethyl)-4,5-dihydropyrazine-2-carboxylate (10 g, 78% yield) as a brownish solid. Calculated M+H: 223.12. Found M+H: 223.0.

Step-4: Preparation of methyl 5-chloro-6-(trifluoromethyl)pyrazine-2-carboxylate

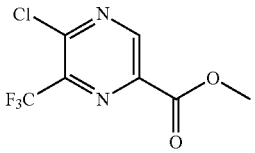

A mixture of methyl 6-trifluoromethyl-5-oxo-4,5-dihydropyrazine-2-carboxylate (3 g, 13.506 mmol), phosphorous oxychloride (15 mL) and N,N-dimethylformamide (0.1 mL) was refluxed for 2 h. The cooled reaction mixture was poured into ice-water and extracted with chloroform (100 mL×2). The combined organic layer was washed with brine, dried over anhydrous sodium sulfate, filtered and concentrated under vacuum to afford the crude compound which was purified by silica gel column chromatography, using 15% ethyl acetate in hexane to obtain the title compound methyl 5-chloro-6-(trifluoromethyl)pyrazine-2-carboxylate (2.6 g, 81% yield) as a colorless liquid. $^1$H NMR (400 MHz, DMSO-$d_6$) δ 9.31 (s, 1H), 3.95 (s, 3H).

Step-5: Preparation of methyl 5-methyl-6-(trifluoromethyl)pyrazine-2-carboxylate

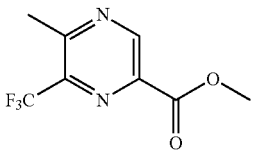

A solution of methyl 5-chloro-6-(trifluoromethyl)pyrazine-2-carboxylate (2.2 g, 9.144 mmol), trimethylboroxine (1.92 g, 13.717 mmol) and potassium carbonate (3.79 g, 27.434 mmol) in dioxane (120 mL) was purged with argon gas for 15 minutes. Then tetrakis(triphenylphosphine)palladium(0) (0.528 g, 0.47 mmol) was added and the reaction mixture was heated at 95° C. for 24 h. The reaction mixture was filtered through celite and the filtrate was concentrated. The crude compound which was purified by silica gel column chromatography, using 12% ethyl acetate in hexane to obtain the title compound methyl 5-methyl-6-(trifluoromethyl)pyrazine-2-carboxylate (1.25 g, 58% yield) as a colorless liquid. Calculated M+H: 221.15. Found M+H: 221.1.

Step-6: Preparation of methyl 5-(bromomethyl)-6-(trifluoromethyl)pyrazine-2-carboxylate

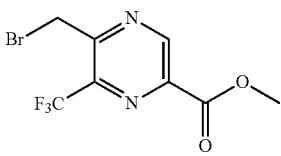 [SMILES: COC(=O)c1cnc(CBr)c(C(F)(F)F)n1]

To a solution of methyl 5-methyl-6-(trifluoromethyl)pyrazine-2-carboxylate (1.58 g, 7.181 mmol) in acetic acid (100 ml) was added bromine (0.41 ml, 7.900 mmol) at room temperature. The reaction mixture was heated at 60° C. for 1.5 h and concentrated to remove acetic acid. The residue was basified with saturated sodium bicarbonate solution and extracted with ethyl acetate (100 mL×2). The combined organic layer was dried and concentrated. The crude was purified by silica gel column chromatography using dichloromethane to afford the title compound methyl 5-(bromomethyl)-6-(trifluoromethyl)pyrazine-2-carboxylate (1.3 g, 61% yield) as a brownish gum. Calculated M+H: 298.96. Found M+H: 299.0.

Step-7: Preparation of methyl 5-(aminomethyl)-6-(trifluoromethyl)pyrazine-2-carboxylate dihydrochloride

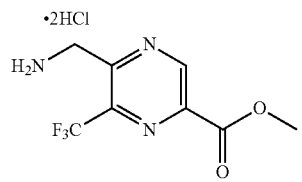 [SMILES: COC(=O)c1cnc(CN)c(C(F)(F)F)n1]

To a solution of 5-(bromomethyl)-6-(trifluoromethyl)pyrazine-2-carboxylate (1.3 g, 4.347 mmol) in chloroform (40 mL) was added hexamethylenetetramine (0.625 g, 4.434 mmol) and the reaction mixture was stirred at room temperature for 18 h. The solid formed was filtered and dried. The solid was suspended in methanol (40 mL), concentrated hydrochloric acid (1.95 ml) was added and the reaction mixture was heated at 75° C. for 3 h. The reaction mixture was concentrated, the residue was triturated with diethyl ether and dried to afford the title compound methyl 5-(aminomethyl)-6-(trifluoromethyl)pyrazine-2-carboxylate dihydrochloride (1 g, crude) as an off-white solid. The crude was as such taken for next step without further purification. Calculated M+H: 236.16. Found M+H: 236.1.

Step-8: Preparation of methyl 5-((3-chloro-4-fluorophenylsulfonamido)methyl)-6-(trifluoromethyl)pyrazine-2-carboxylate

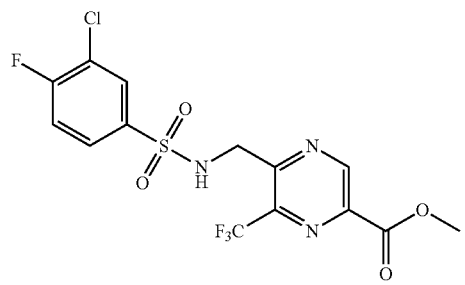 [SMILES: COC(=O)c1cnc(CNS(=O)(=O)c2ccc(F)c(Cl)c2)c(C(F)(F)F)n1]

To a solution of methyl 5-(aminomethyl)-6-(trifluoromethyl)pyrazine-2-carboxylate dihydrochloride (0.5 g, 1.622 mmol) and triethylamine (0.7 mL, 4.868 mmol) in tetrahydrofuran (40 mL) cooled at 0° C., was added 4-fluoro-3-chlorobenzenesulfonyl chloride (2.81 ml, 19.73 mmol) dropwise. The reaction mixture was stirred at the same temperature for 45 minutes. Then the reaction mixture was diluted with water (35 mL) and extracted with ethyl acetate (60 mL×2). The combined organic layer was dried over anhydrous sodium sulfate, filtered and concentrated. The crude was purified by silica gel column chromatography using 30% ethyl acetate in hexane to afford the title compound methyl 5-((3-chloro-4-fluorophenylsulfonamido) methyl)-6-(trifluoromethyl)pyrazine-2-carboxylate (0.23 g, 33%) as a greenish semi solid. Calculated M+H: 428.76. Found M+H: 428.0.

Step-9: Preparation of 5-((3-chloro-4-fluorophenyl-sulfonamido)methyl)-6-(trifluoromethyl)pyrazine-2-carboxylic acid

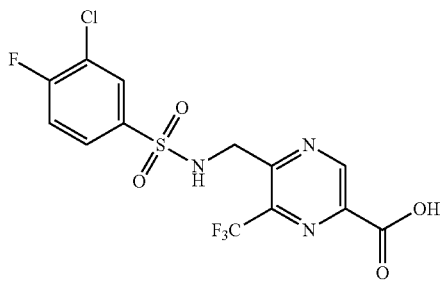 [SMILES: O=C(O)c1cnc(CNS(=O)(=O)c2ccc(F)c(Cl)c2)c(C(F)(F)F)n1]

To a solution of methyl 5-((3-chloro-4-fluorophenylsulfonamido)methyl)-6-(trifluoromethyl)pyrazine-2-carboxylate (0.2 g, 0.468 mmol) in 1,2-dichloroethane (40 mL) was added trimethyl tin hydroxide (0.11 g, 0.608 mmol) and the reaction mixture was heated at 80° C. for 18 h. The reaction mixture was concentrated to afford the title compound 5-((3-chloro-4-fluorophenylsulfonamido)methyl)-6-(trifluoromethyl)pyrazine-2-carboxylic acid (0.19 g, crude) as an off-white solid. The crude was as such taken for next step without further purification. Calculated M+H: 414.73. Found M+H: 414.0.

Step-10: Preparation of 5-((3-chloro-4-fluorophenylsulfonamido)methyl)-N-((2-methylthiazol-5-yl)methyl)-6-(trifluoromethyl)pyrazine-2-carboxamide

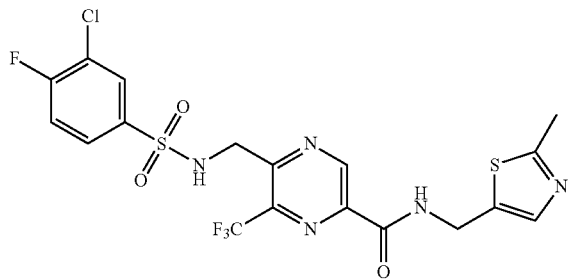 [SMILES: Cc1ncc(CNC(=O)c2cnc(CNS(=O)(=O)c3ccc(F)c(Cl)c3)c(C(F)(F)F)n2)s1]

To a solution of 5-((3-chloro-4-fluorophenylsulfonamido) methyl)-6-(trifluoromethyl)pyrazine-2-carboxylic acid (0.1 g, 0.241 mmol) and triethylamine (0.35 mL, 2.537 mmol) in dichloromethane (40 mL) cooled at 0° C., was added a solution of 1-propanephosphonic acid cyclic anhydride (0.46 mL, 0.61 mmol) and the reaction mixture was stirred at 0° C. for 15 minutes. Then (2-methylthiazol-5-yl)methanamine hydrochloride (0.048 g, 0.241 mmol) was added and the reaction mixture was stirred at room temperature for 1 h. Then the solution was diluted with dichloromethane (50 mL), washed with water (30 mL), brine (30 mL), dried over anhydrous sodium sulfate, filtered and concentrated. The crude was purified by preparative HPLC (analytical conditions: method-050314, column: Eclipse XDB-C18 (150 mm×4.6 mm×3.5 m), mobile phase (A): 0.01% ammonium hydroxide, mobile phase (B): acetonitrile, flow rate: 1.0 mL/min, gradient T/% B: 0/10, 2.5/10, 5/70, 11/70, 13/10, 15/10) to afford the title compound 5-((3-chloro-4-fluorophenylsulfonamido)methyl)-N-((2-methylthiazol-5-yl) methyl)-6-(trifluoromethyl)pyrazine-2-carboxamide (0.026 g, 20% yield) as an off-white solid. Calculated M+H: 524.91. Found M+H: 524.2.

Example 17—Biological Examples

Cell Culture and plating: HEK293 cells expressing NR1/NR2A (Chantest, Cleveland, Ohio) were grown to 70-80% confluency as an adherent monolayer in standard tissue culture flasks at 37° C., 5% $CO_2$ per supplier's instructions. NR2A expression was induced by incubation with 0.3-0.4 μg/ml tetracycline in the presence of 4 mM ARL-15896 for 18-24 hours under the same growth conditions, then transferred to 30° C. for another 3-5 hours.

After induction, cell culture medium was removed and cells were rinsed once with $Ca^{2+}$ and $Mg^{2+}$-free Dulbecco's phosphate buffered saline. Cells were then removed from the flask using TrypLE™ Express (Life Technologies) according to the manufacturer's instructions and collected to 50 ml centrifuge tubes. Following two washes in $Ca^{2+}/Mg^{2+}$-free HBSS with 20 mM HEPES (HHnoCa), cells were counted and viability assessed using trypan blue. To load cells with $Ca^{2+}$-sensitive dye, they were resuspended in fluo-8 plus Component B (AAT Bioquest Products) diluted in HHnoCa and incubated 15 minutes at 37° C., followed by 30 minutes at room temp (in dark). Cells were then washed and resuspended in HHnoCa to remove extracellular dye and plated in 384-well plates (Falcon, uncoated) at 20,000-30,000 cells/well in a final volume of 25 μL/well.

FDSS Assay: To each well of the plate, 10 μL test compound, control (MK801) or HHnoCa buffer was added to a final concentration of 10 μM with a final concentration of DMSO of 0.1%. Following 10 minutes pre-incubation in the dark, plates are loaded onto the Hamamatsu FDSS 6000. After collecting baseline fluorescence images, 3 μM glutamate, 3 μM glycine, and 1 mM $Ca^{2+}$ in HHnoCa buffer is added to each well, and $Ca^{2+}$ is recorded for 3 minutes. Data were processed by computing ratio of fluorescence at the end of data collection to baseline fluorescence to assess degree of $Ca^{2+}$ influx inhibition relative to that observed in MK801.

Table 14 below provides activity of each compound according to the legend that "++++" indicates inhibition at a concentration <100 nM; "+++" indicates inhibition at a concentration between 100 nM and 1 μM of the disclosed compound; "++" indicates inhibition at a concentration of from 1 μM to 10 μM; and "+" indicates inhibition at a concentration >10 μM.

TABLE 12

Biological Activity of Compounds of the Invention

| Structure | IUPAC | NR2A IC$_{50}$ (M) | Binned Activity |
|---|---|---|---|
| 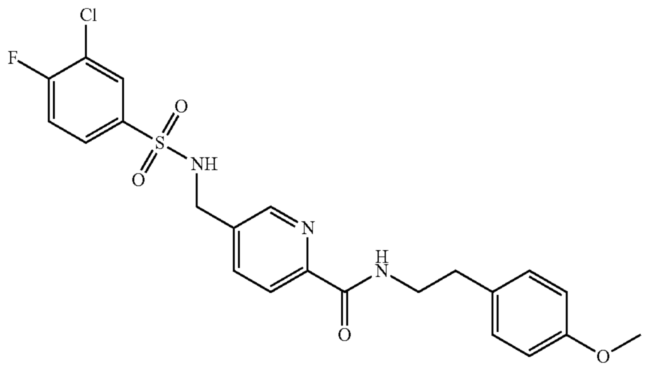 [SMILES: COc1ccc(CCNC(=O)c2ccc(CNS(=O)(=O)c3ccc(F)c(Cl)c3)cn2)cc1] | 5-(3-chloro-4-fluorobenzenesulfon-amidomethyl)-N-[2-(4-methoxyphenyl)ethyl]pyridine-2-carboxamide | 1.00E−05 | + |
| | 5-(3-chloro-4-fluorobenzenesulfon-amidomethyl)-N-[(3-methoxyphenyl)methyl]pyridine-2-carboxamide | 3.37E−06 | ++ |
| 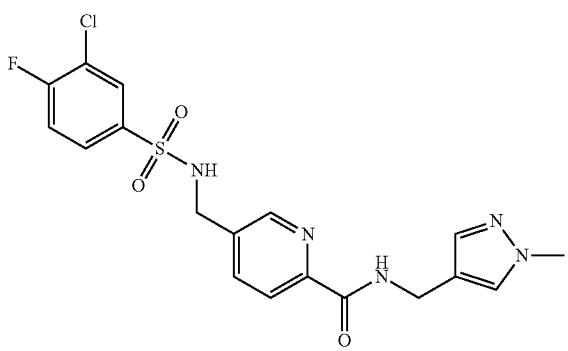 | 5-(3-chloro-4-fluorobenzenesulfon-amidomethyl)-N-[(1-methyl-1H-pyrazol-4-yl)methyl]pyridine-2-carboxamide | 4.59E−06 | ++ |
| 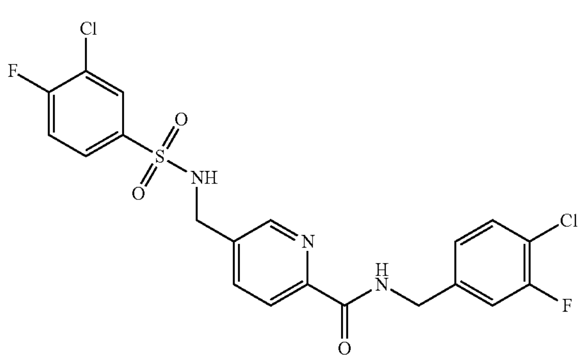 [SMILES: O=C(NCc1ccc(Cl)c(F)c1)c1ccc(CNS(=O)(=O)c2ccc(F)c(Cl)c2)cn1] | N-[(4-chloro-3-fluorophenyl)methyl]-5-(3-chloro-4-fluorobenzenesulfon-amidomethyl)pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 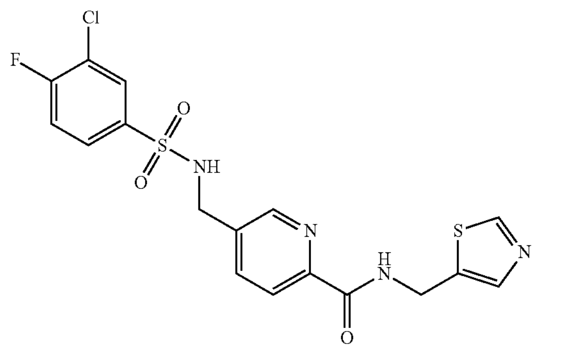 [SMILES: O=C(NCc1cncs1)c1ccc(CNS(=O)(=O)c2ccc(F)c(Cl)c2)cn1] | 5-(3-chloro-4-fluorobenzenesulfon-amidomethyl)-N-(1,3-thiazol-5-ylmethyl)pyridine-2-carboxamide | 3.47E−07 | +++ |
| 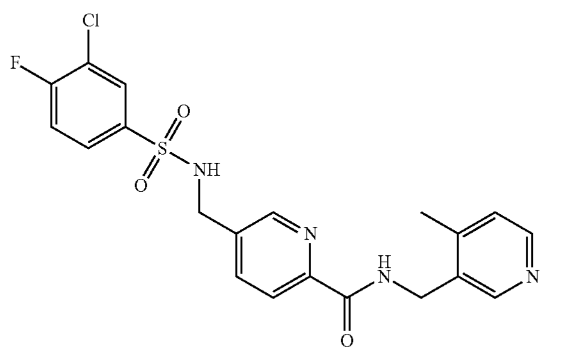 | 5-(3-chloro-4-fluorobenzenesulfon-amidomethyl)-N-[(4-methylpyridin-3-yl)methyl]pyridine-2-carboxamide | 1.87E−07 | +++ |
| 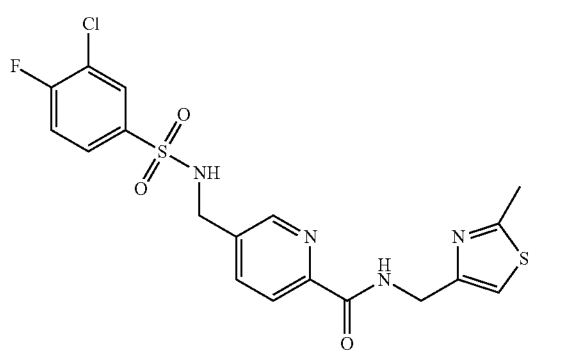 | 5-(3-chloro-4-fluorobenzenesulfon-amidomethyl)-N-[(2-methyl-1,3-thiazol-4-yl)methyl]pyridine-2-carboxamide | 1.00E−05 | + |
| 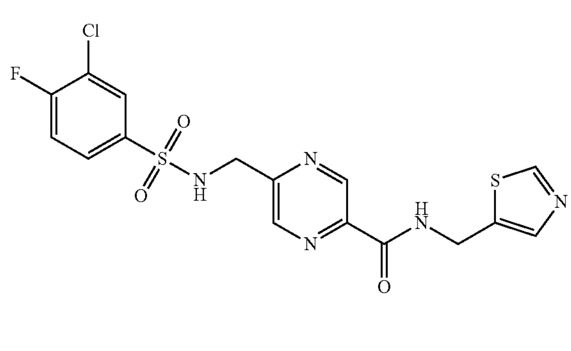 | 5-(3-chloro-4-fluorobenzenesulfon-amidomethyl)-N-(1,3-thiazol-5-ylmethyl)pyrazine-2-carboxamide | 9.29E−07 | +++ |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfonamidomethyl)-N-[(4-methoxyphenyl)methyl]pyrazine-2-carboxamide | 1.00E−05 | + |
| | 5-(3-chloro-4-fluorobenzenesulfonamidomethyl)-N-(pyridin-3-ylmethyl)pyridine-2-carboxamide | 7.58E−07 | +++ |
| | 5-(3-chloro-4-fluorobenzenesulfonamidomethyl)-N-[(4-methoxyphenyl)methyl]pyridine-2-carboxamide | 1.00E−05 | + |
| | 5-(3-chloro-4-fluorobenzenesulfonamidomethyl)-N-(pyrimidin-4-ylmethyl)pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfon-amidomethyl)-N-[(2-methyl-1,3-thiazol-5-yl)methyl]pyridine-2-carboxamide | 2.04E−07 | +++ |
| | 5-(3-chloro-4-fluorobenzenesulfon-amidomethyl)-N-(1,3-oxazol-4-ylmethyl)pyridine-2-carboxamide | 1.00E−05 | + |
| | 5-(3-chloro-4-fluorobenzenesulfon-amidomethyl)-N-(1,1-dioxo-1λ$^6$-thiolan-3-yl)pyridine-2-carboxamide | 1.00E−05 | + |
| | 6-(3-chloro-4-fluorobenzenesulfon-amidomethyl)-N-(1,3-thiazol-5-ylmethyl)pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
|  | 5-(3-chloro-4-fluorobenzenesulfon-amidomethyl)-N-[(4-methyl-1,3-thiazol-5-yl)methyl]pyridine-2-carboxamide | 1.00E−05 | + |
|  | 5-(3-chloro-4-fluorobenzenesulfon-amidomethyl)-N-[(dimethyl-1,3-thiazol-5-yl)methyl]pyridine-2-carboxamide | 1.00E−05 | + |
|  | 5-(3-chloro-4-fluorobenzenesulfon-amidomethyl)-N-(thiophen-2-ylmethyl)pyridine-2-carboxamide | 1.00E−05 | + |
|  | 5-(3-chloro-4-fluorobenzenesulfon-amidomethyl)-N-[(4-methylpyridin-3-yl)methyl]pyrazine-2-carboxamide | 1.08E−07 | +++ |

TABLE 12-continued

Biological Activity of Compounds of the Invention

| Structure | IUPAC | NR2A IC$_{50}$ (M) | Binned Activity |
|---|---|---|---|
|  | 5-(3-chloro-4-fluorobenzenesulfon-amidomethyl)-N-(pyrimidin-4-ylmethyl)pyrazine-2-carboxamide | 1.00E−05 | + |
|  | 5-(3-chloro-4-fluorobenzenesulfon-amidomethyl)-N-(1,3-oxazol-4-ylmethyl)pyrazine-2-carboxamide | 1.00E−05 | + |
|  | 5-(3-chloro-4-fluorobenzenesulfon-amidomethyl)-N-[(2-methyl-1,3-thiazol-4-yl)methyl]pyrazine-2-carboxamide | 1.00E−05 | + |
|  | 5-(3-chloro-4-fluorobenzenesulfon-amidomethyl)-N-(1,1-dioxo-1λ$^6$-thiolan-3-yl)pyrazine-2-carboxamide | 1.00E−05 | + |
|  | 5-(3-chloro-4-fluorobenzenesulfon-amidomethyl)-N-[(1-methyl-1H-imidazol-4-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 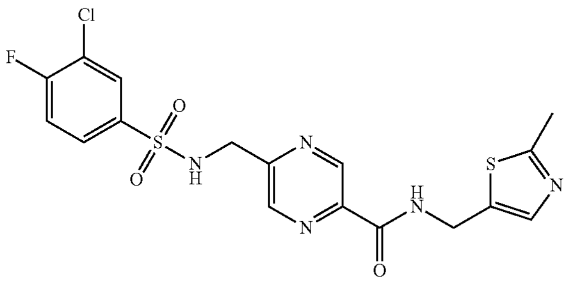 | 5-(3-chloro-4-fluorobenzenesulfonamidomethyl)-N-[(2-methyl-1,3-thiazol-5-yl)methyl]pyrazine-2-carboxamide | 6.10E−08 | ++++ |
| 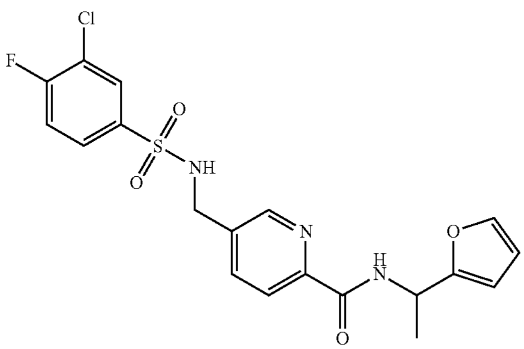 [SMILES: CC(NC(=O)c1ccc(CNS(=O)(=O)c2ccc(F)c(Cl)c2)cn1)c1ccco1] | 5-(3-chloro-4-fluorobenzenesulfonamidomethyl)-N-[1-(furan-2-yl)ethyl]pyridine-2-carboxamide | 5.51E−06 | ++ |
| 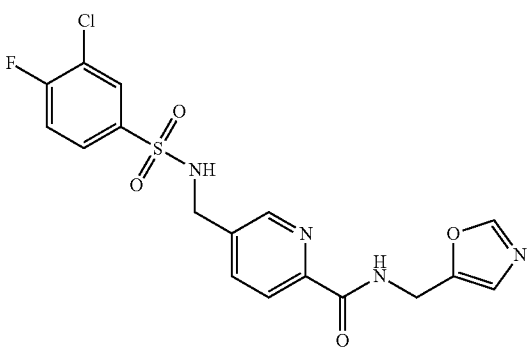 | 5-(3-chloro-4-fluorobenzenesulfonamidomethyl)-N-(1,3-oxazol-5-ylmethyl)pyridine-2-carboxamide | 1.95E−06 | ++ |
| 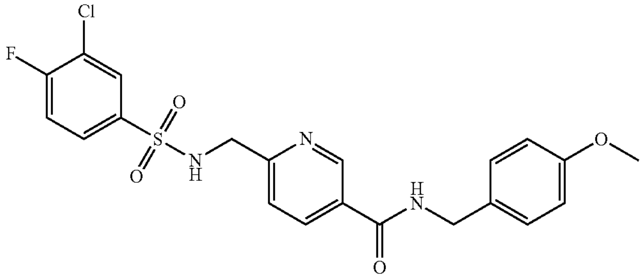 | 6-(3-chloro-4-fluorobenzenesulfonamidomethyl)-N-[(4-methoxyphenyl)methyl]pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 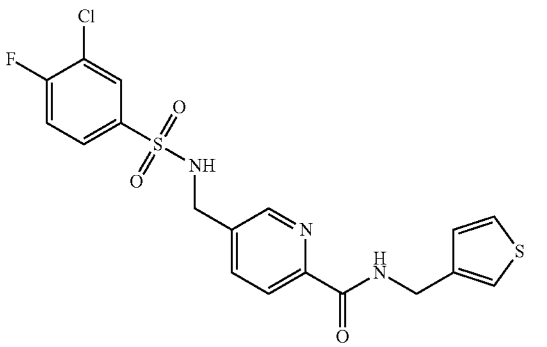 | 5-(3-chloro-4-fluorobenzenesulfonamidomethyl)-N-(thiophen-3-ylmethyl)pyridine-2-carboxamide | 1.00E−05 | + |
| 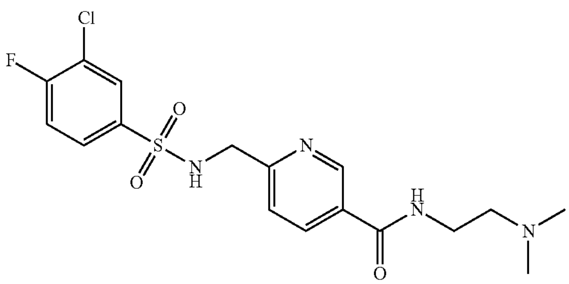 [SMILES: CN(C)CCNC(=O)c1ccc(CNS(=O)(=O)c2ccc(F)c(Cl)c2)nc1] | 6-(3-chloro-4-fluorobenzenesulfonamidomethyl)-N-[2-(dimethylamino)ethyl]pyridine-3-carboxamide | 1.00E−05 | + |
| 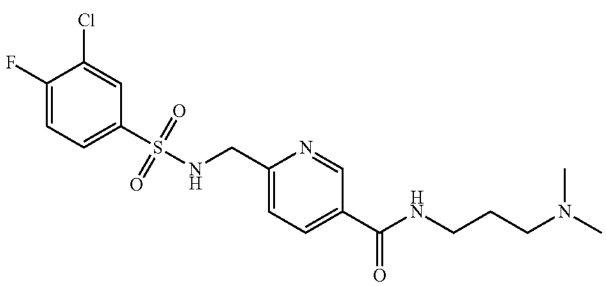 [SMILES: CN(C)CCCNC(=O)c1ccc(CNS(=O)(=O)c2ccc(F)c(Cl)c2)nc1] | 6-(3-chloro-4-fluorobenzenesulfonamidomethyl)-N-[3-(dimethylamino)propyl]pyridine-3-carboxamide | 1.00E−05 | + |
| 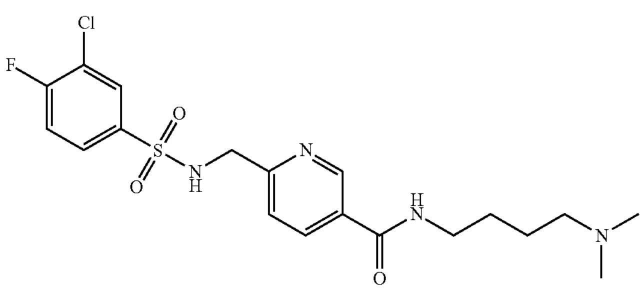 [SMILES: CN(C)CCCCNC(=O)c1ccc(CNS(=O)(=O)c2ccc(F)c(Cl)c2)nc1] | 6-(3-chloro-4-fluorobenzenesulfonamidomethyl)-N-[4-(dimethylamino)butyl]pyridine-3-carboxamide | 1.00E−05 | + |
| 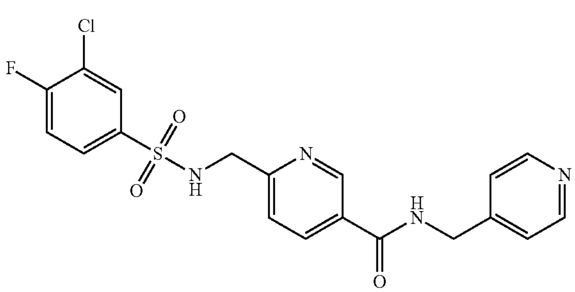 | 6-(3-chloro-4-fluorobenzenesulfonamidomethyl)-N-(pyridin-4-ylmethyl)pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-(pyridin-3-ylmethyl)pyridine-3-carboxamide | 1.10E−05 | + |
| | 6-(3-chloro-4-fluorobenzenesulfon-amidomethyl)-N-[(4-methylpyridin-3-yl)methyl]pyridine-3-carboxamide | 9.75E−06 | ++ |
| | 6-(3-chloro-4-fluorobenzenesulfon-amidomethyl)-N-[(1-methyl-1H-imidazol-4-yl)methyl]pyridine-3-carboxamide | 1.00E−05 | + |
| | 6-(3-chloro-4-fluorobenzenesulfon-amidomethyl)-N-(1,3-oxazol-4-ylmethyl)pyridine-3-carboxamide | 1.00E−05 | + |
| | 6-(3-chloro-4-fluorobenzenesulfon-amidomethyl)-N-(pyridin-2-ylmethyl)pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 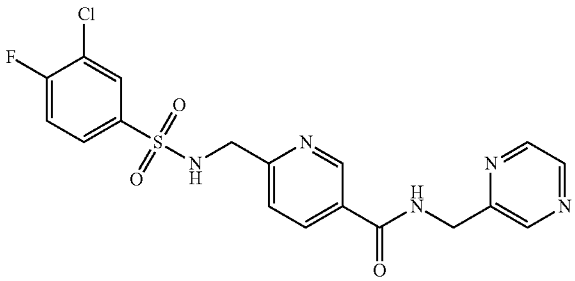 | 6-(3-chloro-4-fluorobenzenesulfonamidomethyl)-N-(pyrazin-2-ylmethyl)pyridine-3-carboxamide | 7.90E−07 | +++ |
| 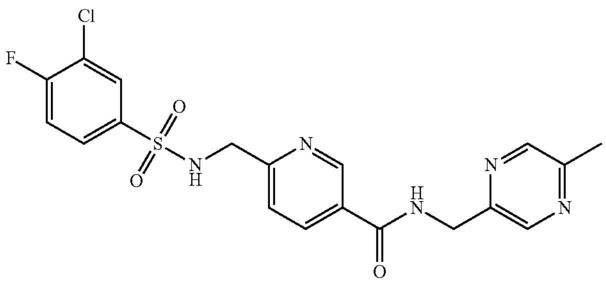 | 6-(3-chloro-4-fluorobenzenesulfonamidomethyl)-N-[(5-methylpyrazin-2-yl)methyl]pyridine-3-carboxamide | 6.30E−07 | +++ |
| 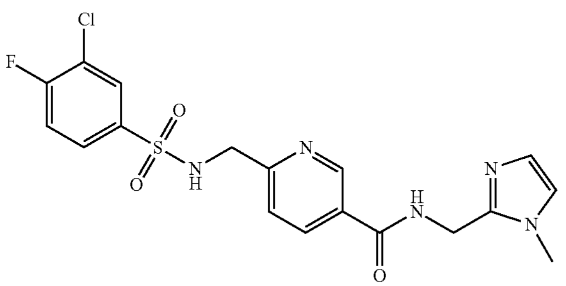 [SMILES: Cn1ccnc1CNC(=O)c1ccc(CNS(=O)(=O)c2ccc(F)c(Cl)c2)nc1] | 6-(3-chloro-4-fluorobenzenesulfonamidomethyl)-N-[(1-methyl-1H-imidazol-2-yl)methyl]pyridine-3-carboxamide | 1.08E−07 | +++ |
| 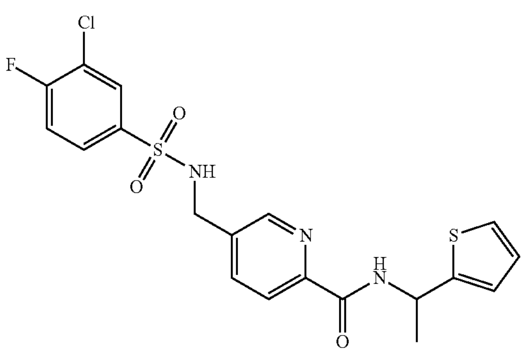 | 5-(3-chloro-4-fluorobenzenesulfonamidomethyl)-N-[1-(thiophen-2-yl)ethyl]pyridine-2-carboxamide | 2.40E−06 | ++ |
| 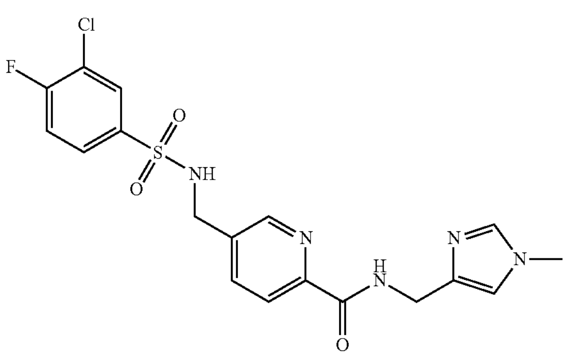 | 5-(3-chloro-4-fluorobenzenesulfonamidomethyl)-N-[(1-methyl-1H-imidazol-4-yl)methyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-(pyrimidin-4-ylmethyl)pyridine-3-carboxamide | 1.00E−05 | + |
| | 5-(3-chloro-4-fluorobenzenesulfon-amidomethyl)-N-(pyridin-3-ylmethyl)pyrazine-2-carboxamide | 4.39E−07 | +++ |
| | 5-(3-chloro-4-fluorobenzenesulfon-amidomethyl)-N-[(4-methyl-1,3-thiazol-5-yl)methyl]pyrazine-2-carboxamide | 1.00E−05 | + |
| | 5-(3-chloro-4-fluorobenzenesulfon-amidomethyl)-N-(pyridin-4-ylmethyl)pyrazine-2-carboxamide | 1.70E−06 | ++ |
| | 5-(3-chloro-4-fluorobenzenesulfon-amidomethyl)-N-(pyrazin-2-ylmethyl)pyrazine-2-carboxamide | 2.10E−06 | ++ |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfon-amidomethyl)-N-[(1-methyl-1H-pyrrol-2-yl)methyl]pyrazine-2-carboxamide | 3.09E−06 | ++ |
| | 5-(3-chloro-4-fluorobenzenesulfon-amidomethyl)-N-[(1,5-dimethyl-1H-pyrrol-2-yl)methyl]pyrazine-2-carboxamide | 7.57E−07 | +++ |
| | 5-(3-chloro-4-fluorobenzenesulfon-amidomethyl)-N-[(1-methyl-1H-pyrazol-5-yl)methyl]pyrazine-2-carboxamide | 1.00E−05 | + |
| | 6-(3-chloro-4-fluorobenzenesulfon-amidomethyl)-N-[(2-methyl-1,3-thiazol-4-yl)methyl]pyridine-3-carboxamide | 1.00E−05 | + |
| | 6-(3-chloro-4-fluorobenzenesulfon-amidomethyl)-N-[(dimethyl-1,3-thiazol-5-yl)methyl]pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
|  | 6-(3-chloro-4-fluorobenzenesulfonamidomethyl)-N-[(6-methylpyridin-2-yl)methyl]pyridine-3-carboxamide | 1.00E−05 | + |
|  | 6-(3-chloro-4-fluorobenzenesulfonamidomethyl)-N-[(1-methyl-1H-pyrrol-2-yl)methyl]pyridine-3-carboxamide | 1.00E−05 | + |
|  | 6-(3-chloro-4-fluorobenzenesulfonamidomethyl)-N-[(1,5-dimethyl-1H-pyrrol-2-yl)methyl]pyridine-3-carboxamide | 1.00E−05 | + |
|  | 5-(3-chloro-4-fluorobenzenesulfonamidomethyl)-N-(furan-3-ylmethyl)pyridine-2-carboxamide | 1.00E−05 | + |
|  | 6-(3-chloro-4-fluorobenzenesulfonamidomethyl)-N-[(1-methyl-1H-pyrazol-5-yl)methyl]pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-[(2-methoxypyridin-4-yl)methyl]pyridine-3-carboxamide | 1.00E−05 | + |
| | 6-(3-chloro-4-fluorobenzenesulfon-amidomethyl)-N-[(6-methoxypyridin-3-yl)methyl]pyridine-3-carboxamide | 1.00E−05 | + |
| | 6-(3-chloro-4-fluorobenzenesulfon-amidomethyl)-N-[(5-methylthiophen-2-yl)methyl]pyridine-3-carboxamide | 1.00E−05 | + |
| | 6-(3-chloro-4-fluorobenzenesulfon-amidomethyl)-N-(1,3-thiazol-2-ylmethyl)pyridine-3-carboxamide | 1.00E−05 | + |
| | 5-(3-chloro-4-fluorobenzenesulfon-amidomethyl)-N-[(1-methyl-1H-imidazol-5-yl)methyl]pyrazine-2-carboxamide | 8.95E−06 | ++ |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-(pyrimidin-2-ylmethyl)pyridine-3-carboxamide | 1.00E−05 | + |
| | 6-(3-chloro-4-fluorobenzenesulfon-amidomethyl)-N-[(2-methoxyphenyl)methyl]pyridine-3-carboxamide | 1.00E−05 | + |
| | 5-(3-chloro-4-fluorobenzenesulfon-amidomethyl)-N-(pyridin-2-ylmethyl)pyrazine-2-carboxamide | 1.00E−05 | + |
| | 5-(3-chloro-4-fluorobenzenesulfon-amidomethyl)-N-[(5-methylpyrazin-2-yl)methyl]pyrazine-2-carboxamide | 1.25E−06 | ++ |
| | 5-(3-chloro-4-fluorobenzenesulfon-amidomethyl)-N-[(6-methylpyridin-2-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfonamidomethyl)-N-[(1R)-1-(1,3-thiazol-5-yl)ethyl]pyridine-3-carboxamide | 1.00E−05 | + |
| | 6-(3-chloro-4-fluorobenzenesulfonamidomethyl)-N-(pyrimidin-5-ylmethyl)pyridine-3-carboxamide | 1.00E−05 | + |
| | 6-(3-chloro-4-fluorobenzenesulfonamidomethyl)-N-[(5-methyl-1,3,4-thiadiazol-2-yl)methyl]pyridine-3-carboxamide | 1.00E−05 | + |
| | 6-(3-chloro-4-fluorobenzenesulfonamidomethyl)-N-{[3-(trifluoromethyl)pyridin-2-yl]methyl}pyridine-3-carboxamide | 1.00E−05 | + |
| | 5-(3-chloro-4-fluorobenzenesulfonamidomethyl)-N-[2-(dimethylamino)ethyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfonamidomethyl)-N-(1,3-thiazol-5-ylmethyl)pyridazine-3-carboxamide | 1.00E−05 | + |
| | 6-(3-chloro-4-fluorobenzenesulfonamidomethyl)-N-(pyridin-2-ylmethyl)pyridazine-3-carboxamide | 1.00E−05 | + |
| | 6-(3-chloro-4-fluorobenzenesulfonamidomethyl)-N-[(2-methyl-1,3-thiazol-5-yl)methyl]pyridazine-3-carboxamide | 1.00E−05 | + |
| | 5-(3-chloro-4-fluorobenzenesulfonamidomethyl)-N-[(1R)-1-(1,3-thiazol-5-yl)ethyl]pyridine-2-carboxamide | 1.00E−05 | + |
| | 5-(3-chloro-4-fluorobenzenesulfonamidomethyl)-N-(furan-2-ylmethyl)pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
|  | 5-(3-chloro-4-fluorobenzenesulfonamidomethyl)-N-(pyridin-4-ylmethyl)pyridine-2-carboxamide | 1.00E−05 | + |
|  | 5-(3-chloro-4-fluorobenzenesulfonamidomethyl)-N-(pyrazin-2-ylmethyl)pyridine-2-carboxamide | 1.69E−06 | ++ |
|  | 5-(3-chloro-4-fluorobenzenesulfonamidomethyl)-N-(pyrimidin-5-ylmethyl)pyridine-2-carboxamide | 7.39E−06 | ++ |
|  | 5-(3-chloro-4-fluorobenzenesulfonamidomethyl)-N-(pyrimidin-2-ylmethyl)pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfon-amidomethyl)-N-[(6-methylpyridin-2-yl)methyl]pyridine-2-carboxamide | 1.00E−05 | + |
| | 5-(3-chloro-4-fluorobenzenesulfon-amidomethyl)-N-{[3-(trifluoromethyl)pyridin-2-yl]methyl}pyridine-2-carboxamide | 1.00E−05 | + |
| | 5-(3-chloro-4-fluorobenzenesulfon-amidomethyl)-N-{[3-chloro-5-(trifluoromethyl)pyridin-2-yl]methyl}pyridine-2-carboxamide | 1.00E−05 | + |
| | 5-(3-chloro-4-fluorobenzenesulfon-amidomethyl)-N-[(2-methoxypyridin-4-yl)methyl]pyridine-2-carboxamide | 3.02E−06 | ++ |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfon-amidomethyl)-N-[(6-methoxypyridin-3-yl)methyl]pyridine-2-carboxamide | 2.00E−06 | ++ |
| | 5-(3-chloro-4-fluorobenzenesulfon-amidomethyl)-N-[(1-methyl-1H-imidazol-5-yl)methyl]pyridine-2-carboxamide | 8.36E−06 | ++ |
| | 5-(3-chloro-4-fluorobenzenesulfon-amidomethyl)-N-[(5-methylthiophen-2-yl)methyl]pyridine-2-carboxamide | 1.00E−05 | + |
| | 5-(3-chloro-4-fluorobenzenesulfon-amidomethyl)-N-[(1-methyl-1H-pyrrol-2-yl)methyl]pyridine-2-carboxamide | 2.55E−06 | ++ |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfonamidomethyl)-N-(pyridin-2-ylmethyl)pyridine-2-carboxamide | 1.00E−05 | + |
| | 6-(3-chloro-4-fluorobenzenesulfonamidomethyl)-N-[(4-methoxyphenyl)methyl]pyridazine-3-carboxamide | 1.00E−05 | + |
| | 6-(3-chloro-4-fluorobenzenesulfonamidomethyl)-N-(furan-2-ylmethyl)pyridazine-3-carboxamide | 1.00E−05 | + |
| | 6-(3-chloro-4-fluorobenzenesulfonamidomethyl)-N-(pyridin-4-ylmethyl)pyridazine-3-carboxamide | 1.00E−05 | + |
| | 6-(3-chloro-4-fluorobenzenesulfonamidomethyl)-N-[(4-methylpyridin-3-yl)methyl]pyridazine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 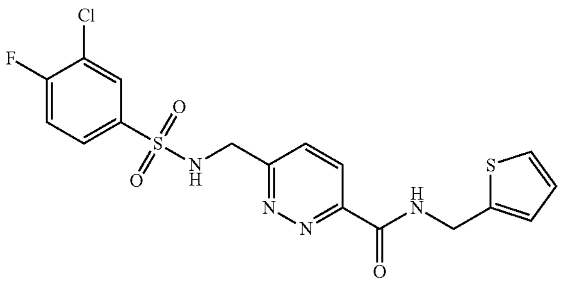 | 6-(3-chloro-4-fluorobenzenesulfon-amidomethyl)-N-(thiophen-2-ylmethyl)pyridazine-3-carboxamide | 1.00E−05 | + |
| 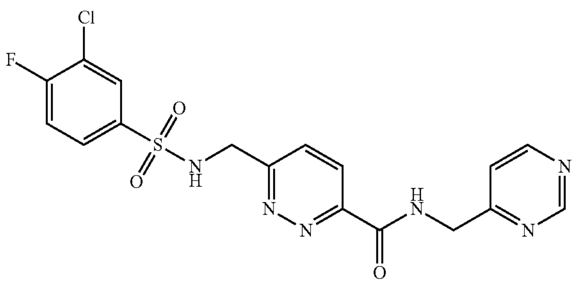 | 6-(3-chloro-4-fluorobenzenesulfon-amidomethyl)-N-(pyrimidin-4-ylmethyl)pyridazine-3-carboxamide | 1.00E−05 | + |
| 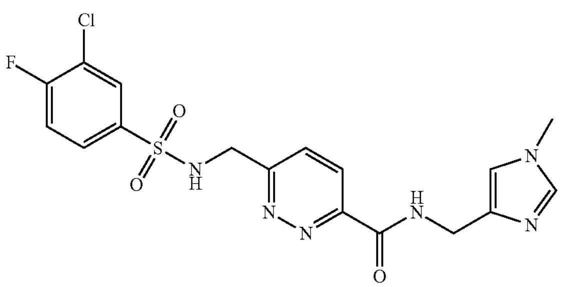 [SMILES: Cn1cnc(CNC(=O)c2ccc(CNS(=O)(=O)c3ccc(F)c(Cl)c3)nn2)c1] | 6-(3-chloro-4-fluorobenzenesulfon-amidomethyl)-N-[(1-methyl-1H-imidazol-4-yl)methyl]pyridazine-3-carboxamide | 1.00E−05 | + |
| 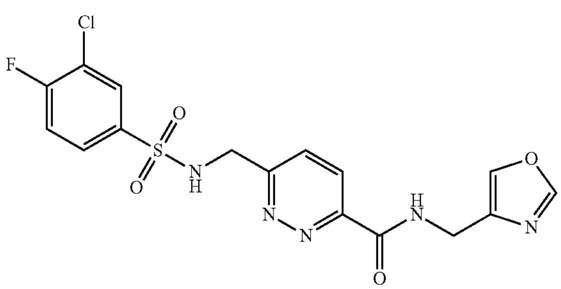 | 6-(3-chloro-4-fluorobenzenesulfon-amidomethyl)-N-(1,3-oxazol-4-ylmethyl)pyridazine-3-carboxamide | 1.00E−05 | + |
| 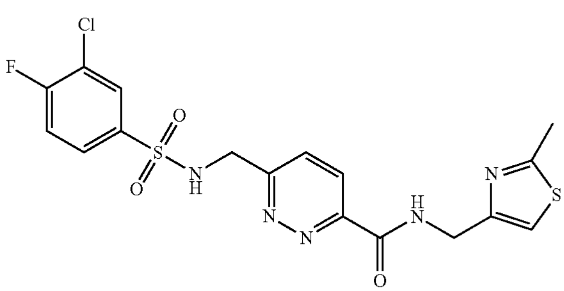 | 6-(3-chloro-4-fluorobenzenesulfon-amidomethyl)-N-[(2-methyl-1,3-thiazol-4-yl)methyl]pyridazine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-[(1R)-1-(1,3-thiazol-5-yl)ethyl]pyridazine-3-carboxamide | 1.00E−05 | + |
| | 6-(3-chloro-4-fluorobenzenesulfon-amidomethyl)-N-[(4-methyl-1,3-thiazol-5-yl)methyl]pyridazine-3-carboxamide | 1.00E−05 | + |
| | 6-(3-chloro-4-fluorobenzenesulfon-amidomethyl)-N-[(dimethyl-1,3-thiazol-5-yl)methyl]pyridazine-3-carboxamide | 1.00E−05 | + |
| | 6-(3-chloro-4-fluorobenzenesulfon-amidomethyl)-N-[1-(furan-2-yl)ethyl]pyridazine-3-carboxamide | 1.00E−05 | + |
| | 6-(3-chloro-4-fluorobenzenesulfon-amidomethyl)-N-(furan-3-ylmethyl)pyridazine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-(pyrazin-2-ylmethyl)pyridazine-3-carboxamide | 1.00E−05 | + |
| | 6-(3-chloro-4-fluorobenzenesulfon-amidomethyl)-N-(pyrimidin-2-ylmethyl)pyridazine-3-carboxamide | 1.00E−05 | + |
| | 5-(3-chloro-4-fluorobenzenesulfon-amidomethyl)-N-[3-(dimethylamino)propyl]pyridine-2-carboxamide | 1.00E−05 | + |
| | 6-(3-chloro-4-fluorobenzenesulfon-amidomethyl)-N-[2-(4-methoxyphenyl)ethyl]pyridazine-3-carboxamide | 1.00E−05 | + |
| | 6-(3-chloro-4-fluorobenzenesulfon-amidomethyl)-N-(pyridin-3-ylmethyl)pyridazine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 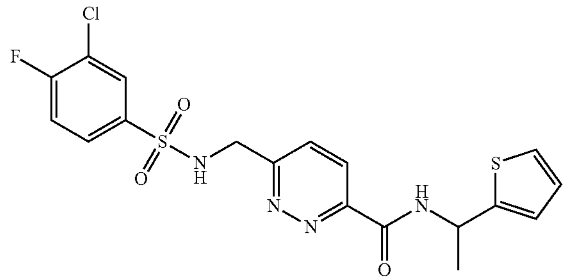 [SMILES: CC(NC(=O)c1ccc(CNS(=O)(=O)c2ccc(F)c(Cl)c2)nn1)c1cccs1] | 6-(3-chloro-4-fluorobenzenesulfon-amidomethyl)-N-[1-(thiophen-2-yl)ethyl]pyridazine-3-carboxamide | 1.00E−05 | + |
| 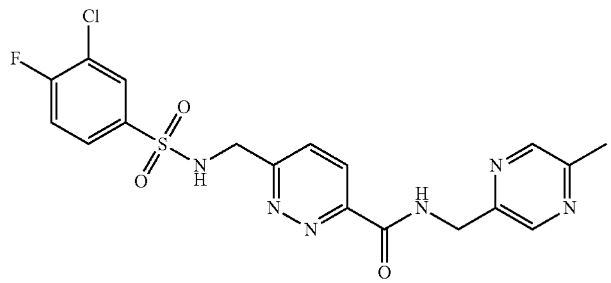 | 6-(3-chloro-4-fluorobenzenesulfon-amidomethyl)-N-[(5-methylpyrazin-2-yl)methyl]pyridazine-3-carboxamide | 1.00E−05 | + |
| 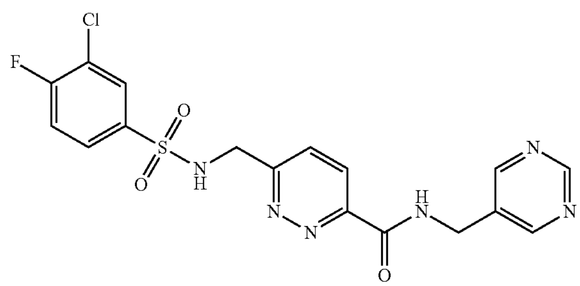 | 6-(3-chloro-4-fluorobenzenesulfon-amidomethyl)-N-(pyrimidin-5-ylmethyl)pyridazine-3-carboxamide | 1.00E−05 | + |
| 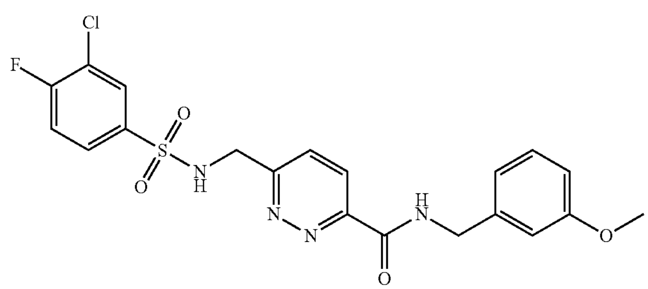 [SMILES: COc1cccc(CNC(=O)c2ccc(CNS(=O)(=O)c3ccc(F)c(Cl)c3)nn2)c1] | 6-(3-chloro-4-fluorobenzenesulfon-amidomethyl)-N-[(3-methoxyphenyl)methyl]pyridazine-3-carboxamide | 1.00E−05 | + |
| 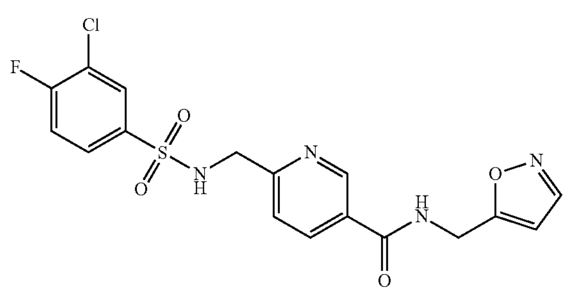 [SMILES: O=C(NCc1ccno1)c1ccc(CNS(=O)(=O)c2ccc(F)c(Cl)c2)nc1] | 6-(3-chloro-4-fluorobenzenesulfon-amidomethyl)-N-(1,2-oxazol-5-ylmethyl)pyridine-3-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 5-(3-chloro-4-fluorobenzenesulfon-amidomethyl)-N-(1,3-thiazol-2-ylmethyl)pyrazine-2-carboxamide | 1.00E−05 | + |
| | 5-(3-chloro-4-fluorobenzenesulfon-amidomethyl)-N-[(4-methyl-1,3-thiazol-2-yl)methyl]pyrazine-2-carboxamide | 1.00E−05 | |
| | 5-(3-chloro-4-fluorobenzenesulfon-amidomethyl)-N-[(5-methyl-1,3,4-oxadiazol-2-yl)methyl]pyridine-2-carboxamide | 2.83E−06 | ++ |
| | 5-(3-chloro-4-fluorobenzenesulfon-amidomethyl)-N-[(5-methyl-1,3,4-thiadiazol-2-yl)methyl]pyridine-2-carboxamide | 1.02E−06 | ++ |

TABLE 12-continued

Biological Activity of Compounds of the Invention

| Structure | IUPAC | NR2A IC$_{50}$ (M) | Binned Activity |
|---|---|---|---|
| 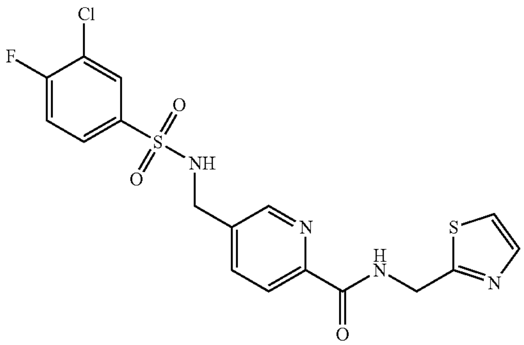 [SMILES: O=C(NCc1nccs1)c1ccc(CNS(=O)(=O)c2ccc(F)c(Cl)c2)cn1] | 5-(3-chloro-4-fluorobenzenesulfonamidomethyl)-N-(1,3-thiazol-2-ylmethyl)pyridine-2-carboxamide | 9.13E−06 | ++ |
| 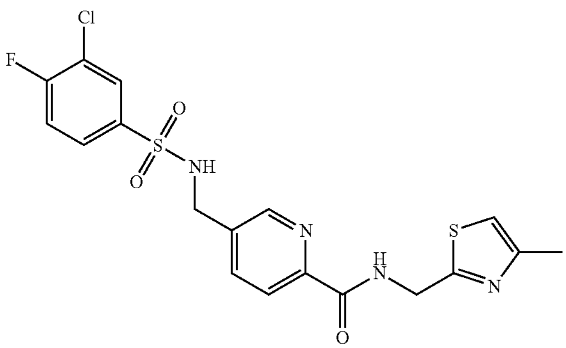 [SMILES: Cc1csc(CNC(=O)c2ccc(CNS(=O)(=O)c3ccc(F)c(Cl)c3)cn2)n1] | 5-(3-chloro-4-fluorobenzenesulfonamidomethyl)-N-[(4-methyl-1,3-thiazol-2-yl)methyl]pyridine-2-carboxamide | 1.00E−05 | + |
| 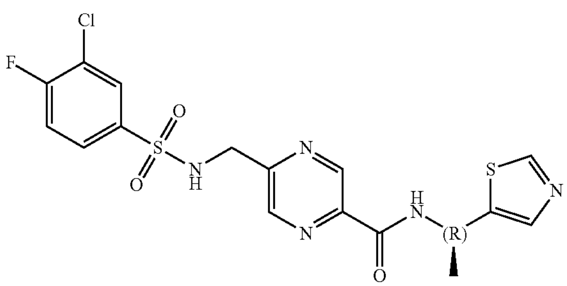 | 5-(3-chloro-4-fluorobenzenesulfonamidomethyl)-N-[(1R)-1-(1,3-thiazol-5-yl)ethyl]pyrazine-2-carboxamide | 1.05E−05 | + |
| 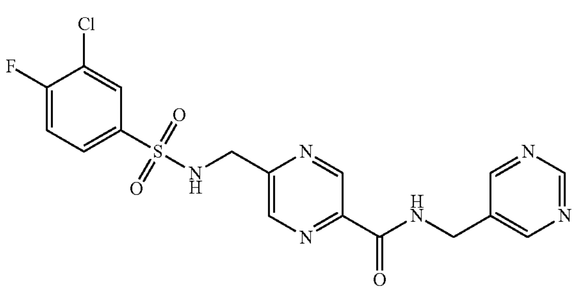 | 5-(3-chloro-4-fluorobenzenesulfonamidomethyl)-N-(pyrimidin-5-ylmethyl)pyrazine-2-carboxamide | 4.84E−06 | ++ |
| 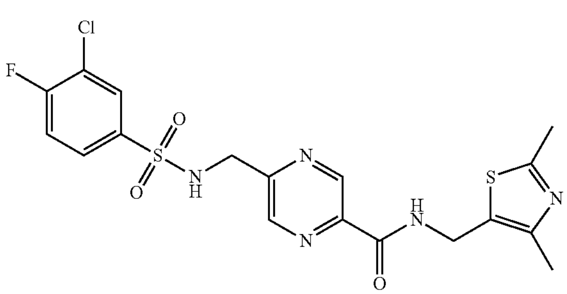 | 5-(3-chloro-4-fluorobenzenesulfonamidomethyl)-N-[(dimethyl-1,3-thiazol-5-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 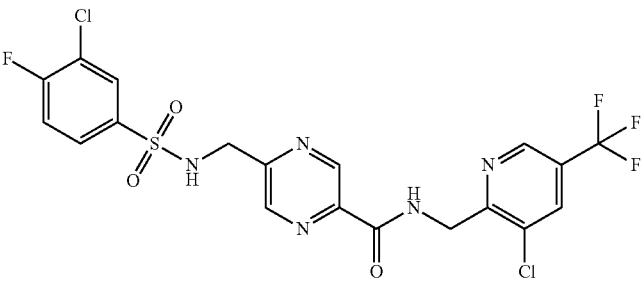 [SMILES: O=C(NCc1ncc(C(F)(F)F)cc1Cl)c1cnc(CNS(=O)(=O)c2ccc(F)c(Cl)c2)cn1] | 5-(3-chloro-4-fluorobenzenesulfon-amidomethyl)-N-{[3-chloro-5-(trifluoromethyl)pyridin-2-yl]methyl}pyrazine-2-carboxamide | 1.00E−05 | + |
| 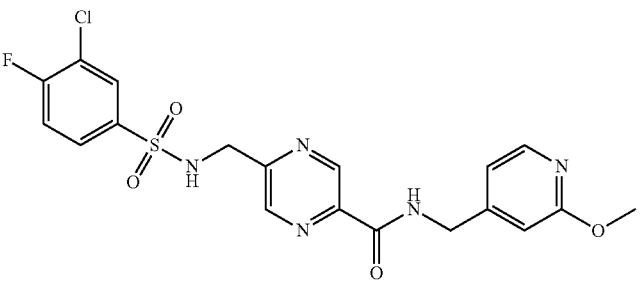 [SMILES: COc1cc(CNC(=O)c2cnc(CNS(=O)(=O)c3ccc(F)c(Cl)c3)cn2)ccn1] | 5-(3-chloro-4-fluorobenzenesulfon-amidomethyl)-N-[(2-methoxypyridin-4-yl)methyl]pyrazine-2-carboxamide | 8.50E−07 | +++ |
| 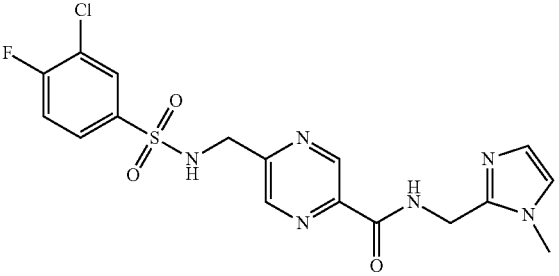 [SMILES: Cn1ccnc1CNC(=O)c1cnc(CNS(=O)(=O)c2ccc(F)c(Cl)c2)cn1] | 5-(3-chloro-4-fluorobenzenesulfon-amidomethyl)-N-[(1-methyl-1H-imidazol-2-yl)methyl]pyrazine-2-carboxamide | 1.00E−05 | + |
| 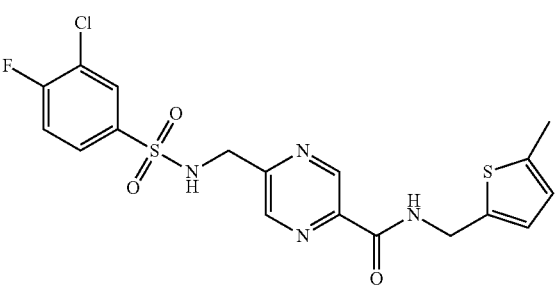 [SMILES: Cc1ccc(CNC(=O)c2cnc(CNS(=O)(=O)c3ccc(F)c(Cl)c3)cn2)s1] | 5-(3-chloro-4-fluorobenzenesulfon-amidomethyl)-N-[(5-methylthiophen-2-yl)methyl]pyrazine-2-carboxamide | 1.00E−05 | + |
| 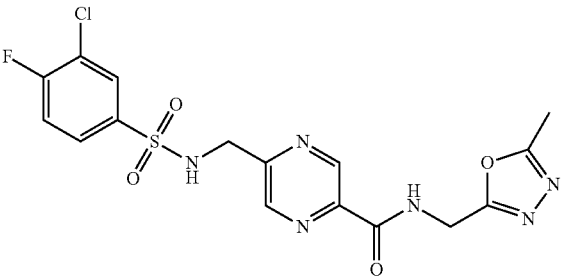 | 5-(3-chloro-4-fluorobenzenesulfon-amidomethyl)-N-[(5-methyl-1,3,4-oxadiazol-2-yl)methyl]pyrazine-2-carboxamide | 2.43E−06 | ++ |

TABLE 12-continued

Biological Activity of Compounds of the Invention

| Structure | IUPAC | NR2A IC$_{50}$ (M) | Binned Activity |
|---|---|---|---|
| 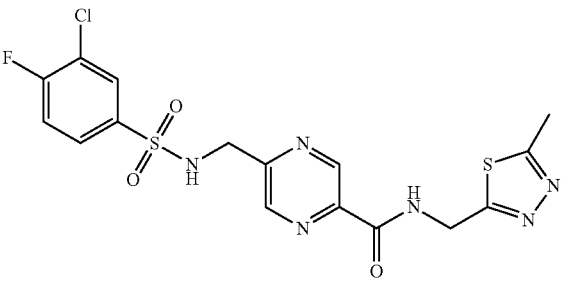 | 5-(3-chloro-4-fluorobenzenesulfonamidomethyl)-N-[(5-methyl-1,3,4-thiadiazol-2-yl)methyl]pyrazine-2-carboxamide | 6.24E−07 | +++ |
| 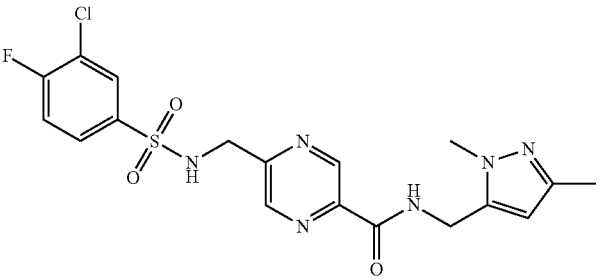 [SMILES: Cc1cc(CNC(=O)c2cnc(CNS(=O)(=O)c3ccc(F)c(Cl)c3)cn2)n(C)n1] | 5-(3-chloro-4-fluorobenzenesulfonamidomethyl)-N-[(1,3-dimethyl-1H-pyrazol-5-yl)methyl]pyrazine-2-carboxamide | 1.00E−05 | + |
| 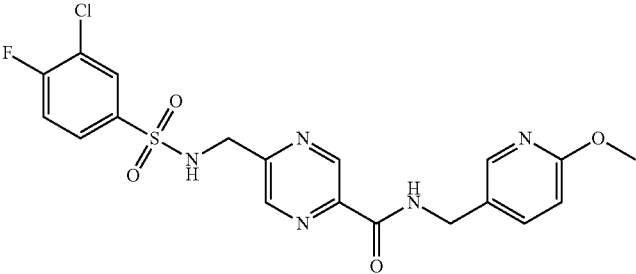 | 5-(3-chloro-4-fluorobenzenesulfonamidomethyl)-N-[(6-methoxypyridin-3-yl)methyl]pyrazine-2-carboxamide | 1.00E−05 | + |
| 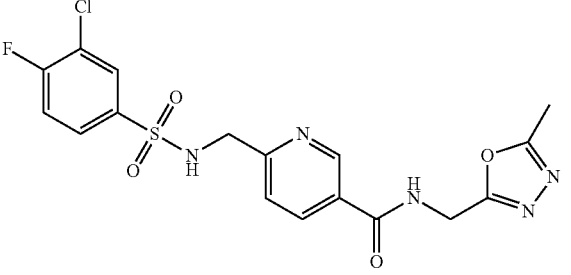 | 6-(3-chloro-4-fluorobenzenesulfonamidomethyl)-N-[(5-methyl-1,3,4-oxadiazol-2-yl)methyl]pyridine-3-carboxamide | 1.00E−05 | + |
| 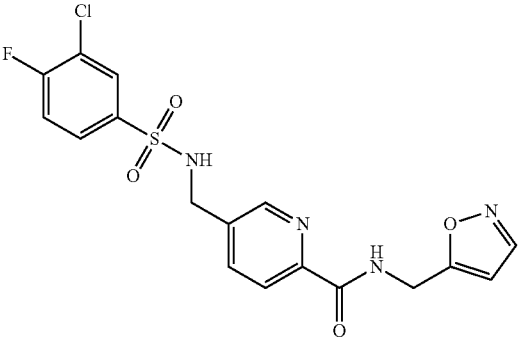 [SMILES: O=C(NCc1ccno1)c1ccc(CNS(=O)(=O)c2ccc(F)c(Cl)c2)cn1] | 5-(3-chloro-4-fluorobenzenesulfonamidomethyl)-N-(1,2-oxazol-5-ylmethyl)pyridine-2-carboxamide | 2.18E−06 | ++ |

TABLE 12-continued

Biological Activity of Compounds of the Invention

| Structure | IUPAC | NR2A IC$_{50}$ (M) | Binned Activity |
|---|---|---|---|
| 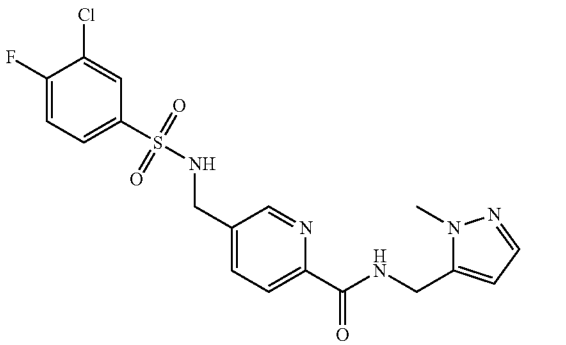 | 5-(3-chloro-4-fluorobenzenesulfon-amidomethyl)-N-[(1-methyl-1H-pyrazol-5-yl)methyl]pyridine-2-carboxamide | 1.00E−05 | + |
| 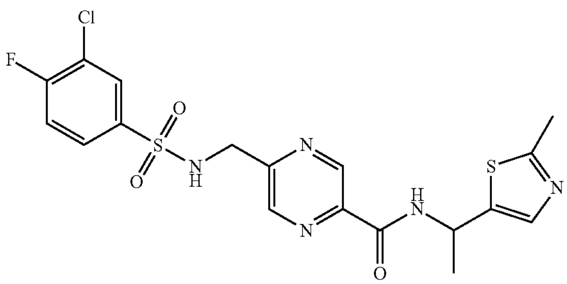 | 5-(3-chloro-4-fluorobenzenesulfon-amidomethyl)-N-[1-(2-methyl-1,3-thiazol-5-yl)ethyl]pyrazine-2-carboxamide | 1.80E−07 | +++ |
| 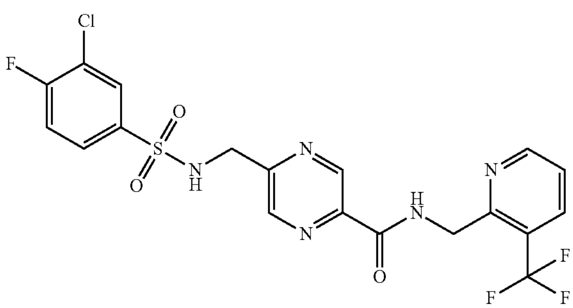 | 5-(3-chloro-4-fluorobenzenesulfon-amidomethyl)-N-{[3-(trifluoromethyl)pyridin-2-yl]methyl}pyrazine-2-carboxamide | 1.00E−05 | + |
| 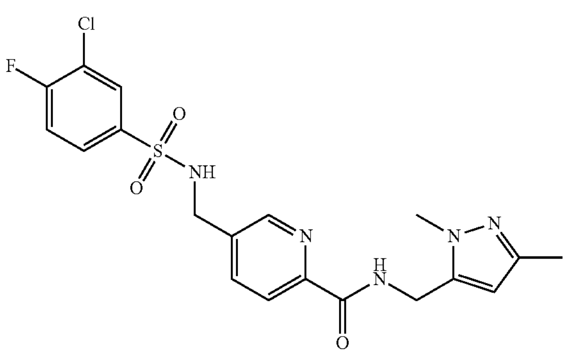 [SMILES: Cc1cc(CNC(=O)c2ccc(CNS(=O)(=O)c3ccc(F)c(Cl)c3)cn2)n(C)n1] | 5-(3-chloro-4-fluorobenzenesulfon-amidomethyl)-N-[(1,3-dimethyl-1H-pyrazol-5-yl)methyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 6-(3-chloro-4-fluorobenzenesulfon-amidomethyl)-N-{[3-chloro-5-(trifluoromethyl)pyridin-2-yl]methyl}pyridine-3-carboxamide | 1.00E−05 | + |
| | 6-(3-chloro-4-fluorobenzenesulfon-amidomethyl)-N-[(4-methyl-1,3-thiazol-2-yl)methyl]pyridine-3-carboxamide | 1.00E−05 | + |
| | 6-(3-chloro-4-fluorobenzenesulfon-amidomethyl)-N-[(1,3-dimethyl-1H-pyrazol-5-yl)methyl]pyridine-3-carboxamide | 1.00E−05 | + |
| | 6-(3-chloro-4-fluorobenzenesulfon-amidomethyl)-N-(1,1-dioxo-1λ$^{6}$-thiolan-3-yl)pyridine-3-carboxamide | 1.00E−05 | + |
| | 5-(2-fluorobenzenesulfon-amidomethyl)-N-[(2-methyl-1,3-thiazol-5-yl)methyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 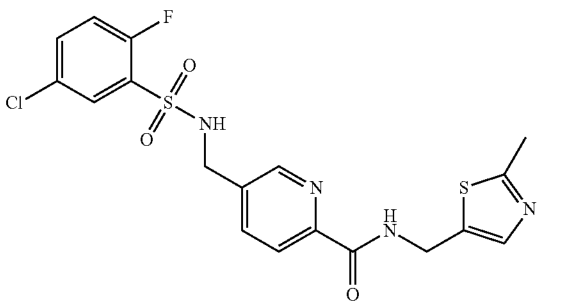 [SMILES: Cc1ncc(CNC(=O)c2ccc(CNS(=O)(=O)c3cc(Cl)ccc3F)cn2)s1] | 5-(5-chloro-2-fluorobenzenesulfon-amidomethyl)-N-[(2-methyl-1,3-thiazol-5-yl)methyl]pyridine-2-carboxamide | 1.00E−05 | + |
| 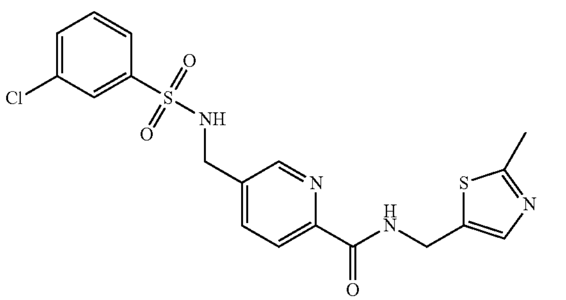 [SMILES: Cc1ncc(CNC(=O)c2ccc(CNS(=O)(=O)c3cccc(Cl)c3)cn2)s1] | 5-(3-chlorobenzenesulfon-amidomethyl)-N-[(2-methyl-1,3-thiazol-5-yl)methyl]pyridine-2-carboxamide | 1.04E−06 | ++ |
| 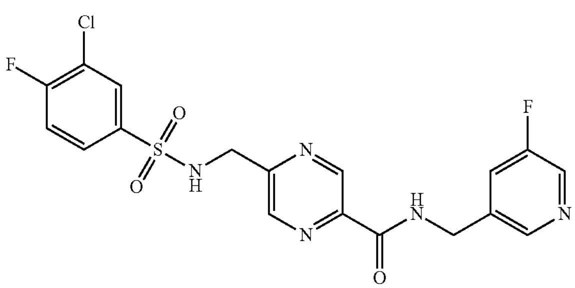 [SMILES: O=C(NCc1cncc(F)c1)c1cnc(CNS(=O)(=O)c2ccc(F)c(Cl)c2)cn1] | 5-(3-chloro-4-fluorobenzenesulfon-amidomethyl)-N-[(5-fluoropyridin-3-yl)methyl]pyrazine-2-carboxamide | 1.10E−06 | ++ |
| 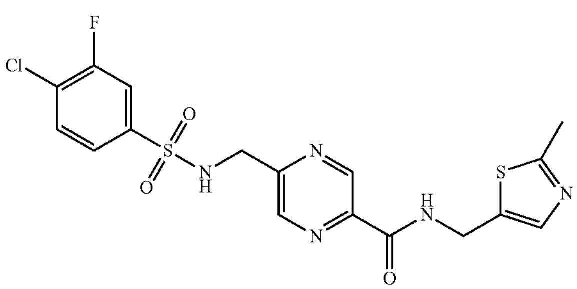 | 5-(4-chloro-3-fluorobenzenesulfon-amidomethyl)-N-[(2-methyl-1,3-thiazol-5-yl)methyl]pyrazine-2-carboxamide | 1.00E−05 | + |
| 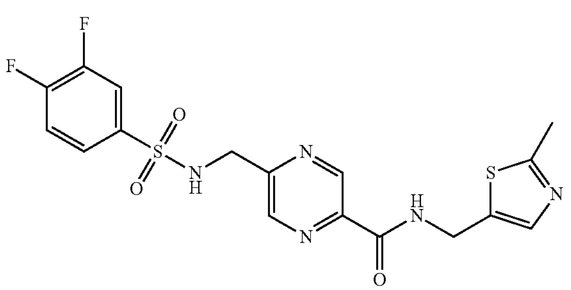 [SMILES: Cc1ncc(CNC(=O)c2cnc(CNS(=O)(=O)c3ccc(F)c(F)c3)cn2)s1] | 5-(3,4-difluorobenzenesulfon-amidomethyl)-N-[(2-methyl-1,3-thiazol-5-yl)methyl]pyrazine-2-carboxamide | 3.13E−07 | +++ |

TABLE 12-continued

Biological Activity of Compounds of the Invention

| Structure | IUPAC | NR2A IC$_{50}$ (M) | Binned Activity |
|---|---|---|---|
| 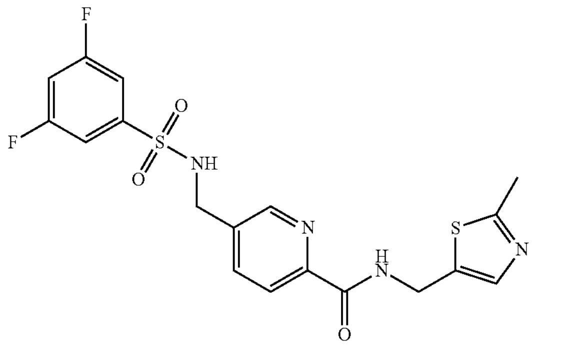 [SMILES: Cc1ncc(CNC(=O)c2ccc(CNS(=O)(=O)c3cc(F)cc(F)c3)cn2)s1] | 5-(3,5-difluorobenzenesulfon-amidomethyl)-N-[(2-methyl-1,3-thiazol-5-yl)methyl]pyridine-2-carboxamide | 1.00E−05 | + |
| 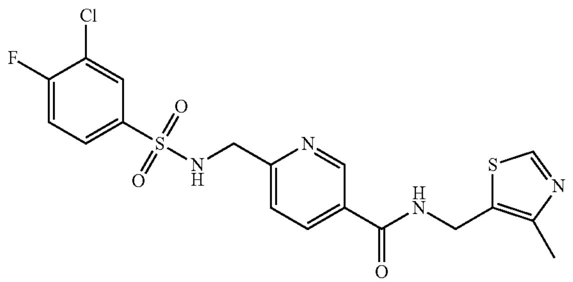 | 6-(3-chloro-4-fluorobenzenesulfon-amidomethyl)-N-[(4-methyl-1,3-thiazol-5-yl)methyl]pyridine-3-carboxamide | 1.00E−05 | + |
| 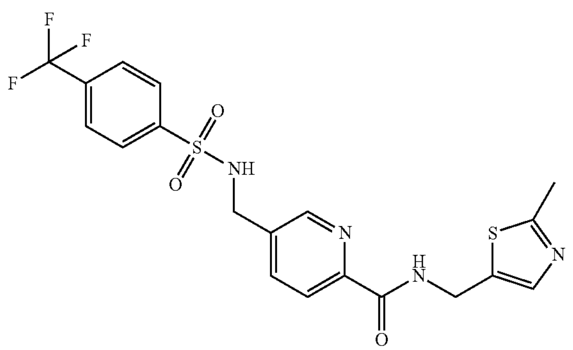 [SMILES: Cc1ncc(CNC(=O)c2ccc(CNS(=O)(=O)c3ccc(C(F)(F)F)cc3)cn2)s1] | N-[(2-methyl-1,3-thiazol-5-yl)methyl]-5-[4-(trifluoromethyl)benzene-sulfonamidomethyl]pyridine-2-carboxamide | 1.00E−05 | + |
| 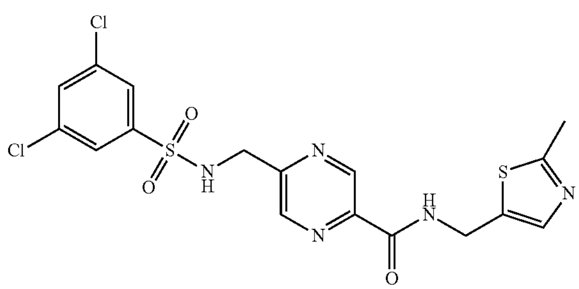 [SMILES: Cc1ncc(CNC(=O)c2cnc(CNS(=O)(=O)c3cc(Cl)cc(Cl)c3)cn2)s1] | 5-(3,5-dichlorobenzenesulfon-amidomethyl)-N-[(2-methyl-1,3-thiazol-5-yl)methyl]pyrazine-2-carboxamide | 1.00E−05 | + |
| 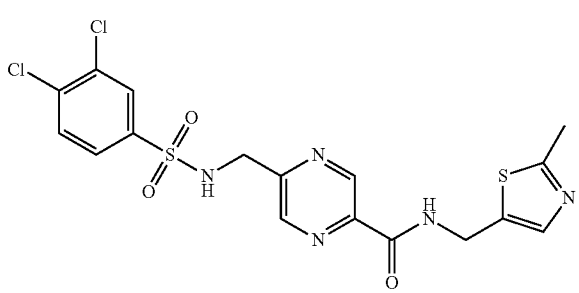 | 5-(3,4-dichlorobenzenesulfon-amidomethyl)-N-[(2-methyl-1,3-thiazol-5-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 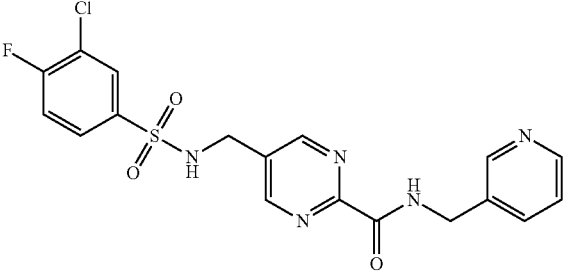 [SMILES: O=C(NCc1cccnc1)c1ncc(CNS(=O)(=O)c2ccc(F)c(Cl)c2)cn1] | 5-(3-chloro-4-fluorobenzenesulfon-amidomethyl)-N-(pyridin-3-ylmethyl)pyrimidine-2-carboxamide | 1.00E−05 | + |
| 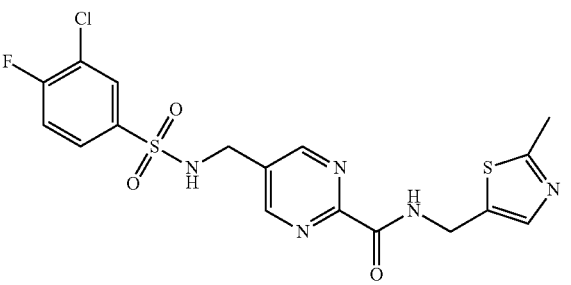 [SMILES: Cc1ncc(CNC(=O)c2ncc(CNS(=O)(=O)c3ccc(F)c(Cl)c3)cn2)s1] | 5-(3-chloro-4-fluorobenzenesulfon-amidomethyl)-N-[(2-methyl-1,3-thiazol-5-yl)methyl]pyrimidine-2-carboxamide | 1.00E−05 | + |
| 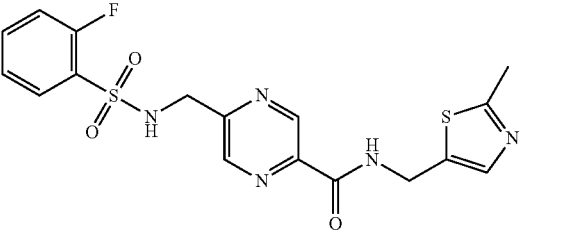 [SMILES: Cc1ncc(CNC(=O)c2cnc(CNS(=O)(=O)c3ccccc3F)cn2)s1] | 5-(2-fluorobenzenesulfon-amidomethyl)-N-[(2-methyl-1,3-thiazol-5-yl)methyl]pyrazine-2-carboxamide | 1.00E−05 | + |
| 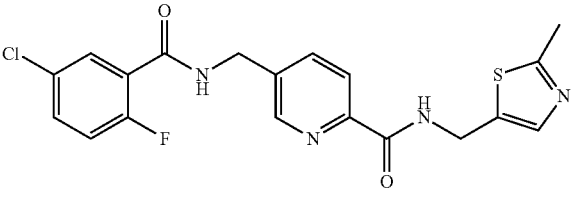 [SMILES: Cc1ncc(CNC(=O)c2ccc(CNC(=O)c3cc(Cl)ccc3F)cn2)s1] | 5-{[(5-chloro-2-fluorophenyl)formamido]methyl}-N-[(2-methyl-1,3-thiazol-5-yl)methyl]pyridine-2-carboxamide | 1.00E−05 | + |
| 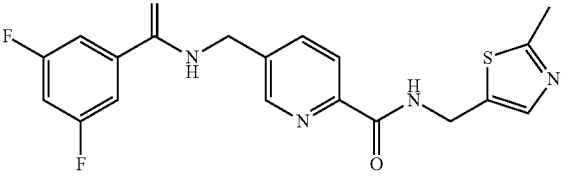 | 5-{[(3,5-difluorophenyl)form-amido]methyl}-N-[(2-methyl-1,3-thiazol-5-yl)methyl]pyridine-2-carboxamide | 1.00E−05 | + |
| 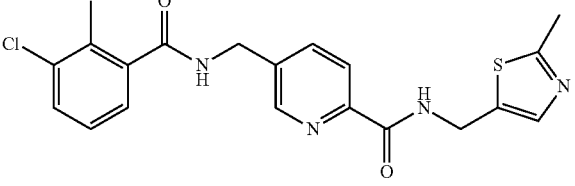 | 5-{[(3-chloro-2-methylphenyl)formamido]methyl}-N-[(2-methyl-1,3-thiazol-5-yl)methyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 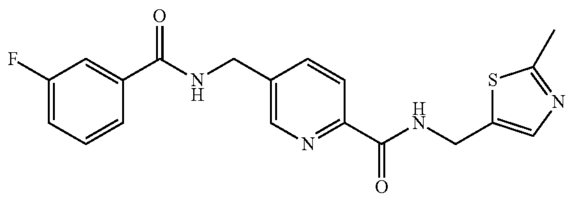 [SMILES: Cc1ncc(CNC(=O)c2ccc(CNC(=O)c3cccc(F)c3)cn2)s1] | 5-{[(3-fluorophenyl)formamido]methyl}-N-[(2-methyl-1,3-thiazol-5-yl)methyl]pyridine-2-carboxamide | 1.00E−05 | + |
| 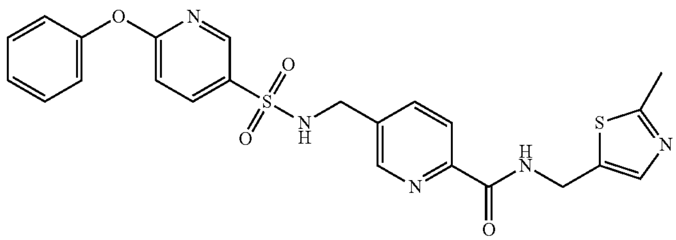 [SMILES: Cc1ncc(CNC(=O)c2ccc(CNS(=O)(=O)c3ccc(Oc4ccccc4)nc3)cn2)s1] | N-[(2-methyl-1,3-thiazol-5-yl)methyl]-5-(6-phenoxypyridine-3-sulfonamidomethyl)pyridine-2-carboxamide | 1.00E−05 | + |
| | 5-(3,5-dichlorobenzenesulfonamidomethyl)-N-[(2-methyl-1,3-thiazol-5-yl)methyl]pyridine-2-carboxamide | 1.00E−05 | + |
| 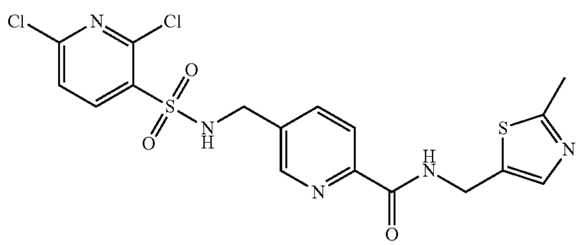 [SMILES: Cc1ncc(CNC(=O)c2ccc(CNS(=O)(=O)c3ccc(Cl)nc3Cl)cn2)s1] | 5-(2,6-dichloropyridine-3-sulfonamidomethyl)-N-[(2-methyl-1,3-thiazol-5-yl)methyl]pyridine-2-carboxamide | 1.00E−05 | + |
| | 5-{[(2,4-dichlorophenyl)formamido]methyl}-N-[(2-methyl-1,3-thiazol-5-yl)methyl]pyridine-2-carboxamide | 1.00E−05 | + |
| | 5-(3,4-dichlorobenzenesulfonamidomethyl)-N-[(2-methyl-1,3-thiazol-5-yl)methyl]pyridine-2-carboxamide | 6.68E−06 | ++ |

TABLE 12-continued

Biological Activity of Compounds of the Invention

| Structure | IUPAC | NR2A IC$_{50}$ (M) | Binned Activity |
|---|---|---|---|
| 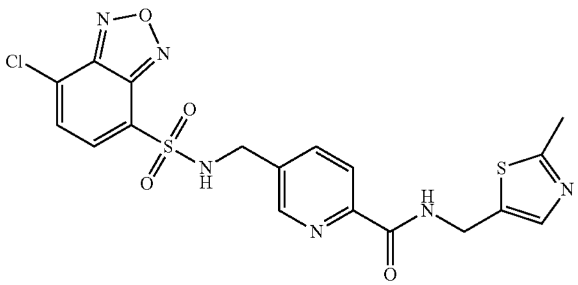 [SMILES: Cc1ncc(CNC(=O)c2ccc(CNS(=O)(=O)c3ccc(Cl)c4nonc34)cn2)s1] | 5-(7-chloro-2,1,3-benzoxadiazole-4-sulfonamidomethyl)-N-[(2-methyl-1,3-thiazol-5-yl)methyl]pyridine-2-carboxamide | 1.00E−05 | + |
| 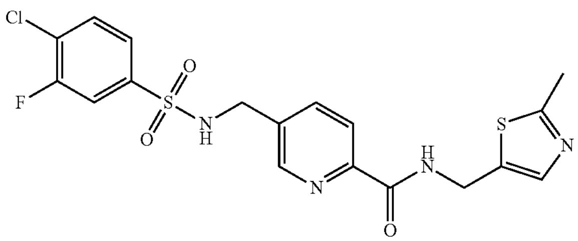 [SMILES: Cc1ncc(CNC(=O)c2ccc(CNS(=O)(=O)c3ccc(Cl)c(F)c3)cn2)s1] | 5-(4-chloro-3-fluorobenzenesulfonamidomethyl)-N-[(2-methyl-1,3-thiazol-5-yl)methyl]pyridine-2-carboxamide | 7.45E−06 | ++ |
| 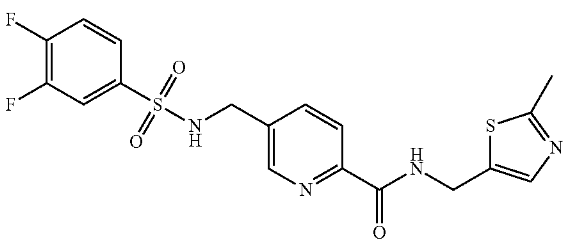 [SMILES: Cc1ncc(CNC(=O)c2ccc(CNS(=O)(=O)c3ccc(F)c(F)c3)cn2)s1] | 5-(3,4-difluorobenzenesulfonamidomethyl)-N-[(2-methyl-1,3-thiazol-5-yl)methyl]pyridine-2-carboxamide | 2.19E−07 | +++ |
| 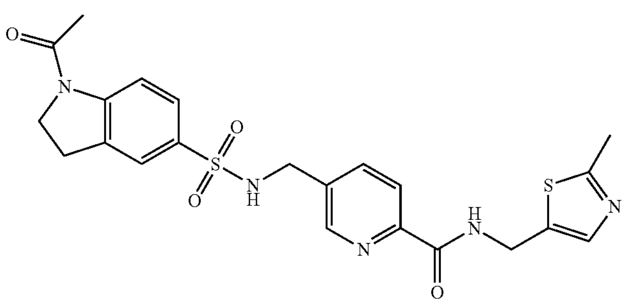 [SMILES: CC(=O)N1CCc2cc(S(=O)(=O)NCc3ccc(C(=O)NCc4cnc(C)s4)nc3)ccc21] | 5-(1-acetyl-2,3-dihydro-1H-indole-5-sulfonamidomethyl)-N-[(2-methyl-1,3-thiazol-5-yl)methyl]pyridine-2-carboxamide | 1.00E−05 | + |
| 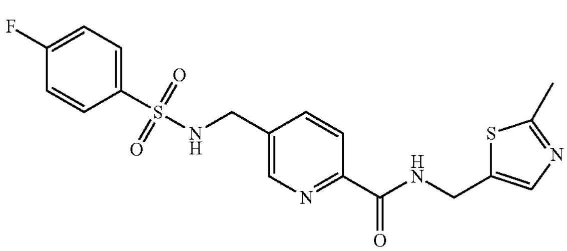 [SMILES: Cc1ncc(CNC(=O)c2ccc(CNS(=O)(=O)c3ccc(F)cc3)cn2)s1] | 5-(4-fluorobenzenesulfonamidomethyl)-N-[(2-methyl-1,3-thiazol-5-yl)methyl]pyridine-2-carboxamide | 2.84E−06 | ++ |
| 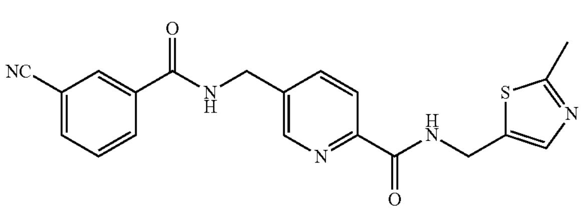 [SMILES: Cc1ncc(CNC(=O)c2ccc(CNC(=O)c3cccc(C#N)c3)cn2)s1] | 5-{[(3-cyanophenyl)formamido]methyl}-N-[(2-methyl-1,3-thiazol-5-yl)methyl]pyridine-2-carboxamide | 1.00E−05 | + |

US 9,963,434 B2

TABLE 12-continued

Biological Activity of Compounds of the Invention

| Structure | IUPAC | NR2A IC$_{50}$ (M) | Binned Activity |
|---|---|---|---|
| 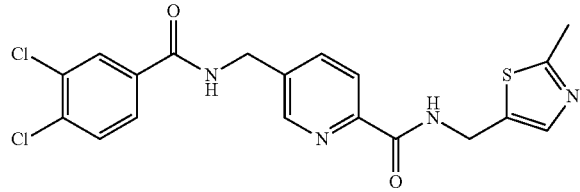 [SMILES: Cc1ncc(CNC(=O)c2ccc(CNC(=O)c3ccc(Cl)c(Cl)c3)cn2)s1] | 5-{[(3,4-dichlorophenyl)form-amido]methyl}-N-[(2-methyl-1,3-thiazol-5-yl)methyl]pyridine-2-carboxamide | 1.00E−05 | + |
| 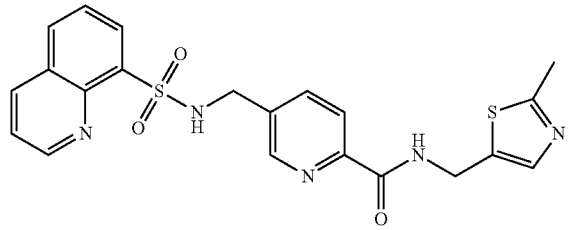 | N-[(2-methyl-1,3-thiazol-5-yl)methyl]-5-(quinoline-8-sulfonamidomethyl)pyridine-2-carboxamide | 1.00E−05 | + |
| 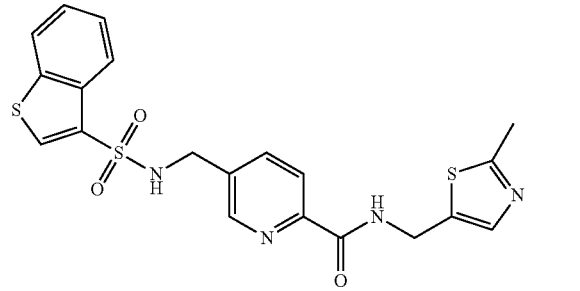 [SMILES: Cc1ncc(CNC(=O)c2ccc(CNS(=O)(=O)c3csc4ccccc34)cn2)s1] | 5-(1-benzothiophene-3-sulfonamidomethyl)-N-[(2-methyl-1,3-thiazol-5-yl)methyl]pyridine-2-carboxamide | 1.00E−05 | + |
| 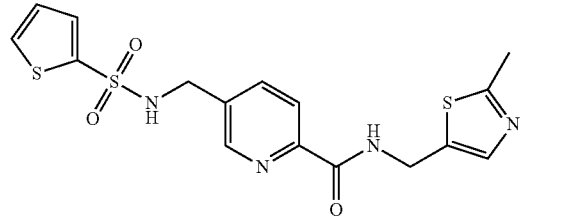 [SMILES: Cc1ncc(CNC(=O)c2ccc(CNS(=O)(=O)c3cccs3)cn2)s1] | N-[(2-methyl-1,3-thiazol-5-yl)methyl]-5-(thiophene-2-sulfonamidomethyl)pyridine-2-carboxamide | 4.02E−06 | ++ |
| 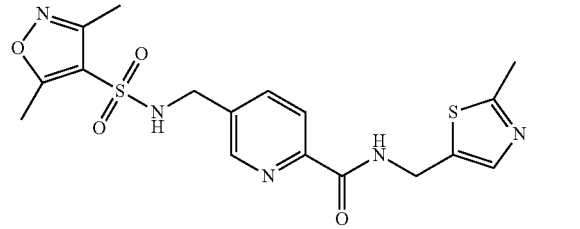 [SMILES: Cc1ncc(CNC(=O)c2ccc(CNS(=O)(=O)c3c(C)noc3C)cn2)s1] | 5-(dimethyl-1,2-oxazole-4-sulfonamidomethyl)-N-[(2-methyl-1,3-thiazol-5-yl)methyl]pyridine-2-carboxamide | 1.00E−05 | + |
| 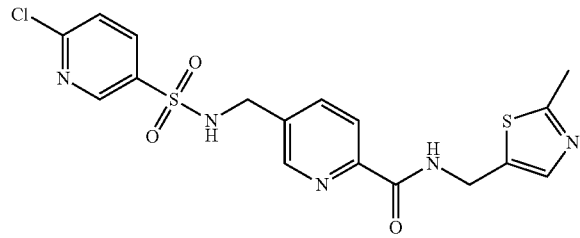 [SMILES: Cc1ncc(CNC(=O)c2ccc(CNS(=O)(=O)c3ccc(Cl)nc3)cn2)s1] | 5-(6-chloropyridine-3-sulfonamidomethyl)-N-[(2-methyl-1,3-thiazol-5-yl)methyl]pyridine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 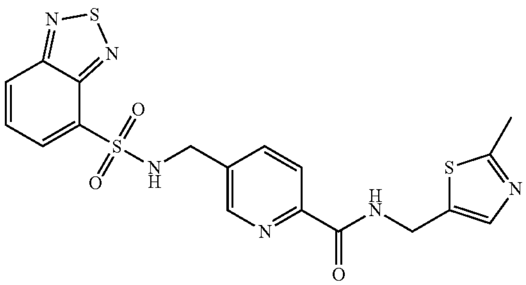 [SMILES: Cc1ncc(CNC(=O)c2ccc(CNS(=O)(=O)c3cccc4nsnc34)cn2)s1] | 5-(2,1,3-benzothiadiazole-4-sulfonamidomethyl)-N-[(2-methyl-1,3-thiazol-5-yl)methyl]pyridine-2-carboxamide | 1.00E−05 | + |
| 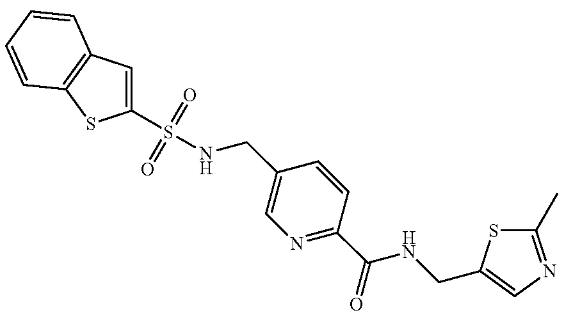 [SMILES: Cc1ncc(CNC(=O)c2ccc(CNS(=O)(=O)c3cc4ccccc4s3)cn2)s1] | 5-(1-benzothiophene-2-sulfonamidomethyl)-N-[(2-methyl-1,3-thiazol-5-yl)methyl]pyridine-2-carboxamide | 1.00E−05 | + |
| 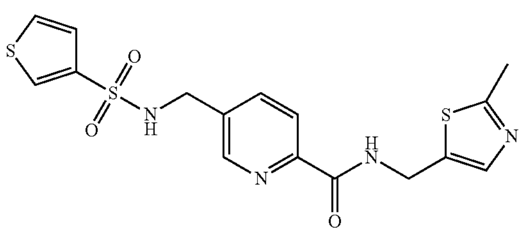 [SMILES: Cc1ncc(CNC(=O)c2ccc(CNS(=O)(=O)c3ccsc3)cn2)s1] | N-[(2-methyl-1,3-thiazol-5-yl)methyl]-5-(thiophene-3-sulfonamidomethyl)pyridine-2-carboxamide | 1.00E−05 | + |
| | 5-(3-chlorobenzenesulfonamidomethyl)-N-[(2-methyl-1,3-thiazol-5-yl)methyl]pyrazine-2-carboxamide | 8.39E−07 | +++ |
| | 5-(3,5-difluorobenzenesulfonamidomethyl)-N-[(2-methyl-1,3-thiazol-5-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 5-(4-fluorobenzenesulfon-amidomethyl)-N-[(2-methyl-1,3-thiazol-5-yl)methyl]pyrazine-2-carboxamide | 5.51E−06 | ++ |
| 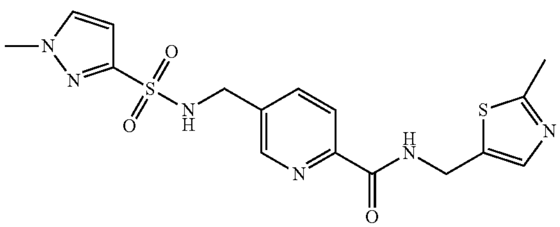 [SMILES: Cc1ncc(CNC(=O)c2ccc(CNS(=O)(=O)c3ccn(C)n3)cn2)s1] | N-[(2-methyl-1,3-thiazol-5-yl)methyl]-5-(1-methyl-1H-pyrazole-3-sulfonamidomethyl)pyridine-2-carboxamide | 1.00E−05 | + |
| 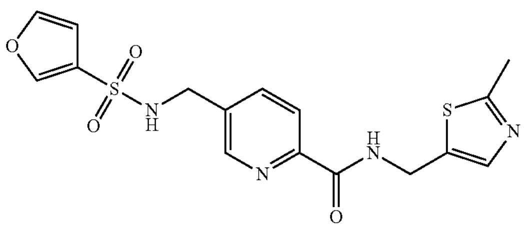 [SMILES: Cc1ncc(CNC(=O)c2ccc(CNS(=O)(=O)c3ccoc3)cn2)s1] | 5-(furan-3-sulfonamidomethyl)-N-[(2-methyl-1,3-thiazol-5-yl)methyl]pyridine-2-carboxamide | 1.00E−05 | + |
| 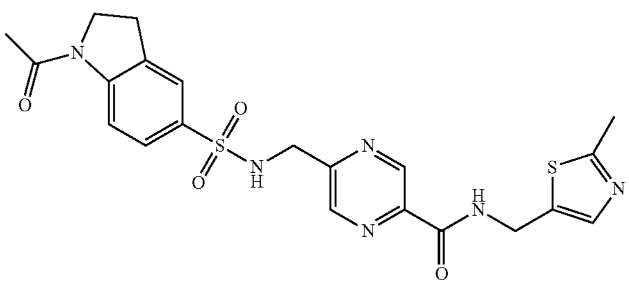 [SMILES: CC(=O)N1CCc2cc(S(=O)(=O)NCc3cnc(C(=O)NCc4cnc(C)s4)cn3)ccc21] | 5-(1-acetyl-2,3-dihydro-1H-indole-5-sulfonamidomethyl)-N-[(2-methyl-1,3-thiazol-5-yl)methyl]pyrazine-2-carboxamide | 1.00E−05 | + |
| 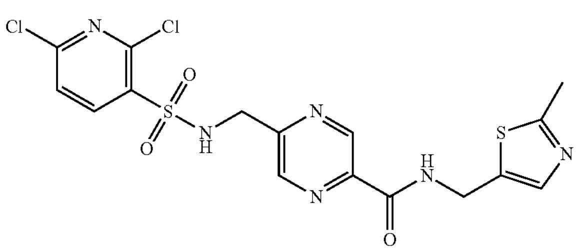 [SMILES: Cc1ncc(CNC(=O)c2cnc(CNS(=O)(=O)c3ccc(Cl)nc3Cl)cn2)s1] | 5-(2,6-dichloropyridine-3-sulfonamidomethyl)-N-[(2-methyl-1,3-thiazol-5-yl)methyl]pyrazine-2-carboxamide | 1.00E−05 | + |
| 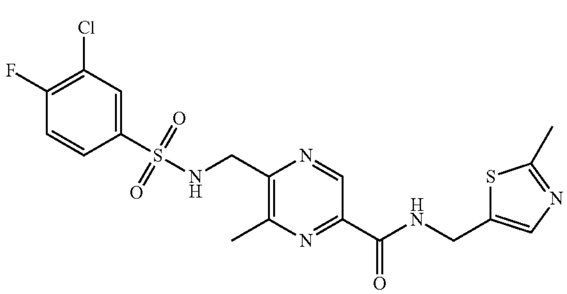 [SMILES: Cc1ncc(CNC(=O)c2cnc(CNS(=O)(=O)c3ccc(F)c(Cl)c3)c(C)n2)s1] | 5-(3-chloro-4-fluorobenzenesulfon-amidomethyl)-6-methyl-N-[(2-methyl-1,3-thiazol-5-yl)methyl]pyrazine-2-carboxamide | 1.96E−08 | ++++ |

TABLE 12-continued

Biological Activity of Compounds of the Invention

| Structure | IUPAC | NR2A IC$_{50}$ (M) | Binned Activity |
|---|---|---|---|
| 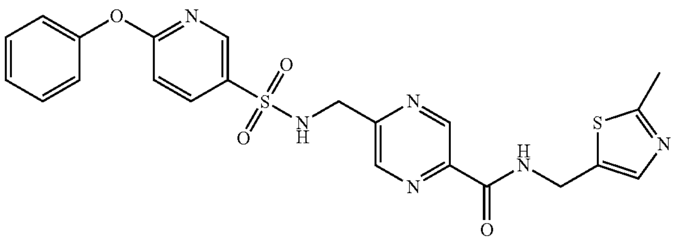 [SMILES: Cc1ncc(CNC(=O)c2cnc(CNS(=O)(=O)c3ccc(Oc4ccccc4)nc3)cn2)s1] | N-[(2-methyl-1,3-thiazol-5-yl)methyl]-5-(6-phenoxypyridine-3-sulfonamidomethyl)pyrazine-2-carboxamide | 1.00E−05 | + |
| 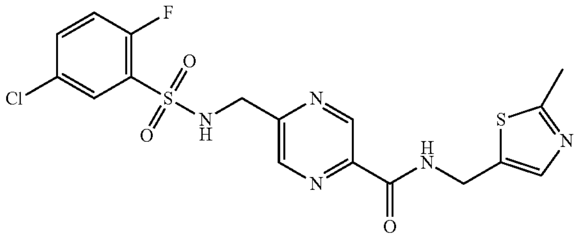 [SMILES: Cc1ncc(CNC(=O)c2cnc(CNS(=O)(=O)c3cc(Cl)ccc3F)cn2)s1] | 5-(5-chloro-2-fluorobenzenesulfon-amidomethyl)-N-[(2-methyl-1,3-thiazol-5-yl)methyl]pyrazine-2-carboxamide | 1.00E−05 | + |
| 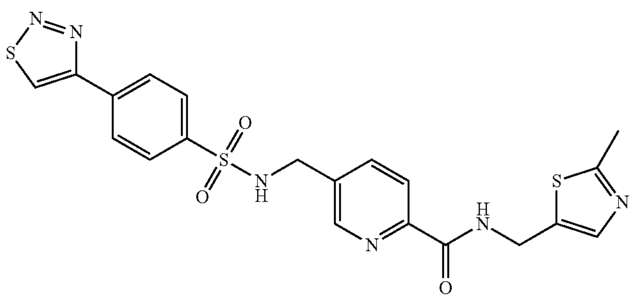 [SMILES: Cc1ncc(CNC(=O)c2ccc(CNS(=O)(=O)c3ccc(-c4csnn4)cc3)cn2)s1] | N-[(2-methyl-1,3-thiazol-5-yl)methyl]-5-[4-(1,2,3-thiadiazol-4-yl)benzenesulfonamido-methyl]pyridine-2-carboxamide | 1.00E−05 | + |
| 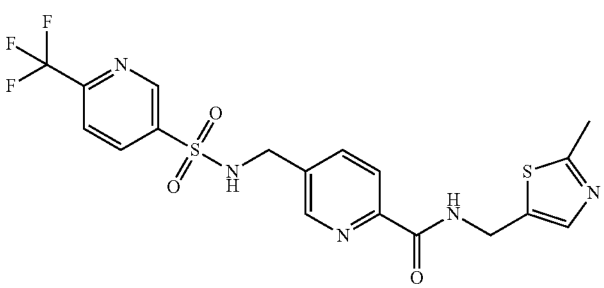 [SMILES: Cc1ncc(CNC(=O)c2ccc(CNS(=O)(=O)c3ccc(C(F)(F)F)nc3)cn2)s1] | N-[(2-methyl-1,3-thiazol-5-yl)methyl]-5-[6-(trifluoromethyl)pyridine-3-sulfonamidomethyl]pyridine-2-carboxamide | 1.00E−05 | + |
| 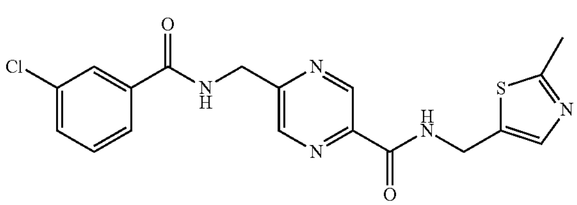 [SMILES: Cc1ncc(CNC(=O)c2cnc(CNC(=O)c3cccc(Cl)c3)cn2)s1] | 5-{[(3-chlorophenyl)formamido]methyl}-N-[(2-methyl-1,3-thiazol-5-yl)methyl]pyrazine-2-carboxamide | 1.00E−05 | + |
| 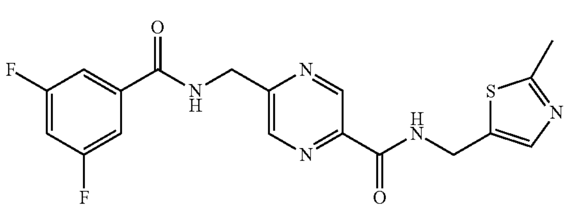 | 5-{[(3,5-difluorophenyl)form-amido]methyl}-N-[(2-methyl-1,3-thiazol-5-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| 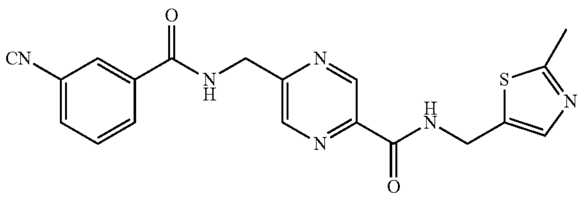 | 5-{[(3-cyanophenyl)formamido]methyl}-N-[(2-methyl-1,3-thiazol-5-yl)methyl]pyrazine-2-carboxamide | 1.00E−05 | + |
| 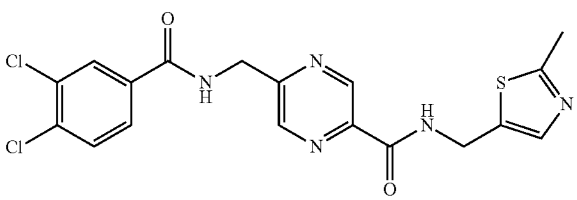 [SMILES: Cc1ncc(CNC(=O)c2cnc(CNC(=O)c3ccc(Cl)c(Cl)c3)cn2)s1] | 5-{[(3,4-dichlorophenyl)formamido]methyl}-N-[(2-methyl-1,3-thiazol-5-yl)methyl]pyrazine-2-carboxamide | 1.00E−05 | + |
| 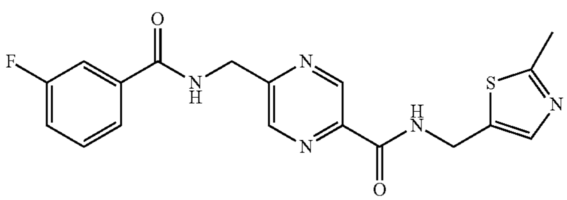 [SMILES: Cc1ncc(CNC(=O)c2cnc(CNC(=O)c3cccc(F)c3)cn2)s1] | 5-{[(3-fluorophenyl)formamido]methyl}-N-[(2-methyl-1,3-thiazol-5-yl)methyl]pyrazine-2-carboxamide | 1.00E−05 | + |
| 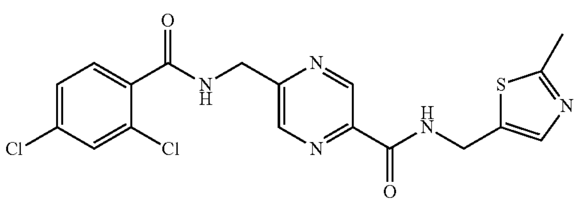 [SMILES: Cc1ncc(CNC(=O)c2cnc(CNC(=O)c3ccc(Cl)cc3Cl)cn2)s1] | 5-{[(2,4-dichlorophenyl)formamido]methyl}-N-[(2-methyl-1,3-thiazol-5-yl)methyl]pyrazine-2-carboxamide | 1.00E−05 | + |
| 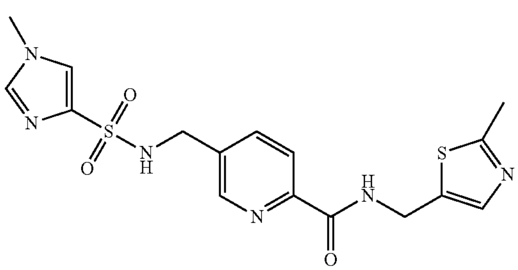 [SMILES: Cc1ncc(CNC(=O)c2ccc(CNS(=O)(=O)c3cn(C)cn3)cn2)s1] | N-[(2-methyl-1,3-thiazol-5-yl)methyl]-5-(1-methyl-1H-imidazole-4-sulfonamidomethyl)pyridine-2-carboxamide | 1.00E−05 | + |
| 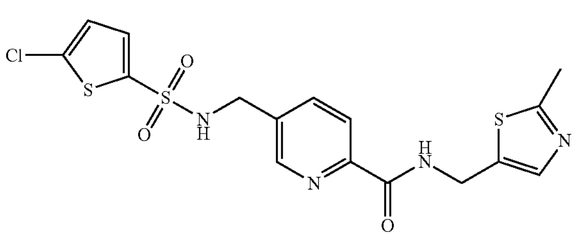 [SMILES: Cc1ncc(CNC(=O)c2ccc(CNS(=O)(=O)c3ccc(Cl)s3)cn2)s1] | 5-(5-chlorothiophene-2-sulfonamidomethyl)-N-[(2-methyl-1,3-thiazol-5-yl)methyl]pyridine-2-carboxamide | 1.00E−05 | + |
| 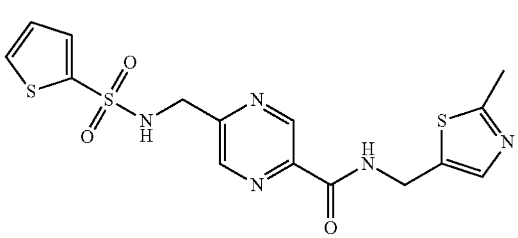 [SMILES: Cc1ncc(CNC(=O)c2cnc(CNS(=O)(=O)c3cccs3)cn2)s1] | N-[(2-methyl-1,3-thiazol-5-yl)methyl]-5-(thiophene-2-sulfonamidomethyl)pyrazine-2-carboxamide | 3.77E−06 | ++ |

TABLE 12-continued

Biological Activity of Compounds of the Invention

| Structure | IUPAC | NR2A IC$_{50}$ (M) | Binned Activity |
|---|---|---|---|
| 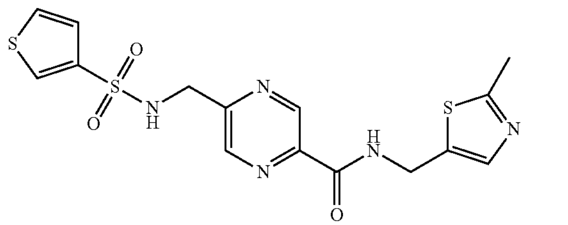 [SMILES: Cc1ncc(CNC(=O)c2cnc(CNS(=O)(=O)c3ccsc3)cn2)s1] | N-[(2-methyl-1,3-thiazol-5-yl)methyl]-5-(thiophene-3-sulfonamidomethyl)pyrazine-2-carboxamide | 1.00E−05 | + |
| 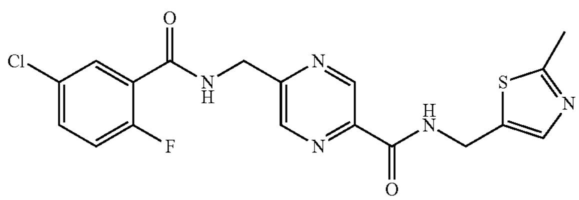 [SMILES: Cc1ncc(CNC(=O)c2cnc(CNC(=O)c3cc(Cl)ccc3F)cn2)s1] | 5-{[(5-chloro-2-fluorophenyl)formamido]methyl}-N-[(2-methyl-1,3-thiazol-5-yl)methyl]pyrazine-2-carboxamide | 1.00E−05 | + |
| 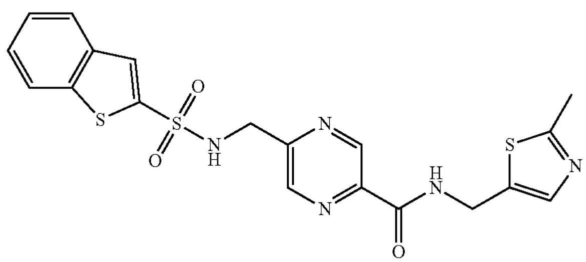 [SMILES: Cc1ncc(CNC(=O)c2cnc(CNS(=O)(=O)c3cc4ccccc4s3)cn2)s1] | 5-(1-benzothiophene-2-sulfonamidomethyl)-N-[(2-methyl-1,3-thiazol-5-yl)methyl]pyrazine-2-carboxamide | 1.00E−05 | + |
| | 5-{[(3,5-difluorophenyl)formamido]methyl}-6-methyl-N-[(2-methyl-1,3-thiazol-5-yl)methyl]pyrazine-2-carboxamide | 1.00E−05 | + |
| 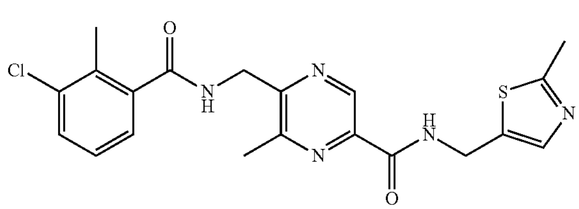 [SMILES: Cc1ncc(CNC(=O)c2cnc(CNC(=O)c3cccc(Cl)c3C)c(C)n2)s1] | 5-{[(3-chloro-2-methylphenyl)formamido]methyl}-6-methyl-N-[(2-methyl-1,3-thiazol-5-yl)methyl]pyrazine-2-carboxamide | 1.00E−05 | + |
| 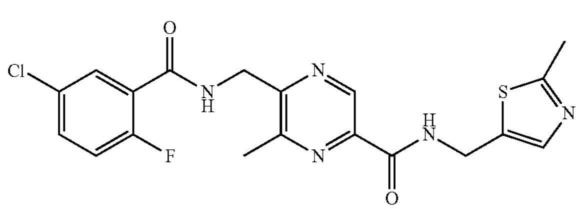 [SMILES: Cc1ncc(CNC(=O)c2cnc(CNC(=O)c3cc(Cl)ccc3F)c(C)n2)s1] | 5-{[(5-chloro-2-fluorophenyl)formamido]methyl}-6-methyl-N-[(2-methyl-1,3-thiazol-5-yl)methyl]pyrazine-2-carboxamide | 1.00E−05 | + |

TABLE 12-continued

Biological Activity of Compounds of the Invention

| Structure | IUPAC | NR2A IC$_{50}$ (M) | Binned Activity |
|---|---|---|---|
| | 5-(3,4-dichlorobenzenesulfon-amidomethyl)-6-methyl-N-[(2-methyl-1,3-thiazol-5-yl)methyl]pyrazine-2-carboxamide | 4.94E−07 | +++ |
| | 5-{[(3-cyanophenyl)formamido]methyl}-6-methyl-N-[(2-methyl-1,3-thiazol-5-yl)methyl]pyrazine-2-carboxamide | 1.00E−05 | + |
| | 5-(3,5-difluorobenzenesulfon-amidomethyl)-6-methyl-N-[(2-methyl-1,3-thiazol-5-yl)methyl]pyrazine-2-carboxamide | 3.66E−07 | +++ |
| | 5-(5-chloro-2-fluorobenzenesulfon-amidomethyl)-6-methyl-N-[(2-methyl-1,3-thiazol-5-yl)methyl]pyrazine-2-carboxamide | 8.06E−06 | ++ |
| | 5-(2-fluorobenzenesulfon-amidomethyl)-6-methyl-N-[(2-methyl-1,3-thiazol-5-yl)methyl]pyrazine-2-carboxamide | 1.00E−05 | + |
| | 5-(4-chloro-3-fluorobenzenesulfon-amidomethyl)-6-methyl-N-[(2-methyl-1,3-thiazol-5-yl)methyl]pyrazine-2-carboxamide | 1.02E−06 | ++ |

TABLE 12-continued

Biological Activity of Compounds of the Invention

| Structure | IUPAC | NR2A IC$_{50}$ (M) | Binned Activity |
|---|---|---|---|
| | 5-(3,5-dichlorobenzenesulfonamidomethyl)-6-methyl-N-[(2-methyl-1,3-thiazol-5-yl)methyl]pyrazine-2-carboxamide | 1.00E−05 | + |
| | 5-(3-chloro-4-fluorobenzenesulfonamidomethyl)-6-ethyl-N-[(2-methyl-1,3-thiazol-5-yl)methyl]pyrazine-2-carboxamide | 8.78E−08 | ++++ |
| | 5-(3-chlorobenzenesulfonmidomethyl)-6-methyl-N-[(2-methyl-1,3-thiazol-5-yl)methyl]pyrazine-2-carboxamide | 3.95E−08 | ++++ |
| | 5-(4-fluorobenzenesulfonamidomethyl)-6-methyl-N-[(2-methyl-1,3-thiazol-5-yl)methyl]pyrazine-2-carboxamide | 1.37E−07 | +++ |
| | 5-(3,4-difluorobenzenesulfonamidomethyl)-6-methyl-N-[(2-methyl-1,3-thiazol-5-yl)methyl]pyrazine-2-carboxamide | 1.62E−08 | ++++ |

TABLE 12-continued

Biological Activity of Compounds of the Invention

| Structure | IUPAC | NR2A IC$_{50}$ (M) | Binned Activity |
|---|---|---|---|
| 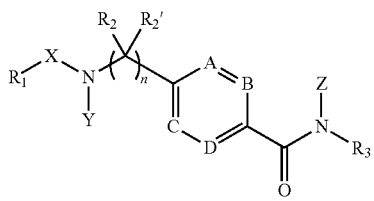 | 5-(3-chloro-4-fluorobenzenesulfon-amidomethyl)-N-[(2-methyl-1,3-thiazol-5-yl)methyl]-6-(trifluoromethyl)pyrazine-2-carboxamide | 1.69E−07 | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What we claim is:

1. A compound of formula I:

I or a pharmaceutically acceptable salt, prodrug, solvate, hydrate, tautomer, or stereoisomer thereof
wherein:
A and D are N;
B and C are CR wherein each R is independently selected from the group consisting of H, halogen, C1-C5 alkyl, CN and O-alkyl;
  $R_1$ is aryl or heteroaryl both of which are optionally substituted with one or more substitutents selected from the group consisting of halogen, $C_1$-$C_5$ alkyl, CN and O-alkyl; or
  $R_1$ is selected from the group consisting of optionally substituted alkyl, optionally substituted cycloalkyl, or optionally substituted heterocycloalkyl;
  $R_2$ and $R_{2'}$ are independently selected from the group consisting of H, and $C_1$-$C_5$ alkyl; or
  $R_2$ and $R_{2'}$ may form, with the carbon to which they are connected, a cycloalkane;
X is C=O or SO$_2$;
Y is selected from the group consisting of H, $C_1$-$C_5$ alkyl, and a group —CHP$_1$P$_2$
  P$_1$ is selected from the group consisting of H, and $C_1$-$C_5$ alkyl;
  P$_2$ is O($C_1$-$C_5$)alkyl optionally substituted by one or more alkoxy and/or hydroxy groups;
  or P$_2$ is selected from the group consisting of OC(O)R$_4$, OC(O)OR$_4$, OC(O)NHR$_4$, OC(O)NR$_4$R$_5$, OC(O)-alkyl-NR$_4$R$_5$, and O(PO)O$_2^{-2}$M$_2$; or P$_1$ and P$_2$, form a cycloalkyl or a heterocycle; M is a monovalent metal cation;
  R$_4$ and R$_5$ are independently selected from the group consisting of H, and C$_1$-C$_5$ alkyl with the proviso that when P$_2$ is OC(O)OR$_4$, R$_4$ is not hydrogen;
  R$_3$ is -L$_1$-Ar$_1$, or

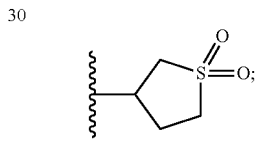

L$_1$ is straight or branched C$_1$-C$_5$ alkyl;
  Z is selected from the group consisting of H and C$_1$-C$_5$ alkyl; or
  Z and R$_3$, with the nitrogen to which they are connected, may form a heterocycle;
  Ar$_1$ is aryl optionally substituted with one or more substitutents selected from the group consisting of C$_1$-C$_5$ alkyl, CN, and O-alkyl; or
  Ar$_1$ is heteroaryl optionally substituted with one or more substitutents selected from the group consisting of C$_1$-C$_5$ alkyl, CN, and O-alkyl; and
  n is 1 or 2.

2. The compound of claim 1 wherein R$_1$ is aryl substituted with one or more substitutents selected from the group consisting of halogen, C$_1$-C$_5$ alkyl, CN and O-alkyl.

3. The compound of claim 1 wherein R$_1$ is heteroaryl substituted with one or more substitutents selected from the group consisting of halogen, C$_1$-C$_5$ alkyl, CN and O-alkyl.

4. The compound of claim 2 wherein R$_1$ is aryl substituted by one or more halogen.

5. The compound of claim 3 wherein R$_1$ is heteroaryl substituted by one or more halogen.

6. The compound of claim 4 wherein R$_1$ is phenyl substituted by one or more halogen.

7. The compound of claim 6 wherein R$_1$ is phenyl substituted by two halogens.

8. The compound of claim 7 wherein $R_1$ is

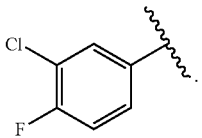 [SMILES: *c1ccc(F)c(Cl)c1]

9. The compound of claim 2 wherein X is $SO_2$.
10. The compound of claim 9 wherein Y is H.
11. The compound of claim 10 wherein n is 1.
12. The compound of claim 11 wherein $R_2$ is H.
13. The compound of claim 11 wherein $R_2$ is H.
14. The compound of claim 1 wherein Z is H.
15. The compound of claim 14 wherein $R_3$ is -$L_1$-$Ar_1$ and $L_1$ is $C_1$-$C_3$ alkyl.
16. The compound of claim 14 wherein $L_1$ is $CH_2$.
17. The compound of claim 15 wherein $Ar_1$ is heteroaryl substituted with one or more of the following features: $C_1$-$C_5$ alkyl, CN, and O-alkyl.
18. The compound of claim 17 wherein $Ar_1$ is pyridyl substituted with one or more of the following features: $C_1$-$C_5$ alkyl, CN, and O-alkyl.
19. The compound of claim 17 wherein $Ar_1$ is pyridinazyl substituted with one or more of the following features: $C_1$-$C_5$ alkyl, CN, and O-alkyl.
20. The compound of claim 17 wherein $Ar_1$ is thiazolyl substituted with one or more of the following features: $C_1$-$C_5$ alkyl, CN, and O-alkyl.
21. The compound of claim 20 wherein thiazolyl is bonded to $L_1$ at the 5 position of the thiazolyl ring:

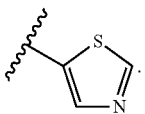 [SMILES: *c1cncs1]

22. A compound selected from the group
5-[(3-chloro-4-fluorobenzene)sulfonamidomethyl]-N-(1,3-thiazol-5-ylmethyl)pyrazine-2-carboxamide;
5-[(3-chloro-4-fluorobenzene)sulfonamidomethyl]-N-[(4-methoxyphenyl)methyl]pyrazine-2-carboxamide;
5-[(3-chloro-4-fluorobenzene)sulfonamidomethyl]-N-[(5-fluoropyridin-3-yl)methyl]pyrazine-2-carboxamide;
5-[(3,5-dichlorobenzene)sulfonamidomethyl]-N-[(2-methyl-1,3-thiazol-5-yl)methyl]pyrazine-2-carboxamide;
5-[(3,4-dichlorobenzene)sulfonamidomethyl]-N-[(2-methyl-1,3-thiazol-5-yl)methyl]pyrazine-2-carboxamide;
5-[(2-fluorobenzene)sulfonamidomethyl]-N-[(2-methyl-1,3-thiazol-5-yl)methyl]pyrazine-2-carboxamide;
5-[(3-chloro-4-fluorobenzene)sulfonamidomethyl]-N-[(4-methylpyridin-3-yl)methyl]pyrazine-2-carboxamide;
5-[(3-chloro-4-fluorobenzene)sulfonamidomethyl]-N-(pyrimidin-4-ylmethyl)pyrazine-2-carboxamide;
5-[(3-chloro-4-fluorobenzene)sulfonamidomethyl]-N-(1,3-oxazol-4-ylmethyl)pyrazine-2-carboxamide;
5-[(3-chloro-4-fluorobenzene)sulfonamidomethyl]-N-[(2-methyl-1,3-thiazol-4-yl)methyl]pyrazine-2-carboxamide;
5-(((3-chloro-4-fluorophenyl)sulfonamido)methyl)-N-(1,1-dioxidotetrahydrothiophen-3-yl)pyrazine-2-carboxamide;
5-[(3-chloro-4-fluorobenzene)sulfonamidomethyl]-N-[(1-methyl-1H-imidazol-4-yl)methyl]pyrazine-2-carboxamide;
5-[(3-chloro-4-fluorobenzene)sulfonamidomethyl]-N-(pyridin-3-ylmethyl)pyrazine-2-carboxamide;
5-[(3-chloro-4-fluorobenzene)sulfonamidomethyl]-N-[(4-methyl-1,3-thiazol-5-yl)methyl]pyrazine-2-carboxamide;
5-[(3-chloro-4-fluorobenzene)sulfonamidomethyl]-N-(pyridin-4-ylmethyl)pyrazine-2-carboxamide;
5-[(3-chloro-4-fluorobenzene)sulfonamidomethyl]-N-(pyrazin-2-ylmethyl)pyrazine-2-carboxamide;
5-[(3-chloro-4-fluorobenzene)sulfonamidomethyl]-N-[(1-methyl-1H-pyrrol-2-yl)methyl]pyrazine-2-carboxamide;
5-[(3-chloro-4-fluorobenzene)sulfonamidomethyl]-N-[(1,5-dimethyl-1H-pyrrol-2-yl)methyl]pyrazine-2-carboxamide;
5-[(3-chloro-4-fluorobenzene)sulfonamidomethyl]-N-[(1-methyl-1H-pyrazol-5-yl)methyl]pyrazine-2-carboxamide;
5-[(3-chloro-4-fluorobenzene)sulfonamidomethyl]-N-[(1-methyl-1H-imidazol-5-yl)methyl]pyrazine-2-carboxamide;
5-[(3-chloro-4-fluorobenzene)sulfonamidomethyl]-N-(pyridin-2-ylmethyl)pyrazine-2-carboxamide;
5-[(3-chloro-4-fluorobenzene)sulfonamidomethyl]-N-[(5-methylpyrazin-2-yl)methyl]pyrazine-2-carboxamide;
5-[(3-chloro-4-fluorobenzene)sulfonamidomethyl]-N-[(6-methylpyridin-2-yl)methyl]pyrazine-2-carboxamide;
5-[(3-chloro-4-fluorobenzene)sulfonamidomethyl]-N-(1,3-thiazol-2-ylmethyl)pyrazine-2-carboxamide;
5-[(3-chloro-4-fluorobenzene)sulfonamidomethyl]-N-[(4-methyl-1,3-thiazol-2-yl)methyl]pyrazine-2-carboxamide;
5-[(3-chloro-4-fluorobenzene)sulfonamidomethyl]-N-[(1R)-1-(1,3-thiazol-5-yl)ethyl]pyrazine-2-carboxamide;
5-[(3-chloro-4-fluorobenzene)sulfonamidomethyl]-N-(pyrimidin-5-ylmethyl)pyrazine-2-carboxamide;
5-[(3-chloro-4-fluorobenzene)sulfonamidomethyl]-N-[(dimethyl-1,3-thiazol-5-yl)methyl]pyrazine-2-carboxamide;
5-[(3-chloro-4-fluorobenzene)sulfonamidomethyl]-N-{[3-chloro-5-(trifluoromethyl)pyridin-2-yl]methyl}pyrazine-2-carboxamide;
5-[(3-chloro-4-fluorobenzene)sulfonamidomethyl]-N-[(2-methoxypyridin-4-yl)methyl]pyrazine-2-carboxamide;
5-[(3-chloro-4-fluorobenzene)sulfonamidomethyl]-N-[(1-methyl-1H-imidazol-2-yl)methyl]pyrazine-2-carboxamide;
5-[(3-chloro-4-fluorobenzene)sulfonamidomethyl]-N-[(5-methylthiophen-2-yl)methyl]pyrazine-2-carboxamide;
5-[(3-chloro-4-fluorobenzene)sulfonamidomethyl]-N-[(5-methyl-1,3,4-oxadiazol-2-yl)methyl]pyrazine-2-carboxamide;
5-[(3-chloro-4-fluorobenzene)sulfonamidomethyl]-N-[(5-methyl-1,3,4-thiadiazol-2-yl)methyl]pyrazine-2-carboxamide;

- 5-[(3-chloro-4-fluorobenzene)sulfonamidomethyl]-N-[(1,3-dimethyl-1H-pyrazol-5-yl)methyl]pyrazine-2-carboxamide;
- 5-[(3-chloro-4-fluorobenzene)sulfonamidomethyl]-N-[(6-methoxypyridin-3-yl)methyl]pyrazine-2-carboxamide;
- 5-[(3-chloro-4-fluorobenzene)sulfonamidomethyl]-N-[1-(2-methyl-1,3-thiazol-5-yl)ethyl]pyrazine-2-carboxamide;
- 5-[(3-chloro-4-fluorobenzene)sulfonamidomethyl]-N-{[3-(trifluoromethyl)pyridin-2-yl]methyl}pyrazine-2-carboxamide;
- 5-[(4-chloro-3-fluorobenzene)sulfonamidomethyl]-N-[(2-methyl-1,3-thiazol-5-yl)methyl]pyrazine-2-carboxamide; and
- 5-[(3,4-difluorobenzene)sulfonamidomethyl]-N-[(2-methyl-1,3-thiazol-5-yl)methyl]pyrazine-2-carboxamide.

23. A pharmaceutical composition comprising a compound according to claim 1 and a pharmaceutically acceptable carrier.

24. The compound 5-[(3-chloro-4-fluorobenzene)sulfonamidomethyl]-N-[(2-methyl-1,3-thiazol-5-yl)methyl]pyrazine-2-carboxamide.

25. The compound:
- 5-(3,4-difluorobenzenesulfonamidomethyl)-6-methyl-N-[(2-methyl-1,3-thiazol-5-yl)methyl]pyrazine-2-carboxamide; or
- 5-(3-chloro-4-fluorobenzenesulfonamidomethyl)-6-methyl-N-[(2-methyl-1,3-thiazol-5-yl)methyl]pyrazine-2-carboxamide.

* * * * *